(12) United States Patent
Fumero et al.

(10) Patent No.: US 8,058,232 B2
(45) Date of Patent: Nov. 15, 2011

(54) HMGB1 HIGH AFFINITY BINDING DOMAIN BOX-A MUTANTS

(75) Inventors: Silvano Fumero, Ivrea (IT); Luisa Bertarione Rava Rossa, Pavone Canaverse (IT); Domenico G. Barone, Turin (IT); Lila Drittanti, Vigneux sur Siene (FR); Thierry Guyon, Palaiseau (FR); Gilles Borrelly, Epinay sous Senart (FR); Barbara Canepa, San Sebastiano da Po (IT); Chiara Lorenzetto, Villafranca Piemonte (IT)

(73) Assignee: Creabilis Therapeutics S.p.A., Colleretto Giacosa (IT)

( * ) Notice: Subject to any disclaimer, the term of this patent is extended or adjusted under 35 U.S.C. 154(b) by 0 days.

(21) Appl. No.: 12/614,805

(22) Filed: Nov. 9, 2009

(65) Prior Publication Data

US 2011/0052493 A1    Mar. 3, 2011

Related U.S. Application Data

(60) Division of application No. 11/713,789, filed on Mar. 5, 2007, now Pat. No. 7,635,679, which is a continuation-in-part of application No. PCT/EP2005/009528, filed on Sep. 5, 2005.

(30) Foreign Application Priority Data

Sep. 3, 2004 (EP) .................................. 04425665

(51) Int. Cl.
*A61K 38/17* (2006.01)
*C07K 14/47* (2006.01)
*C12N 15/00* (2006.01)
*C12P 21/02* (2006.01)

(52) U.S. Cl. ........................ 514/1.4; 435/69.1; 530/350
(58) Field of Classification Search .................. None
See application file for complete search history.

(56) References Cited

U.S. PATENT DOCUMENTS 7,304,034 B2   12/2007  Tracey et al. ................... 514/12

FOREIGN PATENT DOCUMENTS

| CH | 694905 A5 | 9/2005 |
|---|---|---|
| WO | 02/074337 A1 | 9/2002 |
| WO | 02/092004 A2 | 11/2002 |
| WO | 2004/022747 A1 | 3/2004 |
| WO | 2004/046345 A2 | 6/2004 |
| WO | 2005/025604 A2 | 3/2005 |

OTHER PUBLICATIONS

Isackson et al., "Production of HMG-3 by Limited Trypsin Digestion of Purified High-Mobility-Group Nonhistone Chromatin Proteins", Biochimica Et Biophysica Acta, 748 (1983), 436-443.
Yang et al., "HMGB1 as a cytokine and therapeutic target", Journal of Endotoxin Research, vol. 8, No. 6, 2002, pp. 469-472.
Kokkola et al, "Successful Treatment of Collagen-Induced Arthritis in Mice and Rats by Targeting Extracellular High Mobility Group Box Chromosomal Protein 1 Activity", Arthritis & Rheumatism, vol. 48, No. 7, Jul. 2003, pp. 2052-2058.
Sparatore et al. "Extracellular processing of amphoterin generates a peptide active on erythroleukaemia cell differentiation", Biochem J., (2001), 357, p. 569-574.
Andersson et al., "HMGB1 is a potent trigger of arthritis", Journal of Internal Medicine, 2004, 255, p. 344-350.
Park et al., "Involvement of Toll-like Receptors 2 and 4 in Cellular Activation by High Mobility Group Box 1 Protein", The Journal of Biological Chemistry, vol. 279, No. 9, Issue of Feb. 27, pp. 7370-7377, 2004.
Farid et al., "Differential Binding of HMG1, HMG2 and a Singe HMG Box to Cisplatin-Damaged DNA", Toxicology and Applied Pharmacology, 141, p. 532-539, (1996).
Falciola et al., "Mutational analysis of the DNA binding domain A of chromosomal protein HMG1", Nucleic Acids Research, 1994, vol. 22, No. 3, pp. 285-292.
Yang et al., "Reversing established sepsis with antagonists of endogenous high-mobility group box 1", PNAS, Jan. 6, 2004, vol. 1, No. 1, pp. 296-301.

*Primary Examiner* — Elly-Gerald Stoica
(74) *Attorney, Agent, or Firm* — Rothwell, Figg, Ernst & Manbeck, P.C.

(57) ABSTRACT

The present invention relates to polypeptide variants of the HMGB-1 high affinity binding domain Box-A (HMGB1 Box-A) or to a biologically active fragment of HMGB1 Box-A, which are obtained through systematic mutations of single amino acids of the wild-type HMGB1 Box-A protein and which show an increased resistance to proteases and which are therefore characterized by more favorable pharmacokinetic and pharmacodynamic profiles. Moreover, the present invention concerns the use of said polypeptide molecules of HMGB1 Box-A to diagnose, prevent, alleviate and/or treat pathologies associated with extracellular HMGB1 and associated with RAGE.

5 Claims, 110 Drawing Sheets

Figure 1

In silico identification of all amino acid positions that are targets for proteolysis using a large number of selected proteases and chemical treatments.

| | | |
|---|---|---|
| AspN | 'D | Endoproteinase Asp-N |
| Chymo | (F,W,Y,M,L)'~P | Chymotrypsin |
| Clos | R' | Clostripain |
| CnBr | M' | Cyanogen Bromide |
| IbzO | W' | IodosoBenzoate |
| Myxo | K' | Myxobacter |
| NH2OH | N'G | Hydroxylamine |
| pH2.5 | D'P | pH 2.5 |
| ProEn | P' | Proline Endopeptidase |
| Staph | E' | Staphylococcal Protease |
| Tryp | (K,R)'~P | Trypsin |
| TrypK | K'~P | Trypsin(Arg blocked) |
| TrypR | R'~P | Trypsin(Lys blocked) |

Figure 2 – Percent Accepted Mutation (PAM 250)

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 2 | -2 | 0 | 0 | -2 | 0 | 0 | 1 | -1 | -1 | -2 | -1 | -1 | -3 | 1 | 1 | 1 | -6 | -3 | 0 |
| R | -2 | 6 | 0 | -1 | -4 | 1 | -1 | -3 | 2 | -2 | -3 | 3 | 0 | -4 | 0 | 0 | -1 | 2 | -4 | -2 |
| N | 0 | 0 | 2 | 2 | -4 | 1 | 1 | 0 | 2 | -2 | -3 | 1 | -2 | -3 | 0 | 1 | 0 | -4 | -2 | -2 |
| D | 0 | -1 | 2 | 4 | -5 | 2 | 3 | 1 | 1 | -2 | -4 | 0 | -3 | -6 | -1 | 0 | 0 | -7 | -4 | -2 |
| C | -2 | -4 | -4 | -5 | 12 | -5 | -5 | -3 | -3 | -2 | -6 | -5 | -5 | -4 | -3 | 0 | -2 | -8 | 0 | -2 |
| Q | 0 | 1 | 1 | 2 | -5 | 4 | 2 | -1 | 3 | -2 | -2 | 1 | -1 | -5 | 0 | -1 | -1 | -5 | -4 | -2 |
| E | 0 | -1 | 1 | 3 | -5 | 2 | 4 | 0 | 1 | -2 | -3 | 0 | -2 | -5 | -1 | 0 | 0 | -7 | -4 | -2 |
| G | 1 | -3 | 0 | 1 | -3 | -1 | 0 | 5 | -2 | -3 | -4 | -2 | -3 | -5 | 0 | 1 | 0 | -7 | -5 | -1 |
| H | -1 | 2 | 2 | 1 | -3 | 3 | 1 | -2 | 6 | -2 | -2 | 0 | -2 | -2 | 0 | -1 | -1 | -3 | 0 | -2 |
| I | -1 | -2 | -2 | -2 | -2 | -2 | -2 | -3 | -2 | 5 | 2 | -2 | 2 | 1 | -2 | -1 | 0 | -5 | -1 | 4 |
| L | -2 | -3 | -3 | -4 | -6 | -2 | -3 | -4 | -2 | 2 | 6 | -3 | 4 | 2 | -3 | -3 | -2 | -2 | -1 | 2 |
| K | -1 | 3 | 1 | 0 | -5 | 1 | 0 | -2 | 0 | -2 | -3 | 5 | 0 | -5 | -1 | 0 | 0 | -3 | -4 | -2 |
| M | -1 | 0 | -2 | -3 | -5 | -1 | -2 | -3 | -2 | 2 | 4 | 0 | 6 | 0 | -2 | -2 | -1 | -4 | -2 | 2 |
| F | -3 | -4 | -3 | -6 | -4 | -5 | -5 | -5 | -2 | 1 | 2 | -5 | 0 | 9 | -5 | -3 | -3 | 0 | 7 | -1 |
| P | 1 | 0 | 0 | -1 | -3 | 0 | -1 | 0 | 0 | -2 | -3 | -1 | -2 | -5 | 6 | 1 | 0 | -6 | -5 | -1 |
| S | 1 | 0 | 1 | 0 | 0 | -1 | 0 | 1 | -1 | -1 | -3 | 0 | -2 | -3 | 1 | 2 | 1 | -2 | -3 | -1 |
| T | 1 | -1 | 0 | 0 | -2 | -1 | 0 | 0 | -1 | 0 | -2 | 0 | -1 | -3 | 0 | 1 | 3 | -5 | -3 | 0 |
| W | -6 | 2 | -4 | -7 | -8 | -5 | -7 | -7 | -3 | -5 | -2 | -3 | -4 | 0 | -6 | -2 | -5 | 17 | 0 | -6 |
| Y | -3 | -4 | -2 | -4 | 0 | -4 | -4 | -5 | 0 | -1 | -1 | -4 | -2 | 7 | -5 | -3 | -3 | 0 | 10 | -2 |
| V | 0 | -2 | -2 | -2 | -2 | -2 | -2 | -1 | -2 | 4 | 2 | -2 | 2 | -1 | -1 | -1 | 0 | -6 | -2 | 4 |

▨ Value given for identical residues.

■ Positive value of substitution between two residues.

Figure 3a

Box A 84 amino acids

\# Protection against proteolysis
If sequence:

GKGDPKKPRGKMSSYAFFVQTCREEHKKKHPDASVNFSEFSKKCSERWKTMSAKE
KGKFEDMAKADKARYEREMKTYIPPKGET

In bold amino acids sensitive to proteases proteolysis

Figure 3b

Box A 84 amino acids
\# Mutant list:

| | | | |
|---|---|---|---|
| K2N   | K27Q  | E55Q  | E73N |
| K2Q   | K28N  | E55H  | M74I |
| D4N   | K28Q  | E55N  | M74V |
| D4Q   | K29N  | K56N  | K75N |
| P5A   | K29Q  | K56Q  | K75Q |
| P5S   | P31A  | K58N  | Y77H |
| K6N   | P31S  | K58Q  | Y77I |
| K6Q   | D32N  | F59I  | P79A |
| K7N   | D32Q  | F59V  | P79S |
| K7Q   | F37I  | E60Q  | P80A |
| P8A   | F37V  | E60H  | P80S |
| P8S   | E39Q  | E60N  | K81N |
| R9H   | E39H  | D61N  | K81Q |
| R9Q   | E39N  | D61Q  | E83Q |
| K11N  | F40I  | M62I  | E83H |
| K11Q  | F40V  | M62V  | E83N |
| M12I  | K42N  | K64N  | |
| M12V  | K42Q  | K64Q  | |
| Y15H  | K43N  | D66N  | |
| Y15I  | K43Q  | D66Q  | |
| F17I  | E46Q  | K67N  | |
| F17V  | E46H  | K67Q  | |
| F18I  | E46N  | R69H  | |
| F18V  | R47H  | R69Q  | |
| R23H  | R47Q  | Y70H  | |
| R23Q  | W48Y  | Y70I  | |
| E24Q  | W48S  | E71Q  | |
| E24H  | K49N  | E71H  | |
| E24N  | K49Q  | E71N  | |
| E25Q  | M51I  | R72H  | |
| E25H  | M51V  | R72Q  | |
| E25N  | K54N  | E73Q  | |
| K27N  | K54Q  | E73H  | |

Figure 3b continued

Box A 84 amino acid sequences:

> sequence 1 Wild type
GKGDPKKPRGKMSSYAFFVQTCREEHKKKHPDASVNFSEFSKKCSERWKTMSAKEKGKFEDMAKAD
KARYEREMKTYIPPKGET > sequence 2 K2N
GNGDPKKPRGKMSSYAFFVQTCREEHKKKHPDASVNFSEFSKKCSERWKTMSAKEKGKFEDMAKAD
KARYEREMKTYIPPKGET > sequence 3 K2Q
GQGDPKKPRGKMSSYAFFVQTCREEHKKKHPDASVNFSEFSKKCSERWKTMSAKEKGKFEDMAKAD
KARYEREMKTYIPPKGET > sequence 4 D4N
GKGNPKKPRGKMSSYAFFVQTCREEHKKKHPDASVNFSEFSKKCSERWKTMSAKEKGKFEDMAKAD
KARYEREMKTYIPPKGET > sequence 5 D4Q
GKGQPKKPRGKMSSYAFFVQTCREEHKKKHPDASVNFSEFSKKCSERWKTMSAKEKGKFEDMAKAD
KARYEREMKTYIPPKGET > sequence 6 P5A
GKGDAKKPRGKMSSYAFFVQTCREEHKKKHPDASVNFSEFSKKCSERWKTMSAKEKGKFEDMAKAD
KARYEREMKTYIPPKGET > sequence 7 P5S
GKGDSKKPRGKMSSYAFFVQTCREEHKKKHPDASVNFSEFSKKCSERWKTMSAKEKGKFEDMAKAD
KARYEREMKTYIPPKGET > sequence 8 K6N
GKGDPNKPRGKMSSYAFFVQTCREEHKKKHPDASVNFSEFSKKCSERWKTMSAKEKGKFEDMAKAD
KARYEREMKTYIPPKGET > sequence 9 K6Q
GKGDPQKPRGKMSSYAFFVQTCREEHKKKHPDASVNFSEFSKKCSERWKTMSAKEKGKFEDMAKAD
KARYEREMKTYIPPKGET > sequence 10 K7N
GKGDPKNPRGKMSSYAFFVQTCREEHKKKHPDASVNFSEFSKKCSERWKTMSAKEKGKFEDMAKAD
KARYEREMKTYIPPKGET > sequence 11 K7Q
GKGDPKQPRGKMSSYAFFVQTCREEHKKKHPDASVNFSEFSKKCSERWKTMSAKEKGKFEDMAKAD
KARYEREMKTYIPPKGET > sequence 12 P8A
GKGDPKKARGKMSSYAFFVQTCREEHKKKHPDASVNFSEFSKKCSERWKTMSAKEKGKFEDMAKAD
KARYEREMKTYIPPKGET > sequence 13 P8S
GKGDPKKSRGKMSSYAFFVQTCREEHKKKHPDASVNFSEFSKKCSERWKTMSAKE

Figure 3b continued

KGKFEDMAKADKARYEREMKTYIPPKGET

> sequence 14 R9H
GKGDPKKPHGKMSSYAFFVQTCREEHKKKHPDASVNFSEFSKKCSERWKTMSAKEKGKFEDMAKAD
KARYEREMKTYIPPKGET > sequence 15 R9Q
GKGDPKKPQGKMSSYAFFVQTCREEHKKKHPDASVNFSEFSKKCSERWKTMSAKEKGKFEDMAKAD
KARYEREMKTYIPPKGET > sequence 16 K11N
GKGDPKKPRGNMSSYAFFVQTCREEHKKKHPDASVNFSEFSKKCSERWKTMSAKEKGKFEDMAKAD
KARYEREMKTYIPPKGET > sequence 17 K11Q
GKGDPKKPRGQMSSYAFFVQTCREEHKKKHPDASVNFSEFSKKCSERWKTMSAKEKGKFEDMAKAD
KARYEREMKTYIPPKGET > sequence 18 M12I
GKGDPKKPRGKISSYAFFVQTCREEHKKKHPDASVNFSEFSKKCSERWKTMSAKEKGKFEDMAKADK
ARYEREMKTYIPPKGET > sequence 19 M12V
GKGDPKKPRGKVSSYAFFVQTCREEHKKKHPDASVNFSEFSKKCSERWKTMSAKEKGKFEDMAKADK
ARYEREMKTYIPPKGET > sequence 20 Y15H
GKGDPKKPRGKMSSHAFFVQTCREEHKKKHPDASVNFSEFSKKCSERWKTMSAKEKGKFEDMAKAD
KARYEREMKTYIPPKGET > sequence 21 Y15I
GKGDPKKPRGKMSSIAFFVQTCREEHKKKHPDASVNFSEFSKKCSERWKTMSAKEKGKFEDMAKADK
ARYEREMKTYIPPKGET > sequence 22 F17I
GKGDPKKPRGKMSSYAIFVQTCREEHKKKHPDASVNFSEFSKKCSERWKTMSAKEKGKFEDMAKADK
ARYEREMKTYIPPKGET > sequence 23 F17V
GKGDPKKPRGKMSSYAVFVQTCREEHKKKHPDASVNFSEFSKKCSERWKTMSAKEKGKFEDMAKAD
KARYEREMKTYIPPKGET > sequence 24 F18I
GKGDPKKPRGKMSSYAFIVQTCREEHKKKHPDASVNFSEFSKKCSERWKTMSAKEKGKFEDMAKADK
ARYEREMKTYIPPKGET > sequence 25 F18V
GKGDPKKPRGKMSSYAFVVQTCREEHKKKHPDASVNFSEFSKKCSERWKTMSAKEKGKFEDMAKAD
KARYEREMKTYIPPKGET > sequence 26 R23H
GKGDPKKPRGKMSSYAFFVQTCHEEHKKKHPDASVNFSEFSKKCSERWKTMSAKEKGKFEDMAKAD
KARYEREMKTYIPPKGET

Figure 3b continued

> sequence 27 R23Q
GKGDPKKPRGKMSSYAFFVQTCQEEHKKKHPDASVNFSEFSKKCSERWKTMSAKEGKFEDMAKADK

AYEREMKTYIPPKKGET

> sequence 28 E24Q
GKGDPKKPRGKMSSYAFFVQTCRQEHKKKHPDASVNFSEFSKKCSERWKTMSAKEKGKFEDMAKAD
KARYEREMKTYIPPKGET > sequence 29 E24H
GKGDPKKPRGKMSSYAFFVQTCRHEHKKKHPDASVNFSEFSKKCSERWKTMSAKEKGKFEDMAKAD
KARYEREMKTYIPPKGET > sequence 30 E24N
GKGDPKKPRGKMSSYAFFVQTCRNEHKKKHPDASVNFSEFSKKCSERWKTMSAKEKGKFEDMAKAD
KARYEREMKTYIPPKGET > sequence 31 E25Q
GKGDPKKPRGKMSSYAFFVQTCREQHKKKHPDASVNFSEFSKKCSERWKTMSAKEKGKFEDMAKAD
KARYEREMKTYIPPKGET > sequence 32 E25H
GKGDPKKPRGKMSSYAFFVQTCREHHKKKHPDASVNFSEFSKKCSERWKTMSAKEKGKFEDMAKAD
KARYEREMKTYIPPKGET > sequence 33 E25N
GKGDPKKPRGKMSSYAFFVQTCRENHKKKHPDASVNFSEFSKKCSERWKTMSAKEKGKFEDMAKAD
KARYEREMKTYIPPKGET > sequence 34 K27N
GKGDPKKPRGKMSSYAFFVQTCREEHNKKHPDASVNFSEFSKKCSERWKTMSAKEKGKFEDMAKAD
KARYEREMKTYIPPKGET > sequence 35 K27Q
GKGDPKKPRGKMSSYAFFVQTCREEHQKKHPDASVNFSEFSKKCSERWKTMSAKEKGKFEDMAKAD
KARYEREMKTYIPPKGET > sequence 36 K28N
GKGDPKKPRGKMSSYAFFVQTCREEHKNKHPDASVNFSEFSKKCSERWKTMSAKEKGKFEDMAKAD
KARYEREMKTYIPPKGET > sequence 37 K28Q
GKGDPKKPRGKMSSYAFFVQTCREEHKQKHPDASVNFSEFSKKCSERWKTMSAKEKGKFEDMAKAD
KARYEREMKTYIPPKGET > sequence 38 K29N
GKGDPKKPRGKMSSYAFFVQTCREEHKKNHPDASVNFSEFSKKCSERWKTMSAKEKGKFEDMAKAD
KARYEREMKTYIPPKGET > sequence 39 K29Q
GKGDPKKPRGKMSSYAFFVQTCREEHKKQHPDASVNFSEFSKKCSERWKTMSAKEKGKFEDMAKAD
KARYEREMKTYIPPKGET

Figure 3b continued

> sequence 40 P31A
GKGDPKKPRGKMSSYAFFVQTCREEHKKKHADASVNFSEFSKKCSERWKTMSAKEKGKFEDMAKAD
KARYEREMKTYIPPKGET > sequence 41 P31S
GKGDPKKPRGKMSSYAFFVQTCREEHKKKHSDASVNFSEFSKKCSERWKTMSAKEKGKFEDMAKAD
KARYEREMKTYIPPKGET > sequence 42 D32N
GKGDPKKPRGKMSSYAFFVQTCREEHKKKHPNASVNFSEFSKKCSERWKTMSAKEKGKFEDMAKAD
KARYEREMKTYIPPKGET > sequence 43 D32Q
GKGDPKKPRGKMSSYAFFVQTCREEHKKKHPQASVNFSEFSKKCSERWKTMSAKEKGKFEDMAKAD
KARYEREMKTYIPPKGET > sequence 44 F37I
GKGDPKKPRGKMSSYAFFVQTCREEHKKKHPDASVNISEFSKKCSERWKTMSAKEKGKFEDMAKADK
ARYEREMKTYIPPKGET > sequence 45 F37V
GKGDPKKPRGKMSSYAFFVQTCREEHKKKHPDASVNVSEFSKKCSERWKTMSAKEKGKFEDMAKAD
KARYEREMKTYIPPKGET > sequence 46 E39Q
GKGDPKKPRGKMSSYAFFVQTCREEHKKKHPDASVNFSQFSKKCSERWKTMSAKEKGKFEDMAKAD
KARYEREMKTYIPPKGET > sequence 47 E39H
GKGDPKKPRGKMSSYAFFVQTCREEHKKKHPDASVNFSHFSKKCSERWKTMSAKEKGKFEDMAKAD
KARYEREMKTYIPPKGET > sequence 48 E39N
GKGDPKKPRGKMSSYAFFVQTCREEHKKKHPDASVNFSNFSKKCSERWKTMSAKEKGKFEDMAKAD
KARYEREMKTYIPPKGET > sequence 49 F40I
GKGDPKKPRGKMSSYAFFVQTCREEHKKKHPDASVNFSEISKKCSERWKTMSAKEKGKFEDMAKADK
ARYEREMKTYIPPKGET > sequence 50 F40V
GKGDPKKPRGKMSSYAFFVQTCREEHKKKHPDASVNFSEVSKKCSERWKTMSAKEKGKFEDMAKAD
KARYEREMKTYIPPKGET > sequence 51 K42N
GKGDPKKPRGKMSSYAFFVQTCREEHKKKHPDASVNFSEFSNKCSERWKTMSAKEKGKFEDMAKAD
KARYEREMKTYIPPKGET > sequence 52 K42Q
GKGDPKKPRGKMSSYAFFVQTCREEHKKKHPDASVNFSEFSQKCSERWKTMSAKEKGKFEDMAKAD
KARYEREMKTYIPPKGET > sequence 53 K43N
GKGDPKKPRGKMSSYAFFVQTCREEHKKKHPDASVNFSEFSKNCSERWKTMSAKEKGKFEDMAKAD
KARYEREMKTYIPPKGET

Figure 3b continued

> sequence 54 K43Q
GKGDPKKPRGKMSSYAFFVQTCREEHKKKHPDASVNFSEFSKQCSERWKTMSAKEKGKFEDMAKAD
KARYEREMKTYIPPKGET > sequence 55 E46Q
GKGDPKKPRGKMSSYAFFVQTCREEHKKKHPDASVNFSEFSKKCSQRWKTMSAKEKGKFEDMAKAD
KARYEREMKTYIPPKGET > sequence 56 E46H
GKGDPKKPRGKMSSYAFFVQTCREEHKKKHPDASVNFSEFSKKCSHRWKTMSAKEKGKFEDMAKAD
KARYEREMKTYIPPKGET > sequence 57 E46N
GKGDPKKPRGKMSSYAFFVQTCREEHKKKHPDASVNFSEFSKKCSNRWKTMSAKEKGKFEDMAKAD
KARYEREMKTYIPPKGET > sequence 58 R47H
GKGDPKKPRGKMSSYAFFVQTCREEHKKKHPDASVNFSEFSKKCSEHWKTMSAKEKGKFEDMAKAD
KARYEREMKTYIPPKGET > sequence 59 R47Q
GKGDPKKPRGKMSSYAFFVQTCREEHKKKHPDASVNFSEFSKKCSEQWKTMSAKEKGKFEDMAKAD
KARYEREMKTYIPPKGET > sequence 60 W48Y
GKGDPKKPRGKMSSYAFFVQTCREEHKKKHPDASVNFSEFSKKCSERYKTMSAKEKGKFEDMAKADK
ARYEREMKTYIPPKGET > sequence 61 W48S
GKGDPKKPRGKMSSYAFFVQTCREEHKKKHPDASVNFSEFSKKCSERSKTMSAKEKGKFEDMAKADK
ARYEREMKTYIPPKGET > sequence 62 K49N
GKGDPKKPRGKMSSYAFFVQTCREEHKKKHPDASVNFSEFSKKCSERWNTMSAKEKGKFEDMAKAD
KARYEREMKTYIPPKGET > sequence 63 K49Q
GKGDPKKPRGKMSSYAFFVQTCREEHKKKHPDASVNFSEFSKKCSERWQTMSAKEKGKFEDMAKAD
KARYEREMKTYIPPKGET > sequence 64 M51I
GKGDPKKPRGKMSSYAFFVQTCREEHKKKHPDASVNFSEFSKKCSERWKTISAKEKGKFEDMAKADK
ARYEREMKTYIPPKGET > sequence 65 M51V
GKGDPKKPRGKMSSYAFFVQTCREEHKKKHPDASVNFSEFSKKCSERWKTVSAKEKGKFEDMAKADK
ARYEREMKTYIPPKGET > sequence 66 K54N
GKGDPKKPRGKMSSYAFFVQTCREEHKKKHPDASVNFSEFSKKCSERWKTMSANEKGKFEDMAKAD
KARYEREMKTYIPPKGET > sequence 67 K54Q
GKGDPKKPRGKMSSYAFFVQTCREEHKKKHPDASVNFSEFSKKCSERWKTMSAQEKGKFEDMAKAD

Figure 3b continued

KARYEREMKTYIPPKGET

> sequence 68 E55Q
GKGDPKKPRGKMSSYAFFVQTCREEHKKKHPDASVNFSEFSKKCSERWKTMSAKQKGKFEDMAKAD
KARYEREMKTYIPPKGET > sequence 69 E55H
GKGDPKKPRGKMSSYAFFVQTCREEHKKKHPDASVNFSEFSKKCSERWKTMSAKHKGKFEDMAKAD
KARYEREMKTYIPPKGET > sequence 70 E55N
GKGDPKKPRGKMSSYAFFVQTCREEHKKKHPDASVNFSEFSKKCSERWKTMSAKNKGKFEDMAKAD
KARYEREMKTYIPPKGET > sequence 71 K56N
GKGDPKKPRGKMSSYAFFVQTCREEHKKKHPDASVNFSEFSKKCSERWKTMSAKENGKFEDMAKAD
KARYEREMKTYIPPKGET > sequence 72 K56Q
GKGDPKKPRGKMSSYAFFVQTCREEHKKKHPDASVNFSEFSKKCSERWKTMSAKEQGKFEDMAKAD
KARYEREMKTYIPPKGET > sequence 73 K58N
GKGDPKKPRGKMSSYAFFVQTCREEHKKKHPDASVNFSEFSKKCSERWKTMSAKEKGNFEDMAKAD
KARYEREMKTYIPPKGET > sequence 74 K58Q
GKGDPKKPRGKMSSYAFFVQTCREEHKKKHPDASVNFSEFSKKCSERWKTMSAKEKGQFEDMAKAD
KARYEREMKTYIPPKGET > sequence 75 F59I
GKGDPKKPRGKMSSYAFFVQTCREEHKKKHPDASVNFSEFSKKCSERWKTMSAKEKGKIEDMAKADK
ARYEREMKTYIPPKGET > sequence 76 F59V
GKGDPKKPRGKMSSYAFFVQTCREEHKKKHPDASVNFSEFSKKCSERWKTMSAKEKGKVEDMAKAD
KARYEREMKTYIPPKGET > sequence 77 E60Q
GKGDPKKPRGKMSSYAFFVQTCREEHKKKHPDASVNFSEFSKKCSERWKTMSAKEKGKFQDMAKAD
KARYEREMKTYIPPKGET > sequence 78 E60H
GKGDPKKPRGKMSSYAFFVQTCREEHKKKHPDASVNFSEFSKKCSERWKTMSAKEKGKFHDMAKAD
KARYEREMKTYIPPKGET > sequence 79 E60N
GKGDPKKPRGKMSSYAFFVQTCREEHKKKHPDASVNFSEFSKKCSERWKTMSAKEKGKFNDMAKAD
KARYEREMKTYIPPKGET > sequence 80 D61N
GKGDPKKPRGKMSSYAFFVQTCREEHKKKHPDASVNFSEFSKKCSERWKTMSAKEKGKFENMAKAD
KARYEREMKTYIPPKGET > sequence 81 D61Q

Figure 3b continued

GKGDPKKPRGKMSSYAFFVQTCREEHKKKHPDASVNFSEFSKKCSERWKTMSAKEKGKFEQMAKAD
KARYEREMKTYIPPKGET

> sequence 82 M62I
GKGDPKKPRGKMSSYAFFVQTCREEHKKKHPDASVNFSEFSKKCSERWKTMSAKEKGKFEDIAKADK
ARYEREMKTYIPPKGET > sequence 83 M62V
GKGDPKKPRGKMSSYAFFVQTCREEHKKKHPDASVNFSEFSKKCSERWKTMSAKEKGKFEDVAKADK
ARYEREMKTYIPPKGET > sequence 84 K64N
GKGDPKKPRGKMSSYAFFVQTCREEHKKKHPDASVNFSEFSKKCSERWKTMSAKEKGKFEDMANAD
KARYEREMKTYIPPKGET > sequence 85 K64Q
GKGDPKKPRGKMSSYAFFVQTCREEHKKKHPDASVNFSEFSKKCSERWKTMSAKEKGKFEDMAQAD
KARYEREMKTYIPPKGET > sequence 86 D66N
GKGDPKKPRGKMSSYAFFVQTCREEHKKKHPDASVNFSEFSKKCSERWKTMSAKEKGKFEDMAKAN
KARYEREMKTYIPPKGET > sequence 87 D66Q
GKGDPKKPRGKMSSYAFFVQTCREEHKKKHPDASVNFSEFSKKCSERWKTMSAKEKGKFEDMAKAQ
KARYEREMKTYIPPKGET > sequence 88 K67N
GKGDPKKPRGKMSSYAFFVQTCREEHKKKHPDASVNFSEFSKKCSERWKTMSAKEKGKFEDMAKAD
NARYEREMKTYIPPKGET > sequence 89 K67Q
GKGDPKKPRGKMSSYAFFVQTCREEHKKKHPDASVNFSEFSKKCSERWKTMSAKEKGKFEDMAKAD
QARYEREMKTYIPPKGET > sequence 90 R69H
GKGDPKKPRGKMSSYAFFVQTCREEHKKKHPDASVNFSEFSKKCSERWKTMSAKEKGKFEDMAKAD
KAHYEREMKTYIPPKGET > sequence 91 R69Q
GKGDPKKPRGKMSSYAFFVQTCREEHKKKHPDASVNFSEFSKKCSERWKTMSAKEKGKFEDMAKAD
KAQYEREMKTYIPPKGET > sequence 92 Y70H
GKGDPKKPRGKMSSYAFFVQTCREEHKKKHPDASVNFSEFSKKCSERWKTMSAKEKGKFEDMAKAD
KARHEREMKTYIPPKGET > sequence 93 Y70I
GKGDPKKPRGKMSSYAFFVQTCREEHKKKHPDASVNFSEFSKKCSERWKTMSAKEKGKFEDMAKAD
KARIEREMKTYIPPKGET > sequence 94 E71Q
GKGDPKKPRGKMSSYAFFVQTCREEHKKKHPDASVNFSEFSKKCSERWKTMSAKEKGKFEDMAKAD
KARYQREMKTYIPPKGET

Figure 3b continued

> sequence 95 E71H
GKGDPKKPRGKMSSYAFFVQTCREEHKKKHPDASVNFSEFSKKCSERWKTMSAKEKGKFEDMAKAD
KARYHREMKTYIPPKGET > sequence 96 E71N
GKGDPKKPRGKMSSYAFFVQTCREEHKKKHPDASVNFSEFSKKCSERWKTMSAKEKGKFEDMAKAD
KARYNREMKTYIPPKGET > sequence 97 R72H
GKGDPKKPRGKMSSYAFFVQTCREEHKKKHPDASVNFSEFSKKCSERWKTMSAKEKGKFEDMAKAD
KARYEHEMKTYIPPKGET > sequence 98 R72Q
GKGDPKKPRGKMSSYAFFVQTCREEHKKKHPDASVNFSEFSKKCSERWKTMSAKEKGKFEDMAKAD
KARYEQEMKTYIPPKGET > sequence 99 E73Q
GKGDPKKPRGKMSSYAFFVQTCREEHKKKHPDASVNFSEFSKKCSERWKTMSAKEKGKFEDMAKAD
KARYERQMKTYIPPKGET > sequence 100 E73H
GKGDPKKPRGKMSSYAFFVQTCREEHKKKHPDASVNFSEFSKKCSERWKTMSAKEKGKFEDMAKAD
KARYERHMKTYIPPKGET > sequence 101 E73N
GKGDPKKPRGKMSSYAFFVQTCREEHKKKHPDASVNFSEFSKKCSERWKTMSAKEKGKFEDMAKAD
KARYERNMKTYIPPKGET > sequence 102 M74I
GKGDPKKPRGKMSSYAFFVQTCREEHKKKHPDASVNFSEFSKKCSERWKTMSAKEKGKFEDMAKAD
KARYEREIKTYIPPKGET > sequence 103 M74V
GKGDPKKPRGKMSSYAFFVQTCREEHKKKHPDASVNFSEFSKKCSERWKTMSAKEKGKFEDMAKAD
KARYEREVKTYIPPKGET > sequence 104 K75N
GKGDPKKPRGKMSSYAFFVQTCREEHKKKHPDASVNFSEFSKKCSERWKTMSAKEKGKFEDMAKAD
KARYEREMNTYIPPKGET > sequence 105 K75Q
GKGDPKKPRGKMSSYAFFVQTCREEHKKKHPDASVNFSEFSKKCSERWKTMSAKEKGKFEDMAKAD
KARYEREMQTYIPPKGET > sequence 106 Y77H
GKGDPKKPRGKMSSYAFFVQTCREEHKKKHPDASVNFSEFSKKCSERWKTMSAKEKGKFEDMAKAD
KARYEREMKTHIPPKGET > sequence 107 Y77I
GKGDPKKPRGKMSSYAFFVQTCREEHKKKHPDASVNFSEFSKKCSERWKTMSAKEKGKFEDMAKAD
KARYEREMKTIIPPKGET > sequence 108 P79A
GKGDPKKPRGKMSSYAFFVQTCREEHKKKHPDASVNFSEFSKKCSERWKTMSAKEKGKFEDMAKAD
KARYEREMKTYIAPKGET

Figure 3b continued

> sequence 109 P79S
GKGDPKKPRGKMSSYAFFVQTCREEHKKKHPDASVNFSEFSKKCSERWKTMSAKEKGKFEDMAKAD
KARYEREMKTYISPKGET > sequence 110 P80A
GKGDPKKPRGKMSSYAFFVQTCREEHKKKHPDASVNFSEFSKKCSERWKTMSAKEKGKFEDMAKAD
KARYEREMKTYIPAKGET > sequence 111 P80S
GKGDPKKPRGKMSSYAFFVQTCREEHKKKHPDASVNFSEFSKKCSERWKTMSAKEKGKFEDMAKAD
KARYEREMKTYIPSKGET > sequence 112 K81N
GKGDPKKPRGKMSSYAFFVQTCREEHKKKHPDASVNFSEFSKKCSERWKTMSAKEKGKFEDMAKAD
KARYEREMKTYIPPNGET > sequence 113 K81Q
GKGDPKKPRGKMSSYAFFVQTCREEHKKKHPDASVNFSEFSKKCSERWKTMSAKEKGKFEDMAKAD
KARYEREMKTYIPPQGET > sequence 114 E83Q
GKGDPKKPRGKMSSYAFFVQTCREEHKKKHPDASVNFSEFSKKCSERWKTMSAKEKGKFEDMAKAD
KARYEREMKTYIPPKGQT > sequence 115 E83H
GKGDPKKPRGKMSSYAFFVQTCREEHKKKHPDASVNFSEFSKKCSERWKTMSAKEKGKFEDMAKAD
KARYEREMKTYIPPKGHT > sequence 116 E83N
GKGDPKKPRGKMSSYAFFVQTCREEHKKKHPDASVNFSEFSKKCSERWKTMSAKEKGKFEDMAKAD
KARYEREMKTYIPPKGNT

Figure 4a

Box A 77 amino acids

Protection against proteolysis
If sequence:

PRGKMSSYAFFVQTCREEHKKKHPDASVNFSEFSKKCSERWKTMSAKEKGKFEDM
AKADKARYEREMKTYIPPKGET

In bold amino acids sensitive to proteases proteolysis

Figure 4b

Box A 77 amino acids

Mutant list:

| | | | |
|---|---|---|---|
| P1A | F30V | E53H | P73S |
| P1S | E32Q | E53N | K74N |
| R2H | E32H | D54N | K74Q |
| R2Q | E32N | D54Q | E76Q |
| K4N | F33I | M55I | E76H |
| K4Q | F33V | M55V | E76N |
| M5I | K35N | K57N | |
| M5V | K35Q | K57Q | |
| Y8H | K36N | D59N | |
| Y8I | K36Q | D59Q | |
| F10I | E39Q | K60N | |
| F10V | E39H | K60Q | |
| F11I | E39N | R62H | |
| F11V | R40H | R62Q | |
| R16H | R40Q | Y63H | |
| R16Q | W41Y | Y63I | |
| E17Q | W41S | E64Q | |
| E17H | K42N | E64H | |
| E17N | K42Q | E64N | |
| E18Q | M44I | R65H | |
| E18H | M44V | R65Q | |
| E18N | K47N | E66Q | |
| K20N | K47Q | E66H | |
| K20Q | E48Q | E66N | |
| K21N | E48H | M67I | |
| K21Q | E48N | M67V | |
| K22N | K49N | K68N | |
| K22Q | K49Q | K68Q | |
| P24A | K51N | Y70H | |
| P24S | K51Q | Y70I | |
| D25N | F52I | P72A | |
| D25Q | F52V | P72S | |
| F30I | E53Q | P73A | |

Figure 4b continued

Box A 77 amino acid sequences

> sequence 117 Wild type

PRGKMSSYAFFVQTCREEHKKKHPDASVNFSEFSKKCSERWKTMSAKEKGKFEDMAKADKARYEREM
KTYIPPKGET

> sequence 118 P1A
ARGKMSSYAFFVQTCREEHKKKHPDASVNFSEFSKKCSERWKTMSAKEKGKFEDMAKADKARYEREM
KTYIPPKGET > sequence 119 P1S
SRGKMSSYAFFVQTCREEHKKKHPDASVNFSEFSKKCSERWKTMSAKEKGKFEDMAKADKARYEREM
KTYIPPKGET > sequence 120 R2H
PHGKMSSYAFFVQTCREEHKKKHPDASVNFSEFSKKCSERWKTMSAKEKGKFEDMAKADKARYEREM
KTYIPPKGET > sequence 121 R2Q
PQGKMSSYAFFVQTCREEHKKKHPDASVNFSEFSKKCSERWKTMSAKEKGKFEDMAKADKARYERE
MKTYIPPKGET > sequence 122 K4N
PRGNMSSYAFFVQTCREEHKKKHPDASVNFSEFSKKCSERWKTMSAKEKGKFEDMAKADKARYEREM
KTYIPPKGET > sequence 123 K4Q
PRGQMSSYAFFVQTCREEHKKKHPDASVNFSEFSKKCSERWKTMSAKEKGKFEDMAKADKARYERE
MKTYIPPKGET > sequence 124 M5I
PRGKISSYAFFVQTCREEHKKKHPDASVNFSEFSKKCSERWKTMSAKEKGKFEDMAKADKARYEREM
KTYIPPKGET > sequence 125 M5V
PRGKVSSYAFFVQTCREEHKKKHPDASVNFSEFSKKCSERWKTMSAKEKGKFEDMAKADKARYEREM
KTYIPPKGET > sequence 126 Y8H
PRGKMSSHAFFVQTCREEHKKKHPDASVNFSEFSKKCSERWKTMSAKEKGKFEDMAKADKARYERE
MKTYIPPKGET > sequence 127 Y8I
PRGKMSSIAFFVQTCREEHKKKHPDASVNFSEFSKKCSERWKTMSAKEKGKFEDMAKADKARYEREM
KTYIPPKGET > sequence 128 F10I
PRGKMSSYAIFVQTCREEHKKKHPDASVNFSEFSKKCSERWKTMSAKEKGKFEDMAKADKARYEREM
KTYIPPKGET > sequence 129 F10V
PRGKMSSYAVFVQTCREEHKKKHPDASVNFSEFSKKCSERWKTMSAKEKGKFEDMAKADKARYERE

Figure 4b continued

MKTYIPPKGET

> sequence 130 F11I
PRGKMSSYAFIVQTCREEHKKKHPDASVNFSEFSKKCSERWKTMSAKEKGKFEDMAKADKARYEREM
KTYIPPKGET > sequence 131 F11V
PRGKMSSYAFVVQTCREEHKKKHPDASVNFSEFSKKCSERWKTMSAKEKGKFEDMAKADKARYERE
MKTYIPPKGET > sequence 132 R16H
PRGKMSSYAFFVQTCHEEHKKKHPDASVNFSEFSKKCSERWKTMSAKEKGKFEDMAKADKARYEREM
KTYIPPKGET > sequence 133 R16Q
PRGKMSSYAFFVQTCQEEHKKKHPDASVNFSEFSKKCSERWKTMSAKEKGKFEDMAKADKARYERE
MKTYIPPKGET > sequence 134 E17Q
PRGKMSSYAFFVQTCRQEHKKKHPDASVNFSEFSKKCSERWKTMSAKEKGKFEDMAKADKARYERE
MKTYIPPKGET > sequence 135 E17H
PRGKMSSYAFFVQTCRHEHKKKHPDASVNFSEFSKKCSERWKTMSAKEKGKFEDMAKADKARYERE
MKTYIPPKGET > sequence 136 E17N
PRGKMSSYAFFVQTCRNEHKKKHPDASVNFSEFSKKCSERWKTMSAKEKGKFEDMAKADKARYERE
MKTYIPPKGET > sequence 137 E18Q
PRGKMSSYAFFVQTCREQHKKKHPDASVNFSEFSKKCSERWKTMSAKEKGKFEDMAKADKARYERE
MKTYIPPKGET > sequence 138 E18H
PRGKMSSYAFFVQTCREHHKKKHPDASVNFSEFSKKCSERWKTMSAKEKGKFEDMAKADKARYERE
MKTYIPPKGET > sequence 139 E18N
PRGKMSSYAFFVQTCRENHKKKHPDASVNFSEFSKKCSERWKTMSAKEKGKFEDMAKADKARYERE
MKTYIPPKGET > sequence 140 K20N
PRGKMSSYAFFVQTCREEHNKKHPDASVNFSEFSKKCSERWKTMSAKEKGKFEDMAKADKARYEREM
KTYIPPKGET > sequence 141 K20Q
PRGKMSSYAFFVQTCREEHQKKHPDASVNFSEFSKKCSERWKTMSAKEKGKFEDMAKADKARYERE
MKTYIPPKGET > sequence 142 K21N
PRGKMSSYAFFVQTCREEHKNKHPDASVNFSEFSKKCSERWKTMSAKEKGKFEDMAKADKARYEREM
KTYIPPKGET > sequence 143 K21Q
PRGKMSSYAFFVQTCREEHKQKHPDASVNFSEFSKKCSERWKTMSAKEKGKFEDMAKADKARYERE

Figure 4b continued

MKTYIPPKGET

> sequence 144 K22N
PRGKMSSYAFFVQTCREEHKKNHPDASVNFSEFSKKCSERWKTMSAKEKGKFEDMAKADKARYEREM
KTYIPPKGET > sequence 145 K22Q
PRGKMSSYAFFVQTCREEHKKQHPDASVNFSEFSKKCSERWKTMSAKEKGKFEDMAKADKARYERE
MKTYIPPKGET > sequence 146 P24A
PRGKMSSYAFFVQTCREEHKKKHADASVNFSEFSKKCSERWKTMSAKEKGKFEDMAKADKARYEREM
KTYIPPKGET > sequence 147 F24S
PRGKMSSYAFFVQTCREEHKKKHSDASVNFSEFSKKCSERWKTMSAKEKGKFEDMAKADKARYEREM
KTYIPPKGET > sequence 148 D25N
PRGKMSSYAFFVQTCREEHKKKHPNASVNFSEFSKKCSERWKTMSAKEKGKFEDMAKADKARYEREM
KTYIPPKGET > sequence 149 D25Q
PRGKMSSYAFFVQTCREEHKKKHPQASVNFSEFSKKCSERWKTMSAKEKGKFEDMAKADKARYERE
MKTYIPPKGET > sequence 150 F30I
PRGKMSSYAFFVQTCREEHKKKHPDASVNISEFSKKCSERWKTMSAKEKGKFEDMAKADKARYEREM
KTYIPPKGET > sequence 151 F30V
PRGKMSSYAFFVQTCREEHKKKHPDASVNVSEFSKKCSERWKTMSAKEKGKFEDMAKADKARYERE
MKTYIPPKGET > sequence 152 E32Q
PRGKMSSYAFFVQTCREEHKKKHPDASVNFSQFSKKCSERWKTMSAKEKGKFEDMAKADKARYERE
MKTYIPPKGET > sequence 153 E32H
PRGKMSSYAFFVQTCREEHKKKHPDASVNFSHFSKKCSERWKTMSAKEKGKFEDMAKADKARYERE
MKTYIPPKGET > sequence 154 E32N
PRGKMSSYAFFVQTCREEHKKKHPDASVNFSNFSKKCSERWKTMSAKEKGKFEDMAKADKARYERE
MKTYIPPKGET > sequence 155 F33I
PRGKMSSYAFFVQTCREEHKKKHPDASVNFSEISKKCSERWKTMSAKEKGKFEDMAKADKARYEREM
KTYIPPKGET > sequence 156 F33V
PRGKMSSYAFFVQTCREEHKKKHPDASVNFSEVSKKCSERWKTMSAKEKGKFEDMAKADKARYERE
MKTYIPPKGET > sequence 157 K35N
PRGKMSSYAFFVQTCREEHKKKHPDASVNFSEFSNKCSERWKTMSAKEKGKFEDMAKADKARYEREM

Figure 4b continued

KTYIPPKGET

> sequence 158 K35Q
PRGKMSSYAFFVQTCREEHKKKHPDASVNFSEFSQKCSERWKTMSAKEKGKFEDMAKADKARYERE
MKTYIPPKGET > sequence 159 K36N
PRGKMSSYAFFVQTCREEHKKKHPDASVNFSEFSKNCSERWKTMSAKEKGKFEDMAKADKARYEREM
KTYIPPKGET > sequence 160 K36Q
PRGKMSSYAFFVQTCREEHKKKHPDASVNFSEFSKQCSERWKTMSAKEKGKFEDMAKADKARYERE
MKTYIPPKGET > sequence 161 E39Q
PRGKMSSYAFFVQTCREEHKKKHPDASVNFSEFSKKCSQRWKTMSAKEKGKFEDMAKADKARYERE
MKTYIPPKGET > sequence 162 E39H
PRGKMSSYAFFVQTCREEHKKKHPDASVNFSEFSKKCSHRWKTMSAKEKGKFEDMAKADKARYERE
MKTYIPPKGET > sequence 163 E39N
PRGKMSSYAFFVQTCREEHKKKHPDASVNFSEFSKKCSNRWKTMSAKEKGKFEDMAKADKARYERE
MKTYIPPKGET > sequence 164 R40H
PRGKMSSYAFFVQTCREEHKKKHPDASVNFSEFSKKCSEHWKTMSAKEKGKFEDMAKADKARYEREM
KTYIPPKGET > sequence 165 R40Q
PRGKMSSYAFFVQTCREEHKKKHPDASVNFSEFSKKCSEQWKTMSAKEKGKFEDMAKADKARYERE
MKTYIPPKGET > sequence 166 W41Y
PRGKMSSYAFFVQTCREEHKKKHPDASVNFSEFSKKCSERYKTMSAKEKGKFEDMAKADKARYEREM
KTYIPPKGET > sequence 167 W41S
PRGKMSSYAFFVQTCREEHKKKHPDASVNFSEFSKKCSERSKTMSAKEKGKFEDMAKADKARYEREM
KTYIPPKGET > sequence 168 K42N
PRGKMSSYAFFVQTCREEHKKKHPDASVNFSEFSKKCSERWNTMSAKEKGKFEDMAKADKARYEREM
KTYIPPKGET > sequence 169 K42Q
PRGKMSSYAFFVQTCREEHKKKHPDASVNFSEFSKKCSERWQTMSAKEKGKFEDMAKADKARYERE
MKTYIPPKGET > sequence 170 M44I
PRGKMSSYAFFVQTCREEHKKKHPDASVNFSEFSKKCSERWKTISAKEKGKFEDMAKADKARYEREM
KTYIPPKGET > sequence 171 M44V

Figure 4b continued

PRGKMSSYAFFVQTCREEHKKKHPDASVNFSEFSKKCSERWKTVSAKEKGKFEDMAKADKARYEREM
KTYIPPKGET

> sequence 172 K47N
PRGKMSSYAFFVQTCREEHKKKHPDASVNFSEFSKKCSERWKTMSANEKGKFEDMAKADKARYEREM
KTYIPPKGET > sequence 173 K47Q
PRGKMSSYAFFVQTCREEHKKKHPDASVNFSEFSKKCSERWKTMSAQEKGKFEDMAKADKARYERE
MKTYIPPKGET > sequence 174 E48Q
PRGKMSSYAFFVQTCREEHKKKHPDASVNFSEFSKKCSERWKTMSAKQKGKFEDMAKADKARYERE
MKTYIPPKGET > sequence 175 E48H
PRGKMSSYAFFVQTCREEHKKKHPDASVNFSEFSKKCSERWKTMSAKHKGKFEDMAKADKARYERE
MKTYIPPKGET > sequence 176 E48N
PRGKMSSYAFFVQTCREEHKKKHPDASVNFSEFSKKCSERWKTMSAKNKGKFEDMAKADKARYERE
MKTYIPPKGET > sequence 177 K49N
PRGKMSSYAFFVQTCREEHKKKHPDASVNFSEFSKKCSERWKTMSAKENGKFEDMAKADKARYEREM
KTYIPPKGET > sequence 178 K49Q
PRGKMSSYAFFVQTCREEHKKKHPDASVNFSEFSKKCSERWKTMSAKEQGKFEDMAKADKARYERE
MKTYIPPKGET > sequence 179 K51N
PRGKMSSYAFFVQTCREEHKKKHPDASVNFSEFSKKCSERWKTMSAKEKGNFEDMAKADKARYEREM
KTYIPPKGET > sequence 180 K51Q
PRGKMSSYAFFVQTCREEHKKKHPDASVNFSEFSKKCSERWKTMSAKEKGQFEDMAKADKARYERE
MKTYIPPKGET > sequence 181 F52I
PRGKMSSYAFFVQTCREEHKKKHPDASVNFSEFSKKCSERWKTMSAKEKGKIEDMAKADKARYEREM
KTYIPPKGET > sequence 182 F52V
PRGKMSSYAFFVQTCREEHKKKHPDASVNFSEFSKKCSERWKTMSAKEKGKVEDMAKADKARYERE
MKTYIPPKGET > sequence 183 E53Q
PRGKMSSYAFFVQTCREEHKKKHPDASVNFSEFSKKCSERWKTMSAKEKGKFQDMAKADKARYERE
MKTYIPPKGET > sequence 184 E53H
PRGKMSSYAFFVQTCREEHKKKHPDASVNFSEFSKKCSERWKTMSAKEKGKFHDMAKADKARYERE
MKTYIPPKGET

*Figure 4b continued*

> sequence 185 E53N
PRGKMSSYAFFVQTCREEHKKKHPDASVNFSEFSKKCSERWKTMSAKEKGKFNDMAKADKARYERE
MKTYIPPKGET > sequence 186 D54N
PRGKMSSYAFFVQTCREEHKKKHPDASVNFSEFSKKCSERWKTMSAKEKGKFENMAKADKARYEREM
KTYIPPKGET > sequence 187 D54Q
PRGKMSSYAFFVQTCREEHKKKHPDASVNFSEFSKKCSERWKTMSAKEKGKFEQMAKADKARYERE
MKTYIPPKGET > sequence 188 M55I
PRGKMSSYAFFVQTCREEHKKKHPDASVNFSEFSKKCSERWKTMSAKEKGKFEDIAKADKARYEREM
KTYIPPKGET > sequence 189 M55V
PRGKMSSYAFFVQTCREEHKKKHPDASVNFSEFSKKCSERWKTMSAKEKGKFEDVAKADKARYEREM
KTYIPPKGET > sequence 190 K57N
PRGKMSSYAFFVQTCREEHKKKHPDASVNFSEFSKKCSERWKTMSAKEKGKFEDMANADKARYEREM
KTYIPPKGET > sequence 191 K57Q
PRGKMSSYAFFVQTCREEHKKKHPDASVNFSEFSKKCSERWKTMSAKEKGKFEDMAQADKARYERE
MKTYIPPKGET > sequence 192 D59N
PRGKMSSYAFFVQTCREEHKKKHPDASVNFSEFSKKCSERWKTMSAKEKGKFEDMAKANKARYEREM
KTYIPPKGET > sequence 193 D59Q
PRGKMSSYAFFVQTCREEHKKKHPDASVNFSEFSKKCSERWKTMSAKEKGKFEDMAKAQKARYERE
MKTYIPPKGET > sequence 194 K60N
PRGKMSSYAFFVQTCREEHKKKHPDASVNFSEFSKKCSERWKTMSAKEKGKFEDMAKADNARYEREM
KTYIPPKGET > sequence 195 K60Q
PRGKMSSYAFFVQTCREEHKKKHPDASVNFSEFSKKCSERWKTMSAKEKGKFEDMAKADQARYERE
MKTYIPPKGET > sequence 196 R62H
PRGKMSSYAFFVQTCREEHKKKHPDASVNFSEFSKKCSERWKTMSAKEKGKFEDMAKADKAHYEREM
KTYIPPKGET > sequence 197 R62Q
PRGKMSSYAFFVQTCREEHKKKHPDASVNFSEFSKKCSERWKTMSAKEKGKFEDMAKADKAQYERE
MKTYIPPKGET > sequence 198 Y63H
PRGKMSSYAFFVQTCREEHKKKHPDASVNFSEFSKKCSERWKTMSAKEKGKFEDMAKADKARHERE
MKTYIPPKGET

Figure 4b continued

> sequence 199 Y63I
PRGKMSSYAFFVQTCREEHKKKHPDASVNFSEFSKKCSERWKTMSAKEKGKFEDMAKADKARIEREM
KTYIPPKGET > sequence 200 E64Q
PRGKMSSYAFFVQTCREEHKKKHPDASVNFSEFSKKCSERWKTMSAKEKGKFEDMAKADKARYQRE
MKTYIPPKGET > sequence 201 E64H
PRGKMSSYAFFVQTCREEHKKKHPDASVNFSEFSKKCSERWKTMSAKEKGKFEDMAKADKARYHRE
MKTYIPPKGET > sequence 202 E64N
PRGKMSSYAFFVQTCREEHKKKHPDASVNFSEFSKKCSERWKTMSAKEKGKFEDMAKADKARYNRE
MKTYIPPKGET > sequence 203 R65H
PRGKMSSYAFFVQTCREEHKKKHPDASVNFSEFSKKCSERWKTMSAKEKGKFEDMAKADKARYEHEM
KTYIPPKGET > sequence 204 R65Q
PRGKMSSYAFFVQTCREEHKKKHPDASVNFSEFSKKCSERWKTMSAKEKGKFEDMAKADKARYEQE
MKTYIPPKGET > sequence 205 E66Q
PRGKMSSYAFFVQTCREEHKKKHPDASVNFSEFSKKCSERWKTMSAKEKGKFEDMAKADKARYERQ
MKTYIPPKGET > sequence 206 E66H
PRGKMSSYAFFVQTCREEHKKKHPDASVNFSEFSKKCSERWKTMSAKEKGKFEDMAKADKARYERH
MKTYIPPKGET > sequence 207 E66N
PRGKMSSYAFFVQTCREEHKKKHPDASVNFSEFSKKCSERWKTMSAKEKGKFEDMAKADKARYERN
MKTYIPPKGET > sequence 208 M67I
PRGKMSSYAFFVQTCREEHKKKHPDASVNFSEFSKKCSERWKTMSAKEKGKFEDMAKADKARYEREI
KTYIPPKGET > sequence 209 M67V
PRGKMSSYAFFVQTCREEHKKKHPDASVNFSEFSKKCSERWKTMSAKEKGKFEDMAKADKARYEREV
KTYIPPKGET > sequence 210 K68N
PRGKMSSYAFFVQTCREEHKKKHPDASVNFSEFSKKCSERWKTMSAKEKGKFEDMAKADKARYEREM
NTYIPPKGET > sequence 211 K68Q
PRGKMSSYAFFVQTCREEHKKKHPDASVNFSEFSKKCSERWKTMSAKEKGKFEDMAKADKARYEREM
QTYIPPKGET > sequence 212 Y70H
PRGKMSSYAFFVQTCREEHKKKHPDASVNFSEFSKKCSERWKTMSAKEKGKFEDMAKADKARYEREM

Figure 4b continued

KTHIPPKGET

> sequence 213 Y70I
PRGKMSSYAFFVQTCREEHKKKHPDASVNFSEFSKKCSERWKTMSAKEKGKFEDMAKADKARYEREM
KTIIPPKGET > sequence 214 P72A
PRGKMSSYAFFVQTCREEHKKKHPDASVNFSEFSKKCSERWKTMSAKEKGKFEDMAKADKARYEREM
KTYIAPKGET > sequence 215 P72S
PRGKMSSYAFFVQTCREEHKKKHPDASVNFSEFSKKCSERWKTMSAKEKGKFEDMAKADKARYEREM
KTYISPKGET > sequence 216 P73A
PRGKMSSYAFFVQTCREEHKKKHPDASVNFSEFSKKCSERWKTMSAKEKGKFEDMAKADKARYEREM
KTYIPAKGET > sequence 217 P73S
PRGKMSSYAFFVQTCREEHKKKHPDASVNFSEFSKKCSERWKTMSAKEKGKFEDMAKADKARYEREM
KTYIPSKGET > sequence 218 K74N
PRGKMSSYAFFVQTCREEHKKKHPDASVNFSEFSKKCSERWKTMSAKEKGKFEDMAKADKARYEREM
KTYIPPNGET > sequence 219 K74Q
PRGKMSSYAFFVQTCREEHKKKHPDASVNFSEFSKKCSERWKTMSAKEKGKFEDMAKADKARYEREM
KTYIPPQGET > sequence 220 E76Q
PRGKMSSYAFFVQTCREEHKKKHPDASVNFSEFSKKCSERWKTMSAKEKGKFEDMAKADKARYEREM
KTYIPPKGQT > sequence 221 E76H
PRGKMSSYAFFVQTCREEHKKKHPDASVNFSEFSKKCSERWKTMSAKEKGKFEDMAKADKARYEREM
KTYIPPKGHT > sequence 222 E76N
PRGKMSSYAFFVQTCREEHKKKHPDASVNFSEFSKKCSERWKTMSAKEKGKFEDMAKADKARYEREM
KTYIPPKGNT

Figure 5a

Box A 54 amino acids

Protection against proteolysis
If sequence:

PDASVNFSEFSKKCSERWKTMSAKEKGKFEDMAKADKARYEREMKTYIPPKGET

In bold amino acids sensitive to proteases proteolysis

Figure 5b

Box A 54 amino acids
Mutant list:

| | | |
|---|---|---|
| P1A | F29I | P50A |
| P1S | F29V | P50S |
| D2N | E30Q | K51N |
| D2Q | E30H | K51Q |
| F7I | E30N | E53Q |
| F7V | D31N | E53H |
| E9Q | D31Q | E53N |
| E9H | M32I | |
| E9N | M32V | |
| F10I | K34N | |
| F10V | K34Q | |
| K12N | D36N | |
| K12Q | D36Q | |
| K13N | K37N | |
| K13Q | K37Q | |
| E16Q | R39H | |
| E16H | R39Q | |
| E16N | Y40H | |
| R17H | Y40I | |
| R17Q | E41Q | |
| W18Y | E41H | |
| W18S | E41N | |
| K19N | R42H | |
| K19Q | R42Q | |
| M21I | E43Q | |
| M21V | E43H | |
| K24N | E43N | |
| K24Q | M44I | |
| E25Q | M44V | |
| E25H | K45N | |
| E25N | K45Q | |
| K26N | Y47H | |
| K26Q | Y47I | |
| K28N | P49A | |
| K28Q | P49S | |

Figure 5b continued

Box A 54 amino acid sequences:

> sequence 223 Wild type

PDASVNFSEFSKKCSERWKTMSAKEKGKFEDMAKADKARYEREMKTYIPPKGET

> sequence 224 P1A
ADASVNFSEFSKKCSERWKTMSAKEKGKFEDMAKADKARYEREMKTYIPPKGET

> sequence 225 P1S
SDASVNFSEFSKKCSERWKTMSAKEKGKFEDMAKADKARYEREMKTYIPPKGET

> sequence 226 D2N
PNASVNFSEFSKKCSERWKTMSAKEKGKFEDMAKADKARYEREMKTYIPPKGET

> sequence 227 D2Q
PQASVNFSEFSKKCSERWKTMSAKEKGKFEDMAKADKARYEREMKTYIPPKGET

> sequence 228 F7I
PDASVNISEFSKKCSERWKTMSAKEKGKFEDMAKADKARYEREMKTYIPPKGET

> sequence 229 F7V
PDASVNVSEFSKKCSERWKTMSAKEKGKFEDMAKADKARYEREMKTYIPPKGET

> sequence 230 E9Q
PDASVNFSQFSKKCSERWKTMSAKEKGKFEDMAKADKARYEREMKTYIPPKGET

> sequence 231 E9H
PDASVNFSHFSKKCSERWKTMSAKEKGKFEDMAKADKARYEREMKTYIPPKGET

> sequence 232 E9N
PDASVNFSNFSKKCSERWKTMSAKEKGKFEDMAKADKARYEREMKTYIPPKGET

> sequence 233 F10I
PDASVNFSEISKKCSERWKTMSAKEKGKFEDMAKADKARYEREMKTYIPPKGET

> sequence 234 F10V
PDASVNFSEVSKKCSERWKTMSAKEKGKFEDMAKADKARYEREMKTYIPPKGET

> sequence 235 K12N
PDASVNFSEFSNKCSERWKTMSAKEKGKFEDMAKADKARYEREMKTYIPPKGET

> sequence 236 K12Q
PDASVNFSEFSQKCSERWKTMSAKEKGKFEDMAKADKARYEREMKTYIPPKGET

> sequence 237 K13N
PDASVNFSEFSKNCSERWKTMSAKEKGKFEDMAKADKARYEREMKTYIPPKGET

> sequence 238 K13Q
PDASVNFSEFSKQCSERWKTMSAKEKGKFEDMAKADKARYEREMKTYIPPKGET

> sequence 239 E16Q
PDASVNFSEFSKKCSQRWKTMSAKEKGKFEDMAKADKARYEREMKTYIPPKGET

Figure 5b continued

> sequence 240 E16H
PDASVNFSEFSKKCSHRWKTMSAKEKGKFEDMAKADKARYEREMKTYIPPKGET

> sequence 241 E16N
PDASVNFSEFSKKCSNRWKTMSAKEKGKFEDMAKADKARYEREMKTYIPPKGET

> sequence 242 R17H
PDASVNFSEFSKKCSEHWKTMSAKEKGKFEDMAKADKARYEREMKTYIPPKGET

> sequence 243 R17Q
PDASVNFSEFSKKCSEQWKTMSAKEKGKFEDMAKADKARYEREMKTYIPPKGET

> sequence 244 W18Y
PDASVNFSEFSKKCSERYKTMSAKEKGKFEDMAKADKARYEREMKTYIPPKGET

> sequence 245 W18S
PDASVNFSEFSKKCSERSKTMSAKEKGKFEDMAKADKARYEREMKTYIPPKGET

> sequence 246 K19N
PDASVNFSEFSKKCSERWNTMSAKEKGKFEDMAKADKARYEREMKTYIPPKGET

> sequence 247 K19Q
PDASVNFSEFSKKCSERWQTMSAKEKGKFEDMAKADKARYEREMKTYIPPKGET

> sequence 248 M21I
PDASVNFSEFSKKCSERWKTISAKEKGKFEDMAKADKARYEREMKTYIPPKGET

> sequence 249 M21V
PDASVNFSEFSKKCSERWKTVSAKEKGKFEDMAKADKARYEREMKTYIPPKGET

> sequence 250 K24N
PDASVNFSEFSKKCSERWKTMSANEKGKFEDMAKADKARYEREMKTYIPPKGET

> sequence 251 K24Q
PDASVNFSEFSKKCSERWKTMSAQEKGKFEDMAKADKARYEREMKTYIPPKGET

> sequence 252 E25Q
PDASVNFSEFSKKCSERWKTMSAKQKGKFEDMAKADKARYEREMKTYIPPKGET

> sequence 253 E25H
PDASVNFSEFSKKCSERWKTMSAKHKGKFEDMAKADKARYEREMKTYIPPKGET

> sequence 254 E25N
PDASVNFSEFSKKCSERWKTMSAKNKGKFEDMAKADKARYEREMKTYIPPKGET

> sequence 255 K26N
PDASVNFSEFSKKCSERWKTMSAKENGKFEDMAKADKARYEREMKTYIPPKGET

> sequence 256 K26Q
PDASVNFSEFSKKCSERWKTMSAKEQGKFEDMAKADKARYEREMKTYIPPKGET

> sequence 257 K28N
PDASVNFSEFSKKCSERWKTMSAKEKGNFEDMAKADKARYEREMKTYIPPKGET

> sequence 258 K28Q

Figure 5b continued

PDASVNFSEFSKKCSERWKTMSAKEKGQFEDMAKADKARYEREMKTYIPPKGET

> sequence 259 F29I
PDASVNFSEFSKKCSERWKTMSAKEKGKIEDMAKADKARYEREMKTYIPPKGET

> sequence 260 F29V
PDASVNFSEFSKKCSERWKTMSAKEKGKVEDMAKADKARYEREMKTYIPPKGET

> sequence 261 E30Q
PDASVNFSEFSKKCSERWKTMSAKEKGKFQDMAKADKARYEREMKTYIPPKGET

> sequence 262 E30H
PDASVNFSEFSKKCSERWKTMSAKEKGKFHDMAKADKARYEREMKTYIPPKGET

> sequence 263 E30N
PDASVNFSEFSKKCSERWKTMSAKEKGKFNDMAKADKARYEREMKTYIPPKGET

> sequence 264 D31N
PDASVNFSEFSKKCSERWKTMSAKEKGKFENMAKADKARYEREMKTYIPPKGET

> sequence 265 D31Q
PDASVNFSEFSKKCSERWKTMSAKEKGKFEQMAKADKARYEREMKTYIPPKGET

> sequence 266 M32I
PDASVNFSEFSKKCSERWKTMSAKEKGKFEDIAKADKARYEREMKTYIPPKGET

> sequence 267 M32V
PDASVNFSEFSKKCSERWKTMSAKEKGKFEDVAKADKARYEREMKTYIPPKGET

> sequence 268 K34N
PDASVNFSEFSKKCSERWKTMSAKEKGKFEDMANADKARYEREMKTYIPPKGET

> sequence 269 K34Q
PDASVNFSEFSKKCSERWKTMSAKEKGKFEDMAQADKARYEREMKTYIPPKGET

> sequence 270 D36N
PDASVNFSEFSKKCSERWKTMSAKEKGKFEDMAKANKARYEREMKTYIPPKGET

> sequence 271 D36Q
PDASVNFSEFSKKCSERWKTMSAKEKGKFEDMAKAQKARYEREMKTYIPPKGET

> sequence 272 K37N
PDASVNFSEFSKKCSERWKTMSAKEKGKFEDMAKADNARYEREMKTYIPPKGET

> sequence 273 K37Q
PDASVNFSEFSKKCSERWKTMSAKEKGKFEDMAKADQARYEREMKTYIPPKGET

> sequence 274 R39H
PDASVNFSEFSKKCSERWKTMSAKEKGKFEDMAKADKAHYEREMKTYIPPKGET

> sequence 275 R39Q
PDASVNFSEFSKKCSERWKTMSAKEKGKFEDMAKADKAQYEREMKTYIPPKGET

> sequence 276 Y40H
PDASVNFSEFSKKCSERWKTMSAKEKGKFEDMAKADKARHEREMKTYIPPKGET

Figure 5b continued

> sequence 277 Y40I
PDASVNFSEFSKKCSERWKTMSAKEKGKFEDMAKADKARIEREMKTYIPPKGET

> sequence 278 E41Q
PDASVNFSEFSKKCSERWKTMSAKEKGKFEDMAKADKARYQREMKTYIPPKGET

> sequence 279 E41H
PDASVNFSEFSKKCSERWKTMSAKEKGKFEDMAKADKARYHREMKTYIPPKGET

> sequence 280 E41N
PDASVNFSEFSKKCSERWKTMSAKEKGKFEDMAKADKARYNREMKTYIPPKGET

> sequence 281 R42H
PDASVNFSEFSKKCSERWKTMSAKEKGKFEDMAKADKARYEHEMKTYIPPKGET

> sequence 282 R42Q
PDASVNFSEFSKKCSERWKTMSAKEKGKFEDMAKADKARYEQEMKTYIPPKGET

> sequence 283 E43Q
PDASVNFSEFSKKCSERWKTMSAKEKGKFEDMAKADKARYERQMKTYIPPKGET

> sequence 284 E43H
PDASVNFSEFSKKCSERWKTMSAKEKGKFEDMAKADKARYERHMKTYIPPKGET

> sequence 285 E43N
PDASVNFSEFSKKCSERWKTMSAKEKGKFEDMAKADKARYERNMKTYIPPKGET

> sequence 286 M44I
PDASVNFSEFSKKCSERWKTMSAKEKGKFEDMAKADKARYEREIKTYIPPKGET

> sequence 287 M44V
PDASVNFSEFSKKCSERWKTMSAKEKGKFEDMAKADKARYEREVKTYIPPKGET

> sequence 288 K45N
PDASVNFSEFSKKCSERWKTMSAKEKGKFEDMAKADKARYEREMNTYIPPKGET

> sequence 289 K45Q
PDASVNFSEFSKKCSERWKTMSAKEKGKFEDMAKADKARYEREMQTYIPPKGET

> sequence 290 Y47H
PDASVNFSEFSKKCSERWKTMSAKEKGKFEDMAKADKARYEREMKTHIPPKGET

> sequence 291 Y47I
PDASVNFSEFSKKCSERWKTMSAKEKGKFEDMAKADKARYEREMKTIIPPKGET

> sequence 292 P49A
PDASVNFSEFSKKCSERWKTMSAKEKGKFEDMAKADKARYEREMKTYIAPKGET

> sequence 293 P49S
PDASVNFSEFSKKCSERWKTMSAKEKGKFEDMAKADKARYEREMKTYISPKGET

> sequence 294 P50A
PDASVNFSEFSKKCSERWKTMSAKEKGKFEDMAKADKARYEREMKTYIPAKGET

Figure 5b continued

> sequence 295 P50S
PDASVNFSEFSKKCSERWKTMSAKEKGKFEDMAKADKARYEREMKTYIPSKGET

> sequence 296 K51N
PDASVNFSEFSKKCSERWKTMSAKEKGKFEDMAKADKARYEREMKTYIPPNGET

> sequence 297 K51Q
PDASVNFSEFSKKCSERWKTMSAKEKGKFEDMAKADKARYEREMKTYIPPQGET

> sequence 298 E53Q
PDASVNFSEFSKKCSERWKTMSAKEKGKFEDMAKADKARYEREMKTYIPPKGQT

> sequence 299 E53H
PDASVNFSEFSKKCSERWKTMSAKEKGKFEDMAKADKARYEREMKTYIPPKGHT

> sequence 300 E53N
PDASVNFSEFSKKCSERWKTMSAKEKGKFEDMAKADKARYEREMKTYIPPKGNT

Figure 6a

Box A 84 amino acid of HMGB1 *Anopheles gambia* (XP_311154)

Protection against proteolysis
If sequence:

GKVKDNKPRGRMTAYAFFVQTCREEHKKKHPEEQVIFAEFSRKCAERWKTMLDKEK
QRFHEMAEKDKARYELEMQSYVPPKGAV

In bold amino acids sensitive to proteases proteolysis

Figure 6b

Box A 84 amino acid
Mutant list:

| | | | | |
|---|---|---|---|---|
| K2N | E24H | F40V | K56N | E71H |
| K2Q | E24N | R42H | K56Q | E71N |
| K4N | E25Q | R42Q | R58H | L72I |
| K4Q | E25H | K43N | R58Q | L72V |
| D5N | E25N | K43Q | F59I | E73Q |
| D5Q | K27N | E46Q | F59V | E73H |
| K7N | K27Q | E46H | E61Q | E73N |
| K7Q | K28N | E46N | E61H | M74I |
| P8A | K28Q | R47H | E61N | M74V |
| P8S | K29N | R47Q | M62I | Y77H |
| R9H | K29Q | W48Y | M62V | Y77I |
| R9Q | P31A | W48S | E64Q | P79A |
| R11H | P31S | K49N | E64H | P79S |
| R11Q | E32Q | K49Q | E64N | P80A |
| M12I | E32H | M51I | K65N | P80S |
| M12V | E32N | M51V | K65Q | K81N |
| Y15H | E33Q | L52I | D66N | K81Q |
| Y15I | E33H | L52V | D66Q | |
| F17I | E33N | D53N | K67N | |
| F17V | F37I | D53Q | K67Q | |
| F18I | F37V | K54N | R69H | |
| F18V | E39Q | K54Q | R69Q | |
| R23H | E39H | E55Q | Y70H | |
| R23Q | E39N | E55H | Y70I | |
| E24Q | F40I | E55N | E71Q | |

Figure 6b continued

> SEQUENCE 301 Wild type
GKVKDNKPRGRMTAYAFFVQTCREEHKKKHPEEQVIFAEFSRKCAERWKTMLDKEKQRFHEMAEKDK
ARYELEMQSYVPPKGAV > > SEQUENCE 302 K2N
GNVKDNKPRGRMTAYAFFVQTCREEHKKKHPEEQVIFAEFSRKCAERWKTMLDKEKQRFHEMAEKDK
ARYELEMQSYVPPKGAV > > SEQUENCE 303 K2Q
GQVKDNKPRGRMTAYAFFVQTCREEHKKKHPEEQVIFAEFSRKCAERWKTMLDKEKQRFHEMAEKDK
ARYELEMQSYVPPKGAV > > SEQUENCE 304 K4N
GKVNDNKPRGRMTAYAFFVQTCREEHKKKHPEEQVIFAEFSRKCAERWKTMLDKEKQRFHEMAEKDK
ARYELEMQSYVPPKGAV > > SEQUENCE 305 K4Q
GKVQDNKPRGRMTAYAFFVQTCREEHKKKHPEEQVIFAEFSRKCAERWKTMLDKEKQRFHEMAEKDK
ARYELEMQSYVPPKGAV > > SEQUENCE 306 D5N
GKVKNNKPRGRMTAYAFFVQTCREEHKKKHPEEQVIFAEFSRKCAERWKTMLDKEKQRFHEMAEKDK
ARYELEMQSYVPPKGAV > > SEQUENCE 307 D5Q
GKVKQNKPRGRMTAYAFFVQTCREEHKKKHPEEQVIFAEFSRKCAERWKTMLDKEKQRFHEMAEKDK
ARYELEMQSYVPPKGAV > > SEQUENCE 308 K7N
GKVKDNNPRGRMTAYAFFVQTCREEHKKKHPEEQVIFAEFSRKCAERWKTMLDKEKQRFHEMAEKDK
ARYELEMQSYVPPKGAV > > SEQUENCE 309 K7Q
GKVKDNQPRGRMTAYAFFVQTCREEHKKKHPEEQVIFAEFSRKCAERWKTMLDKEKQRFHEMAEKDK
ARYELEMQSYVPPKGAV > > SEQUENCE 310 P8A
GKVKDNKARGRMTAYAFFVQTCREEHKKKHPEEQVIFAEFSRKCAERWKTMLDKEKQRFHEMAEKDK
ARYELEMQSYVPPKGAV > > SEQUENCE 311 P8S
GKVKDNKSRGRMTAYAFFVQTCREEHKKKHPEEQVIFAEFSRKCAERWKTMLDKEKQRFHEMAEKDK
ARYELEMQSYVPPKGAV > > SEQUENCE 312 R9H
GKVKDNKPHGRMTAYAFFVQTCREEHKKKHPEEQVIFAEFSRKCAERWKTMLDKEKQRFHEMAEKDK
ARYELEMQSYVPPKGAV > > SEQUENCE 313 R9Q
GKVKDNKPQGRMTAYAFFVQTCREEHKKKHPEEQVIFAEFSRKCAERWKTMLDKEKQRFHEMAEKDK
ARYELEMQSYVPPKGAV > > SEQUENCE 314 R11H
GKVKDNKPRGHMTAYAFFVQTCREEHKKKHPEEQVIFAEFSRKCAERWKTMLDKEKQRFHEMAEKDK

Figure 6b continued

ARYELEMQSYVPPKGAV

>> SEQUENCE 315 R11Q
GKVKDNKPRGQMTAYAFFVQTCREEHKKKHPEEQVIFAEFSRKCAERWKTMLDKEKQRFHEMAEKDK
ARYELEMQSYVPPKGAV

>> SEQUENCE 316 M12I
GKVKDNKPRGRITAYAFFVQTCREEHKKKHPEEQVIFAEFSRKCAERWKTMLDKEKQRFHEMAEKDKA
RYELEMQSYVPPKGAV

>> SEQUENCE 317 M12V
GKVKDNKPRGRVTAYAFFVQTCREEHKKKHPEEQVIFAEFSRKCAERWKTMLDKEKQRFHEMAEKDK
ARYELEMQSYVPPKGAV

>> SEQUENCE 318 Y15H
GKVKDNKPRGRMTAHAFFVQTCREEHKKKHPEEQVIFAEFSRKCAERWKTMLDKEKQRFHEMAEKDK
ARYELEMQSYVPPKGAV

>> SEQUENCE 319 Y15I
GKVKDNKPRGRMTAIAFFVQTCREEHKKKHPEEQVIFAEFSRKCAERWKTMLDKEKQRFHEMAEKDKA
RYELEMQSYVPPKGAV

>> SEQUENCE 320 F17I
GKVKDNKPRGRMTAYAIFVQTCREEHKKKHPEEQVIFAEFSRKCAERWKTMLDKEKQRFHEMAEKDKA
RYELEMQSYVPPKGAV

>> SEQUENCE 321 F17V
GKVKDNKPRGRMTAYAVFVQTCREEHKKKHPEEQVIFAEFSRKCAERWKTMLDKEKQRFHEMAEKDK
ARYELEMQSYVPPKGAV

>> SEQUENCE 322 F18I
GKVKDNKPRGRMTAYAFIVQTCREEHKKKHPEEQVIFAEFSRKCAERWKTMLDKEKQRFHEMAEKDKA
RYELEMQSYVPPKGAV

>> SEQUENCE 323 F18V
GKVKDNKPRGRMTAYAFVVQTCREEHKKKHPEEQVIFAEFSRKCAERWKTMLDKEKQRFHEMAEKDK
ARYELEMQSYVPPKGAV

>> SEQUENCE 324 R23H
GKVKDNKPRGRMTAYAFFVQTCHEEHKKKHPEEQVIFAEFSRKCAERWKTMLDKEKQRFHEMAEKDK
ARYELEMQSYVPPKGAV

>> SEQUENCE 325 R23Q
GKVKDNKPRGRMTAYAFFVQTCQEEHKKKHPEEQVIFAEFSRKCAERWKTMLDKEKQRFHEMAEKDK
ARYELEMQSYVPPKGAV

>> SEQUENCE 326 E24Q
GKVKDNKPRGRMTAYAFFVQTCRQEHKKKHPEEQVIFAEFSRKCAERWKTMLDKEKQRFHEMAEKDK
ARYELEMQSYVPPKGAV

>> SEQUENCE 327 E24H
GKVKDNKPRGRMTAYAFFVQTCRHEHKKKHPEEQVIFAEFSRKCAERWKTMLDKEKQRFHEMAEKDK
ARYELEMQSYVPPKGAV

>> SEQUENCE 328 E24N

Figure 6b continued

GKVKDNKPRGRMTAYAFFVQTCRNEHKKKHPEEQVIFAEFSRKCAERWKTMLDKEKQRFHEMAEKDK
ARYELEMQSYVPPKGAV

>> SEQUENCE 329 E25Q
GKVKDNKPRGRMTAYAFFVQTCREQHKKKHPEEQVIFAEFSRKCAERWKTMLDKEKQRFHEMAEKDK
ARYELEMQSYVPPKGAV

>> SEQUENCE 330 E25H
GKVKDNKPRGRMTAYAFFVQTCREHHKKKHPEEQVIFAEFSRKCAERWKTMLDKEKQRFHEMAEKDK
ARYELEMQSYVPPKGAV

>> SEQUENCE 331 E25N
GKVKDNKPRGRMTAYAFFVQTCRENHKKKHPEEQVIFAEFSRKCAERWKTMLDKEKQRFHEMAEKDK
ARYELEMQSYVPPKGAV

>> SEQUENCE 332 K27N
GKVKDNKPRGRMTAYAFFVQTCREEHNKKHPEEQVIFAEFSRKCAERWKTMLDKEKQRFHEMAEKDK
ARYELEMQSYVPPKGAV

>> SEQUENCE 333 K27Q
GKVKDNKPRGRMTAYAFFVQTCREEHQKKHPEEQVIFAEFSRKCAERWKTMLDKEKQRFHEMAEKDK
ARYELEMQSYVPPKGAV

>> SEQUENCE 334 K28N
GKVKDNKPRGRMTAYAFFVQTCREEHKNKHPEEQVIFAEFSRKCAERWKTMLDKEKQRFHEMAEKDK
ARYELEMQSYVPPKGAV

>> SEQUENCE 335 K28Q
GKVKDNKPRGRMTAYAFFVQTCREEHKQKHPEEQVIFAEFSRKCAERWKTMLDKEKQRFHEMAEKDK
ARYELEMQSYVPPKGAV

>> SEQUENCE 336 K29N
GKVKDNKPRGRMTAYAFFVQTCREEHKKNHPEEQVIFAEFSRKCAERWKTMLDKEKQRFHEMAEKDK
ARYELEMQSYVPPKGAV

>> SEQUENCE 337 K29Q
GKVKDNKPRGRMTAYAFFVQTCREEHKKQHPEEQVIFAEFSRKCAERWKTMLDKEKQRFHEMAEKDK
ARYELEMQSYVPPKGAV

>> SEQUENCE 338 P31A
GKVKDNKPRGRMTAYAFFVQTCREEHKKKHAEEQVIFAEFSRKCAERWKTMLDKEKQRFHEMAEKDK
ARYELEMQSYVPPKGAV

>> SEQUENCE 339 P31S
GKVKDNKPRGRMTAYAFFVQTCREEHKKKHSEEQVIFAEFSRKCAERWKTMLDKEKQRFHEMAEKDK
ARYELEMQSYVPPKGAV

>> SEQUENCE 340 E32Q
GKVKDNKPRGRMTAYAFFVQTCREEHKKKHPQEQVIFAEFSRKCAERWKTMLDKEKQRFHEMAEKDK
ARYELEMQSYVPPKGAV

>> SEQUENCE 341 E32H
GKVKDNKPRGRMTAYAFFVQTCREEHKKKHPHEQVIFAEFSRKCAERWKTMLDKEKQRFHEMAEKDK

Figure 6b continued

ARYELEMQSYVPPKGAV

>> SEQUENCE 342 E32N
GKVKDNKPRGRMTAYAFFVQTCREEHKKKHPNEQVIFAEFSRKCAERWKTMLDKEKQRFHEMAEKDK
ARYELEMQSYVPPKGAV

>> SEQUENCE 343 E33Q
GKVKDNKPRGRMTAYAFFVQTCREEHKKKHPEQQVIFAEFSRKCAERWKTMLDKEKQRFHEMAEKDK
ARYELEMQSYVPPKGAV

>> SEQUENCE 344 E33H
GKVKDNKPRGRMTAYAFFVQTCREEHKKKHPEHQVIFAEFSRKCAERWKTMLDKEKQRFHEMAEKDK
ARYELEMQSYVPPKGAV

>> SEQUENCE 345 E33N
GKVKDNKPRGRMTAYAFFVQTCREEHKKKHPENQVIFAEFSRKCAERWKTMLDKEKQRFHEMAEKDK
ARYELEMQSYVPPKGAV

>> SEQUENCE 346 F37I
GKVKDNKPRGRMTAYAFFVQTCREEHKKKHPEEQVIIAEFSRKCAERWKTMLDKEKQRFHEMAEKDKA
RYELEMQSYVPPKGAV

>> SEQUENCE 347 F37V
GKVKDNKPRGRMTAYAFFVQTCREEHKKKHPEEQVIVAEFSRKCAERWKTMLDKEKQRFHEMAEKDK
ARYELEMQSYVPPKGAV

>> SEQUENCE 348 E39Q
GKVKDNKPRGRMTAYAFFVQTCREEHKKKHPEEQVIFAQFSRKCAERWKTMLDKEKQRFHEMAEKDK
ARYELEMQSYVPPKGAV

>> SEQUENCE 349 E39H
GKVKDNKPRGRMTAYAFFVQTCREEHKKKHPEEQVIFAHFSRKCAERWKTMLDKEKQRFHEMAEKDK
ARYELEMQSYVPPKGAV

>> SEQUENCE 350 E39N
GKVKDNKPRGRMTAYAFFVQTCREEHKKKHPEEQVIFANFSRKCAERWKTMLDKEKQRFHEMAEKDK
ARYELEMQSYVPPKGAV

>> SEQUENCE 351 F40I
GKVKDNKPRGRMTAYAFFVQTCREEHKKKHPEEQVIFAEISRKCAERWKTMLDKEKQRFHEMAEKDKA
RYELEMQSYVPPKGAV

>> SEQUENCE 352 F40V
GKVKDNKPRGRMTAYAFFVQTCREEHKKKHPEEQVIFAEVSRKCAERWKTMLDKEKQRFHEMAEKDK
ARYELEMQSYVPPKGAV

>> SEQUENCE 353 R42H
GKVKDNKPRGRMTAYAFFVQTCREEHKKKHPEEQVIFAEFSHKCAERWKTMLDKEKQRFHEMAEKDK
ARYELEMQSYVPPKGAV

>> SEQUENCE 354 R42Q
GKVKDNKPRGRMTAYAFFVQTCREEHKKKHPEEQVIFAEFSQKCAERWKTMLDKEKQRFHEMAEKDK
ARYELEMQSYVPPKGAV

>> SEQUENCE 355 K43N

Figure 6b continued

GKVKDNKPRGRMTAYAFFVQTCREEHKKKHPEEQVIFAEFSRNCAERWKTMLDKEKQRFHEMAEKDK
ARYELEMQSYVPPKGAV

>> SEQUENCE 356 K43Q
GKVKDNKPRGRMTAYAFFVQTCREEHKKKHPEEQVIFAEFSRQCAERWKTMLDKEKQRFHEMAEKDK
ARYELEMQSYVPPKGAV

>> SEQUENCE 357 E46Q
GKVKDNKPRGRMTAYAFFVQTCREEHKKKHPEEQVIFAEFSRKCAQRWKTMLDKEKQRFHEMAEKDK
ARYELEMQSYVPPKGAV

>> SEQUENCE 358 E46H
GKVKDNKPRGRMTAYAFFVQTCREEHKKKHPEEQVIFAEFSRKCAHRWKTMLDKEKQRFHEMAEKDK
ARYELEMQSYVPPKGAV

>> SEQUENCE 359 E46N
GKVKDNKPRGRMTAYAFFVQTCREEHKKKHPEEQVIFAEFSRKCANRWKTMLDKEKQRFHEMAEKDK
ARYELEMQSYVPPKGAV

>> SEQUENCE 360 R47H
GKVKDNKPRGRMTAYAFFVQTCREEHKKKHPEEQVIFAEFSRKCAEHWKTMLDKEKQRFHEMAEKDK
ARYELEMQSYVPPKGAV

>> SEQUENCE 361 R47Q
GKVKDNKPRGRMTAYAFFVQTCREEHKKKHPEEQVIFAEFSRKCAEQWKTMLDKEKQRFHEMAEKDK
ARYELEMQSYVPPKGAV

>> SEQUENCE 362 W48Y
GKVKDNKPRGRMTAYAFFVQTCREEHKKKHPEEQVIFAEFSRKCAERYKTMLDKEKQRFHEMAEKDK
ARYELEMQSYVPPKGAV

>> SEQUENCE 363 W48S
GKVKDNKPRGRMTAYAFFVQTCREEHKKKHPEEQVIFAEFSRKCAERSKTMLDKEKQRFHEMAEKDK
ARYELEMQSYVPPKGAV

>> SEQUENCE 364 K49N
GKVKDNKPRGRMTAYAFFVQTCREEHKKKHPEEQVIFAEFSRKCAERWNTMLDKEKQRFHEMAEKDK
ARYELEMQSYVPPKGAV

>> SEQUENCE 365 K49Q
GKVKDNKPRGRMTAYAFFVQTCREEHKKKHPEEQVIFAEFSRKCAERWQTMLDKEKQRFHEMAEKDK
ARYELEMQSYVPPKGAV

>> SEQUENCE 366 M51I
GKVKDNKPRGRMTAYAFFVQTCREEHKKKHPEEQVIFAEFSRKCAERWKTILDKEKQRFHEMAEKDKA
RYELEMQSYVPPKGAV

>> SEQUENCE 367 M51V
GKVKDNKPRGRMTAYAFFVQTCREEHKKKHPEEQVIFAEFSRKCAERWKTVLDKEKQRFHEMAEKDK
ARYELEMQSYVPPKGAV

>>> SEQUENCE 368 L52I
GKVKDNKPRGRMTAYAFFVQTCREEHKKKHPEEQVIFAEFSRKCAERWKTMIDKEKQRFHEMAEKDKA
RYELEMQSYVPPKGAV

Figure 6b continued

>> SEQUENCE 369 L52V
GKVKDNKPRGRMTAYAFFVQTCREEHKKKHPEEQVIFAEFSRKCAERWKTMVDKEKQRFHEMAEKDK
ARYELEMQSYVPPKGAV

>> SEQUENCE 370 D53N
GKVKDNKPRGRMTAYAFFVQTCREEHKKKHPEEQVIFAEFSRKCAERWKTMLNKEKQRFHEMAEKDK
ARYELEMQSYVPPKGAV

>> SEQUENCE 371 D53Q
GKVKDNKPRGRMTAYAFFVQTCREEHKKKHPEEQVIFAEFSRKCAERWKTMLQKEKQRFHEMAEKDK
ARYELEMQSYVPPKGAV

>> SEQUENCE 372 K54N
GKVKDNKPRGRMTAYAFFVQTCREEHKKKHPEEQVIFAEFSRKCAERWKTMLDNEKQRFHEMAEKDK
ARYELEMQSYVPPKGAV

>> SEQUENCE 373 K54Q
GKVKDNKPRGRMTAYAFFVQTCREEHKKKHPEEQVIFAEFSRKCAERWKTMLDQEKQRFHEMAEKDK
ARYELEMQSYVPPKGAV

>> SEQUENCE 374 E55Q
GKVKDNKPRGRMTAYAFFVQTCREEHKKKHPEEQVIFAEFSRKCAERWKTMLDKQKQRFHEMAEKDK
ARYELEMQSYVPPKGAV

>> SEQUENCE 375 E55H
GKVKDNKPRGRMTAYAFFVQTCREEHKKKHPEEQVIFAEFSRKCAERWKTMLDKHKQRFHEMAEKDK
ARYELEMQSYVPPKGAV

>> SEQUENCE 376 E55N
GKVKDNKPRGRMTAYAFFVQTCREEHKKKHPEEQVIFAEFSRKCAERWKTMLDKNKQRFHEMAEKDK
ARYELEMQSYVPPKGAV

>> SEQUENCE 377 K56N
GKVKDNKPRGRMTAYAFFVQTCREEHKKKHPEEQVIFAEFSRKCAERWKTMLDKENQRFHEMAEKDK
ARYELEMQSYVPPKGAV

>> SEQUENCE 378 K56Q
GKVKDNKPRGRMTAYAFFVQTCREEHKKKHPEEQVIFAEFSRKCAERWKTMLDKEQQRFHEMAEKDK
ARYELEMQSYVPPKGAV

>> SEQUENCE 379 R58H
GKVKDNKPRGRMTAYAFFVQTCREEHKKKHPEEQVIFAEFSRKCAERWKTMLDKEKQHFHEMAEKDK
ARYELEMQSYVPPKGAV

>> SEQUENCE 380 R58Q
GKVKDNKPRGRMTAYAFFVQTCREEHKKKHPEEQVIFAEFSRKCAERWKTMLDKEKQQFHEMAEKDK
ARYELEMQSYVPPKGAV

>> SEQUENCE 381 F59I
GKVKDNKPRGRMTAYAFFVQTCREEHKKKHPEEQVIFAEFSRKCAERWKTMLDKEKQRIHEMAEKDKA
RYELEMQSYVPPKGAV

>> SEQUENCE 382 F59V
GKVKDNKPRGRMTAYAFFVQTCREEHKKKHPEEQVIFAEFSRKCAERWKTMLDKEKQRVHEMAEKDK
ARYELEMQSYVPPKGAV

Figure 6b continued

>>SEQUENCE 383 E61Q
GKVKDNKPRGRMTAYAFFVQTCREEHKKKHPEEQVIFAEFSRKCAERWKTMLDKEKQRFHQMAEKDK
ARYELEMQSYVPPKGAV

>>SEQUENCE 384 E61H
GKVKDNKPRGRMTAYAFFVQTCREEHKKKHPEEQVIFAEFSRKCAERWKTMLDKEKQRFHHMAEKDK
ARYELEMQSYVPPKGAV

>>SEQUENCE 385 E61N
GKVKDNKPRGRMTAYAFFVQTCREEHKKKHPEEQVIFAEFSRKCAERWKTMLDKEKQRFHNMAEKDK
ARYELEMQSYVPPKGAV

>>SEQUENCE 386 M62I
GKVKDNKPRGRMTAYAFFVQTCREEHKKKHPEEQVIFAEFSRKCAERWKTMLDKEKQRFHEIAEKDKA
RYELEMQSYVPPKGAV

>>SEQUENCE 387 M62V
GKVKDNKPRGRMTAYAFFVQTCREEHKKKHPEEQVIFAEFSRKCAERWKTMLDKEKQRFHEVAEKDK
ARYELEMQSYVPPKGAV

>>SEQUENCE 388 E64Q
GKVKDNKPRGRMTAYAFFVQTCREEHKKKHPEEQVIFAEFSRKCAERWKTMLDKEKQRFHEMAQKDK
ARYELEMQSYVPPKGAV

>>SEQUENCE 389 E64H
GKVKDNKPRGRMTAYAFFVQTCREEHKKKHPEEQVIFAEFSRKCAERWKTMLDKEKQRFHEMAHKDK
ARYELEMQSYVPPKGAV

>>SEQUENCE 390 E64N
GKVKDNKPRGRMTAYAFFVQTCREEHKKKHPEEQVIFAEFSRKCAERWKTMLDKEKQRFHEMANKDK
ARYELEMQSYVPPKGAV

>>SEQUENCE 391 K65N
GKVKDNKPRGRMTAYAFFVQTCREEHKKKHPEEQVIFAEFSRKCAERWKTMLDKEKQRFHEMAENDK
ARYELEMQSYVPPKGAV

>>SEQUENCE 392 K65Q
GKVKDNKPRGRMTAYAFFVQTCREEHKKKHPEEQVIFAEFSRKCAERWKTMLDKEKQRFHEMAEQDK
ARYELEMQSYVPPKGAV

>>SEQUENCE 393 D66N
GKVKDNKPRGRMTAYAFFVQTCREEHKKKHPEEQVIFAEFSRKCAERWKTMLDKEKQRFHEMAEKNK
ARYELEMQSYVPPKGAV

>>SEQUENCE 394 D66Q
GKVKDNKPRGRMTAYAFFVQTCREEHKKKHPEEQVIFAEFSRKCAERWKTMLDKEKQRFHEMAEKQK
ARYELEMQSYVPPKGAV

>>SEQUENCE 395 K67N
GKVKDNKPRGRMTAYAFFVQTCREEHKKKHPEEQVIFAEFSRKCAERWKTMLDKEKQRFHEMAEKDN
ARYELEMQSYVPPKGAV

>>SEQUENCE 396 K67Q
GKVKDNKPRGRMTAYAFFVQTCREEHKKKHPEEQVIFAEFSRKCAERWKTMLDKEKQRFHEMAEKDQ

Figure 6b continued

ARYELEMQSYVPPKGAV

>> SEQUENCE 397 R69H
GKVKDNKPRGRMTAYAFFVQTCREEHKKKHPEEQVIFAEFSRKCAERWKTMLDKEKQRFHEMAEKDK
AHYELEMQSYVPPKGAV

>> SEQUENCE 398 R69Q
GKVKDNKPRGRMTAYAFFVQTCREEHKKKHPEEQVIFAEFSRKCAERWKTMLDKEKQRFHEMAEKDK
AQYELEMQSYVPPKGAV

>> SEQUENCE 399 Y70H
GKVKDNKPRGRMTAYAFFVQTCREEHKKKHPEEQVIFAEFSRKCAERWKTMLDKEKQRFHEMAEKDK
ARHELEMQSYVPPKGAV

>> SEQUENCE 400 Y70I
GKVKDNKPRGRMTAYAFFVQTCREEHKKKHPEEQVIFAEFSRKCAERWKTMLDKEKQRFHEMAEKDK
ARIELEMQSYV

>> SEQUENCE 401 E71Q
GKVKDNKPRGRMTAYAFFVQTCREEHKKKHPEEQVIFAEFSRKCAERWKTMLDKEKQRFHEMAEKDK
ARYQLEMQSYVPPKGAV

>> SEQUENCE 402 E71H
GKVKDNKPRGRMTAYAFFVQTCREEHKKKHPEEQVIFAEFSRKCAERWKTMLDKEKQRFHEMAEKDK
ARYHLEMQSYVPPKGAV

>> SEQUENCE 403 E71N
GKVKDNKPRGRMTAYAFFVQTCREEHKKKHPEEQVIFAEFSRKCAERWKTMLDKEKQRFHEMAEKDK
ARYNLEMQSYVPPKGAV

>> SEQUENCE 404 L72I
GKVKDNKPRGRMTAYAFFVQTCREEHKKKHPEEQVIFAEFSRKCAERWKTMLDKEKQRFHEMAEKDK
ARYEIEMQSYVPPKGAV

>> SEQUENCE 405 L72V
GKVKDNKPRGRMTAYAFFVQTCREEHKKKHPEEQVIFAEFSRKCAERWKTMLDKEKQRFHEMAEKDK
ARYEVEMQSYVPPKGAV

>> SEQUENCE 406 E73Q
GKVKDNKPRGRMTAYAFFVQTCREEHKKKHPEEQVIFAEFSRKCAERWKTMLDKEKQRFHEMAEKDK
ARYELQMQSYVPPKGAV

>> SEQUENCE 407 E73H
GKVKDNKPRGRMTAYAFFVQTCREEHKKKHPEEQVIFAEFSRKCAERWKTMLDKEKQRFHEMAEKDK
ARYELHMQSYVPPKGAV

>> SEQUENCE 408 E73N
GKVKDNKPRGRMTAYAFFVQTCREEHKKKHPEEQVIFAEFSRKCAERWKTMLDKEKQRFHEMAEKDK
ARYELNMQSYVPPKGAV

>> SEQUENCE 409 M74I
GKVKDNKPRGRMTAYAFFVQTCREEHKKKHPEEQVIFAEFSRKCAERWKTMLDKEKQRFHEMAEKDK
ARYELEIQSYVPPKGAV

>> SEQUENCE 410 M74V
GKVKDNKPRGRMTAYAFFVQTCREEHKKKHPEEQVIFAEFSRKCAERWKTMLDKEKQRFHEMAEKDK

Figure 6b continued

ARYELEVQSYVPPKGAV

>> SEQUENCE 411 Y77H
GKVKDNKPRGRMTAYAFFVQTCREEHKKKHPEEQVIFAEFSRKCAERWKTMLDKEKQRFHEMAEKDK
ARYELEMQSHVPPKGAV

>> SEQUENCE 412 Y77I
GKVKDNKPRGRMTAYAFFVQTCREEHKKKHPEEQVIFAEFSRKCAERWKTMLDKEKQRFHEMAEKDK
ARYELEMQSIVPPKGAV

>> SEQUENCE 413 P79A
GKVKDNKPRGRMTAYAFFVQTCREEHKKKHPEEQVIFAEFSRKCAERWKTMLDKEKQRFHEMAEKDK
ARYELEMQSYVAPKGAV

>> SEQUENCE 414 P79S
GKVKDNKPRGRMTAYAFFVQTCREEHKKKHPEEQVIFAEFSRKCAERWKTMLDKEKQRFHEMAEKDK
ARYELEMQSYVSPKGAV

>> SEQUENCE 415 P80A
GKVKDNKPRGRMTAYAFFVQTCREEHKKKHPEEQVIFAEFSRKCAERWKTMLDKEKQRFHEMAEKDK
ARYELEMQSYVPAKGAV

>> SEQUENCE 416 P80S
GKVKDNKPRGRMTAYAFFVQTCREEHKKKHPEEQVIFAEFSRKCAERWKTMLDKEKQRFHEMAEKDK
ARYELEMQSYVPSKGAV

>> SEQUENCE417 K81N
GKVKDNKPRGRMTAYAFFVQTCREEHKKKHPEEQVIFAEFSRKCAERWKTMLDKEKQRFHEMAEKDK
ARYELEMQSYVPPNGAV

>> SEQUENCE 418 K81Q
GKVKDNKPRGRMTAYAFFVQTCREEHKKKHPEEQVIFAEFSRKCAERWKTMLDKEKQRFHEMAEKDK
ARYELEMQSYVPPQGAV

Figure 7a

Box A 77 amino acid of HMGB1 *Anopheles gambia* (XP_311154)

Protection against proteolysis
If sequence:

PRGRMTAYAFFVQTCREEHKKKHPEEQVIFAEFSRKCAERWKTMLDKEKQRFHEMA
EKDKARYELEMQSYVPPKGAV

In bold amino acids sensitive to proteases proteolysis

Figure 7b

Box A 77 amino acid of HMGB1 *Anopheles gambia* (XP_311154)

Mutant list:

| | | | |
|---|---|---|---|
| P1A | E26N | R51Q | P73A |
| P1S | F30I | F52I | P73S |
| R2H | F30V | F52V | K74N |
| R2Q | E32Q | E54Q | K74Q |
| R4H | E32H | E54H | |
| R4Q | E32N | E54N | |
| M5I | F33I | M55I | |
| M5V | F33V | M55V | |
| Y8H | R35H | E57Q | |
| Y8I | R35Q | E57H | |
| F10I | K36N | E57N | |
| F10V | K36Q | K58N | |
| F11I | E39Q | K58Q | |
| F11V | E39H | D59N | |
| R16H | E39N | D59Q | |
| R16Q | R40H | K60N | |
| E17Q | R40Q | K60Q | |
| E17H | W41Y | R62H | |
| E17N | W41S | R62Q | |
| E18Q | K42N | Y63H | |
| E18H | K42Q | Y63I | |
| E18N | M44I | E64Q | |
| K20N | M44V | E64H | |
| K20Q | L45I | E64N | |
| K21N | L45V | L65I | |
| K21Q | D46N | L65V | |
| K22N | D46Q | E66Q | |
| K22Q | K47N | E66H | |
| P24A | K47Q | E66N | |
| P24S | E48Q | M67I | |
| E25Q | E48H | M67V | |
| E25H | E48N | Y70H | |
| E25N | K49N | Y70I | |
| E26Q | K49Q | P72A | |
| E26H | R51H | P72S | |

Figure 7b continued

> SEQUENCE 419 Wild type
PRGRMTAYAFFVQTCREEHKKKHPEEQVIFAEFSRKCAERWKTMLDKEKQRFHEMAEKDKARYELEM
QSYVPPKGAV > > SEQUENCE 420 P1A
ARGRMTAYAFFVQTCREEHKKKHPEEQVIFAEFSRKCAERWKTMLDKEKQRFHEMAEKDKARYELEM
QSYVPPKGAV > SEQUENCE 421 P1S
SRGRMTAYAFFVQTCREEHKKKHPEEQVIFAEFSRKCAERWKTMLDKEKQRFHEMAEKDKARYELEM
QSYVPPKGAV > SEQUENCE 422 R2H
PHGRMTAYAFFVQTCREEHKKKHPEEQVIFAEFSRKCAERWKTMLDKEKQRFHEMAEKDKARYELEM
QSYVPPKGAV > SEQUENCE 423 R2Q
PQGRMTAYAFFVQTCREEHKKKHPEEQVIFAEFSRKCAERWKTMLDKEKQRFHEMAEKDKARYELEM
QSYVPPKGAV > SEQUENCE 424 R4H
PRGHMTAYAFFVQTCREEHKKKHPEEQVIFAEFSRKCAERWKTMLDKEKQRFHEMAEKDKARYELEM
QSYVPPKGAV > SEQUENCE 425 R4Q
PRGQMTAYAFFVQTCREEHKKKHPEEQVIFAEFSRKCAERWKTMLDKEKQRFHEMAEKDKARYELEM
QSYVPPKGAV > SEQUENCE 426 M5I
PRGRITAYAFFVQTCREEHKKKHPEEQVIFAEFSRKCAERWKTMLDKEKQRFHEMAEKDKARYELEMQ
SYVPPKGAV > SEQUENCE 427 M5V
PRGRVTAYAFFVQTCREEHKKKHPEEQVIFAEFSRKCAERWKTMLDKEKQRFHEMAEKDKARYELEM
QSYVPPKGAV > SEQUENCE 428 Y8H
PRGRMTAHAFFVQTCREEHKKKHPEEQVIFAEFSRKCAERWKTMLDKEKQRFHEMAEKDKARYELEM
QSYVPPKGAV > SEQUENCE 429 Y8I
PRGRMTAIAFFVQTCREEHKKKHPEEQVIFAEFSRKCAERWKTMLDKEKQRFHEMAEKDKARYELEMQ
SYVPPKGAV > SEQUENCE 430 F10I
PRGRMTAYAIFVQTCREEHKKKHPEEQVIFAEFSRKCAERWKTMLDKEKQRFHEMAEKDKARYELEMQ
SYVPPKGAV > SEQUENCE 431 F10V
PRGRMTAYAVFVQTCREEHKKKHPEEQVIFAEFSRKCAERWKTMLDKEKQRFHEMAEKDKARYELEM
QSYVPPKGAV

*Figure 7b continued*

> SEQUENCE 432 F11I
PRGRMTAYAFIVQTCREEHKKKHPEEQVIFAEFSRKCAERWKTMLDKEKQRFHEMAEKDKARYELEMQ
SYVPPKGAV

> SEQUENCE 433 F11V
PRGRMTAYAFVVQTCREEHKKKHPEEQVIFAEFSRKCAERWKTMLDKEKQRFHEMAEKDKARYELEM
QSYVPPKGAV

> SEQUENCE 434 R16H
PRGRMTAYAFFVQTCHEEHKKKHPEEQVIFAEFSRKCAERWKTMLDKEKQRFHEMAEKDKARYELEM
QSYVPPKGAV

> SEQUENCE 435 R16Q
PRGRMTAYAFFVQTCQEEHKKKHPEEQVIFAEFSRKCAERWKTMLDKEKQRFHEMAEKDKARYELEM
QSYVPPKGAV

> SEQUENCE 436 E17Q
PRGRMTAYAFFVQTCRQEHKKKHPEEQVIFAEFSRKCAERWKTMLDKEKQRFHEMAEKDKARYELEM
QSYVPPKGAV

> SEQUENCE 437 E17H
PRGRMTAYAFFVQTCRHEHKKKHPEEQVIFAEFSRKCAERWKTMLDKEKQRFHEMAEKDKARYELEM
QSYVPPKGAV

> SEQUENCE 438 E17N
PRGRMTAYAFFVQTCRNEHKKKHPEEQVIFAEFSRKCAERWKTMLDKEKQRFHEMAEKDKARYELEM
QSYVPPKGAV

> SEQUENCE 439 E18Q
PRGRMTAYAFFVQTCREQHKKKHPEEQVIFAEFSRKCAERWKTMLDKEKQRFHEMAEKDKARYELEM
QSYVPPKGAV

> SEQUENCE 440 E18H
PRGRMTAYAFFVQTCREHHKKKHPEEQVIFAEFSRKCAERWKTMLDKEKQRFHEMAEKDKARYELEM
QSYVPPKGAV

> SEQUENCE 441 E18N
PRGRMTAYAFFVQTCRENHKKKHPEEQVIFAEFSRKCAERWKTMLDKEKQRFHEMAEKDKARYELEM
QSYVPPKGAV

> SEQUENCE 442 K20N
PRGRMTAYAFFVQTCREEHNKKHPEEQVIFAEFSRKCAERWKTMLDKEKQRFHEMAEKDKARYELEM
QSYVPPKGAV

> SEQUENCE 443 K20Q
PRGRMTAYAFFVQTCREEHQKKHPEEQVIFAEFSRKCAERWKTMLDKEKQRFHEMAEKDKARYELEM
QSYVPPKGAV

> SEQUENCE 444 K21N
PRGRMTAYAFFVQTCREEHKNKHPEEQVIFAEFSRKCAERWKTMLDKEKQRFHEMAEKDKARYELEM
QSYVPPKGAV

> SEQUENCE 445 K21Q
PRGRMTAYAFFVQTCREEHKQKHPEEQVIFAEFSRKCAERWKTMLDKEKQRFHEMAEKDKARYELEM
QSYVPPKGAV

Figure 7b continued

> SEQUENCE 446 K22N
PRGRMTAYAFFVQTCREEHKKNHPEEQVIFAEFSRKCAERWKTMLDKEKQRFHEMAEKDKARYELEM
QSYVPPKGAV

> SEQUENCE 447 K22Q
PRGRMTAYAFFVQTCREEHKKQHPEEQVIFAEFSRKCAERWKTMLDKEKQRFHEMAEKDKARYELEM
QSYVPPKGAV

> SEQUENCE 448 P24A
PRGRMTAYAFFVQTCREEHKKKHAEEQVIFAEFSRKCAERWKTMLDKEKQRFHEMAEKDKARYELEM
QSYVPPKGAV

> SEQUENCE 449 P24S
PRGRMTAYAFFVQTCREEHKKKHSEEQVIFAEFSRKCAERWKTMLDKEKQRFHEMAEKDKARYELEM
QSYVPPKGAV

> SEQUENCE 450 E25Q
PRGRMTAYAFFVQTCREEHKKKHPQEQVIFAEFSRKCAERWKTMLDKEKQRFHEMAEKDKARYELEM
QSYVPPKGAV

> SEQUENCE 451 E25H
PRGRMTAYAFFVQTCREEHKKKHPHEQVIFAEFSRKCAERWKTMLDKEKQRFHEMAEKDKARYELEM
QSYVPPKGAV

> SEQUENCE 452 E25N
PRGRMTAYAFFVQTCREEHKKKHPNEQVIFAEFSRKCAERWKTMLDKEKQRFHEMAEKDKARYELEM
QSYVPPKGAV

> SEQUENCE 453 E26Q
PRGRMTAYAFFVQTCREEHKKKHPEQQVIFAEFSRKCAERWKTMLDKEKQRFHEMAEKDKARYELEM
QSYVPPKGAV

> SEQUENCE 454 E26H
PRGRMTAYAFFVQTCREEHKKKHPEHQVIFAEFSRKCAERWKTMLDKEKQRFHEMAEKDKARYELEM
QSYVPPKGAV

> SEQUENCE 455 E26N
PRGRMTAYAFFVQTCREEHKKKHPENQVIFAEFSRKCAERWKTMLDKEKQRFHEMAEKDKARYELEM
QSYVPPKGAV

> SEQUENCE 456 F30I
PRGRMTAYAFFVQTCREEHKKKHPEEQVIIAEFSRKCAERWKTMLDKEKQRFHEMAEKDKARYELEMQ
SYVPPKGAV

> SEQUENCE 457 F30V
PRGRMTAYAFFVQTCREEHKKKHPEEQVIVAEFSRKCAERWKTMLDKEKQRFHEMAEKDKARYELEM
QSYVPPKGAV

> SEQUENCE 458 E32Q
PRGRMTAYAFFVQTCREEHKKKHPEEQVIFAQFSRKCAERWKTMLDKEKQRFHEMAEKDKARYELEM
QSYVPPKGAV

> SEQUENCE 459 E32H
PRGRMTAYAFFVQTCREEHKKKHPEEQVIFAHFSRKCAERWKTMLDKEKQRFHEMAEKDKARYELEM
QSYVPPKGAV

Figure 7b continued

> SEQUENCE 460 E32N
PRGRMTAYAFFVQTCREEHKKKHPEEQVIFANFSRKCAERWKTMLDKEKQRFHEMAEKDKARYELEM
QSYVPPKGAV

> SEQUENCE 461 F33I
PRGRMTAYAFFVQTCREEHKKKHPEEQVIFAEISRKCAERWKTMLDKEKQRFHEMAEKDKARYELEMQ
SYVPPKGAV

> SEQUENCE 462 F33V
PRGRMTAYAFFVQTCREEHKKKHPEEQVIFAEVSRKCAERWKTMLDKEKQRFHEMAEKDKARYELEM
QSYVPPKGAV

> SEQUENCE 463 R35H
PRGRMTAYAFFVQTCREEHKKKHPEEQVIFAEFSHKCAERWKTMLDKEKQRFHEMAEKDKARYELEM
QSYVPPKGAV

> SEQUENCE 464 R35Q
PRGRMTAYAFFVQTCREEHKKKHPEEQVIFAEFSQKCAERWKTMLDKEKQRFHEMAEKDKARYELEM
QSYVPPKGAV

> SEQUENCE 465 K36N
PRGRMTAYAFFVQTCREEHKKKHPEEQVIFAEFSRNCAERWKTMLDKEKQRFHEMAEKDKARYELEM
QSYVPPKGAV

> SEQUENCE 466 K36Q
PRGRMTAYAFFVQTCREEHKKKHPEEQVIFAEFSRQCAERWKTMLDKEKQRFHEMAEKDKARYELEM
QSYVPPKGAV

> SEQUENCE 467 E39Q
PRGRMTAYAFFVQTCREEHKKKHPEEQVIFAEFSRKCAQRWKTMLDKEKQRFHEMAEKDKARYELEM
QSYVPPKGAV

> SEQUENCE 468 E39H
PRGRMTAYAFFVQTCREEHKKKHPEEQVIFAEFSRKCAHRWKTMLDKEKQRFHEMAEKDKARYELEM
QSYVPPKGAV

> SEQUENCE 469 E39N
PRGRMTAYAFFVQTCREEHKKKHPEEQVIFAEFSRKCANRWKTMLDKEKQRFHEMAEKDKARYELEM
QSYVPPKGAV

> SEQUENCE 470 R40H
PRGRMTAYAFFVQTCREEHKKKHPEEQVIFAEFSRKCAEHWKTMLDKEKQRFHEMAEKDKARYELEM
QSYVPPKGAV

> SEQUENCE 471 R40Q
PRGRMTAYAFFVQTCREEHKKKHPEEQVIFAEFSRKCAEQWKTMLDKEKQRFHEMAEKDKARYELEM
QSYVPPKGAV

> SEQUENCE 472 W41Y
PRGRMTAYAFFVQTCREEHKKKHPEEQVIFAEFSRKCAERYKTMLDKEKQRFHEMAEKDKARYELEMQ
SYVPPKGAV

> SEQUENCE 473 W41S

Figure 7b continued

PRGRMTAYAFFVQTCREEHKKKHPEEQVIFAEFSRKCAERSKTMLDKEKQRFHEMAEKDKARYELEMQ
SYVPPKGAV

> SEQUENCE 474 K42N
PRGRMTAYAFFVQTCREEHKKKHPEEQVIFAEFSRKCAERWNTMLDKEKQRFHEMAEKDKARYELEM
QSYVPPKGAV

> SEQUENCE 475 K42Q
PRGRMTAYAFFVQTCREEHKKKHPEEQVIFAEFSRKCAERWQTMLDKEKQRFHEMAEKDKARYELEM
QSYVPPKGAV

> SEQUENCE 476 M44I
PRGRMTAYAFFVQTCREEHKKKHPEEQVIFAEFSRKCAERWKTILDKEKQRFHEMAEKDKARYELEMQ
SYVPPKGAV

> SEQUENCE 477 M44V
PRGRMTAYAFFVQTCREEHKKKHPEEQVIFAEFSRKCAERWKTVLDKEKQRFHEMAEKDKARYELEM
QSYVPPKGAV

> SEQUENCE 478 L45I
PRGRMTAYAFFVQTCREEHKKKHPEEQVIFAEFSRKCAERWKTMIDKEKQRFHEMAEKDKARYELEMQ
SYVPPKGAV

> SEQUENCE 479 L45V
PRGRMTAYAFFVQTCREEHKKKHPEEQVIFAEFSRKCAERWKTMVDKEKQRFHEMAEKDKARYELEM
QSYVPPKGAV

> SEQUENCE 480 D46N
PRGRMTAYAFFVQTCREEHKKKHPEEQVIFAEFSRKCAERWKTMLNKEKQRFHEMAEKDKARYELEM
QSYVPPKGAV

> SEQUENCE 481 D46Q
PRGRMTAYAFFVQTCREEHKKKHPEEQVIFAEFSRKCAERWKTMLQKEKQRFHEMAEKDKARYELEM
QSYVPPKGAV

> SEQUENCE 482 K47N
PRGRMTAYAFFVQTCREEHKKKHPEEQVIFAEFSRKCAERWKTMLDNEKQRFHEMAEKDKARYELEM
QSYVPPKGAV

> SEQUENCE 483 K47Q
PRGRMTAYAFFVQTCREEHKKKHPEEQVIFAEFSRKCAERWKTMLDQEKQRFHEMAEKDKARYELEM
QSYVPPKGAV

> SEQUENCE 484 E48Q
PRGRMTAYAFFVQTCREEHKKKHPEEQVIFAEFSRKCAERWKTMLDKQKQRFHEMAEKDKARYELEM
QSYVPPKGAV

> SEQUENCE 485 E48H
PRGRMTAYAFFVQTCREEHKKKHPEEQVIFAEFSRKCAERWKTMLDKHKQRFHEMAEKDKARYELEM
QSYVPPKGAV

> SEQUENCE 486 E48N
PRGRMTAYAFFVQTCREEHKKKHPEEQVIFAEFSRKCAERWKTMLDKNKQRFHEMAEKDKARYELEM
QSYVPPKGAV

Figure 7b continued

> SEQUENCE 487 K49N
PRGRMTAYAFFVQTCREEHKKKHPEEQVIFAEFSRKCAERWKTMLDKENQRFHEMAEKDKARYELEM
QSYVPPKGAV

> SEQUENCE 488 K49Q
PRGRMTAYAFFVQTCREEHKKKHPEEQVIFAEFSRKCAERWKTMLDKEQQRFHEMAEKDKARYELEM
QSYVPPKGAV

> SEQUENCE 489 R51H
PRGRMTAYAFFVQTCREEHKKKHPEEQVIFAEFSRKCAERWKTMLDKEKQHFHEMAEKDKARYELEM
QSYVPPKGAV

> SEQUENCE 490 R51Q
PRGRMTAYAFFVQTCREEHKKKHPEEQVIFAEFSRKCAERWKTMLDKEKQQFHEMAEKDKARYELEM
QSYVPPKGAV

> SEQUENCE 491 F52I
PRGRMTAYAFFVQTCREEHKKKHPEEQVIFAEFSRKCAERWKTMLDKEKQRIHEMAEKDKARYELEMQ
SYVPPKGAV

> SEQUENCE 492 F52V
PRGRMTAYAFFVQTCREEHKKKHPEEQVIFAEFSRKCAERWKTMLDKEKQRVHEMAEKDKARYELEM
QSYVPPKGAV

> SEQUENCE 493 E54Q
PRGRMTAYAFFVQTCREEHKKKHPEEQVIFAEFSRKCAERWKTMLDKEKQRFHQMAEKDKARYELEM
QSYVPPKGAV

> SEQUENCE 494 E54H
PRGRMTAYAFFVQTCREEHKKKHPEEQVIFAEFSRKCAERWKTMLDKEKQRFHHMAEKDKARYELEM
QSYVPPKGAV

> SEQUENCE 495 E54N
PRGRMTAYAFFVQTCREEHKKKHPEEQVIFAEFSRKCAERWKTMLDKEKQRFHNMAEKDKARYELEM
QSYVPPKGAV

> SEQUENCE 496 M55I
PRGRMTAYAFFVQTCREEHKKKHPEEQVIFAEFSRKCAERWKTMLDKEKQRFHEIAEKDKARYELEMQ
SYVPPKGAV

> SEQUENCE 497 M55V
PRGRMTAYAFFVQTCREEHKKKHPEEQVIFAEFSRKCAERWKTMLDKEKQRFHEVAEKDKARYELEM
QSYVPPKGAV

> SEQUENCE 498 E57Q
PRGRMTAYAFFVQTCREEHKKKHPEEQVIFAEFSRKCAERWKTMLDKEKQRFHEMAQKDKARYELEM
QSYVPPKGAV

> SEQUENCE 499 E57H
PRGRMTAYAFFVQTCREEHKKKHPEEQVIFAEFSRKCAERWKTMLDKEKQRFHEMAHKDKARYELEM
QSYVPPKGAV

> SEQUENCE 500 E57N
PRGRMTAYAFFVQTCREEHKKKHPEEQVIFAEFSRKCAERWKTMLDKEKQRFHEMANKDKARYELEM
QSYVPPKGAV

Figure 7b continued

> SEQUENCE 501 K58N
PRGRMTAYAFFVQTCREEHKKKHPEEQVIFAEFSRKCAERWKTMLDKEKQRFHEMAENDKARYELEM
QSYVPPKGAV

> SEQUENCE 502 K58Q
PRGRMTAYAFFVQTCREEHKKKHPEEQVIFAEFSRKCAERWKTMLDKEKQRFHEMAEQDKARYELEM
QSYVPPKGAV

> SEQUENCE 503 D59N
PRGRMTAYAFFVQTCREEHKKKHPEEQVIFAEFSRKCAERWKTMLDKEKQRFHEMAEKNKARYELEM
QSYVPPKGAV

> SEQUENCE 504 D59Q
PRGRMTAYAFFVQTCREEHKKKHPEEQVIFAEFSRKCAERWKTMLDKEKQRFHEMAEKQKARYELEM
QSYVPPKGAV

> SEQUENCE 505 K60N
PRGRMTAYAFFVQTCREEHKKKHPEEQVIFAEFSRKCAERWKTMLDKEKQRFHEMAEKDNARYELEM
QSYVPPKGAV

> SEQUENCE 506 K60Q
PRGRMTAYAFFVQTCREEHKKKHPEEQVIFAEFSRKCAERWKTMLDKEKQRFHEMAEKDQARYELEM
QSYVPPKGAV

> SEQUENCE 507 R62H
PRGRMTAYAFFVQTCREEHKKKHPEEQVIFAEFSRKCAERWKTMLDKEKQRFHEMAEKDKAHYELEM
QSYVPPKGAV

> SEQUENCE 508 R62Q
PRGRMTAYAFFVQTCREEHKKKHPEEQVIFAEFSRKCAERWKTMLDKEKQRFHEMAEKDKAQYELEM
QSYVPPKGAV

> SEQUENCE 509 Y63H
PRGRMTAYAFFVQTCREEHKKKHPEEQVIFAEFSRKCAERWKTMLDKEKQRFHEMAEKDKARHELEM
QSYVPPKGAV

> SEQUENCE 510 Y63I
PRGRMTAYAFFVQTCREEHKKKHPEEQVIFAEFSRKCAERWKTMLDKEKQRFHEMAEKDKARIELEMQ
SYVPPKGAV

> SEQUENCE 511 E64Q
PRGRMTAYAFFVQTCREEHKKKHPEEQVIFAEFSRKCAERWKTMLDKEKQRFHEMAEKDKARYQLEM
QSYVPPKGAV

> SEQUENCE 512 E64H
PRGRMTAYAFFVQTCREEHKKKHPEEQVIFAEFSRKCAERWKTMLDKEKQRFHEMAEKDKARYHLEM
QSYVPPKGAV

> SEQUENCE 513 E64N
PRGRMTAYAFFVQTCREEHKKKHPEEQVIFAEFSRKCAERWKTMLDKEKQRFHEMAEKDKARYNLEM
QSYVPPKGAV

> SEQUENCE 514 L65I
PRGRMTAYAFFVQTCREEHKKKHPEEQVIFAEFSRKCAERWKTMLDKEKQRFHEMAEKDKARYEIEMQ

Figure 7b continued

SYVPPKGAV

> SEQUENCE 515 L65V
PRGRMTAYAFFVQTCREEHKKKHPEEQVIFAEFSRKCAERWKTMLDKEKQRFHEMAEKDKARYEVEM
QSYVPPKGAV

> SEQUENCE 516 E66Q
PRGRMTAYAFFVQTCREEHKKKHPEEQVIFAEFSRKCAERWKTMLDKEKQRFHEMAEKDKARYELQM
QSYVPPKGAV

> SEQUENCE 517 E66H
PRGRMTAYAFFVQTCREEHKKKHPEEQVIFAEFSRKCAERWKTMLDKEKQRFHEMAEKDKARYELHM
QSYVPPKGAV

> SEQUENCE 518 E66N
PRGRMTAYAFFVQTCREEHKKKHPEEQVIFAEFSRKCAERWKTMLDKEKQRFHEMAEKDKARYELNM
QSYVPPKGAV

> SEQUENCE 519 M67I
PRGRMTAYAFFVQTCREEHKKKHPEEQVIFAEFSRKCAERWKTMLDKEKQRFHEMAEKDKARYELEIQ
SYVPPKGAV

> SEQUENCE 520 M67V
PRGRMTAYAFFVQTCREEHKKKHPEEQVIFAEFSRKCAERWKTMLDKEKQRFHEMAEKDKARYELEV
QSYVPPKGAV

> SEQUENCE 521 Y70H
PRGRMTAYAFFVQTCREEHKKKHPEEQVIFAEFSRKCAERWKTMLDKEKQRFHEMAEKDKARYELEM
QSHVPPKGAV

> SEQUENCE 522 Y70I
PRGRMTAYAFFVQTCREEHKKKHPEEQVIFAEFSRKCAERWKTMLDKEKQRFHEMAEKDKARYELEM
QSIVPPKGAV

> SEQUENCE 523 P72A
PRGRMTAYAFFVQTCREEHKKKHPEEQVIFAEFSRKCAERWKTMLDKEKQRFHEMAEKDKARYELEM
QSYVAPKGAV

> SEQUENCE 524 P72S
PRGRMTAYAFFVQTCREEHKKKHPEEQVIFAEFSRKCAERWKTMLDKEKQRFHEMAEKDKARYELEM
QSYVSPKGAV

> SEQUENCE 525 P73A
PRGRMTAYAFFVQTCREEHKKKHPEEQVIFAEFSRKCAERWKTMLDKEKQRFHEMAEKDKARYELEM
QSYVPAKGAV

> SEQUENCE 526 P73S
PRGRMTAYAFFVQTCREEHKKKHPEEQVIFAEFSRKCAERWKTMLDKEKQRFHEMAEKDKARYELEM
QSYVPSKGAV

> SEQUENCE 527 K74N
PRGRMTAYAFFVQTCREEHKKKHPEEQVIFAEFSRKCAERWKTMLDKEKQRFHEMAEKDKARYELEM
QSYVPPNGAV

> SEQUENCE 528 K74Q
PRGRMTAYAFFVQTCREEHKKKHPEEQVIFAEFSRKCAERWKTMLDKEKQRFHEMAEKDKARYELEM

Figure 7b continued

QSYVPPQGAV

Figure 8a

Box A 54 amino acid of HMGB1 *Anopheles gambia* (XP_311154)

Protection against proteolysis
If sequence:

PEEQVIFAEFSRKCAERWKTMLDKEKQRFHEMAEKDKARYELEMQSYVPPKGAV

In bold amino acids sensitive to proteases proteolysis

Figure 8b

Box A 54 amino acid of HMGB1 *Anopheles gambia* (XP_311154)

Mutant list:

| | | |
|---|---|---|
| P1A | K24N | E43Q |
| P1S | K24Q | E43H |
| E2Q | E25Q | E43N |
| E2H | E25H | M44I |
| E2N | E25N | M44V |
| E3Q | K26N | Y47H |
| E3H | K26Q | Y47I |
| E3N | R28H | P49A |
| F7I | R28Q | P49S |
| F7V | F29I | P50A |
| E9Q | F29V | P50S |
| E9H | E31Q | K51N |
| E9N | E31H | K51Q |
| F10I | E31N | |
| F10V | M32I | |
| R12H | M32V | |
| R12Q | E34Q | |
| K13N | E34H | |
| K13Q | E34N | |
| E16Q | K35N | |
| E16H | K35Q | |
| E16N | D36N | |
| R17H | D36Q | |
| R17Q | K37N | |
| W18Y | K37Q | |
| W18S | R39H | |
| K19N | R39Q | |
| K19Q | Y40H | |
| M21I | Y40I | |
| M21V | E41Q | |
| L22I | E41H | |
| L22V | E41N | |
| D23N | L42I | |
| D23Q | L42V | |

Figure 8b continued

> SEQUENCE 529 Wild type

PEEQVIFAEFSRKCAERWKTMLDKEKQRFHEMAEKDKARYELEMQSYVPPKGAV

> SEQUENCE 530 P1A

AEEQVIFAEFSRKCAERWKTMLDKEKQRFHEMAEKDKARYELEMQSYVPPKGAV

> SEQUENCE 531 P1S

SEEQVIFAEFSRKCAERWKTMLDKEKQRFHEMAEKDKARYELEMQSYVPPKGAV

> SEQUENCE 532 E2Q

PQEQVIFAEFSRKCAERWKTMLDKEKQRFHEMAEKDKARYELEMQSYVPPKGAV

> SEQUENCE 533 E2H

PHEQVIFAEFSRKCAERWKTMLDKEKQRFHEMAEKDKARYELEMQSYVPPKGAV

> SEQUENCE 534 E2N

PNEQVIFAEFSRKCAERWKTMLDKEKQRFHEMAEKDKARYELEMQSYVPPKGAV

> SEQUENCE 535 E3Q

PEQQVIFAEFSRKCAERWKTMLDKEKQRFHEMAEKDKARYELEMQSYVPPKGAV

> SEQUENCE 536 E3H

PEHQVIFAEFSRKCAERWKTMLDKEKQRFHEMAEKDKARYELEMQSYVPPKGAV

> SEQUENCE 537 E3N

PENQVIFAEFSRKCAERWKTMLDKEKQRFHEMAEKDKARYELEMQSYVPPKGAV

> SEQUENCE 538 F7I

PEEQVIIAEFSRKCAERWKTMLDKEKQRFHEMAEKDKARYELEMQSYVPPKGAV

> SEQUENCE 539 F7V

PEEQVIVAEFSRKCAERWKTMLDKEKQRFHEMAEKDKARYELEMQSYVPPKGAV

> SEQUENCE 540 E9Q

PEEQVIFAQFSRKCAERWKTMLDKEKQRFHEMAEKDKARYELEMQSYVPPKGAV

> SEQUENCE 541 E9H

PEEQVIFAHFSRKCAERWKTMLDKEKQRFHEMAEKDKARYELEMQSYVPPKGAV

> SEQUENCE 542 E9N

PEEQVIFANFSRKCAERWKTMLDKEKQRFHEMAEKDKARYELEMQSYVPPKGAV

> SEQUENCE 543 F10I

PEEQVIFAEISRKCAERWKTMLDKEKQRFHEMAEKDKARYELEMQSYVPPKGAV

> SEQUENCE 544 F10V

PEEQVIFAEVSRKCAERWKTMLDKEKQRFHEMAEKDKARYELEMQSYVPPKGAV

> SEQUENCE 545 R12H

PEEQVIFAEFSHKCAERWKTMLDKEKQRFHEMAEKDKARYELEMQSYVPPKGAV

> SEQUENCE 546 R12Q

PEEQVIFAEFSQKCAERWKTMLDKEKQRFHEMAEKDKARYELEMQSYVPPKGAV

Figure 8b continued

> SEQUENCE 547 K13N
PEEQVIFAEFSRNCAERWKTMLDKEKQRFHEMAEKDKARYELEMQSYVPPKGAV

> SEQUENCE 548 K13Q
PEEQVIFAEFSRQCAERWKTMLDKEKQRFHEMAEKDKARYELEMQSYVPPKGAV

> SEQUENCE 549 E16Q
PEEQVIFAEFSRKCAQRWKTMLDKEKQRFHEMAEKDKARYELEMQSYVPPKGAV

> SEQUENCE 550 E16H
PEEQVIFAEFSRKCAHRWKTMLDKEKQRFHEMAEKDKARYELEMQSYVPPKGAV

> SEQUENCE 551 E16N
PEEQVIFAEFSRKCANRWKTMLDKEKQRFHEMAEKDKARYELEMQSYVPPKGAV

> SEQUENCE 552 R17H
PEEQVIFAEFSRKCAEHWKTMLDKEKQRFHEMAEKDKARYELEMQSYVPPKGAV

> SEQUENCE 553 R17Q
PEEQVIFAEFSRKCAEQWKTMLDKEKQRFHEMAEKDKARYELEMQSYVPPKGAV

> SEQUENCE 554 W18Y
PEEQVIFAEFSRKCAERYKTMLDKEKQRFHEMAEKDKARYELEMQSYVPPKGAV

> SEQUENCE 555 W18S
PEEQVIFAEFSRKCAERSKTMLDKEKQRFHEMAEKDKARYELEMQSYVPPKGAV

> SEQUENCE 556 K19N
PEEQVIFAEFSRKCAERWNTMLDKEKQRFHEMAEKDKARYELEMQSYVPPKGAV

> SEQUENCE 557 K19Q
PEEQVIFAEFSRKCAERWQTMLDKEKQRFHEMAEKDKARYELEMQSYVPPKGAV

> SEQUENCE 558 M21I
PEEQVIFAEFSRKCAERWKTILDKEKQRFHEMAEKDKARYELEMQSYVPPKGAV

> SEQUENCE 559 M21V
PEEQVIFAEFSRKCAERWKTVLDKEKQRFHEMAEKDKARYELEMQSYVPPKGAV

> SEQUENCE 560 L22I
PEEQVIFAEFSRKCAERWKTMIDKEKQRFHEMAEKDKARYELEMQSYVPPKGAV

> SEQUENCE 561 L22V
PEEQVIFAEFSRKCAERWKTMVDKEKQRFHEMAEKDKARYELEMQSYVPPKGAV

> SEQUENCE 562 D23N
PEEQVIFAEFSRKCAERWKTMLNKEKQRFHEMAEKDKARYELEMQSYVPPKGAV

> SEQUENCE 563 D23Q
PEEQVIFAEFSRKCAERWKTMLQKEKQRFHEMAEKDKARYELEMQSYVPPKGAV

> SEQUENCE 564 K24N
PEEQVIFAEFSRKCAERWKTMLDNEKQRFHEMAEKDKARYELEMQSYVPPKGAV

> SEQUENCE 565 K24Q
PEEQVIFAEFSRKCAERWKTMLDQEKQRFHEMAEKDKARYELEMQSYVPPKGAV

> SEQUENCE 566 E25Q

Figure 8b continued

PEEQVIFAEFSRKCAERWKTMLDKQKQRFHEMAEKDKARYELEMQSYVPPKGAV

>SEQUENCE 567 E25H
PEEQVIFAEFSRKCAERWKTMLDKHKQRFHEMAEKDKARYELEMQSYVPPKGAV

>SEQUENCE 568 E25N
PEEQVIFAEFSRKCAERWKTMLDKNKQRFHEMAEKDKARYELEMQSYVPPKGAV

>SEQUENCE 569 K26N
PEEQVIFAEFSRKCAERWKTMLDKENQRFHEMAEKDKARYELEMQSYVPPKGAV

>SEQUENCE 570 K26Q
PEEQVIFAEFSRKCAERWKTMLDKEQQRFHEMAEKDKARYELEMQSYVPPKGAV

>SEQUENCE 571 R28H
PEEQVIFAEFSRKCAERWKTMLDKEKQHFHEMAEKDKARYELEMQSYVPPKGAV

>SEQUENCE 572 R28Q
PEEQVIFAEFSRKCAERWKTMLDKEKQQFHEMAEKDKARYELEMQSYVPPKGAV

>SEQUENCE 573 F29I
PEEQVIFAEFSRKCAERWKTMLDKEKQRIHEMAEKDKARYELEMQSYVPPKGAV

>SEQUENCE 574; F29V
PEEQVIFAEFSRKCAERWKTMLDKEKQRVHEMAEKDKARYELEMQSYVPPKGAV

>SEQUENCE 575 E31Q
PEEQVIFAEFSRKCAERWKTMLDKEKQRFHQMAEKDKARYELEMQSYVPPKGAV

>SEQUENCE 576 E31H
PEEQVIFAEFSRKCAERWKTMLDKEKQRFHHMAEKDKARYELEMQSYVPPKGAV

>SEQUENCE 577 E31N
PEEQVIFAEFSRKCAERWKTMLDKEKQRFHNMAEKDKARYELEMQSYVPPKGAV

>SEQUENCE 578 M32I
PEEQVIFAEFSRKCAERWKTMLDKEKQRFHEIAEKDKARYELEMQSYVPPKGAV

>SEQUENCE 579 M32V
PEEQVIFAEFSRKCAERWKTMLDKEKQRFHEVAEKDKARYELEMQSYVPPKGAV

>SEQUENCE 580 E34Q
PEEQVIFAEFSRKCAERWKTMLDKEKQRFHEMAQKDKARYELEMQSYVPPKGAV

>SEQUENCE 581 E34H
PEEQVIFAEFSRKCAERWKTMLDKEKQRFHEMAHKDKARYELEMQSYVPPKGAV

>SEQUENCE 582 E34N
PEEQVIFAEFSRKCAERWKTMLDKEKQRFHEMANKDKARYELEMQSYVPPKGAV

>SEQUENCE 583 K35N
PEEQVIFAEFSRKCAERWKTMLDKEKQRFHEMAENDKARYELEMQSYVPPKGAV

>SEQUENCE 584 K35Q
PEEQVIFAEFSRKCAERWKTMLDKEKQRFHEMAEQDKARYELEMQSYVPPKGAV

>SEQUENCE 585 D36N

Figure 8b continued

PEEQVIFAEFSRKCAERWKTMLDKEKQRFHEMAEKNKARYELEMQSYVPPKGAV

> SEQUENCE 586 D36Q
PEEQVIFAEFSRKCAERWKTMLDKEKQRFHEMAEKQKARYELEMQSYVPPKGAV

> SEQUENCE 587 K37N
PEEQVIFAEFSRKCAERWKTMLDKEKQRFHEMAEKDNARYELEMQSYVPPKGAV

> SEQUENCE 588 K37Q
PEEQVIFAEFSRKCAERWKTMLDKEKQRFHEMAEKDQARYELEMQSYVPPKGAV

> SEQUENCE 589 R39H
PEEQVIFAEFSRKCAERWKTMLDKEKQRFHEMAEKDKAHYELEMQSYVPPKGAV

> SEQUENCE 590 R39Q
PEEQVIFAEFSRKCAERWKTMLDKEKQRFHEMAEKDKAQYELEMQSYVPPKGAV

> SEQUENCE 591 Y40H
PEEQVIFAEFSRKCAERWKTMLDKEKQRFHEMAEKDKARHELEMQSYVPPKGAV

> SEQUENCE 592 Y40I
PEEQVIFAEFSRKCAERWKTMLDKEKQRFHEMAEKDKARIELEMQSYVPPKGAV

> SEQUENCE 593 E41Q
PEEQVIFAEFSRKCAERWKTMLDKEKQRFHEMAEKDKARYQLEMQSYVPPKGAV

> SEQUENCE 594 E41H
PEEQVIFAEFSRKCAERWKTMLDKEKQRFHEMAEKDKARYHLEMQSYVPPKGAV

> SEQUENCE 595 E41N
PEEQVIFAEFSRKCAERWKTMLDKEKQRFHEMAEKDKARYNLEMQSYVPPKGAV

> SEQUENCE 596 L42I
PEEQVIFAEFSRKCAERWKTMLDKEKQRFHEMAEKDKARYEIEMQSYVPPKGAV

> SEQUENCE 597 L42V
PEEQVIFAEFSRKCAERWKTMLDKEKQRFHEMAEKDKARYEVEMQSYVPPKGAV

> SEQUENCE 598 E43Q
PEEQVIFAEFSRKCAERWKTMLDKEKQRFHEMAEKDKARYELQMQSYVPPKGAV

> SEQUENCE 599 E43H
PEEQVIFAEFSRKCAERWKTMLDKEKQRFHEMAEKDKARYELHMQSYVPPKGAV

> SEQUENCE 600 E43N
PEEQVIFAEFSRKCAERWKTMLDKEKQRFHEMAEKDKARYELNMQSYVPPKGAV

> SEQUENCE 601 M44I
PEEQVIFAEFSRKCAERWKTMLDKEKQRFHEMAEKDKARYELEIQSYVPPKGAV

> SEQUENCE 602 M44V
PEEQVIFAEFSRKCAERWKTMLDKEKQRFHEMAEKDKARYELEVQSYVPPKGAV

> SEQUENCE 603 Y47H
PEEQVIFAEFSRKCAERWKTMLDKEKQRFHEMAEKDKARYELEMQSHVPPKGAV

> SEQUENCE 604 Y47I
PEEQVIFAEFSRKCAERWKTMLDKEKQRFHEMAEKDKARYELEMQSIVPPKGAV

Figure 8b continued

> SEQUENCE 605 P49A
PEEQVIFAEFSRKCAERWKTMLDKEKQRFHEMAEKDKARYELEMQSYVAPKGAV

> SEQUENCE 606 P49S
PEEQVIFAEFSRKCAERWKTMLDKEKQRFHEMAEKDKARYELEMQSYVSPKGAV

> SEQUENCE 607 P50A
PEEQVIFAEFSRKCAERWKTMLDKEKQRFHEMAEKDKARYELEMQSYVPAKGAV

> SEQUENCE 608 P50S
PEEQVIFAEFSRKCAERWKTMLDKEKQRFHEMAEKDKARYELEMQSYVPSKGAV

> SEQUENCE 609 K51N
PEEQVIFAEFSRKCAERWKTMLDKEKQRFHEMAEKDKARYELEMQSYVPPNGAV

> SEQUENCE 610 K51Q
PEEQVIFAEFSRKCAERWKTMLDKEKQRFHEMAEKDKARYELEMQSYVPPQGAV

Fig. 12A

|  | MEAN (cells/filter) | Std deviation | SEM |
|---|---|---|---|
| w/o FBS | 22,04 | 1,119 | 0,3956 |
| HMGB1 1 nM | 51,13 | 2,702 | 0,9552 |
| HMGB1 1 nM + CT500 1nM | 21,71 | 1,803 | 0,6376 |
| HMGB1 1 nM + CT501 1nM | 19,94 | 1,400 | 0,4950 |
| HMGB1 1 nM + CT568 1 nM | 29,19 | 2,506 | 0,8861 |
| HMGB1 1 nM + CT5691 nM | 28,06 | 3,812 | 1,348 |
| HMGB1 1 nM + CT570 1 nM | 30,00 | 4,559 | 1,612 |
| HMGB1 1 nM + CT571 1 nM | 35,94 | 2,528 | 0,8936 |
| HMGB1 1 nM + CT502 1 nM | 25,31 | 3,218 | 1,138 |
| HMGB1 1 nM + CT572 1 nM | 26,63 | 2,489 | 0,8801 |
| HMGB1 1 nM + CT503 1 nM | 18,75 | 3,012 | 1,065 |
| HMGB1 1 nM + CT573 1 nM | 26,31 | 4,383 | 1,550 |
| HMGB1 1 nM + CT504 1 nM | 26,00 | 4,149 | 1,467 |
| HMGB1 1 nM + CT574 1 nM | 31,19 | 2,789 | 0,9862 |
| HMGB1 1 nM + CT575 1 nM | 29,13 | 3,824 | 1,352 |
| HMGB1 1 nM + CT576 1 nM | 30,19 | 2,404 | 0,8501 |
| HMGB1 1 nM + CT505 1 nM | 18,13 | 2,900 | 1,025 |

Fig. 12C

|  | MEAN (cells/filter) | Std deviation | SEM |
|---|---|---|---|
| w/o FBS | 20,25 | 1,035 | 0,3660 |
| HMGB1 1 nM | 64,42 | 8,556 | 3,025 |
| HMGB1 1 nM + CT500 1nM | 23,33 | 3,505 | 1,239 |
| HMGB1 1 nM + CT577 1 nM | 34,75 | 2,171 | 0,7676 |
| HMGB1 1 nM + CT578 1 nM | 29,56 | 3,396 | 1,201 |
| HMGB1 1 nM + CT506 1 nM | 25,31 | 3,936 | 1,392 |
| HMGB1 1 nM + CT579 1 nM | 51,31 | 4,140 | 1,464 |
| HMGB1 1 nM + CT580 1 nM | 30,44 | 3,469 | 1,226 |
| HMGB1 1 nM + CT581 1 nM | 30,44 | 3,469 | 1,226 |
| HMGB1 1 nM + CT507 1 nM | 24,81 | 4,183 | 1,479 |
| HMGB1 1 nM + CT582 1 nM | 38,22 | 5,205 | 1,840 |
| HMGB1 1 nM + CT584 1 nM | 30,56 | 2,796 | 0,9885 |
| HMGB1 1 nM + CT508 1 nM | 25,63 | 2,838 | 1,003 |
| HMGB1 1 nM + CT509 1 nM | 28,88 | 1,827 | 0,6461 |
| HMGB1 1 nM + CT510 1 nM | 25,50 | 5,285 | 1,868 |
| HMGB1 1 nM + CT585 1 nM | 40,63 | 4,719 | 1,668 |

Fig. 12E

|  | MEAN (cells/filter) | Std deviation | SEM |
|---|---|---|---|
| w/o FBS | 20,38 | 2,285 | 0,8078 |
| HMGB1 1 nM | 72,54 | 5,188 | 1,834 |
| HMGB1 1 nM + CT500 0.5 nM | 33,31 | 2,375 | 0,8395 |
| HMGB1 1 nM + CT511 0.5 nM | 26,31 | 5,669 | 2,004 |
| HMGB1 1 nM + CT512 0.5 nM | 26,56 | 2,872 | 1,015 |
| HMGB1 1 nM + CT513 0.5 nM | 25,93 | 1,512 | 0,5714 |
| HMGB1 1 nM + CT514 0.5 nM | 35,29 | 2,233 | 0,8441 |
| HMGB1 1 nM + CT586 0.5 nM | 60,06 | 5,179 | 1,831 |
| HMGB1 1 nM + CT515 0.5 nM | 24,56 | 3,959 | 1,400 |
| HMGB1 1 nM + CT516 0.5 nM | 29,09 | 2,949 | 1,043 |
| HMGB1 1 nM + CT517 0.5 nM | 27,25 | 3,229 | 1,142 |
| HMGB1 1 nM + CT518 0.5 nM | 29,25 | 2,632 | 0,9306 |
| HMGB1 1 nM + CT519 0.5 nM | 26,81 | 3,712 | 1,313 |
| HMGB1 1 nM + CT520 0.5 nM | 27,31 | 3,047 | 1,077 |
| HMGB1 1 nM + CT521 0.5 nM | 29,13 | 2,888 | 1,021 |
| HMGB1 1 nM + CT522 0.5 nM | 25,69 | 3,391 | 1,199 |

Fig. 12G

| | MEAN (cells/filter) | Std deviation | SEM |
|---|---|---|---|
| w/o FBS | 20,27 | 2,250 | 0,7955 |
| HMGB1 1 nM | 66,58 | 6,732 | 2,380 |
| HMGB1 1 nM + CT500 0.5 nM | 36,50 | 3,045 | 1,076 |
| HMGB1 1 nM + CT523 0.5 nM | 34,06 | 3,849 | 1,361 |
| HMGB1 1 nM + CT524 0.5 nM | 39,57 | 6,380 | 2,411 |
| HMGB1 1 nM + CT525 0.5 nM | 41,06 | 4,229 | 1,495 |
| HMGB1 1 nM + CT526 0.5 nM | 34,13 | 4,764 | 1,684 |
| HMGB1 1 nM + CT527 0.5 nM | 29,88 | 3,182 | 1,125 |
| HMGB1 1 nM + CT528 0.5 nM | 41,50 | 2,878 | 1,018 |
| HMGB1 1 nM + CT588 0.5 nM | 60,13 | 5,848 | 2,067 |
| HMGB1 1 nM + CT529 0.5 nM | 30,13 | 3,357 | 1,187 |
| HMGB1 1 nM + CT530 0.5 nM | 35,63 | 2,504 | 0,8851 |
| HMGB1 1 nM + CT589 0.5 nM | 43,88 | 3,227 | 1,141 |
| HMGB1 1 nM + CT590 0.5 nM | 47,00 | 2,535 | 0,8964 |
| HMGB1 1 nM + CT531 0.5 nM | 35,25 | 8,045 | 2,844 |
| HMGB1 1 nM + CT591 0.5 nM | 43,56 | 3,267 | 1,155 |
| HMGB1 1 nM + CT532 0.5 nM | 26,50 | 3,094 | 1,094 |

Fig. 12I

|  | MEAN (cells/filter) | Std deviation | SEM |
|---|---|---|---|
| w/o FBS | 18,48 | 1,694 | 0,5988 |
| HMGB1 1 nM | 76,81 | 5,000 | 1,768 |
| HMGB1 1 nM + CT500 0.5 nM | 35,90 | 0,738 | 0,2790 |
| HMGB1 1 nM + CT592 0.5 nM | 43,00 | 4,041 | 1,528 |
| HMGB1 1 nM + CT533 0.5 nM | 35,88 | 4,883 | 1,726 |
| HMGB1 1 nM + CT593 0.5 nM | 47,14 | 1,574 | 0,5948 |
| HMGB1 1 nM + CT534 0.5 nM | 34,00 | 3,742 | 1,323 |
| HMGB1 1 nM + CT535 0.5 nM | 33,21 | 3,534 | 1,336 |
| HMGB1 1 nM + CT536 0.5 nM | 28,00 | 1,558 | 0,5510 |
| HMGB1 1 nM + CT537 0.5 nM | 28,88 | 2,925 | 1,034 |
| HMGB1 1 nM + CT594 0.5 nM | 45,31 | 3,391 | 1,199 |
| HMGB1 1 nM + CT538 0.5 nM | 31,93 | 3,421 | 1,293 |
| HMGB1 1 nM + CT539 0.5 nM | 34,41 | 3,265 | 1,154 |
| HMGB1 1 nM + CT540 0.5 nM | 29,81 | 1,850 | 0,6542 |
| HMGB1 1 nM + CT541 0.5 nM | 27,44 | 2,195 | 0,7760 |
| HMGB1 1 nM + CT542 0.5 nM | 32,19 | 5,411 | 1,913 |

Fig. 12K

| | MEAN (cells/filter) | Std deviation | SEM |
|---|---|---|---|
| w/o FBS | 15,25 | 2,231 | 0,7887 |
| HMGB1 1 nM | 90,04 | 5,400 | 1,909 |
| HMGB1 1 nM + CT500 0.5 nM | 34,04 | 1,713 | 0,6057 |
| HMGB1 1 nM + CT596 0.5 nM | 55,56 | 3,479 | 1,230 |
| HMGB1 1 nM + CT597 0.5 nM | 92,79 | 11,77 | 4,449 |
| HMGB1 1 nM + CT598 0.5 nM | 64,38 | 4,446 | 1,572 |
| HMGB1 1 nM + CT599 0.5 nM | 58,81 | 6,681 | 2,362 |
| HMGB1 1 nM + CT600 0.5 nM | 95,86 | 7,063 | 2,670 |
| HMGB1 1 nM + CT601 0.5 nM | 67,44 | 7,302 | 2,582 |
| HMGB1 1 nM + CT602 0.5 nM | 49,63 | 2,532 | 0,8952 |
| HMGB1 1 nM + CT603 0.5 nM | 41,56 | 3,923 | 1,387 |
| HMGB1 1 nM + CT543 0.5 nM | 41,44 | 2,884 | 1,020 |
| HMGB1 1 nM + CT544 0.5 nM | 30,63 | 1,620 | 0,5728 |
| HMGB1 1 nM + CT545 0.5 nM | 40,13 | 3,583 | 1,267 |
| HMGB1 1 nM + CT546 0.5 nM | 34,88 | 4,051 | 1,432 |
| HMGB1 1 nM + CT547 0.5 nM | 41,64 | 4,661 | 1,762 |
| HMGB1 1 nM + CT604 0.5 nM | 61,88 | 5,330 | 1,885 |

Fig. 12M

|  | MEAN (cells/filter) | Std deviation | SEM |
|---|---|---|---|
| w/o FBS | 24,33 | 1,869 | 0,6607 |
| HMGB1 1 nM | 90,58 | 2,888 | 1,021 |
| HMGB1 1 nM + CT500 0.5 nM | 44,33 | 4,673 | 1,652 |
| HMGB1 1 nM + CT548 0.5 nM | 45,38 | 3,068 | 1,085 |
| HMGB1 1 nM + CT549 0.5 nM | 44,56 | 4,362 | 1,542 |
| HMGB1 1 nM + CT605 0.5 nM | 84,63 | 5,643 | 1,995 |
| HMGB1 1 nM + CT606 0.5 nM | 83,19 | 5,182 | 1,832 |
| HMGB1 1 nM + CT607 0.5 nM | 68,00 | 4,132 | 1,461 |
| HMGB1 1 nM + CT608 0.5 nM | 89,50 | 6,503 | 2,299 |
| HMGB1 1 nM + CT609 0.5 nM | 89,56 | 3,110 | 1,100 |
| HMGB1 1 nM + CT610 0.5 nM | 82,19 | 5,398 | 1,908 |
| HMGB1 1 nM + CT550 0.5 nM | 28,06 | 3,479 | 1,230 |
| HMGB1 1 nM + CT551 0.5 nM | 37,50 | 4,862 | 1,719 |
| HMGB1 1 nM + CT611 0.5 nM | 55,88 | 4,060 | 1,435 |
| HMGB1 1 nM + CT552 0.5 nM | 42,94 | 3,510 | 1,241 |
| HMGB1 1 nM + CT553 0.5 nM | 40,25 | 4,097 | 1,449 |
| HMGB1 1 nM + CT554 0.5 nM | 43,69 | 2,235 | 0,7902 |

Fig. 12O

|  | MEAN (cells/filter) | Std deviation | SEM |
|---|---|---|---|
| w/o FBS | 17,10 | 2,428 | 0, 859 |
| HMGB1 1 nM | 75,90 | 3,613 | 1,277 |
| HMGB1 1 nM + CT500 0.5 nM | 33,33 | 2,643 | 0,934 |
| HMGB1 1 nM + CT555 0.5 nM | 26,13 | 2,151 | 0,760 |
| HMGB1 1 nM + CT556 0.5 nM | 30,13 | 2,774 | 0,981 |
| HMGB1 1 nM + CT557 0.5 nM | 33,63 | 5,397 | 1,908 |
| HMGB1 1 nM + CT558 0.5 nM | 25,00 | 3,064 | 1,573 |
| HMGB1 1 nM + CT559 0.5 nM | 26,94 | 4,448 | 1,083 |
| HMGB1 1 nM + CT612 0.5 nM | 65,13 | 4,948 | 1,749 |
| HMGB1 1 nM + CT560 0.5 nM | 27,50 | 2,891 | 1,022 |
| HMGB1 1 nM + CT561 0.5 nM | 27,13 | 2,973 | 1,051 |
| HMGB1 1 nM + CT613 0.5 nM | 43,06 | 2,337 | 0,826 |
| HMGB1 1 nM + CT562 0.5 nM | 28,19 | 1,602 | 0,567 |
| HMGB1 1 nM + CT563 0.5 nM | 27,75 | 3,381 | 1,195 |
| HMGB1 1 nM + CT564 0.5 nM | 23,38 | 1,747 | 0,618 |
| HMGB1 1 nM + CT565 0.5 nM | 29,00 | 2,121 | 0,750 |
| HMGB1 1 nM + CT566 0.5 nM | 27,75 | 2,220 | 0,785 |

Fig. 12Q

|  | MEAN (cells/filter) | Std deviation | SEM |
|---|---|---|---|
| w/o FBS | 14,04 | 1,315 | 0,4648 |
| HMGB1 1 nM | 62,96 | 1,864 | 0,659 |
| HMGB1 1 nM + CT500 0.5 nM | 21,71 | 2,155 | 0,815 |
| HMGB1 1 nM + CT567 0.5 nM | 19,31 | 2,052 | 0,725 |
| HMGB1 1 nM + CT614 0.5 nM | 28,71 | 2,119 | 0,801 |
| HMGB1 1 nM + CT615 0.5 nM | 39,81 | 2,154 | 0,761 |

Fig. 81: CT500 and variants protease resistance summary table

| Variants | TIMEPOINTS | | | | | | | |
|---|---|---|---|---|---|---|---|---|
| | 0 | 5' | 15' | 30' | 1h | 1.5h | 2h | 4h |
| CT500 | x | x | x | x | | | | |
| CT501 | x | x | x | x | | | | |
| CT502 | x | x | x | x | | | | |
| CT503 | x | x | x | x | | | | |
| CT504 | x | x | x | | | | | |
| CT505 | x | x | x | x | | | | |
| CT506 | x | x | x | | | | | |
| CT507 | x | x | | | | | | |
| CT508 | x | x | x | x | | | | |
| CT509 | x | x | x | | | | | |
| CT510 | x | x | x | x | | | | |
| CT511 | x | x | x | x | | | | |
| CT512 | x | x | x | x | | | | |
| CT513 | x | x | x | x | | | | |
| CT514 | x | x | x | x | x | | | |
| CT515 | x | x | x | x | x | | | |
| CT516 | x | x | x | x | x | | | |
| CT517 | x | x | x | x | x | | | |
| CT518 | x | x | x | x | x | | | |
| CT519 | x | x | x | | | | | |
| CT520 | x | x | x | x | | | | |
| CT521 | x | x | x | x | x | | | |

| Variants | TIMEPOINTS | | | | | | | |
|---|---|---|---|---|---|---|---|---|
| | 0 | 5' | 15' | 30' | 1h | 1.5h | 2h | 4h |
| CT522 | x | x | x | x | x | | | |
| CT523 | x | x | x | x | x | | | |
| CT524 | x | x | x | x | x | x | | |
| CT525 | x | x | x | x | | | | |
| CT526 | x | x | x | x | x | | | |
| CT527 | x | x | x | x | x | | | |
| CT528 | x | x | x | x | x | x | | |
| CT529 | x | x | x | x | | | | |
| CT530 | x | x | x | x | x | x | | |
| CT531 | x | x | x | x | x | x | | |
| CT532 | x | x | x | x | x | | | |
| CT533 | x | x | x | x | x | x | x | |
| CT534 | x | | | | | | | |
| CT535 | x | x | x | x | x | | | |
| CT536 | x | x | x | x | | | | |
| CT537 | x | x | x | x | x | x | x | |
| CT538 | x | x | x | x | | | | |
| CT539 | x | x | x | x | x | x | | |
| CT540 | x | x | x | x | x | | | |
| CT541 | x | x | x | x | | | | |
| CT542 | x | | | | | | | |
| CT543 | x | x | x | x | | | | |
| CT544 | x | x | x | x | | | | |
| CT545 | x | x | x | | | | | |
| CT546 | x | x | x | | | | | |
| CT547 | x | x | x | x | | | | |
| CT548 | x | x | | | | | | |
| CT549 | x | x | | | | | | |

| Variants | | | | | | | | |
|---|---|---|---|---|---|---|---|---|
| CT550 | x | x | x | | | | | |
| CT551 | x | x | | | | | | |
| CT552 | x | x | x | x | | | | |
| CT553 | x | x | x | x | | | | |
| CT554 | x | x | | | | | | |

Fig. 81 (continued)

| Variants | TIMEPOINTS | | | | | | | |
|---|---|---|---|---|---|---|---|---|
| CT555 | x | | | | | | | |
| CT556 | x | | | | | | | |
| CT557 | x | x | | | | | | |
| CT558 | x | x | | | | | | |
| CT559 | x | x | x | x | x | | | |
| CT560 | x | x | x | x | | | | |
| CT561 | x | x | x | x | | | | |
| CT562 | x | x | x | x | | | | |
| CT563 | x | x | x | x | | | | |
| CT564 | x | x | x | x | | | | |
| CT565 | x | x | x | x | | | | |
| CT566 | x | x | x | x | | | | |
| CT567 | x | x | x | x | | | | |

HMGB1 HIGH AFFINITY BINDING DOMAIN BOX-A MUTANTS

This application is a divisional of Ser. No. 11/713,789 filed Mar. 5, 2007, granted as U.S. Pat. No. 7,635,679, which is a continuation in part of PCT/EP2005/009528 filed Sep. 5, 2005; which claims the benefit of European Patent Application No. 04 425 665.9 filed on Sep. 3, 2004, the disclosure of which is incorporated herein in its entirety by reference.

The present invention relates to polypeptide variants of the HMGB-1 high affinity binding domain Box-A (HMGB1 Box-A) or to a biologically active fragment of HMGB1 Box-A, which are obtained through systematic mutations of single amino acids of the wild-type HMGB1 Box-A protein and which show an increased resistance to proteases and which are therefore characterized by more favourable pharmacokinetic and pharmacodynamic profiles. Moreover, the present invention concerns the use of said polypeptide molecules of HMGB1 Box-A to diagnose, prevent, alleviate and/or treat pathologies associated with extracellular HMGB1 and associated with the receptor RAGE.

Recent research in the field of sepsis and inflammation has led to an improved understanding of the pathogenic mechanisms and events underlying their clinical onset and development. In the early stages of sepsis, for instance, bacterial endotoxins stimulate cells of the innate immune system which release pro-inflammatory cytokines (TNF, IL-1α and IL-6). These early cytokines in turn induce the release of a later-acting downstream mediator (identified as the known protein HMGB1) that triggers the pathological sequelae mediated by the subsequent release of cytokines such as TNF, IL-1α, IL-1β, IL-1Ra, IL-6, IL-8, IL-18, IFN-γ, PAF, etc., leading to a multisystem pathogenesis or to a lethal systemic inflammation (Andersson et al., 2002).

The HMGB1 protein belongs to the family of high mobility group (HMG) proteins. HMG proteins, so-called due to their high electrophoretic mobility in polyacrylamide gels, are the most ubiquitous non-histone proteins associated with isolated chromatin in eukaryotic cells. These proteins play a generalized "architectural" role in DNA bending, looping, folding and wrapping, since they either distort, bend or modify DNA structures and complexes with transcription factors or histones (Andersson et al., 2002; Agresti et al., 2003; Degryse et al., 2003). The high mobility group 1 (HMGB1) protein is usually a nuclear factor, in particular a transcriptional regulatory molecule causing DNA bending and facilitating the binding of several transcriptional complexes.

Structurally, the HMGB1 protein is a protein of approximately 25 kDa with a highly conserved sequence among mammals, whereby 2 out of 214 amino acids have conservative substitutions in all mammalian species. HMGB1 is ubiquitously present in all vertebrate nuclei and in particular can be found in fibroblasts, neurons, hepatocytes, glia and in cells derived from hematopoietic stem cells, including monocytes/macrophages, neutrophils and platelets. The HMGB1 molecule has a tripartite structure composed of three distinct domains: two DNA binding domains called HMG Box-A and Box-B, and an acid carboxyl terminus, making it bipolarly charged.

The two HMGB1 boxes are involved in the protein's function as non-sequence-specific architectural DNA-binding elements, conferring the ability to bind DNA into recognized distorted DNA structures and stabilizing nucleosome assembly, remodelling and sliding. Both the A- and B-HMG boxes are made up of highly conserved 84 amino acid residues, are strongly positively charged and are arranged in three α-helices having a similar L-shaped fold. The long arm of the "L" contains the N-terminal extended strand and helix III (Andersson et al. 2002; Agresti et al., 2003; Thomas, J. O. 2001), while the short arm comprises helices I and II. Structure-function analysis reveals that the pro-inflammatory cytokine domain of HMGB1 is the B-Box and in particular the sequence of its first 20 amino acids. The A-Box is an extremely weak agonist of the inflammatory cytokine release triggered by HMGB1 and competitively inhibits the pro-inflammatory activities of the B-Box and of the whole protein. Therefore, from a pharmacological point of view, the A-Box acts as an antagonist of the pathological conditions induced and/or sustained by the B-Box and HMGB1.

The third domain, the carboxyl terminus or acidic tail, is extremely negatively charged since it contains 30 repetitive aspartic and glutamic acid residues, and is linked to the boxes by a basic region of about 20 residues. Mouse and rat HMGB1 differ from the human form by only two substitutions that are located in this continuous C-terminal stretch.

HMGB1 binds rather weakly to the B-form variety of linear double-stranded DNA with no sequence specificity, while it binds in the interior of the nucleus with high affinity to supercoiled DNA, to unusual DNA structures like 4-way junctions (cruciform DNA), bulged DNA and bent DNA (Ferrari et al., 1992; Pontiggia et al., 1993 and PCT/EP2005/007198 in the name of Creabilis Therapeutics).

Besides its nuclear location and role as a transcription factor regulator, HMGB1 has also been found in the extracellular medium, actively released by activated cells of the immune systems (monocytes and macrophages) or passively released by damaged or necrotic cells (Andersson et al., 2002; Scaffidi et al., 2002; Bonaldi et al., 2002; Taniguchi et al., 2003; Friedman et al., 2003; Palumbo et al., 2004).

Extracellularly released HMGB1 acts as a potent cytokine and as an extremely potent macrophage-stimulating factor. HMGB1 acts directly by binding to the cell membrane, inducing signaling and chemotaxis, having a chemokine-like function (Yang et al., 2001) and further acting indirectly by up-regulating the expression and secretion of pro-inflammatory cytokines. This makes extracellular HMGB1 protein a potent chemotactic and immunoregulatory protein which promotes an effective inflammatory immune response. Furthermore, other proteins belonging to the family of HMG proteins, and which are able to bend DNA, are released together with HMGB1 in the extracellular medium. These proteins are inter alia HMGB2, HMGB3, HMG-1L10, HMG-4L and SP100-HMG. They share with HMGB1 highly homologous amino acid sequences. Like HMGB1, they trigger/sustain inflammatory pathologies interacting with the same receptors, leading to the same downstream pathways of interaction.

In healthy cells, HMGB1 migrates to the cytoplasm both by passive and active transport. However, all cultured cells and resting monocytes contain the vast majority of HMGB1 in the nucleus, indicating that in baseline conditions import is much more effective than export. Cells might transport HMGB1 from the nucleus by acetylating lysine residues which are abundant in HMGB1, thereby neutralizing their basic charge and rendering them unable to function as nuclear localization signals. Nuclear HMGB1 hyperacetylation determines the relocation of this protein from the nucleus to the cytoplasm (in the fibroblasts, for example) or its accumulation into secretory endolysosomes (in activated monocytes and macrophages, for example) and subsequent redirection towards release through a non-classical vesicle-mediated secretory pathway. HMGB1 secretion by already activated monocytes is then triggered by bioactive lysophosphatidylcholine (LPC), which is generated later in the inflammation site from phosphatidylcholine through the action of the secretory phospholipase sPLA2 produced by monocytes several hours after activation. Therefore, secretion of HMGB1 seems to be induced by two signals (Bonaldi et al., 2003) and to take place in three steps: 1) at first, an inflammatory signal promotes HMGB1 acetylation and its relocation from the nucleus to the cytoplasm (step 1) and storage in cytoplasmic secretory vesicles (step 2); then, a secretion signal (extracellular ATP or lysophosphatidylcholine) promotes exocytosis (third step) (Andersson et al., 2002; Scaffidi et al. 2002; Gardella et al., 2002; Bonaldi et al., 2003; Friedman et al., 2003).

Released HMGB1 has been identified as one of the ligands binding to the RAGE receptor. This receptor is expressed in most cell types, and at a high level mainly in endothelial cells, in vascular smooth muscle cells, in monocytes and macrophages and in mononuclear phagocytes. Recognition involves the C-terminal of HMGB1. The interaction of HMGB1 and RAGE triggers a sustained period of cellular activation mediated by RAGE up-regulation and receptor-dependent signaling. In particular, the interaction of HMGB1 and RAGE activates several intracellular signal transduction pathways, including mitogen-activated protein kinases (MAPKs), Cdc-42, p21ras, Rac and the nuclear translocation factor KB (NF-κB), the transcription factor classically linked to inflammatory processes (Schmidt et al., 2001).

According to several experimental evidences, released HMGB1 may also interact with receptors belonging to one or more subclasse(s) of the family of the Toll-like receptors. Further, HMGB1 may also interact with the functional N-terminal lectin-like domain (D1) of thrombomodulin. Due to the ability of the functional D1 domain of thrombomodulin to intercept and bind circulating HMGB1, the interaction with the RAGE receptors and the Toll-like receptors is prevented.

In the context of the present invention, "HMGB1" includes the non-acetylated form or/and the acetylated form of HMGB1. Likewise, "HMGB1 homologous proteins" include the non-acetylated form or/and the acetylated form of HMGB1 homologous proteins. Preferred HMGB1 homologous proteins are HMGB2, HMGB3, HMG-1L10, HMG-4L or/and SP100-HMG.

When released in vivo, HMGB1 is an extremely potent cytokine and a potent macrophage-stimulating factor. In fact, like other cytokine mediators of endotoxemia, HMGB1 activates in vitro a cascade of multiple pro-inflammatory cytokines (TNF, IL-1α, IL-1β, IL-1Ra IL-6, IL-8, MIP-1α and MIP-1β) from human macrophages. Therefore, HMGB1 acts as a late mediator during acute inflammation and participates in an important way in the pathogenesis of systemic inflammation after the early mediator response has been resolved.

The observed pro-inflammatory effects of HMGB1 in vitro and the correlation between circulating HMGB1 levels and the development of the pathogenic sequence of systemic inflammation in vivo indicate that therapeutically targeting of this cytokine-like molecule should be of relevant clinical value, suggesting novel therapeutic approaches by a "late" administration of (selective) antagonists/inhibitors of the extracellular activities of HMGB1.

Moreover the observed RAGE upregulation in proinflammatory environments and the proved increased expression of this receptor in a variety of acute and chronic inflammatory diseases provide support for RAGE as an attractive target for future clinical interventions related to inflammation.

Therefore, several attempts were performed in order to block this extracellular HMGB1 chemo-cytokine protein. Several important approaches were addressed to the administration of antibodies against HMGB1, of HMGB1 fragments (for example HMGB1 A-Box), of antibodies to RAGE, of soluble RAGE (sRAGE) and of ethyl pyruvate (Czura et al., 2003; Lotze et al., 2003).

The passive immunization of mice with HMGB1-neutralizing antibodies conferred a highly significant, dose-dependent and lasting protection against lethal doses of endotoxin, even when the first doses of antibodies were given after the TNF peak had passed, suggesting that antagonizing HMGB1 activity late in the clinical course may be an effective treatment approach to potentially lethal sepsis (Yang et al., 2004).

Another possibility is to administer mono- or oligoclonal antibodies against the HMGB1 B-Box, or its 20 amino acid relevant core which signals through RAGE. Furthermore, HMGB1 A-Box, one of the two DNA-binding domains in HMGB1, has been identified as a specific antagonist of HMGB1: highly purified recombinant A-Box has protected mice from lethal experimental sepsis even when initial treatment has been delayed for 24 hours after pathology induction, further suggesting that HMGB1 antagonists may be administered successfully in a clinically relevant window wider than the one used for other known cytokines (Yang et al., 2004).

Structural function analysis of HMGB1-truncated mutants has revealed that the A-Box domain of HMGB1 competitively displaces the saturable binding of HMGB1 to macrophages, specifically antagonizing HMGB1 activities. As has been already seen with the protective activity of anti-HMGB1 antibodies, the administration of the A-Box rescues mice from sepsis even when treatment has been initiated as late as 24 hours after surgical induction of sepsis (Yang H. et al., 2004). HMGB1 antagonists or inhibitors selected from the group of antibodies or antibody fragments that bind to an HMGB1 protein, HMGB1 gene antisense sequences and HMGB1 receptor antagonists are known from U.S. Pat. No. 6,468,533, WO 02/074337 and US 2003/0144201.

Moreover, saturation of circulating HMGB1 by the administration of sRAGE leads to the block of its activities mediated by cellular RAGE, a result which can also be obtained by inhibiting RAGE itself with the administration of anti-RAGE antibodies.

Furthermore, a similar protective response late in the course of sepsis has been observed by administering ethylpyruvate, a stable lipophilic derivative and relatively non-toxic food additive also used as an experimental anti-inflammatory agent, which attenuates the systemic inflammation of ischemia/reperfusion tissue injury and lethal hemorrhagic shock. Ethyl-pyruvate inhibited HMGB1 and TNF release in vitro from endotoxin-stimulated murine macrophages, while in vivo protected mice from peritonitis-induced lethal sepsis, again when dosing was begun 24 hours after this pathology was experimentally induced.

Finally, it has been shown that the N-terminal lectin-like domain (D1) of thrombomodulin is an inhibitor of HMGB1, since it binds to and sequesters this chemokine, preventing the binding of HMGB1 to RAGE and Toll-like receptors such that the downstream cascade of events leading to inflammatory pathologies is inhibited.

As described above, several attempts were performed with the aim of inhibiting and/or antagonising the extracellular HMGB1 chemo-cytokine protein. The present invention is based on the experimental evidence that the two high affinity binding domains for DNA, i.e. HMGB1 Box-A and HMGB1 Box-A, which are present in the HMGB1 molecule, have two opposing roles in the protein released in the extracellular space. The main activity of HMGB1 Box-B is to mediate the pro-inflammatory activities attributed to the HMGB1 protein.

On the other hand, HMGB1 Box-A acts as an antagonist competing with the pro-inflammatory activity of the Box-B domain.

The problem underlying the present invention was therefore the provision of novel agents for the prevention, alleviation and/or treatment of HMGB1-associated pathologies. In particular, the problem of the present invention was to develop novel agents as selective extracellular HMGB1 antagonist and/or inhibitors, in order to prevent, alleviate and/or treat the broad spectrum of pathological effects induced by the HMGB1 chemokine itself and/or by the cascade of multiple inflammatory cytokines caused by the extracellular release of the HMGB1 protein.

The inventors of the present invention based their studies on the evidence that HMGB1 Box-A behaves as an antagonist in the pathological conditions induced and/or sustained by HMGB1 and as inhibitors of RAGE. Hence HMGB1 Box-A represents a high potential therapeutic approach to block both the contribution of HMGB1 and of RAGE to inflammatory disorders.

However, the delivery of therapeutic proteins for clinical use is a major challenge to pharmaceutical science. Most natural proteins, as such, are inefficient drugs due to suboptimal performance in terms of potency, stability, immunogenicity, side effects or toxicity. Once in the blood stream, these proteins are constantly eliminated from circulation within a short time. Different physiological processes involving metabolism as well as clearance through normal pathways of protein elimination (such as glomerular filtration in the kidneys or proteolysis in blood) are involved. Consequently, also the therapeutic use is limited by a very short half-life in plasma.

Hence the need to identify a HMGB1 Box-A variant specifically designed to maintain the same or a higher pharmacological activity of wild type but characterized by a consistent increased resistance to proteases and consequently improved pharmacokinetic and pharmacodynamic performance exists in the art.

The solution to the above problem is therefore the provision of a polypeptide variant of the human and/or non-human HMGB1 high affinity binding domain Box-A (HMGB1 Box-A) or of a biologically active fragment of human and/or non-human HMGB1 Box-A, characterized in that the amino acid sequence of said polypeptide variant differs from the amino acid sequence of the wild type HMGB1 Box-A protein by the mutation of one or more single amino acids. Surprisingly, it was found by the inventors of the present invention that said polypeptide variant exhibits an increased resistance to proteolysis compared to wild type HMGB1 Box-A or to the biological active fragment of the wild type HMGB1 Box-A together with the maintenance of the same or development of even higher pharmacological activity.

By increasing the resistance to the proteolytic activity of the proteases, a more favourable pharmacokinetic and pharmacodynamic profile can be achieved, since an increased stability in body fluids is obtained for the inventive polypeptide variants. As a result thereof, an increase in the half-life in body fluids of the protein's variants of the present invention is observed as well. It is known that the estimated half-life of proteins in vivo can be as short as a few minutes. The variants of the present invention preferably have an increased half-life, e.g. because they are more resistant to proteases.

In a most preferred embodiment of the present invention, polypeptide variants are obtained by using a directed evolution process, which technology is extensively described in WO 2004/7022593 and in several further patent applications (PCT/FR00/03503, PCT/FR01/01366, U.S. Ser. No. 10/022, 249, U.S. Ser. No. 10/022,390, U.S. Ser. No. 10/375,192, U.S. 60/409,898, U.S. 60/457,135, U.S. 60/410,258 and U.S. 60/410,263), all in the name of Nautilus Biotech S.A. (Paris, France), which are herein incorporated by reference.

In general, the term "directed evolution" refers to biotechnological processes devoted to the improvement of target protein features by means of specific changes introduced into their amino acid sequences. The directed evolution process includes the generation of a library of mutant versions of the gene of interest, followed by the selection of those variants that display the desired features. These processes can be iterative when gene products having an improvement in a desired property are subjected to further cycles of mutation and screening.

In order to optimise the Box-A of HMGB1 protein and to obtain the polypeptide variants of the present invention with higher stability against proteases, a particular Nautilus proprietary technology for directed evolution has been applied. In particular, a so-called two-dimensional rational mutagenesis scanning approach ("2-D scanning") has been applied, which is described in the Nautilus patent application WO 2004/022593, said application being herein incorporated by reference.

Nautilus 2-D scanning approach for protein rational evolution is based on a process, in which two dimensions of the target protein are scanned by serial mutagenesis in order to find the right amino acid change that is needed at the right amino acid position. The first dimension that is scanned is the amino acid position along the target protein sequence, in order to identify those specific amino acid residues to be replaced with different amino acids. These amino acid positions are referred to as is-HIT target positions. The second dimension is the specific amino acid type selected for replacing a particular is-HIT target position. According to a particular approach of the 2-D scanning method, a number of target positions along the protein sequence are selected, in silico. As used herein, in silico refers to research and experiments performed using a computer. In this context, in silico methods include, but are not limited to, molecular modeling studies and biomolecular docking experiments. Therefore, the amino acid target positions on the protein sequence are identified without use of experimental biological methods. Once a protein feature to be optimised is selected, diverse sources of information or previous knowledge are exploited in order to determine those amino acid positions that may be amenable to improve the protein's fitness by replacement with a different amino acid. In particular the "is-HIT target positions" are identified based on three factors, being (i) the protein feature to be evolved and optimised, (ii) the protein's amino acid sequence and/or (iii) the known properties of the individual amino acids.

In the specific context of the present invention, the "in silico HITs" ("is-HITs") are all possible candidate amino acid positions along the target protein's primary sequence that might be involved as target for the proteolytic activity of proteases. Based on the specific list of proteases considered in the context of the present invention (FIG. 1), the complete list of all amino acid sequences that could potentially be targeted within the wild type HMGB1-Box-A amino acid sequence is determined.

Once the is-HIT target positions have been selected, mutagenesis then is performed by the replacement of single amino acid residues at the specific acid target positions on the protein backbone. The mutagenesis is performed by residue replacement "one-by-one" in addressable arrays and molecules containing the preselected amino acid changes at each of the target amino acid positions are produced.

The choice of the replacing amino acid takes into account the need to preserve the physicochemical properties such as hydrophobicity, charge and/or polarity of essential residues (such as catalytic and binding residues). Numerous methods of selecting replacing amino acids are well known in the art, in particular, amino acid substitution matrixes are used for this purpose. A very preferred technology according to the present invention makes use of the so-called "Percent Accepted Mutation" (PAM) (Dayhoff et al., Atlas of protein sequence and structure, 5(3):345-352, 1978), as shown in FIG. 2. PAM values are used in order to select an appropriate group of replacement amino acids. PAM values, originally developed to produce alignments between protein sequences, are available in the form of probability matrixes, which reflect an evolutionary distance. "Conservative substitutions" of a residue in a reference sequence are those substitutions that are physically and functionally similar to the corresponding reference residues, e.g. those that have a similar size, shape, electric charge, chemical properties, including the ability to form covalent or hydrogen bonds, or the like. Preferred conservative substitutions show the highest scores fitting with the PAM matrix criteria in the form of "accepted point mutations". The PAM250 matrix is used in 2-D scanning to identify the replacing amino acids for the is-HITs in order to generate conservative mutations without affecting the protein function. At least, the two amino acids with the highest values in PAM250 matrix, corresponding to "conservative substitutions" or "accepted point mutations", are chosen. The replacement of amino acids by cysteine residues is explicitly avoided, since this change would potentially lead to the formation of intermolecular disulfide bonds.

Using the above-resumed Nautilus Biotech directed evolution technology, the inventors of the present application were able to obtain polypeptide variants of the HMGB1 Box-A which differ from the amino acid sequence of the native target polypeptide by one or more mutation.

In the context of the present invention, where reference is made to the term "HMGB1 Box-A or amino acid sequence of HMGB1 Box-A", it is referred to both human and non-human HMGB1 Box-A. In a preferred embodiment of the present invention, the systematic mutation of single amino acid on the critical is-HITs positions for proteases has been obtained on the wild type of human HMGB1 Box-A protein and on the wild type of *Anopheles gambia* HMGB1 Box-A protein. The choice of the species *Anopheles gambia* was made by the inventors of the present application after a proper structural and phylogenetic analysis showing a 68% identity and a 88% homology of the human and *Anopheles* HMGB1 Box-A.

"Biologically active fragments of HMGB1 Box-A" as used herein are meant to encompass parts of the known wild type HMGB1 Box-A protein, for which at least one of the biological activities of the corresponding mature protein is still observable when known tests are being used. Preferably, a fragment of the mature protein is considered as biologically active if an antagonist activity with respect to the pro-inflammatory activity of the HMGB1 B-Box and the HMGB1 protein as a whole can be determined. Biologically active fragments of native HMGB1 Box-A are fragments of at least 20, 25, 30, 35, 45, 50, 55, 60, 65, 70, 75 or 80 amino acids. Preferred biologically active fragments of native HMGB1 Box-A used in the context of the present invention comprises fragments of at least 77 or of at least 54 amino acids, respectively.

The term "mutation" as used in the context of the present invention can be understood as substitution, deletion and/or addition of single amino acid in the target sequence. Preferably, the mutation of the target sequence in the present invention is a substitution. The substitution can occur with different genetically encoded amino acid or by non-genetically encoded amino acids. Examples for non-genetically encoded amino acids are homocystein, hydroxyproline, ornithin, hydroxylysine, citrulline, carnitine, etc.

The polypeptide variants of the present invention obtained by using directed evolution technology are mutant proteins which differ from the amino acid sequence of the wild type HMGB1 Box-A by the mutation of one or more single amino acid. In a very preferred embodiment of the present invention, only one amino acid replacement occurs on the sequence of the native protein. In this case, the polypeptide variant of the invention is obtained by the modification of the native protein, such that the amino acid sequence of the variant differs from that of the native protein by a single amino acid change at only one of the is-HIT target positions. It is, however, encompassed by the subject of the present invention that the native protein can be further optimised by replacement of a plurality, e.g two or more, of is-HIT target positions on the same protein molecule. According to this variant of the invention, polypeptide variants are obtained by combining the single mutation into a single protein molecule. The modified polypeptide variants having more single amino acid replacement can differ from the wild type protein sequence by amino acid replacements on 1-10, preferably 2, 3, 4, 5 and 6 different amino acid target positions.

The selection of the candidate lead of the series of polypeptide variants produced with the technology used in the present invention is based both on the more favourable pharmacokinetic profile, obtained thanks to the longer resistance to proteases and on a better pharmacodynamic profile thanks to an increased intrinsic activity and binding affinity which gives a greater antagonistic activity than the native HMGB1 Box-A protein.

In a particular embodiment of the invention, starting from Human HMGB1 Box-A as starting native protein, three groups of polypeptide variants are obtained. In particular, one group of polypeptide variants is derived from single mutations introduced into the full-length amino acid sequence (84 amino acids) from Human HMGB1 Box-A (SEQ ID NO:1). The other two groups of inventive polypeptide variants are generated starting from biologically active fragments of Human HMGB1 Box-A of 77 amino acids (SEQ ID NO:117) and 54 amino acids (SEQ ID NO:223), respectively.

In a further particular embodiment of the invention, starting from *Anopheles gambia* HMGB1 Box-A as starting native protein, three groups of polypeptide variants are obtained. In particular, one group of polypeptide variants is derived from single mutations introduced into the full-length amino acid sequence (84 amino acids) from *Anopheles gambia* HMGB1 Box-A (SEQ ID NO:301). The other two groups of inventive polypeptide variants are generated starting from biologically active fragments of *Anopheles gambia* HMGB1 Box-A of 77 amino acids (SEQ ID NO:419) and 54 amino acids (SEQ ID NO:529), respectively.

Hence, the above-mentioned very preferred polypeptide variants of this invention are defined as below.

1) On the human HMGB1 Box-A full-length fragment of 84 amino acids defined by the sequence SEQ ID NO:1 (FIG. 3a), 53 amino acid positions, recognized as substrate for different proteases (cf. FIG. 1), are identified. The numbering corresponds to that in the wild type protein:

K2, D4, P5, K6, K7, P8, R9, K11, M12, Y15, F17, F18, R23, E24, E25, K27, K28, K29, P31, D32, F37, E39, F40, K42, K43, E46, R47, W48, K49, M51, K54, E55, K56, K58, F59, E60, D61, M62, K64, D66, K67, R69, Y70, E71, R72, E73, M74, K75, Y77, P79, P80, K81, E83.

The native amino acid at each of these positions is replaced by residues defined by the substitution matrix PAM250 (cf. FIG. 2). In particular, the performed residue substitutions are as listed below.
R to H, Q
E to H, Q, N
K to Q, T
D to N, Q
M to I, V
P to A, S
Y to I, H
F to I, V
W to Y, S A total of 115 polypeptide variants of Box-A of human HMGB1 are generated (FIG. 3a). These polypeptide variants are defined in sequences SEQ ID NOs:2 to 116.

2) On the Human HMGB1 Box-A biologically active fragment of 77 amino acids, defined in sequence SEQ ID NO:117 (FIG. 4a), 48 amino acid positions, recognized as substrate for different proteases (cf. FIG. 1), are identified. The numbering is in accordance to their position in SEQ ID NO:117:

P1, R2, K4, M5, Y8, F10, F11, R16, E17, E18, K20, K21, K22, P24, D25, F30, E32, F33, K35, K36, E39, R40, W41, K42, M44, K47, E48, K49, K51, F52, E53, D54, M55, K56, D59, K60, R62, Y63, E64, R65, E66, M67, K68, Y70, P72, P73, K74, E76.

The native amino acid in each of these positions is replaced by residues defined by the substitution matrix PAM250 (cf. FIG. 2). In particular, the performed residue substitutions are as listed below.
R to H, Q
E to H, Q, N
K to Q, T
D to N, Q
M to I, V
P to A, S
Y to I, H
F to I, V
W to Y, S A total of 105 polypeptide variants of Box-A of human HMGB1 fragment of 77 amino acids are generated (FIG. 4b) and defined as in sequences SEQ ID NOs:118 to 222.

3) On the Human HMGB1 Box-A biologically active fragment of 54 amino acids defined in sequence SEQ ID NO:223 (FIG. 5a), 35 amino acid positions, recognized as substrate for different proteases (FIG. 1), are identified. The numbering is in accordance to their position in SEQ ID NO:223:

P1, D2, F7, E9, F10, K12, K13, E16, R17, W18, K19, M21, K24, E25, K26, K28, F29, E30, D31, M32, K34, D36, K37, R39, Y40, E41, R42, E43, M44, K45, Y47, P49, P50, K51, E53.

The native amino acid at each of these positions is replaced by residues defined by the substitution matrix PAM250 (cf. FIG. 2). In particular, the performed residue substitutions are as listed below.
R to H, Q
E to H, Q, N
K to Q, T
D to N, Q
M to I, V
P to A, S
Y to I, H
F to I, V
W to Y, S A total of 77 polypeptide variants of Box-A of human HMGB1 fragment of 54 amino acids are generated (FIG. 5b) and defined as in sequences SEQ ID NOs:224 to 300.

4) On the *Anopheles gambia* (XP_311154) HMGB1 Box-A full-length fragment of 84 amino acids, defined by the sequence SEQ ID NO:301 (FIG. 6a), 53 amino acid positions, recognized as substrate for different proteases (FIG. 1), were identified. The numbering is in accordance with the position in the native protein.

K2, K4, D5, K7, P8, R9, R11, M12, Y15, F17, F18, R23, E24, E25, K27, K28, K29, P31, E32, E33, F37, E39, F40, R42, K43, E46, R47, W48, K49, M51, L52, D53, K54, E55, K56, R58, F59, E61, M62, E64, K65, D66, K67, R69, Y70, E71, L72, E73, M74, Y77, P79, P80, K81.

The native amino acid at each of these positions was replaced by residues defined by the substitution matrix PAM250 (cf. FIG. 2).

The performed actual residue substitutions are as listed below.
R to H, Q
E to H, Q, N
K to Q, T
D to N, Q
M to I, V
P to A, S
Y to I, H
F to I, V
W to Y, S A total of 117 variants of Box-A of HMGB1 *Anopheles gambia* (XP_311154) were generated (FIG. 6b) and identified in the sequences as defined in SEQ ID NOs:302 to 418.

5) On the *Anopheles gambia* (XP_311154) HMGB1 Box-A biologically active fragment of 77 amino acids, defined in sequence SEQ ID NO:419 (FIG. 7a), 49 amino acid positions, recognized as substrate for different proteases (cf. FIG. 1), were identified. The numbering is in accordance with the position in the sequence as defined in SEQ ID NO:419.

P1, R2, R4, M5, Y8, F10, F11, R16, E17, E18, K20, K21, K22, P24, E25, E26, F30, E32, F33, R35, K36, E39, R40, W41, K42, M44, L45, D46, K47, E48, K49, R51, F52, E54, M55, E57, K58, D59, K60, R62, Y63, E64, L65, E66, M67, Y70, P72, P73, K74.

The native amino acid at each of these positions was replaced by residues defined by the substitution matrix PAM250 (cf. FIG. 2).

The performed actual residue substitutions are as listed below.
R to H, Q
E to H, Q, N
K to Q, T
D to N, Q
M to I, V
P to A, S
Y to I, H
F to I, V
W to Y, S A total of 109 polypeptide variants of Box-A of HMGB1 fragment of 77 amino acids were generated (FIG. 7b) and identified as defined in sequences SEQ ID NOs:420 to 528.

6) On the *Anopheles gambia* (XP_311154) HMGB1 Box-A biologically active fragment of 54 amino acids defined in sequence SEQ ID NO:529 (FIG. 8a), 36 amino acid positions, recognized as substrate for different proteases (cf. FIG. 1), were identified. The numbering is in accordance with the position on the sequence as defined in SEQ ID NO:529.

P1, E2, E3, F7, E9, F10, R12, K13, E16, R17, W18, K19, M21, L22, D23, K24, E25, K26, R28, F29, E31, M32, E34, K35, D36, K37, R39, Y40, E41, L42, E43, M44, Y47, P49, P50, K51.

The native amino acid in each of these positions was replaced by residues defined by the substitution matrix PAM250 (cf. FIG. 2).

The performed actual residue substitutions are as listed below.
R to H, Q
E to H, Q, N
K to Q, T
D to N, Q
M to I, V
P to A, S
Y to I, H
F to I, V
W to Y, S A total of 81 polypeptide variants of Box-A of HMGB1 *Anopheles gambia* (XP_311154) fragment of 54 amino acids were generated (FIG. 8*b*) and identified in the sequences as defined in SEQ ID NOs:530 to 610.

It is noted that the amino acids which occur in the various amino acid sequences appearing herein are identified according to their known one-letter code abbreviations. It should be further noted that all amino acid residue sequences represented herein by their one-letter abbreviation code have a left-to-right orientation in the conventional direction of amino-terminus to carboxyl-terminus.

Accordingly, the present invention provides modified polypeptide variants that exhibit increased resistance to the proteolytic activity of proteases and/or peptidases compared to the wild type HMGB1 Box-A protein together with a similar or even higher antagonistic activity than the native HMGB1 Box-A protein. The polypeptide variants of the invention in particular exhibit an increase in the resistance to the proteolytic activity of the human proteases and/or peptidases, in particular of the human serum proteases and/or human gastro-intestinal proteases or peptidases. Preferred proteases are listed in FIG. 1. In a more preferred embodiment of the invention, polypeptide variants exhibit an increase in the resistance to the proteolytic activity of at least a protease selected from the group comprising chymotrypsin, trypsin, endoprotease, endopeptidases or a combination thereof.

In particular, the resistance to proteolysis is at least 10%, 20%, 30%, 40%, 50%, 70%, 80%, 90%, 95% or higher compared to the unmodified wild type HMGB1 Box-A. Protease resistance was measured at different timepoints (between 5 minutes and 8 hours) at 25° C. after incubation of 20 µg of Box-A wild type or variants with a mixture of proteases at 1% w/w of total proteins. The mixture of the proteases was prepared freshly at each assay from stock solutions of endoproteinase Glu-C (SIGMA) 200 µg/ml; trypsin (SIGMA) 400 µg/ml and α-chymotrypsin (SIGMA) 400 µg/ml. After protease incubation the reaction was stopped adding 10 µl of anti-proteases solution (Roche) and the samples were stored at −20° C. for the biological activity assay.

In particular, in order to identify the most preferred polypeptide variants of the invention, studies have been conducted to determine the variants which show both a similar or even improved activity and an increased protease resistance compared to the wild-type HMGB1 Box-A protein. For this purpose, the activity of Box-A polypeptide variants of human HMGB1 Box-A full-length fragment in inhibiting HMGB1-induced NIH/3T3 cell migration was determined in chemotaxis assays in comparison to Box-A wild-type (Example 6 and FIGS. 12A to 12R). Moreover for the polypeptide variants, which show a similar or even higher antagonistic activity than the native HMGB1 Box-A protein of SEQ ID NO:1 the in vitro resistance to protease digestion was determined by incubation of each of these polypeptide variants with a mixture of trypsin, α-chymotrypsin, endoproteinase Asp-N and endoproteinase Glu-C (sigma). This protease resistance test is described in Example 7 and the results of protease resistance profile of said variants are shown in FIGS. 14 to 81.

From the results it can be gathered that the preferred polypeptide variants of the present invention are those variants which show a similar or higher antagonistic activity together with an increased protease resistance. In particular, the preferred polypeptide variants are the polypeptides of SEQ ID NOs: 33, 35, 37-39, 42-45, 47-49, 52, 55, 57, 59, 62, 64, 67, 69 and 104. Among these preferred polypeptide variants, the most preferred variants are those defined in SEQ ID Nos:45, 49, 52, 55, 59, 64 and 67. These very preferred polypeptide variants show a dramatically improved proteinase resistance profile compared with the wild-type human HMGB1 Box-A of SEQ ID NO:1 (cf. results of Example 7).

As a consequence of the increased stability due to the increased resistance to proteases activity, the polypeptide variants of the present invention also exhibit a longer half-life in body fluids compared to the wild type HMGB1 Box-A. In particular, the half-life in serum and/or in blood is increased, whereby an increase of at least 10 minutes, 20 minutes, 30 minutes, 60 minutes or even longer, compared to the wild type HMGB1 Box-A is observed.

A further aspect of the present invention is a nucleic acid molecule encoding a polypeptide variant of the present invention. In particular, the present invention refers to nucleic acid molecules encoding polypeptide variants as defined in SEQ ID NO:2 to 116, 118 to 222, 224 to 300, 302 to 418, 420 to 528 and 530 to 610. Even more preferably, the present invention refers to nucleic acid molecules encoding for the preferred polypeptide variants as defined above.

A still further aspect of the present invention is a vector comprising a nucleic acid molecule as defined above.

Furthermore, the present invention refers to a method for producing a polypeptide variant as described above comprising (i) introducing a nucleic acid molecule as defined above into a host cell and (ii) culturing the cell, under conditions in which the encoded polypeptide variant is expressed. Preferably the host cell is a mammalian, insect or bacterial cell, in particular *E. Coli*, preferably the M15 strain.

A further method for producing a polypeptide variant as described above is the use of chemical peptide synthesis, e.g. a solid phase peptide synthesis according to standard methods.

The polypeptide variants of the present invention exhibit an increased resistance to proteolysis and thus a higher stability compared to the unmodified wild type protein. Consequently, the peptides of the invention also exhibit improved therapeutic and biological properties and activity. In fact, they show a more favorable pharmacokinetic and pharmacodynamic profile than native HMGB1 Box-A.

The invention is therefore directed to the use of the above-mentioned polypeptide variants of HMGB1 Box-A, obtained through systematic mutations of single amino acids in the sequence of HMGB1 Box-A or of its biologically active fragments as active agent in a medicament. In a preferred embodiment, the present invention refers to the use of the preferred polypeptide variants as defined above as active agent in a medicament.

A still further aspect of the invention is hence the use of the inventive polypeptide variants, in particular of the preferred polypeptide variants of the present invention as defined above, for the manufacture of a medicament for the prevention and/or treatment of extracellular HMGB1-associated pathologies or pathologies associated with the HMGB1 homologous proteins. In particular, the HMGB1 associated pathologies are pathologies which are mediated by a multiple inflammatory cytokine cascade.

The broad spectrum of pathological conditions induced by the HMGB1-chemokine and by the HMGB1-induced cascade of inflammatory cytokines are grouped in the following categories: inflammatory disease, autoimmune disease, systemic inflammatory response syndrome, reperfusion injury after organ transplantation, cardiovascular affections, obstetric and gynecologic disease, infectious (viral and bacterial) disease, allergic and atopic disease, solid and liquid tumor pathologies, transplant rejection diseases, congenital diseases, dermatological diseases, neurological diseases, cachexia, renal diseases, iatrogenic intoxication conditions, metabolic and iodiopathic diseases.

HMGB1-associated pathologies according to the present invention are preferably pathological conditions mediated by activation of the inflammatory cytokine cascade. Non limiting examples of conditions which can be usefully treated using the present invention include the broad spectrum of pathological conditions induced by the HMGB1-chemokine and by the HMGB1-induced cascade of inflammatory cytokines grouped in the following categories: restenosis and other cardiovascular diseases, reperfusion injury, inflammation diseases such as inflammatory bowel disease, systemic inflammation response syndrome, e.g. sepsis, adult respiratory distress syndrome, etc, autoimmune diseases such as rheumatoid arthritis and osteoarthritis, obstetric and gynaecological diseases, infectious diseases, atopic diseases, such as asthma, eczema, etc, tumor pathologies, e.g. solid or non-solid tumor diseases associated with organ or tissue transplants, such as reperfusion injuries after organ transplantation, organ rejection and graft-versus-host disease, congenital diseases, dermatological diseases such as psoriasis or alopecia, neurological diseases, ophthalmological diseases, renal, metabolic or idiopathic diseases and intoxication conditions, e.g. iatrogenic toxicity, wherein the above diseases are caused by, associated with and/or accompanied by HMGB1 protein release.

In particular, the pathologies belonging to inflammatory and autoimmune diseases include rheumatoid arthritis/seronegative arthropathies, osteoarthritis, inflammatory bowel disease, Crohn's disease, intestinal infarction, systemic lupus erythematosus, iridoeyelitis/uveitis, optic neuritis, idiopathic pulmonary fibrosis, systemic vasculitis/Wegener's granulomatosis, sarcoidosis, orchitis/vasectomy reversal procedures, systemic sclerosis and scleroderma. Systemic sclerosis and scleroderma systemic inflammatory response includes sepsis syndrome (including gram positive sepsis, gram negative sepsis, culture negative sepsis, fungal sepsis, neutropenic fever, urosepsis, septic conjunctivitis), meningococcemia, trauma hemorrhage, hums, ionizing radiation exposure, acute and chronic prostatitis, acute and chronic pancreatitis, appendicitis, peptic, gastric and duodenal ulcers, peritonitis, ulcerative, pseudomembranous, acute and ischemic cholitis, diverticulitis, achalasia, cholangitis, cholecystitis, enteritis, adult respiratory distress syndrome (ARDS). Reperfusion injury includes post-pump syndrome and ischemia-reperfusion injury. Cardiovascular disease includes cardiac stun syndrome, myocardial infarction and ischemia, atherosclerosis, thrombophlebitis, endocarditis, pericarditis, congestive heart failure and restenosis. Obstetric and gynecologic diseases include premature labour, endometriosis, miscarriage, vaginitis and infertility. Infectious diseases include HIV infection/HIV neuropathy, meningitis, B- and C-hepatitis, herpes simplex infection, septic arthritis, peritonitis, *E. coli* 0157:H7, pneumonia epiglottitis, haemolytic uremic syndrome/thrombolytic thrombocytopenic purpura, candidiasis, filariasis, amebiasis, malaria, Dengue hemorrhagic fever, leishmaniasis, leprosy, toxic shock syndrome, streptococcal myositis, gas gangrene, mycobacterium tuberculosis, mycobacterium avium intracellulare, pneumocystis carinii pneumonia, pelvic inflammatory disease, orchitis/epidydimitis, legionella, Lyme disease, influenza A, Epstein-Barr Virus, Cytomegalovirus, viral associated hemiaphagocytic syndrome, viral encephalitis/aseptic meningitis. Allergic and atopic disease include asthma, allergy, anaphylactic shock, immune complex disease, hay fever, allergic rhinitis, eczema, allergic contact dermatitis, allergic conjunctivitis, hypersensitivity pneumonitis. Malignancies (liquid and solid tumor pathologies) include ALL, AML, CML, CLL, Hodgkin's disease, non Hodgkin's lymphoma, Kaposi's sarcoma, colorectal carcinoma, nasopharyngeal carcinoma, malignant histiocytosis and paraneoplastic syndrome/hypercalcemia of malignancy. Transplant diseases include organ transplant rejection and graft-versus-host disease. Congenital disease includes cystic fibrosis, familial hematophagocytic lymphohistiocytosis and sickle cell anemia. Dermatologic disease includes psoriasis, psoriatic arthritis and alopecia. Neurologic disease includes neurodegenerative diseases (multiple sclerosis, migraine, headache, amyloid-associated pathologies, prion diseases/Creutzfeld-Jacob disease, Alzheimer and Parkinson's diseases, multiple sclerosis, amyotrophic emilateral sclerosis) and peripheral neuropathies, migraine, headache. Renal disease includes nephrotic syndrome, hemodialysis and uremia. Iatrogenic intoxication condition includes OKT3 therapy, Anti-CD3 therapy, Cytokine therapy, Chemotherapy, Radiation therapy and chronic salicylate intoxication. Metabolic and idiopathic disease includes Wilson's disease, hemochromatosis, antitrypsin deficiency, diabetes and diabetes complications, weight loss, anorexia, cachexia, obesity, Hashimoto's thyroiditis, osteoporosis, hypothalamic-pituitary-adrenal axis evaluation and primary biliary cirrhosis. Ophtalmological disease include glaucoma, retinopathies and dry-eye. A miscellanea of other pathologies comprehends: multiple organ dysfunction syndrome, muscular dystrophy, septic meningitis, atherosclerosis, epiglottitis, Whipple's disease, asthma, allergy, allergic rhinitis, organ necrosis, fever, septicaemia, endotoxic shock, hyperpyrexia, eosinophilic granuloma, granulomatosis, sarcoidosis, septic abortion, urethritis, emphysema, rhinitis, alveolitis, bronchiolitis, pharyngitis, epithelial barrier dysfunctions, pneumoultramicropicsilicovolcanoconiosis, pleurisy, sinusitis, influenza, respiratory syncytial virus infection, disseminated bacteremia, hydatid cyst, dermatomyositis, burns, sunburn, urticaria, warst, wheal, vasulitis, angiitis, myocarditis, arteritis, periarteritis nodosa, rheumatic fever, celiac disease, encephalitis, cerebral embolism, Guillame-Barre syndrome, neuritis, neuralgia, iatrogenic complications/peripheral nerve lesions, spinal cord injury, paralysis, uveitis, arthriditis, arthralgias, osteomyelitis, fasciitis, Paget's disease, gout, periodontal disease, synovitis, myasthenia gravis, Goodpasture's syndrome, Babcets's syndrome, ankylosing spondylitis, Barger's disease, Retier's syndrome, bullous dermatitis (bullous pemphigoid), pemphigous and pemphigous vulgaris and alopecia.

In a further aspect of the invention, the use of the polypeptide variants obtained through systematic mutations of amino acid sequences of human and non-human Box-A of HMGB1, or of its biologically relevant fragments described above, is in combination with a further agent.

The further agent is preferably an agent capable of inhibiting an early mediator of the inflammatory cytokine cascade. Preferably, this further agent is an antagonist or inhibitor of a cytokine selected from the group consisting of TNF, IL-1α, IL-1β, IL-Ra, IL-6, IL-8, IL-10, IL 13, IL-18, IFN-γ MIP-1α, MIP-1β, MIP-2, MIF and PAF.

The further agent used in combination with the polypeptide variants of HMGB1 Box-A, or of its biologically relevant fragments, may also be an inhibitor of RAGE, e.g. an antibody directed to RAGE, a nucleic acid or nucleic acid analogue capable of inhibiting RAGE expression, e.g. an antisense molecule, a ribozyme or a RNA interference molecule, or a small synthetic molecule antagonist of the interaction of HMGB1 with RAGE, preferably of the interaction of the non-acetylated or/and acetylated form of HMGB1 with RAGE, or soluble RAGE (sRAGE). The antibody to RAGE is preferably a monoclonal antibody, more preferably a chimeric or humanised antibody or a recombinant antibody, such as a single chain antibody or an antigen-binding fragment of such an antibody. The soluble RAGE analog may be optionally present as a fusion protein, e.g. with the Fc domain of a human antibody. The small synthetic molecular antagonist of the HMGB1 interaction with RAGE preferably has a molecular weight of less than 1000 Dalton. The small synthetic molecular antagonist preferably inhibits the interaction of RAGE with the non-acetylated form or/and with the acetylated form of HMGB1 and with the non-acetylated form or/and with the acetylated form of HMGB1 homologous proteins, particularly HMGB2, HMGB3, HMG-1L10, HMG-4L or/and SP100-HMG.

The further agent used in combination with the polypeptide variants of HMGB1 Box-A, or of its biologically relevant fragments, may also be an inhibitor of the interaction of a Toll-like receptor (TLR), e.g. of TLR2, TLR4, TLR7, TLR8 or/and TLR9, with HMGB1, which inhibitor is preferably a monoclonal or polyclonal antibody, a nucleic acid or nucleic acid analogue capable of inhibiting TLR expression, e.g. an antisense molecule, a ribozyme or a RNA interference molecule, or a synthetic molecule preferably having a size of less than 1000 Dalton. The inhibitor may be a known inhibitor of a Toll-like receptor, in particular of TLR2, TLR4, TLR7, TLR8 or/and TLR9. The inhibitor preferably inhibits the interaction of the Toll-like receptor with the non-acetylated form or/and the acetylated form of HMGB1 and with the non-acetylated form or/and with the acetylated form of HMGB1 homologous proteins, in particular HMGB2, HMGB3, HMG-1L10, HMG-4L or/and SP100-HMG.

In still another embodiment, the further agent used in combination with the polypeptide variants of HMGB1 Box-A, or of its biologically relevant fragments, is the functional N-terminal lectin-like domain (D1) of thrombomodulin. The D1 domain of thrombomodulin is able to intercept the non-acetylated form and/or the acetylated form of released HMGB1 and of released HMGB1 homologous proteins, in particular HMGB2, HMGB3, HMG-1L10, HMG-4L or/and SP100-HMG, preventing thus their interaction with RAGE and Toll-like receptors. The D1 domain of thrombomodulin may be native or mutated in order to make it resistant to proteases.

The further agent may also be a synthetic double-stranded nucleic acid or nucleic acid analogue molecule with a bent shape structure, particularly a double-stranded bent DNA, PNA or DNA/PNA chimera or hybrid or a double-stranded cruciform DNA, PNA or DNA/PNA chimera or hybrid structure, capable of binding to the HMGB1 protein. Preferred nucleic acids and nucleic analogue molecules are disclosed in a co-owned and co-pending international patent application No. PCT/EP2005/007198 filed on 4 Jul. 2005 (claiming the priority of U.S. provisional application No. 60/584,678 filed on 2 Jul. 2004), which are incorporated herein by reference. The synthetic double-stranded nucleic acid or nucleic acid analogue molecule with a bent shape structure is preferably capable of binding to the non-acetylated or/and to the acetylated form of HMGB1 and the non-acetylated or/and the acetylated form of HMGB1 homologous proteins, in particular HMGB2, HMGB3, HMG-1L10, HMG4L or/and SP100-HMG.

In a still further embodiment, the further agent used in combination with the inventive polypeptide variants is K-252a or/and a salt or derivative thereof or a polymer conjugate of K-252a or/and of a derivative thereof. The use of K-252a or polymer conjugate of K-252a and derivatives thereof is disclosed in a co-owned and co-pending international patent application No. PCT/EP2005/008258 and US provisional application filed on 25 Aug. 2005.

Therefore, a further aspect of the present invention is a pharmaceutical composition comprising an effective amount of at least one of the polypeptide variants of HMGB1 Box-A or a biologically active fragment thereof in particular of the preferred polypeptide variants of the invention as defined above as an active ingredient for the treatment of HMGB1-associated pathologies and pharmaceutically acceptable carriers, diluents and/or adjuvants. The pharmaceutical composition of the present invention is preferably suitable for the treatment of pathologies associated with the non-acetylated or/and the acetylated form of HMGB1 and/or of HMGB1 homologous proteins. In a further preferred embodiment, the pharmaceutical composition of the present invention comprising the at least one polypeptide variant also comprises a further agent as defined above. The pharmaceutical composition of the present invention may be used for diagnostic or for therapeutic applications.

The exact formulation, route of administration and dosage can be chosen by the individual physician in view of the patient's conditions. Administration may be achieved in a single dose or repeated doses at intervals. Dosage amount and interval may be adjusted individually in order to provide the therapeutical effect which results in amelioration of symptoms or a prolongation of the survival in a patient. The actual amount of composition administered will, of course, be dependent on the subject being treated, on the subject's weight, the severity of the affliction, the manner of administration and the judgement of the prescribing physician. A suitable daily dosage will be between 0.001 to 10 mg/kg, particularly 0.1 to 5 mg/kg.

The administration may be carried out by known methods, e.g. by injection, in particular by intravenous, intramuscular, transmucosal, subcutaneous or intraperitoneal injection and/or by oral, topical, nasal, inhalation, aerosol and/or rectal application, etc. The administration may be local or systemic.

In addition, the variants of Box-A of HMGB1, or of its pharmacologically active fragments, object of this invention can be reversibly immobilized and/or adsorbed on the surface and/or inside medical devices or drug release/vehicling systems (microspheres). Medical devices and microspheres can be reversibly loaded with the polypeptide variants of Box-A object of this invention, through their binding, impregnation and/or adsorption on the surface of the medical device or of the microsphere or on a layer that coats its surface. When the medical device or the microsphere come into contact with biological fluids, the reversibly immobilized variant of Box-A is released. Therefore, the medical device and the microsphere act as drug-releasing tools that elute the molecule object of this invention in such a way that their release kinetics can be controlled, ensuring controlled or sustained release, as required by the treatment. The methods for coating/impregnating the medical devices and loading microspheres are well known by experts in these technologies.

Thus, a further aspect of this invention is the way of using the variants of Box-A of HMGB1 or its pharmacologically relevant fragments, wherein the mutated polypeptide molecules are reversibly immobilized on the surface of medical devices or of microspheres or are adsorbed within them. These medical instruments are preferably surgical tools, implants, catheters or stents, for example stents for angioplasty and, in particular, medicated drug-eluting stents.

Another aspect of the invention concerns a medical device reversibly coated with at least one polypeptide variant of the invention. Such a device can be selected from surgical instruments, implants, catheters or stents. Such a device may be useful for angioplasty.

The invention is further illustrated by the following Figures and Examples. The examples are intended to exemplify generic processes and are included for illustrative purpose only, without intention of limiting the scope of the present invention.

FIG. 1 shows the proteases used for the in silico identification of the amino acid positions (is-HITs) on the HMGB1 Box-A amino acid sequence which are targets for the proteolytic activity.

FIG. 2 depicts the "Percent Accepted Mutation" (PAM 250) matrix. Values given to identical residues are shown in grey square. Highest values in the matrix are shown in black square and correspond to the highest occurrence of substitution between two residues.

FIG. 3a displays the amino acid sequence of the native Human HMGB1 Box-A made of 84 amino acid residues [SEQ ID NO: 1]. In bold, the amino acids sensitive to proteases proteolysis are identified, showing the is-HIT residue positions.

FIG. 3b shows the type of replacing amino acids on the respective is-HITs target positions selected to generate the polypeptide variant of the full-length human HMGB1 Box-A. Further, the specific amino acid sequences of the generated polypeptide variant are displayed in SEQ ID NOs:2 to 116.

FIG. 4a displays the amino acid sequence of the biologically active fragment of Human HGB1 Box-A made of 77 amino acid residues [SEQ ID NO: 117]. In bold, the amino acids sensitive to proteases proteolysis are identified, showing the is-HIT residue positions.

FIG. 4b shows the type of replacing amino acids on the respective is-HITs target positions selected to generate the polypeptide variant of the biologically active fragment of Human HMGB1 Box-A made of 77 amino acid residues. Further the specific amino acid sequences of the generated polypeptide variant are displayed in SEQ ID NOs: 118 to 222.

FIG. 5a displays the amino acid sequence of the biologically active fragment of Human HMGB1 Box-A made of 54 amino acid residues [SEQ ID NO: 223]. In bold, the amino acids sensitive to proteases proteolysis are identified, showing the is-HIT residue positions.

FIG. 5b shows the type of replacing amino acids on the respective is-HITs target positions selected to generate the polypeptide variant of the biologically active fragment of Human HMGB1 Box-A made of 54 amino acid residues. Further, the specific amino acid sequences of the generated polypeptide variant are displayed in SEQ ID NOs: 224 to 300.

FIG. 6a displays the amino acid sequence of the native *Anopheles gambia* HMGB1 Box-A made of 84 amino acid residues [SEQ ID NO: 301]. In bold, the amino acids sensitive to proteases proteolysis are identified, showing the is-HIT residue positions.

FIG. 6b shows the type of replacing amino acids on the respective is-HITs target positions selected to generate the polypeptide variant of the full-length *Anopheles gambia* HMGB1 Box-A. Further, the specific amino acid sequences of the generated polypeptide variant are displayed in SEQ ID NOs: 302 to 418.

FIG. 7*a* displays the amino acid sequence of the biologically active fragment of *Anopheles gambia* HMGB1 Box-A made of 77 amino acid residues [SEQ ID NO: 419]. In bold, the amino acids sensitive to proteases proteolysis are identified, showing the is-HIT residue positions.

FIG. 7*b* shows the type of replacing amino acids on the respective is-HITs target positions selected to generate the polypeptide variant of the biologically active fragment of *Anopheles gambia* HMGB1 Box-A made of 77 amino acid residues. Further the specific amino acid sequences of the generated polypeptide variant are displayed in SEQ ID NOs: 420 to 528.

FIG. 8*a* displays the amino acid sequence of the biologically active fragment of *Anopheles gambia* HMGB1 Box-A made of 54 amino acid residues [SEQ ID NO: 529]. In bold, the amino acids sensitive to proteases proteolysis are identified, showing the is-HIT residue positions.

FIG. 8*b* shows the type of replacing amino acids on the respective is-HITs target positions selected to generate the polypeptide variant of the biologically active fragment of *Anopheles gambia* HMGB1 Box-A made of 54 amino acid residues. Further, the specific amino acid sequences of the generated polypeptide variant are displayed in SEQ ID NOs: 530 to 610.

FIG. 9 shows the plasmid vector containing the nucleic acid sequence encoding for the polypeptide variant of the present invention. The plasmid contains the gene encoding for the polypeptide variant of the present invention, which is under control of the IPTG inducible T5 promoter. The plasmid further contains an ampicillin resistant gene, a 6×His-tag and several restriction sites.

FIG. 10 shows a graph displaying the correlation between the TNF-alpha release induced by the stimulation of HMGB1 in RAW 264.7 cells.

FIG. 11 displays a dose-dependent inhibition of HMGB1-induced TNF-alpha release by a Box-A His-tagged protein.

FIGS. 12A to 12R show the results of the chemotaxis assay described of Example 6 performed on the HMGB1 Box-A polypeptide variants of SEQ ID NO:2 to SEQ ID NO:116 of the present invention. In each figure the activity of a set of polypeptide variants is tested compared to the activity of human wild-type HMGB1 Box-A full-length fragment of SEQ ID NO:1 in the inhibition of HMGB1 induced NIH/3T3 cell migration. Each figure shows a table reporting the statistical analysis numerical data and a column bar graph showing the chemotaxis assay results.

FIGS. 12A and 12B show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID NO:2 to 15 (identified in the Figures with the code CT501, CT568, CT569, CT570, CT571, CT502, CT572, CT503, CT573, CT504, CT574, CT575, CT576 and CT505, respectively).

FIGS. 12C and 12D show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID NOs:16-23 and 25-29 (identified in the Figures with the code CT577, CT578, CT506, CT579, CT580, C1581, CT507, CT582, CT584, CT508, CT509, CT510 and CT585, respectively).

FIGS. 12E and 12F show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:30-35 and 37-43 (identified in the Figures with the code CT511, CT512, CT513, CT514, CT586, CT515, CT516, CT517, CT518, CT519, CT520, CT521 and CT522, respectively).

FIGS. 12G and 12H show the bar graph and statistical data of chemotaxis migration assay results in the inhibition of HMGB1-induced NIH/3T3 cells by human HMGB1 Box-A wild type of SEQ ID NOs:44-57 (identified in the Figures with the code CT523, CT524, CT525, CT526, CT527, CT528, CT588, CT529, CT530, CT589, CT590, CT531, CT591 and CT532, respectively).

FIGS. 12I and 12J show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:58-67 and 69-71 (identified in the Figures with the code CT592, CT533, CT593, CT534, CT535, CT536, CT537, CT594, CT538, CT539, CT540, CT541 and CT542, respectively).

Figure 12B:
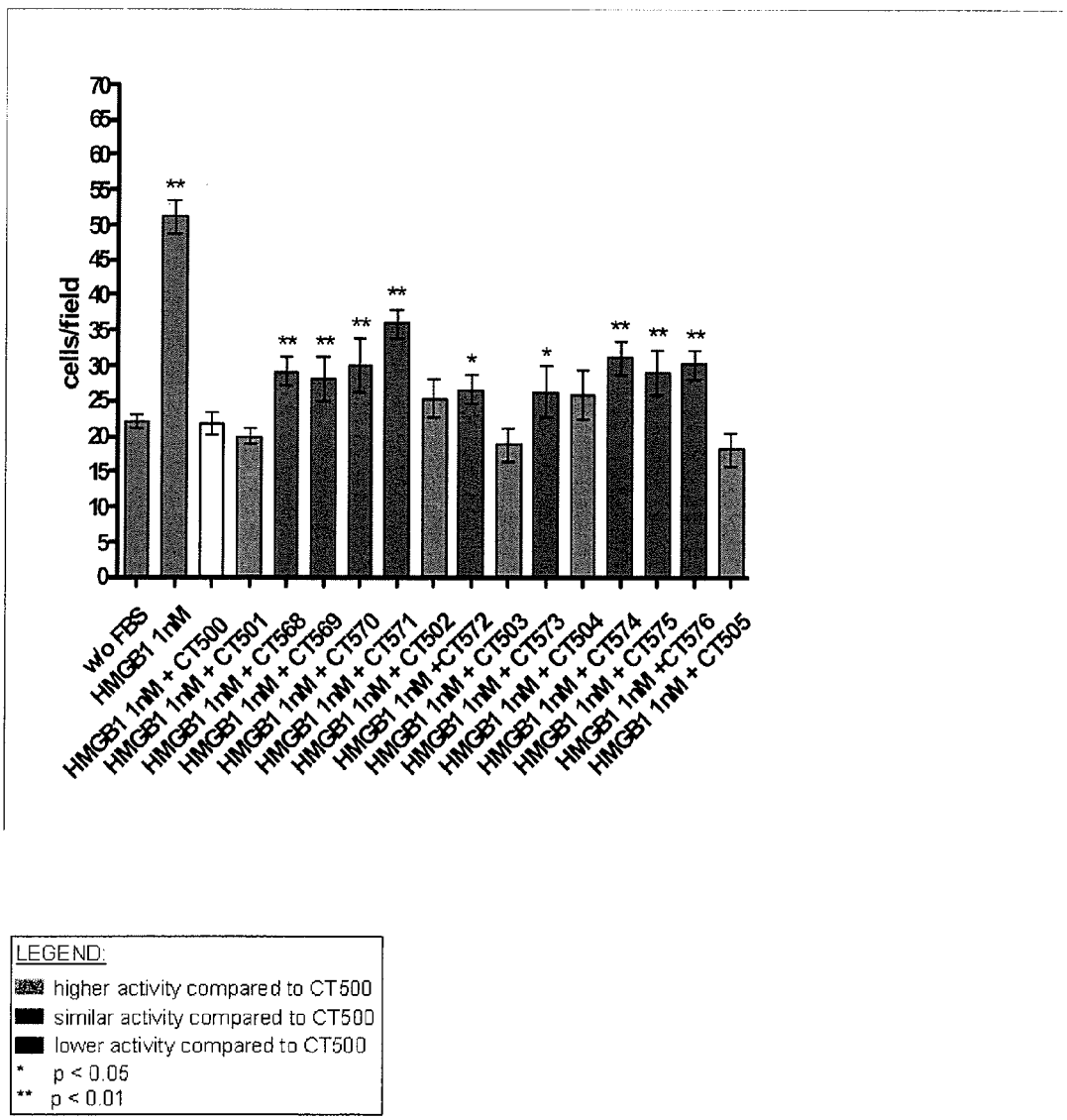
FIGS. 12K and 12L show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:72-85 (identified in the Figures with the code CT596, CT597, CT598, CT599, CT600, CT601, CT602, CT603, CT543, CT544, CT545, CT546, CT547 and CT604, respectively).
FIGS. 12M and 12N show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID NOs:86-99 (identified in the Figures with the code CT548, CT549, CT605, CT606, CT607, CT608, CT609, CT610, CT550, CT551, CT611, CT552, CT553 and CT554, respectively).
Figure 12D:
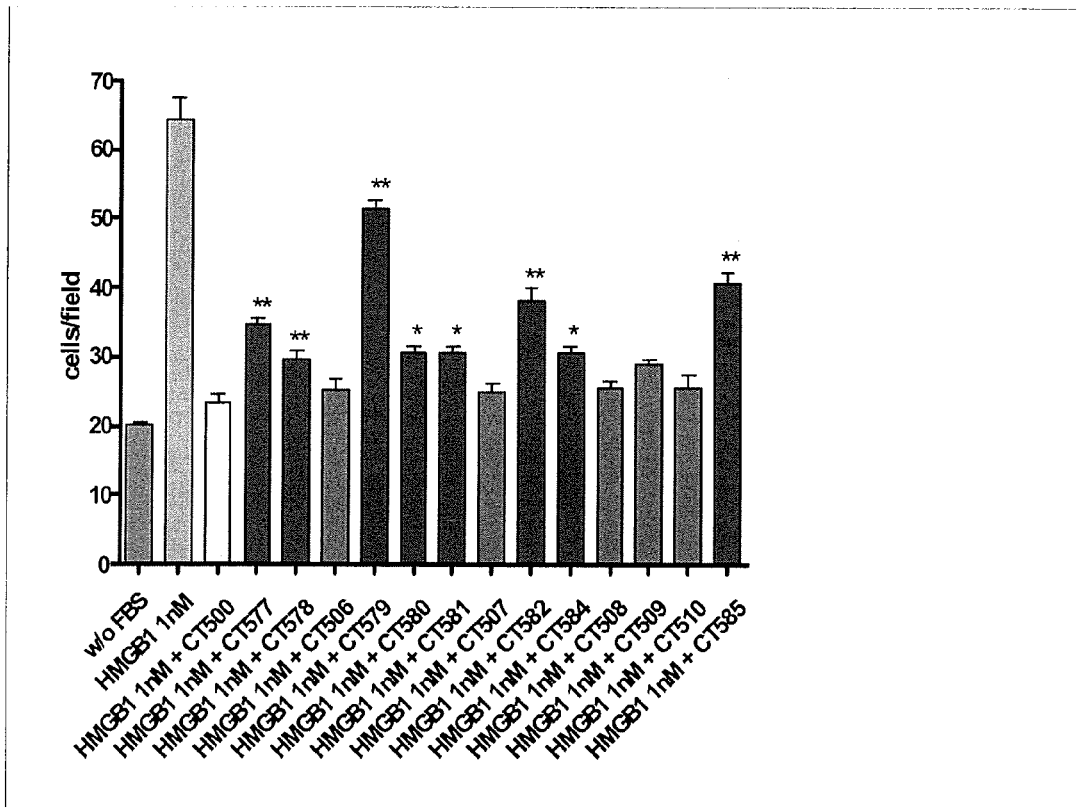
Figure 12F:
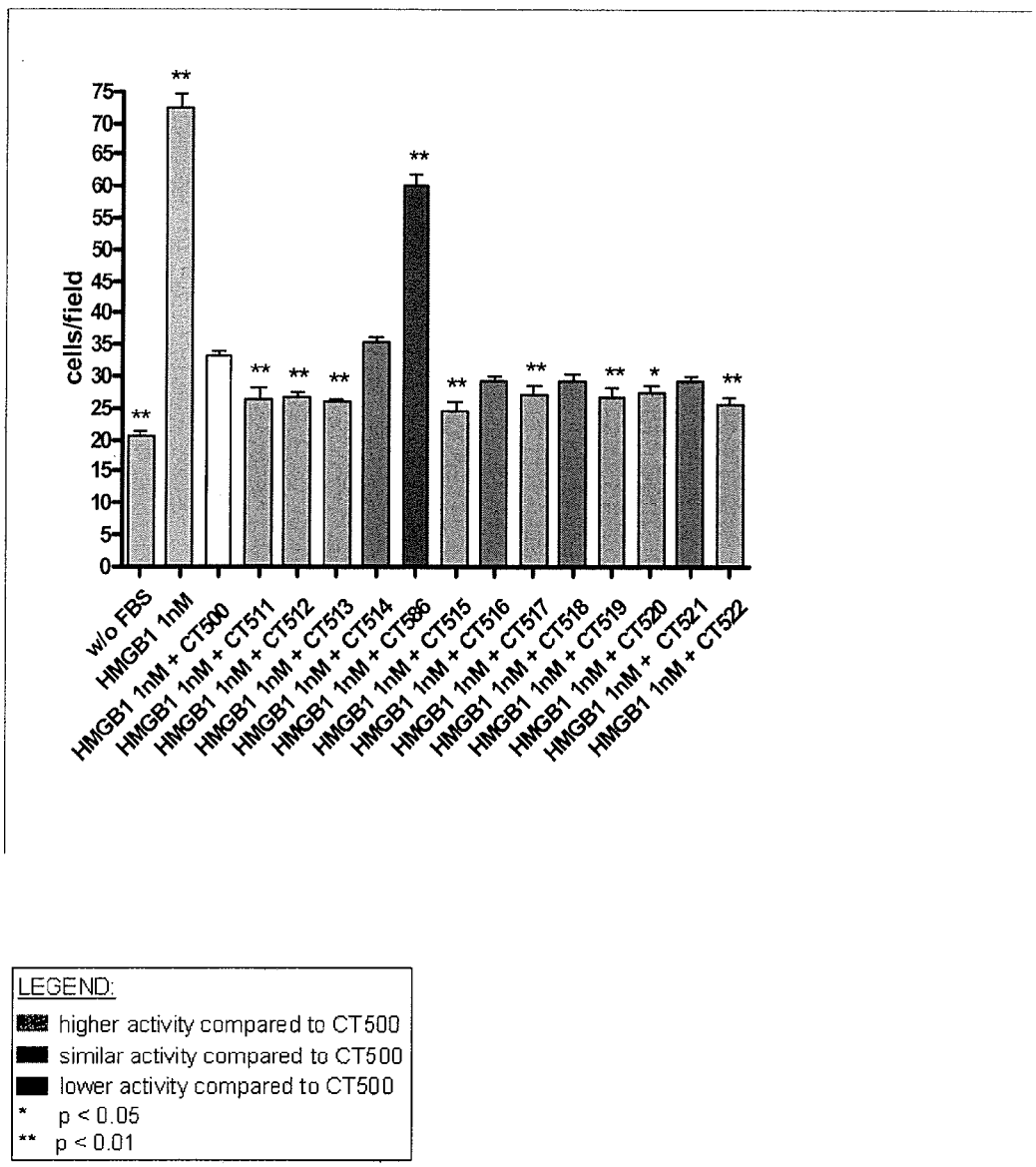
Figure 12H:
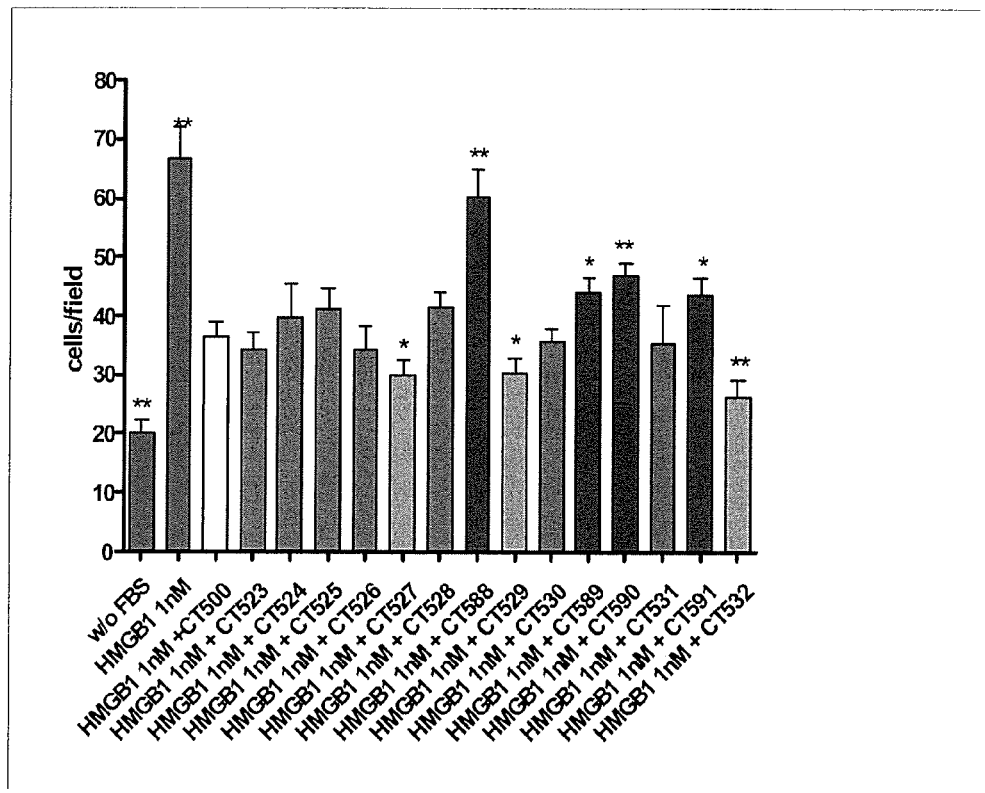
Figure 12J:
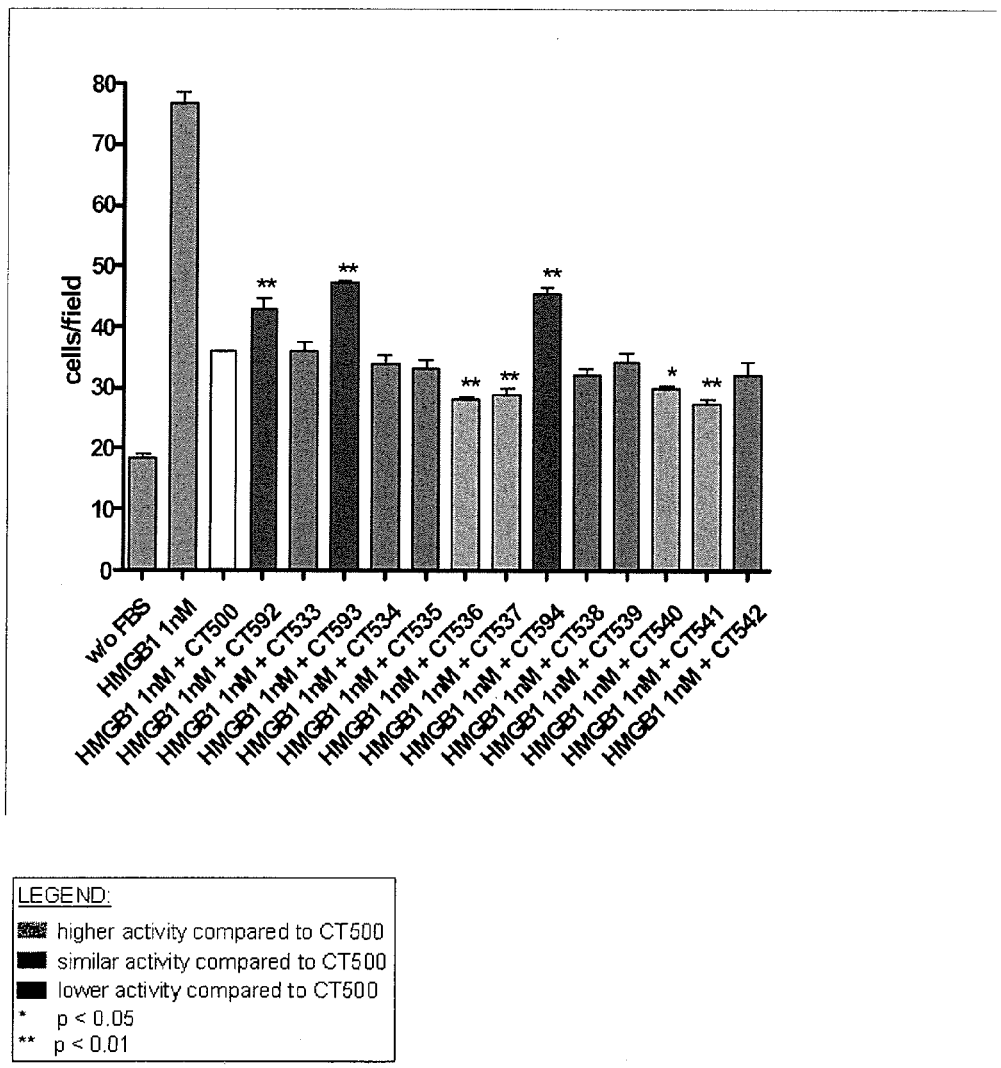
Figure 12L:
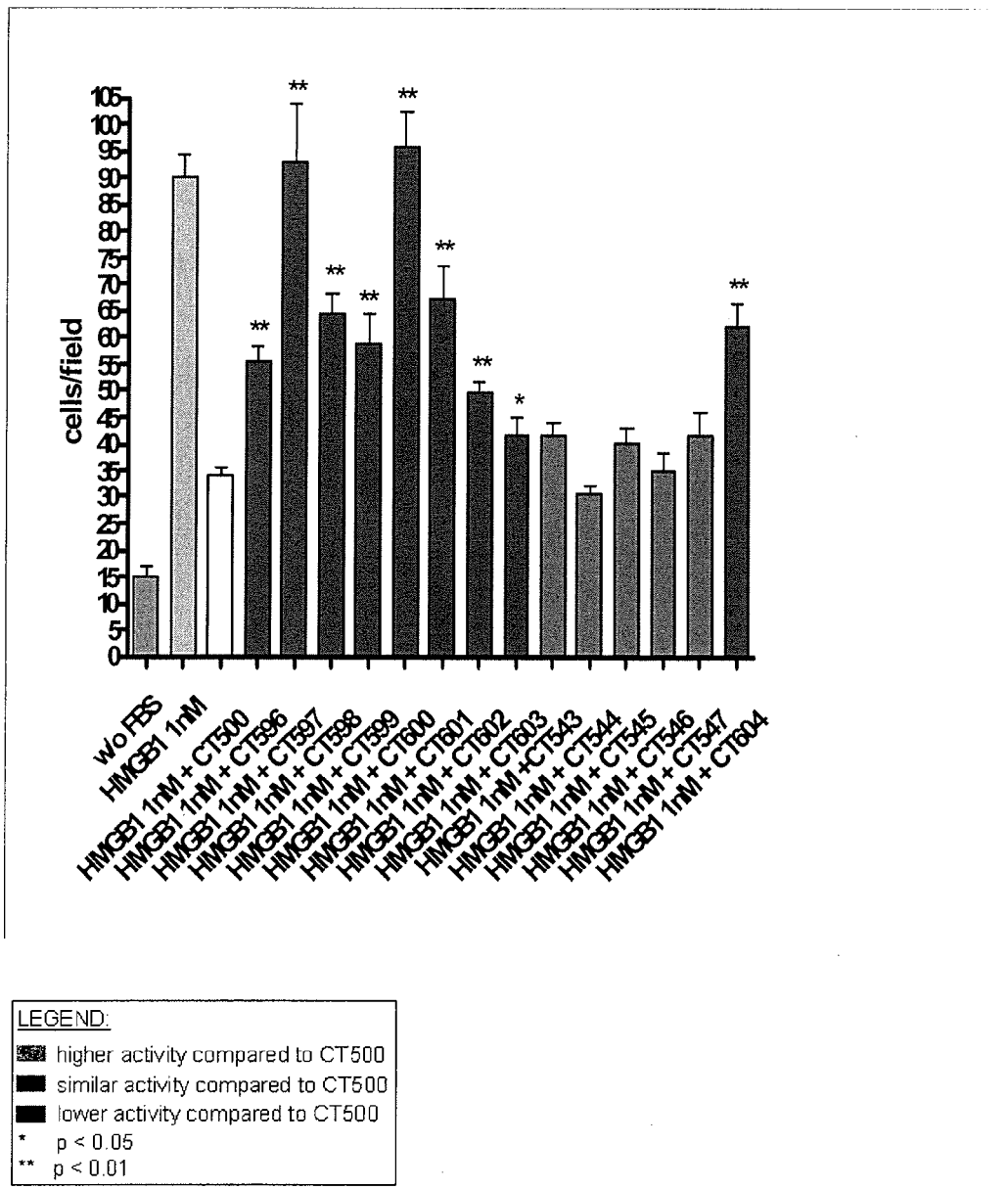
Figure 12N:
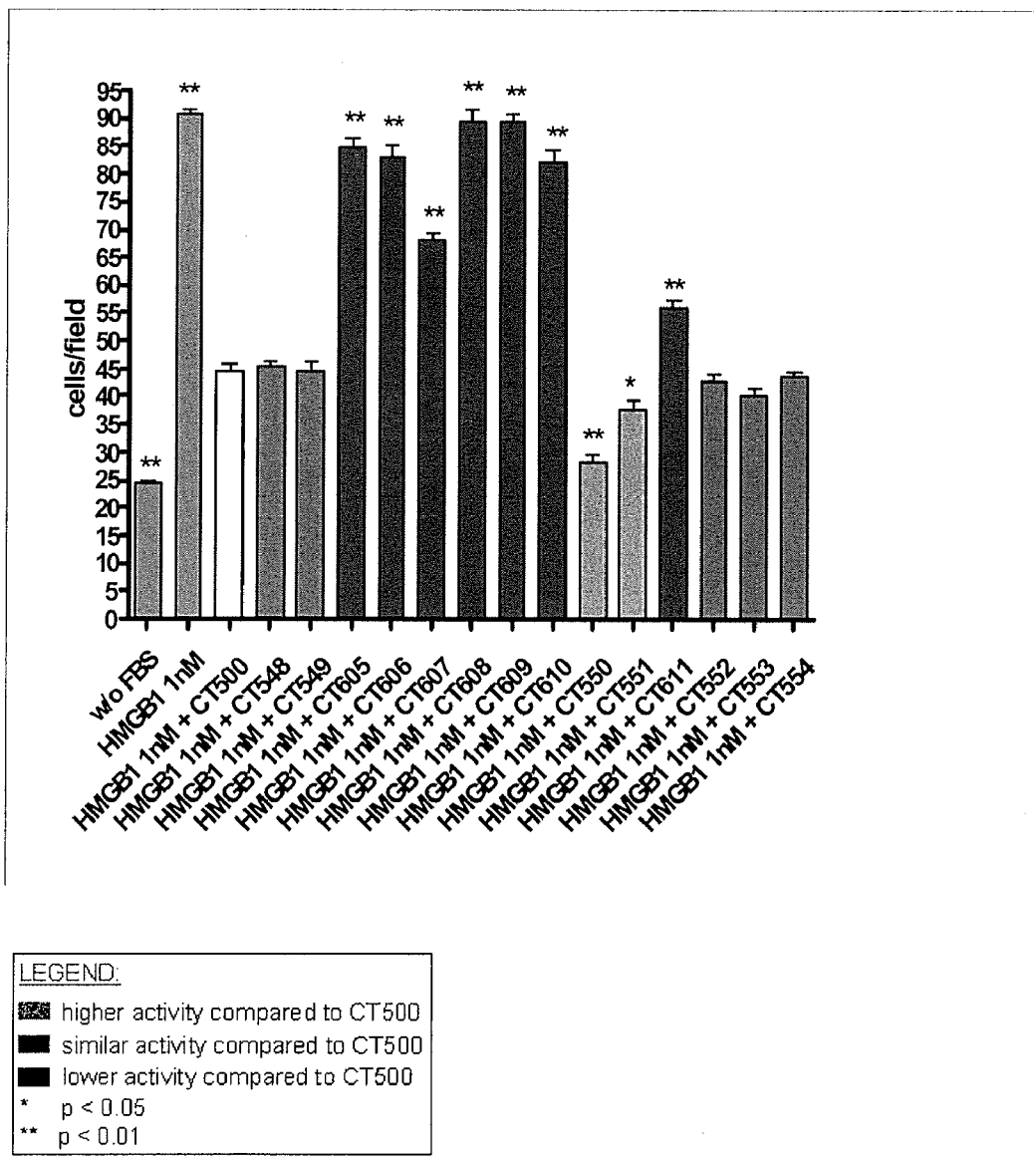
Figure 12P:
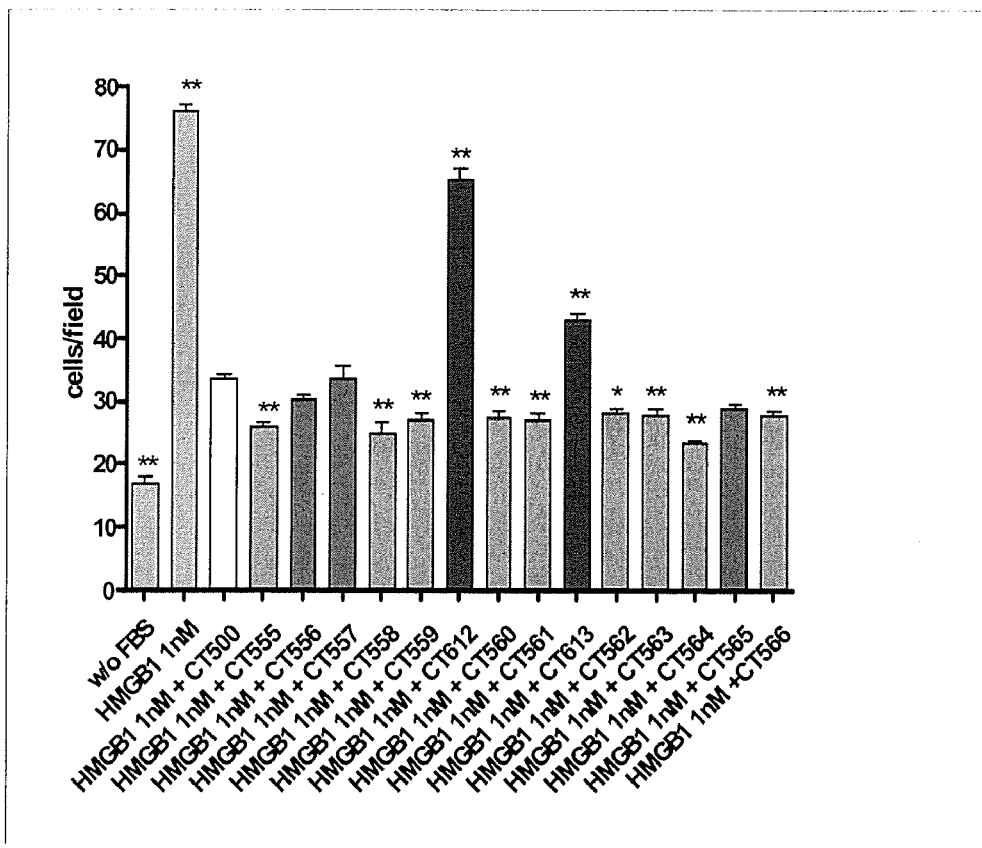

FIGS. 12O and 12P show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:100-113 (identified in the Figures with the code CT555, CT556, CT557, CT558, CT559, CT612, CT560, CT561, CT613, CT562, CT563, CT564, CT565 and CT566, respectively).

Figure 12R:
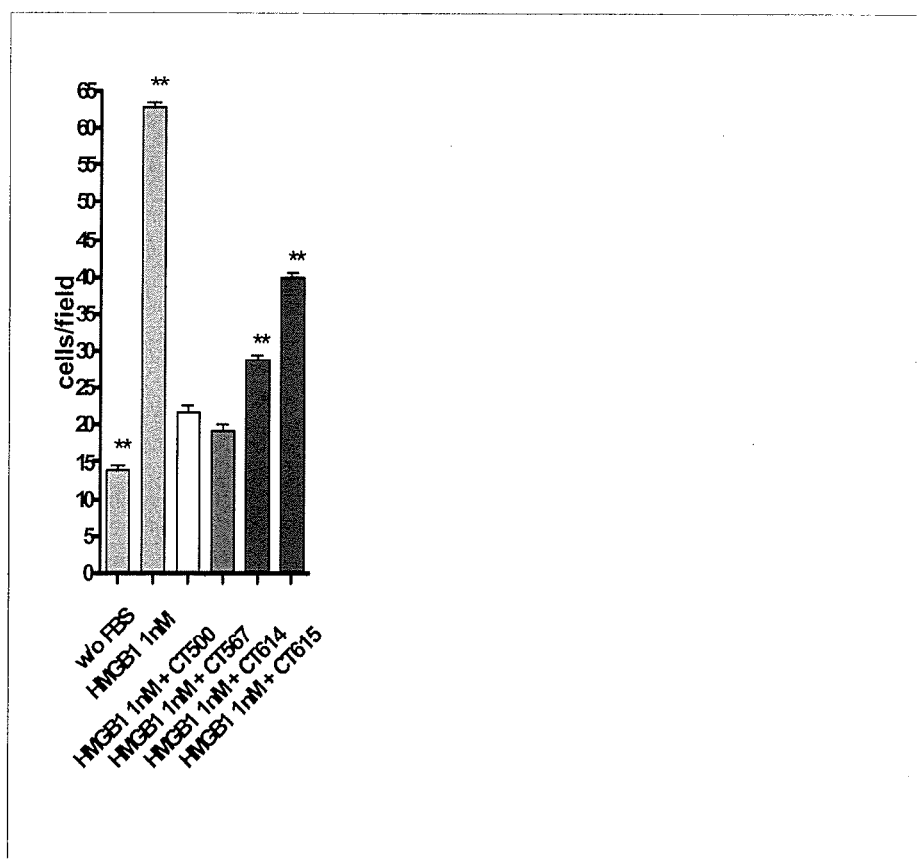

FIGS. 12Q and 12R show the bar graph and statistical data of chemotaxis migration assay results in the inhibition of HMGB1-induced NIH/3T3 cells by human HMGB1 Box-A wild type of SEQ ID NO:1 (CT500) and polypeptide variants of SEQ ID Nos:114-116 (identified in the Figures with the code CT567, CT614 and CT615, respectively).

Figure 13:
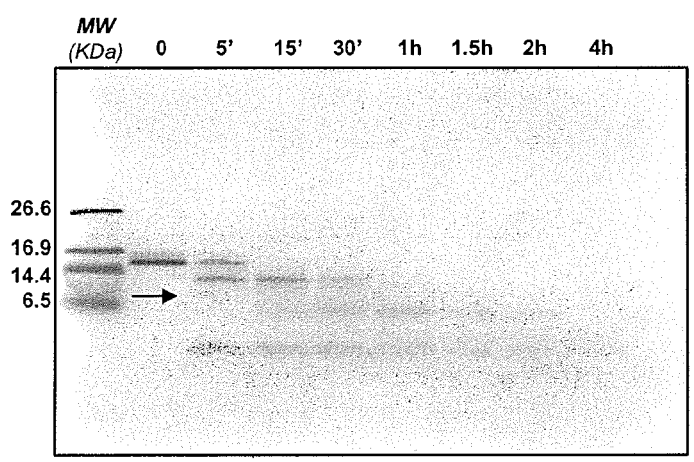

FIG. 13 shows the image of the Tricine SDS-PAGE gel loaded with human HMGB1 Box-A wild type of SEQ ID NO:1 (CT500) at different timepoints after protease digestion of the protease resistance testing described in Example 7. The Box-A wild type protein tested for protease resistance is a His-tagged protein. After 5 minutes of digestion CT500 shows two major bands, one corresponding to the original protein in the sample and the second corresponding to the 84-aminoacid protein without the N-term His-tag (indicated on the figure with an arrow). The profile of this second band shows resistance to proteases for 30 minutes. Minor bands present on this and other gels of FIG. 14 to FIG. 81 correspond to Box-A digested fragments.

Figure 14:
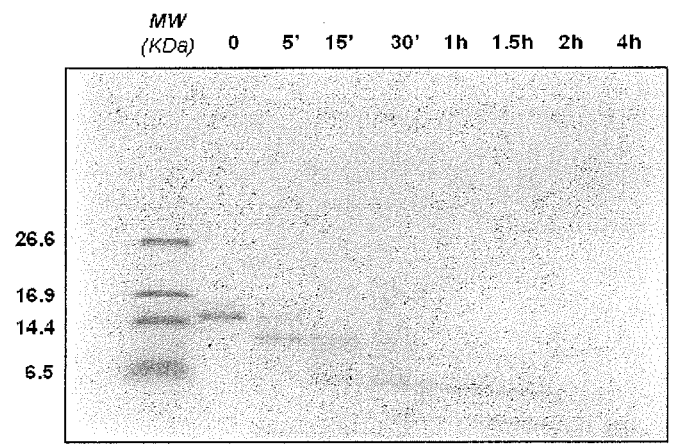

FIG. 14 to FIG. 81 show the image of the Tricine SDS-PAGE gel loaded with the polypeptide variants of the present invention at different timepoints after protease digestion of the protease resistance testing described in Example 7. Box-A polypeptide variants tested for protease resistance are His-tagged proteins. After 5 minutes of digestion the SDS-PAGE gel image of the polypeptide variants show two major bands, one corresponding to the original protein variant in the sample and the second corresponding to the Box-A 84 amino acid protein variant without the N-term His-tag.

FIG. 14 shows the Tricine SDS-PAGE of the polypeptide variant of SEQ ID NO:2 (CT501) at different timepoints after protease digestion.

Figure 15:
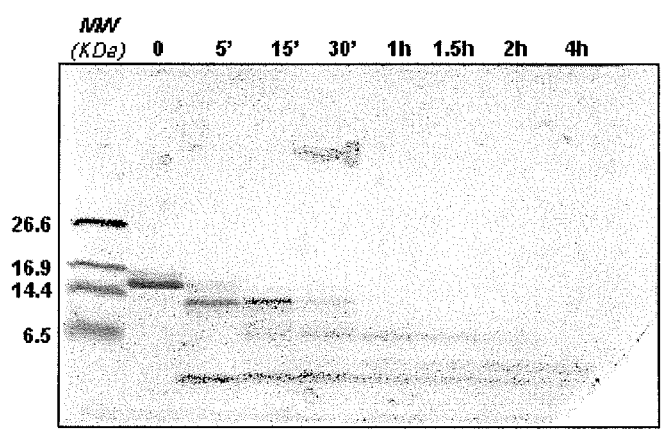

FIG. 15 shows the Tricine SDS-PAGE of the polypeptide variant of SEQ ID NO:7 (CT502) at different timepoints after protease digestion.

Figure 16:
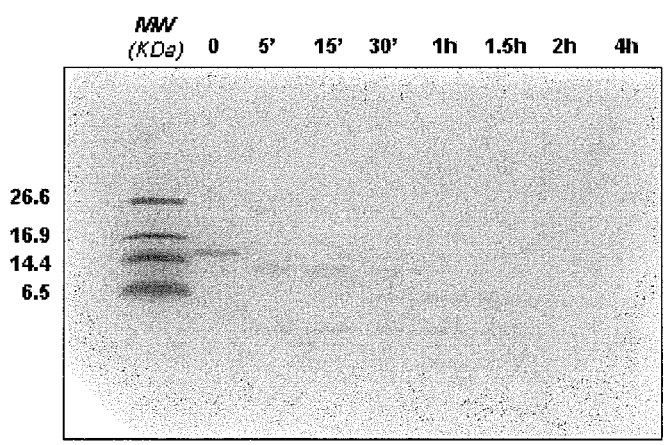

FIG. 16 shows the Tricine SDS-PAGE of the polypeptide variant of SEQ ID NO:9 (CT503) at different timepoints after protease digestion.

Figure 17:

FIG. 17 shows the Tricine SDS-PAGE of the polypeptide variant of SEQ ID NO:11 (CT504) at different timepoints after protease digestion.

Figure 18:
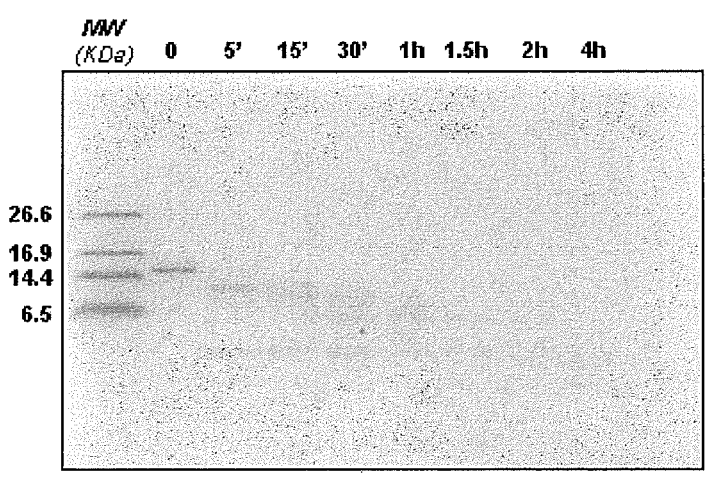

FIG. 18 shows the Tricine SDS-PAGE of the polypeptide variant of SEQ ID NO:15 (CT505) at different timepoints after protease digestion.

Figure 19:
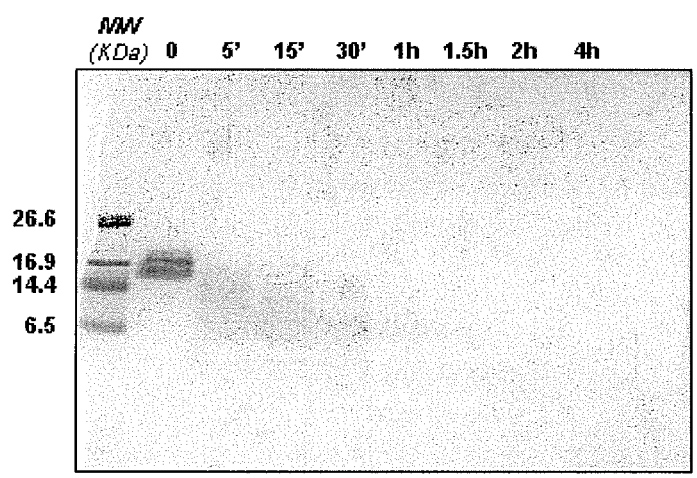

FIG. 19 shows the Tricine SDS-PAGE of the polypeptide variant of SEQ ID NO:18 (CT506) at different timepoints after protease digestion.

Figure 20:
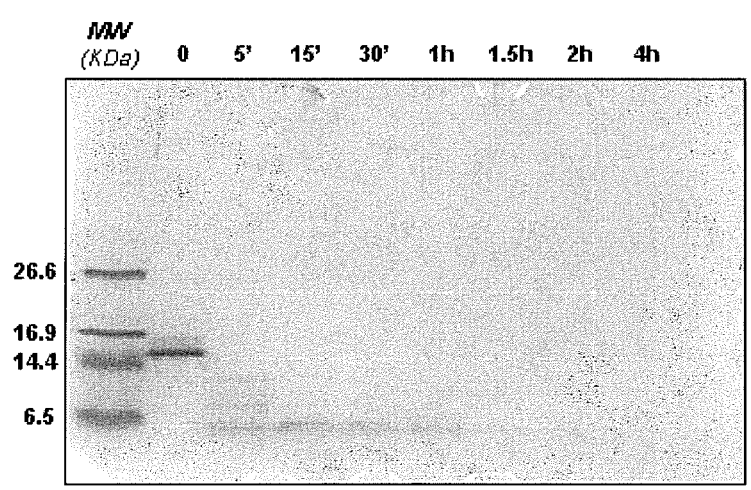

FIG. 20: Tricine SDS-PAGE of the polypeptide variant of SEQ ID NO:22 (CT507) at different timepoints after protease digestion.

Figure 21:
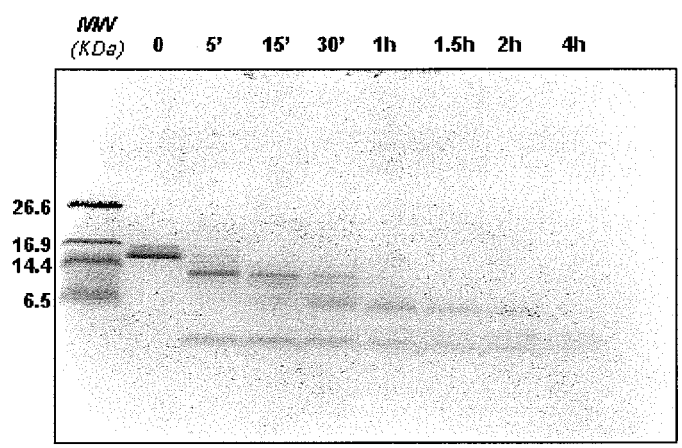

FIG. 21 shows the Tricine SDS-PAGE of the polypeptide variant of SEQ ID NO:26 (CT508) at different timepoints after protease digestion.

Figure 22:
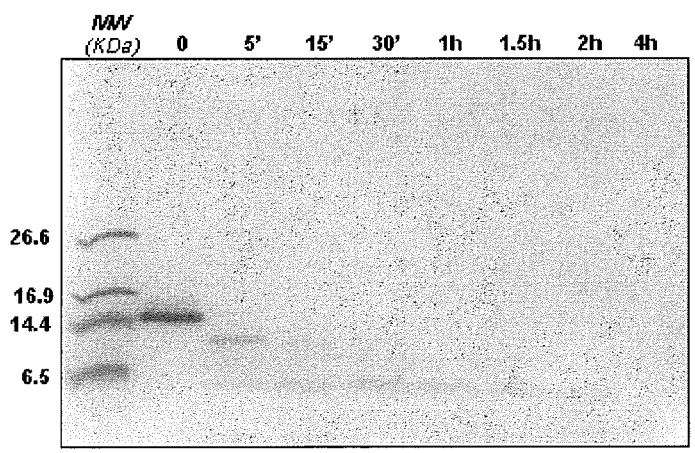

FIG. 22 shows the Tricine SDS-PAGE of the polypeptide variant of SEQ ID NO:27 (CT509) at different timepoints after protease digestion.

Figure 23:
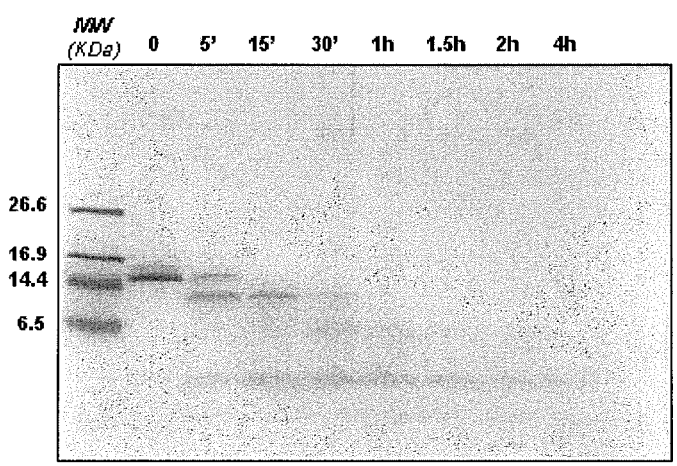

FIG. 23 shows the Tricine SDS-PAGE of the polypeptide variant of SEQ ID NO:28 (CT510) at different timepoints after protease digestion.

Figure 24:
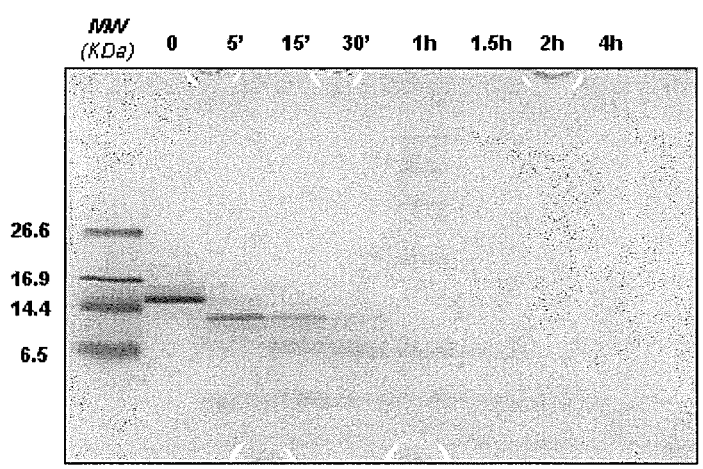

FIG. 24 shows the Tricine SDS-PAGE of the polypeptide variant of SEQ ID NO:30 (CT511) at different timepoints after protease digestion.

Figure 25:
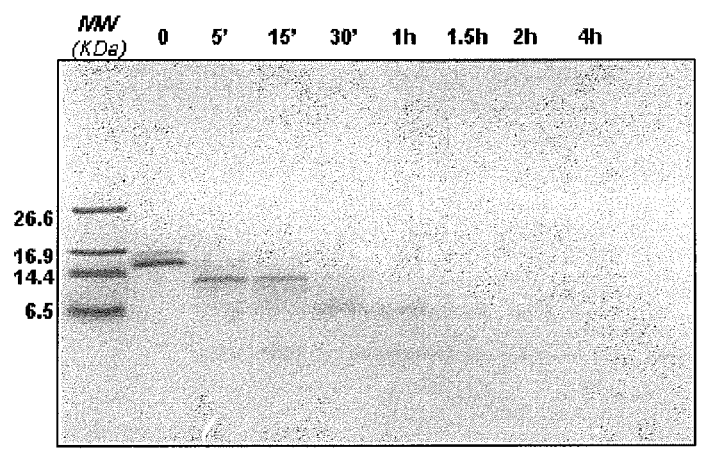

FIG. 25 shows the Tricine SDS-PAGE of the polypeptide variant of SEQ ID NO:31 (CT512) at different timepoints after protease digestion.

Figure 26:
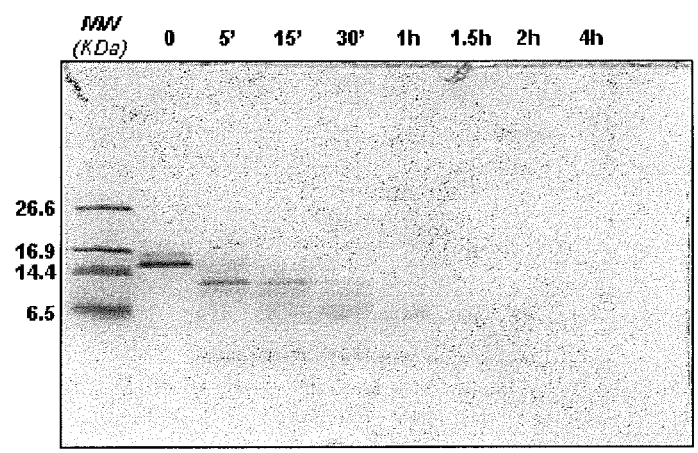

FIG. 26 shows the Tricine SDS-PAGE of the polypeptide variant of SEQ ID NO:32 (CT513) at different timepoints after protease digestion.

Figure 27:
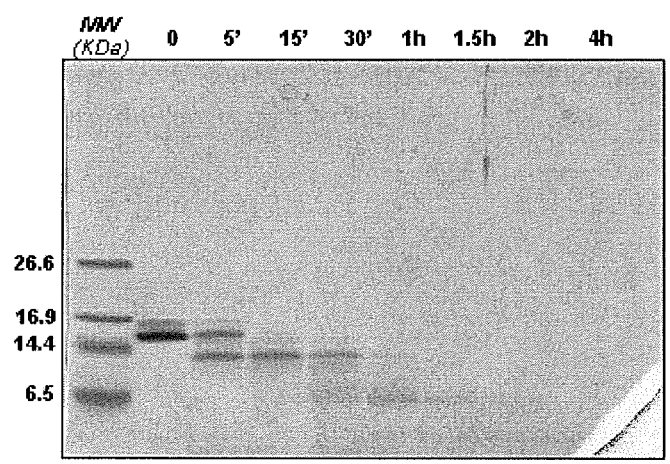

FIG. 27 shows the Tricine SDS-PAGE of the polypeptide variant of SEQ ID NO:33 (CT514) at different timepoints after protease digestion.

Figure 28:
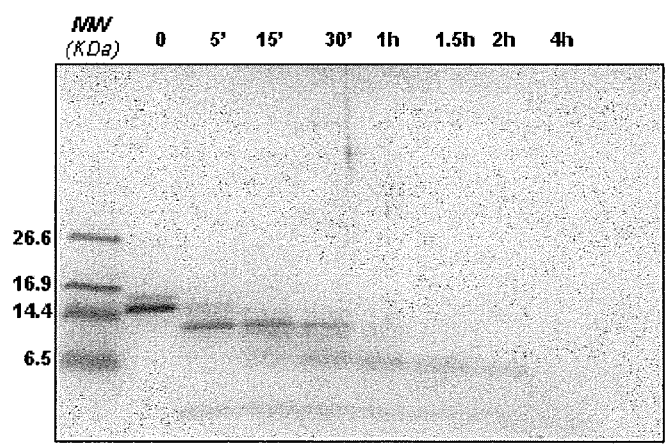

FIG. 28 shows the Tricine SDS-PAGE of the polypeptide variant of SEQ ID NO:35 (CT515) at different timepoints after protease digestion.

Figure 29:
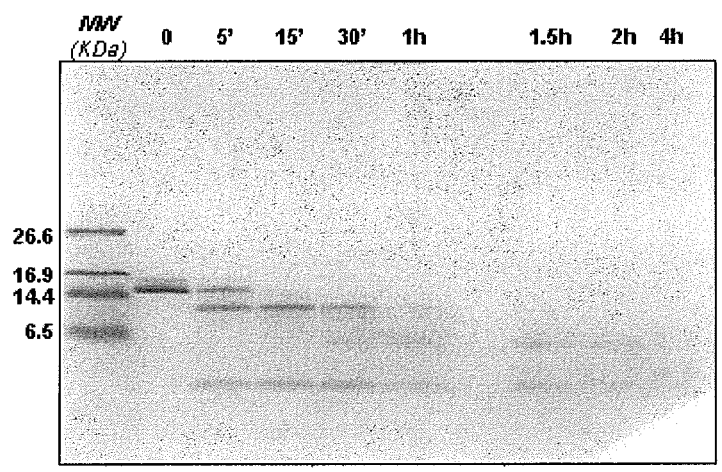

FIG. 29 shows the Tricine SDS-PAGE of the polypeptide variant of SEQ ID NO:37 (CT516) at different timepoints after protease digestion.

Figure 30:
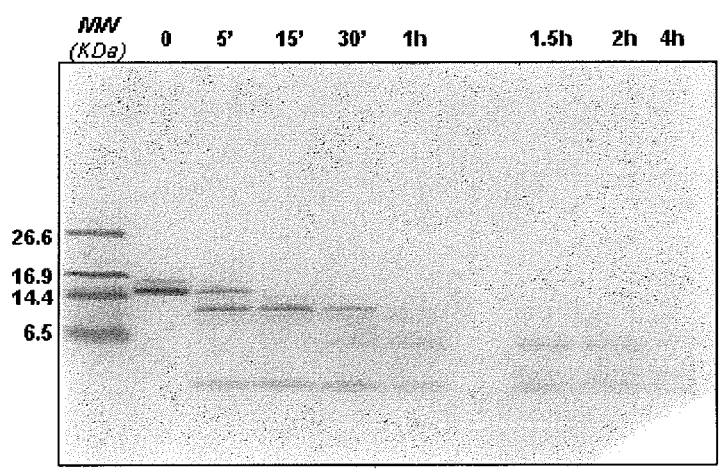

FIG. 30 shows the Tricine SOS-PAGE of the polypeptide variant of SEQ ID NO:38 (CT517) at different timepoints after protease digestion.

Figure 31:
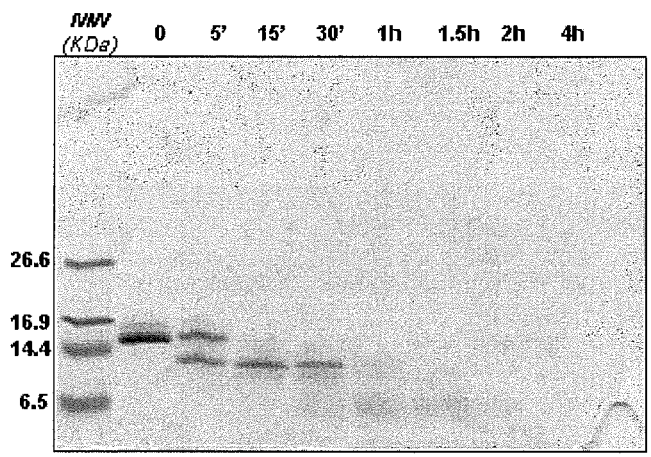

FIG. 31 shows the Tricine SDS-PAGE of the polypeptide variant of SEQ ID NO:39 (CT518) at different timepoints after protease digestion.

Figure 32:
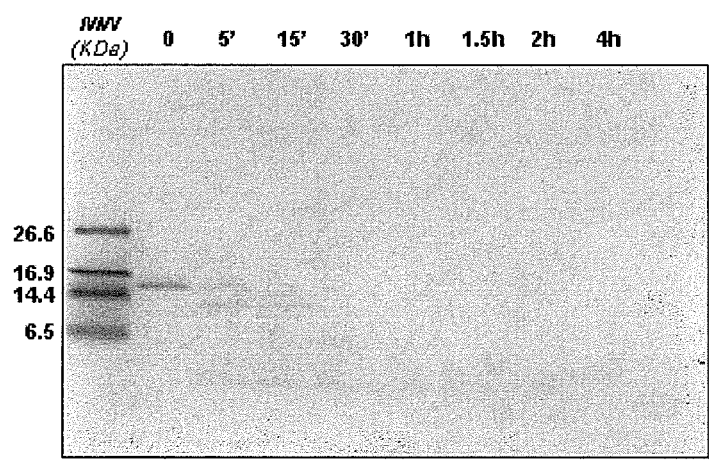

FIG. 32 shows the Tricine SDS-PAGE of the polypeptide variant of SEQ ID NO:40 (CT519) at different timepoints after protease digestion.

Figure 33:
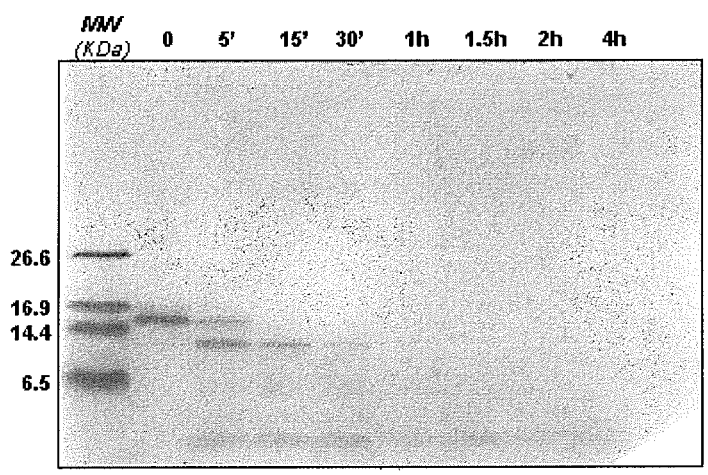

FIG. 33 shows the Tricine SDS-PAGE of the polypeptide variant of SEQ ID NO:41 (CT520) at different timepoints after protease digestion.

Figure 34:
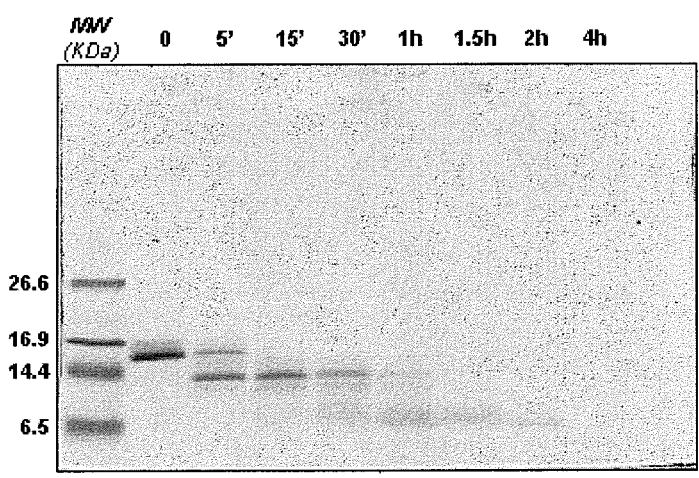

FIG. 34 shows the Tricine SDS-PAGE of the polypeptide variant of SEQ ID NO:42 (CT521) at different timepoints after protease digestion.

Figure 35:
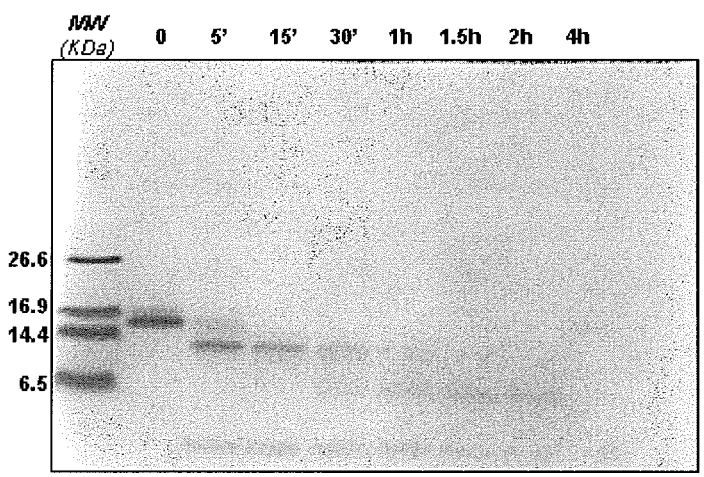

FIG. 35 shows the Tricine SDS-PAGE of the polypeptide variant of SEQ ID NO:43 (CT522) at different timepoints after protease digestion.

Figure 36:
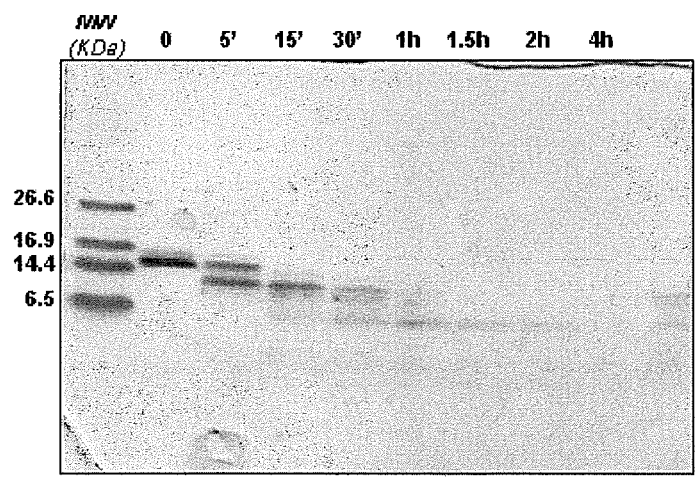

FIG. 36 shows the Tricine SDS-PAGE of the polypeptide variant of SEQ ID NO:44 (CT523) at different timepoints after protease digestion.

Figure 37:
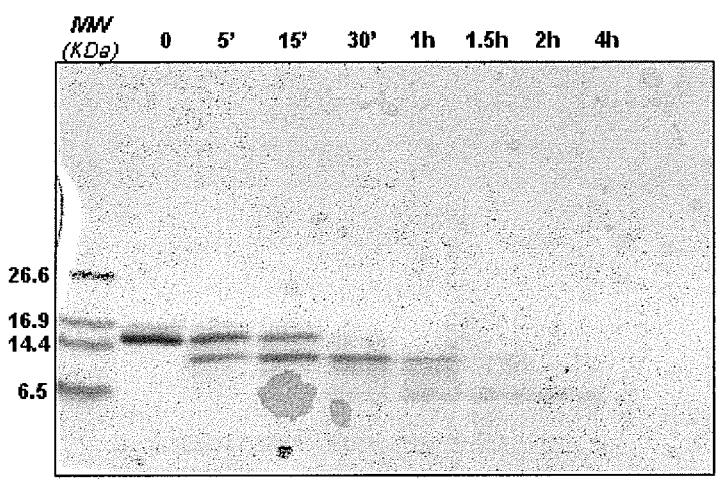

FIG. 37 shows the Tricine SDS-PAGE of the polypeptide variant of SEQ ID NO:45 (CT524) at different timepoints after protease digestion.

Figure 38:
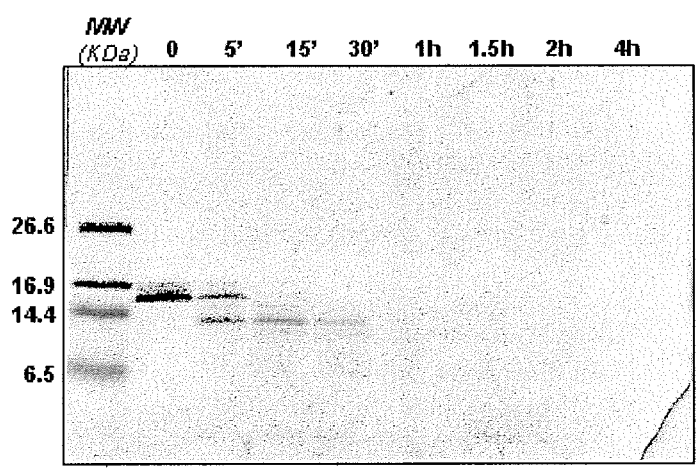

FIG. 38 shows the Tricine SDS-PAGE of the polypeptide variant of SEQ ID NO:46 (CT525) at different timepoints after protease digestion.

Figure 39:
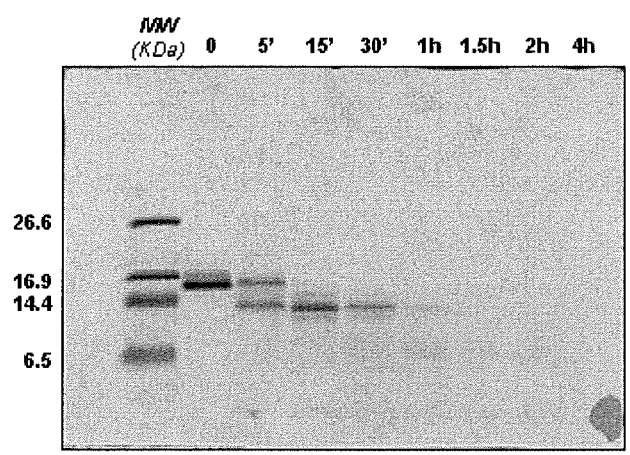

FIG. 39 shows the Tricine SDS-PAGE of the polypeptide variant of SEQ ID NO:47 (CT526) at different timepoints after protease digestion.

Figure 40:
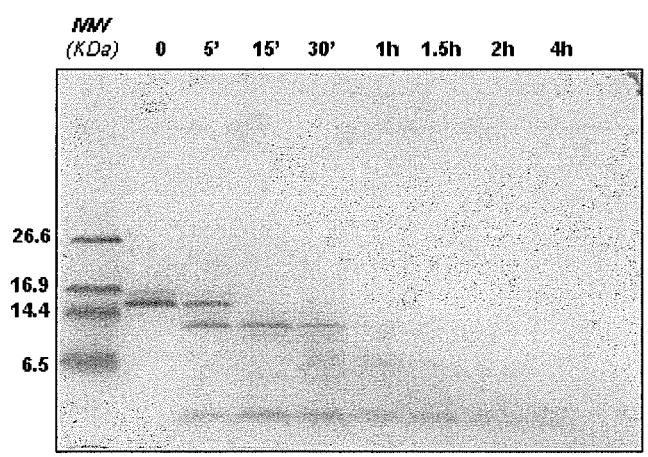

FIG. 40 shows the Tricine SDS-PAGE of the polypeptide variant of SEQ ID NO:48 (CT527) at different timepoints after protease digestion.

Figure 41:
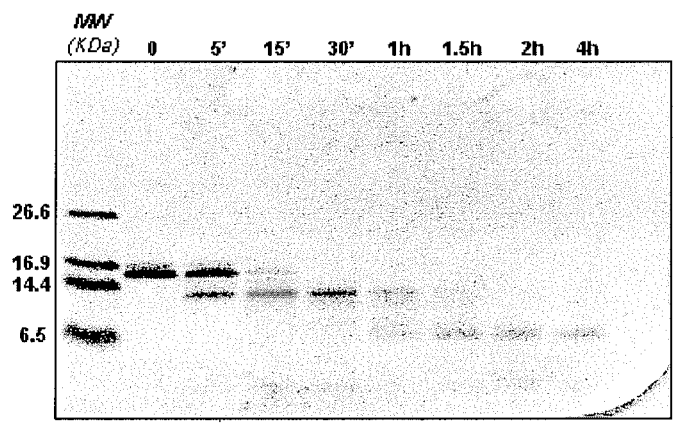

FIG. 41 shows the Tricine SDS-PAGE of the polypeptide variant of SEQ ID NO:49 (CT528) at different timepoints after protease digestion.

Figure 42:
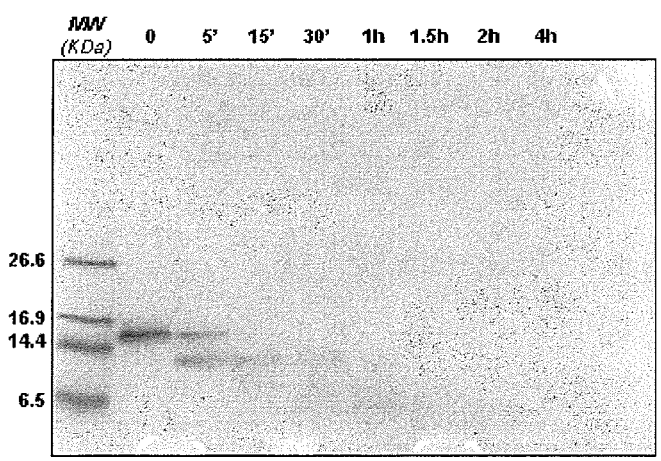

FIG. 42 shows the Tricine SDS-PAGE of the polypeptide variant of SEQ ID NO:51 (CT529) at different timepoints after protease digestion.

Figure 43:
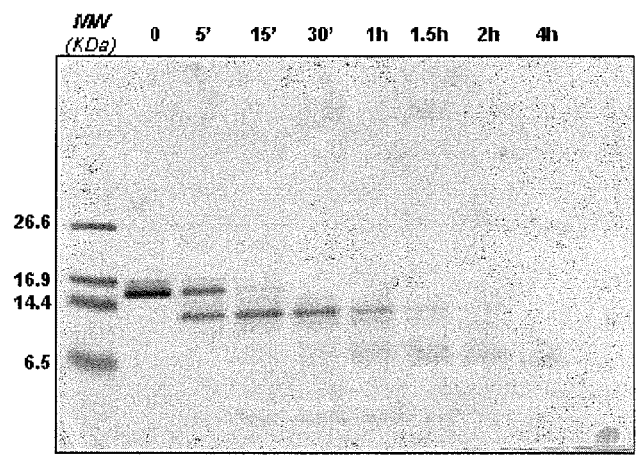

FIG. 43 shows the Tricine SDS-PAGE of the polypeptide variant of SEQ ID NO:52 (CT530) at different timepoints after protease digestion.

Figure 44:
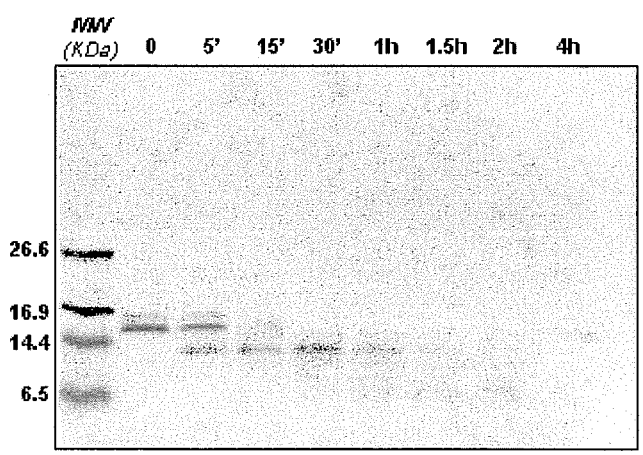

FIG. 44 shows the Tricine SDS-PAGE of the polypeptide variant of SEQ ID NO:55 (CT531) at different timepoints after protease digestion.

Figure 45:
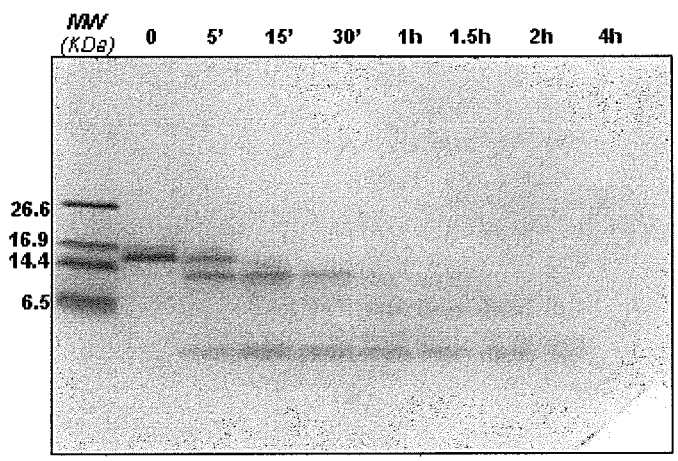

FIG. 45 shows the Tricine SDS-PAGE of the polypeptide variant of SEQ ID NO:57 (CT532) at different timepoints after protease digestion.

Figure 46:
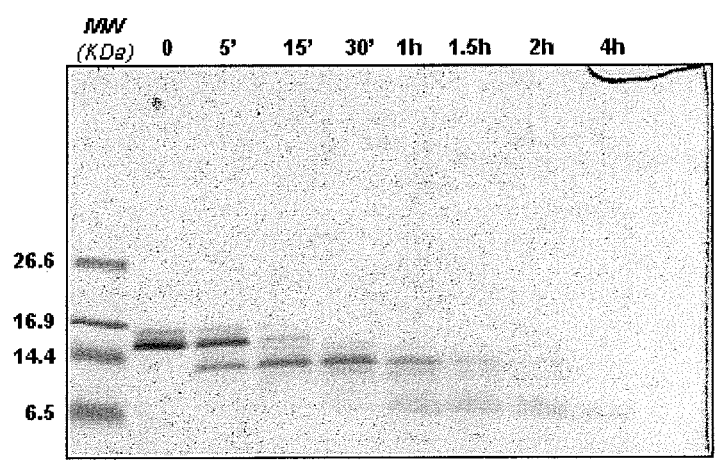

FIG. 46 shows the Tricine SDS-PAGE of the polypeptide variant of SEQ ID NO:59 (CT533) at different timepoints after protease digestion.

Figure 47:
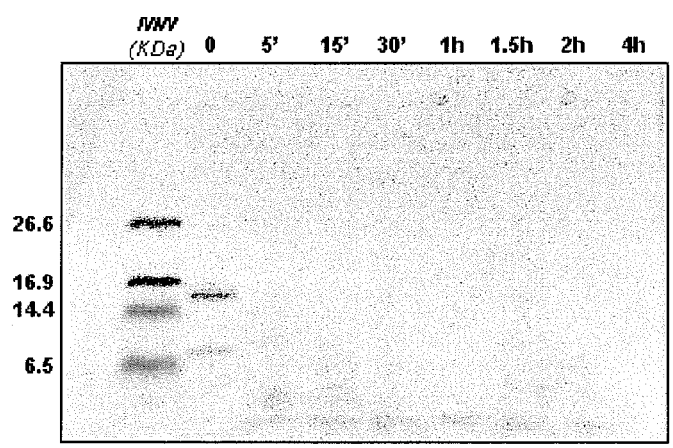

FIG. 47 shows the Tricine SDS-PAGE of the polypeptide variant of SEQ ID NO:61 (CT534) at different timepoints after protease digestion.

Figure 48:
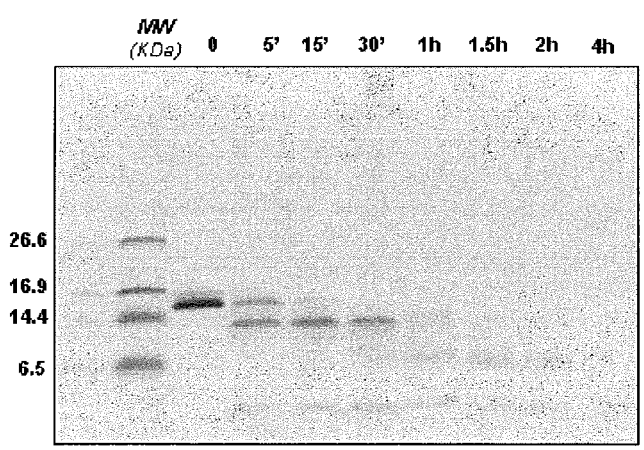

FIG. 48 shows the Tricine SDS-PAGE of the polypeptide variant of SEQ ID NO:62 (CT535) at different timepoints after protease digestion.

Figure 49:
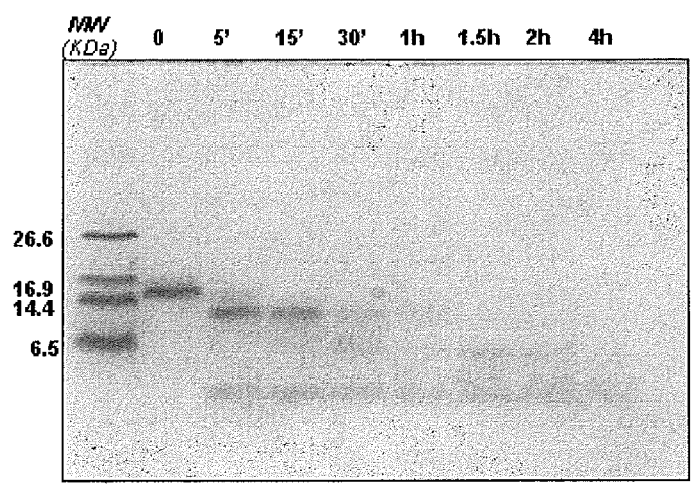

FIG. 49 shows the Tricine SDS-PAGE of the polypeptide variant of SEQ ID NO:63 (CT536) at different timepoints after protease digestion.

Figure 50:
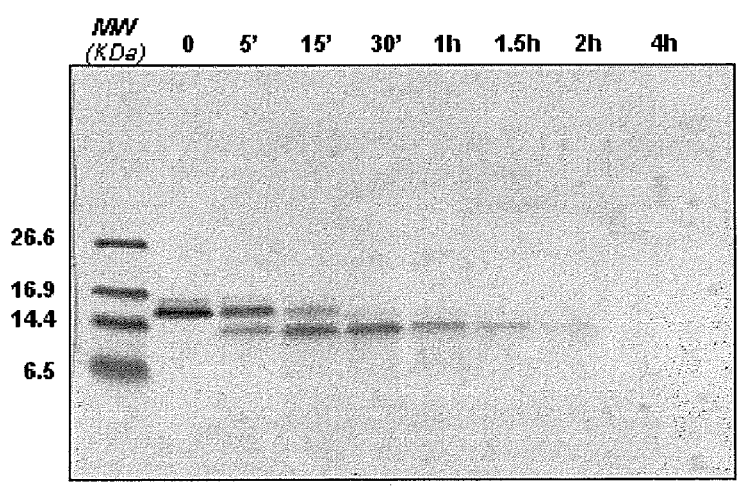

FIG. 50 shows the Tricine SDS-PAGE of the polypeptide variant of SEQ ID NO:64 (CT537) at different timepoints after protease digestion.

Figure 51:
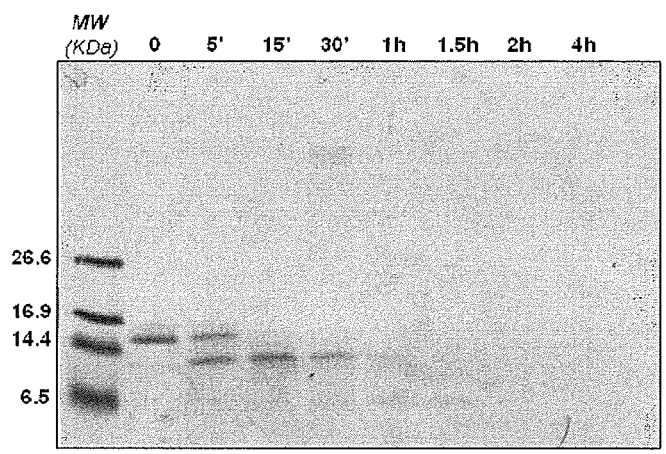

FIG. 51 shows the Tricine SDS-PAGE of the polypeptide variant of SEQ ID NO:66 (CT538) at different timepoints after protease digestion.

Figure 52:
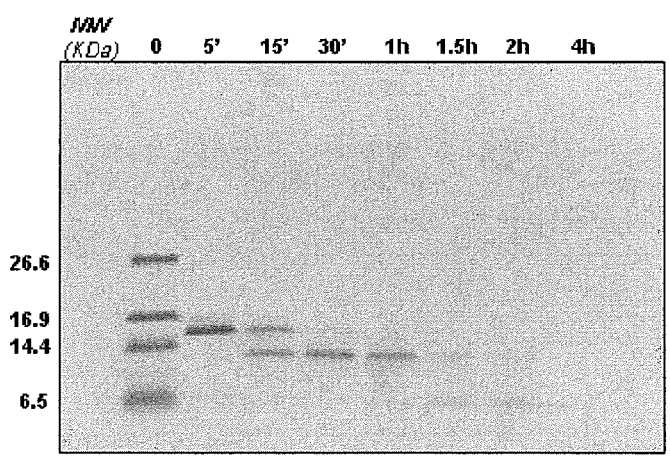

FIG. 52 shows the Tricine SDS-PAGE of the polypeptide variant of SEQ ID NO:67 (CT539) at different timepoints after protease digestion.

Figure 53:
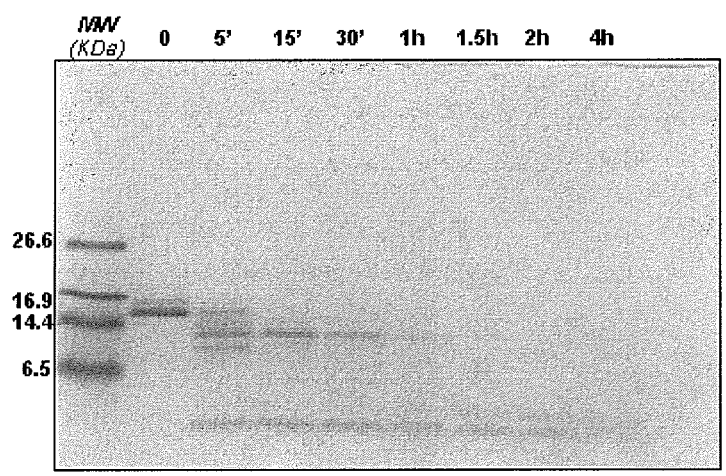

FIG. 53 shows the Tricine SDS-PAGE of the polypeptide variant of SEQ ID NO:69 (CT540) at different timepoints after protease digestion.

Figure 54:
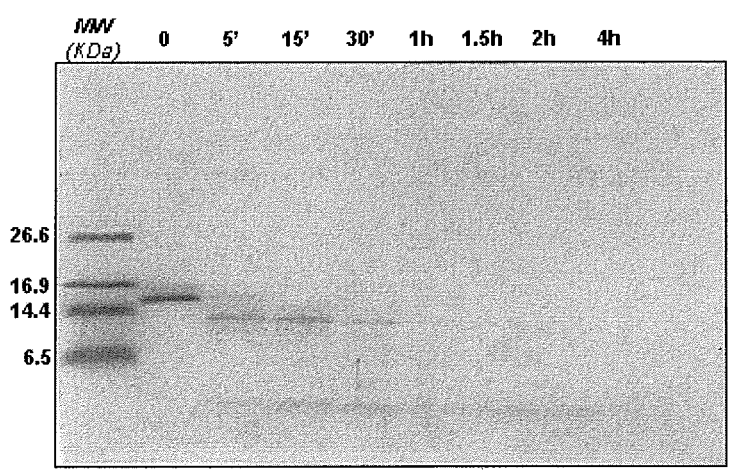

FIG. 54 shows the Trickle SDS-PAGE of the polypeptide variant of SEQ ID NO:70 (CT541) at different timepoints after protease digestion.

Figure 55:
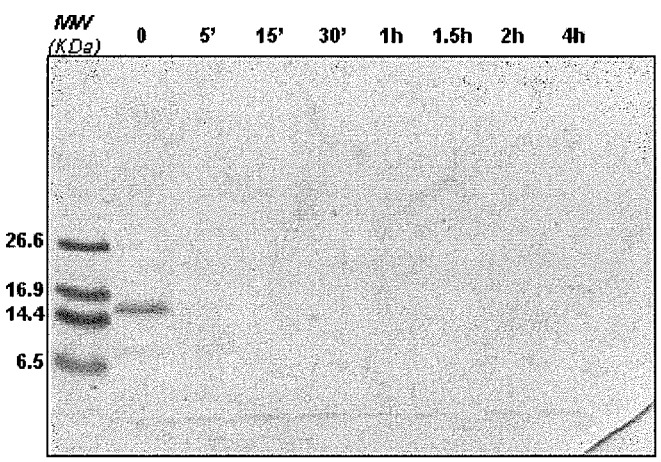

FIG. 55 shows the Tricine SDS-PAGE of the polypeptide variant of SEQ ID NO:71 (CT542) at different timepoints after protease digestion.

Figure 56:
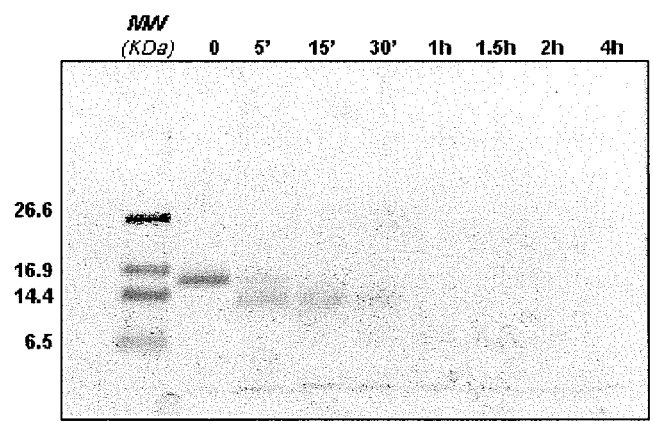

FIG. 56 shows the Tricine SDS-PAGE of the polypeptide variant of SEQ ID NO:80 (CT543) at different timepoints after protease digestion.

Figure 57:
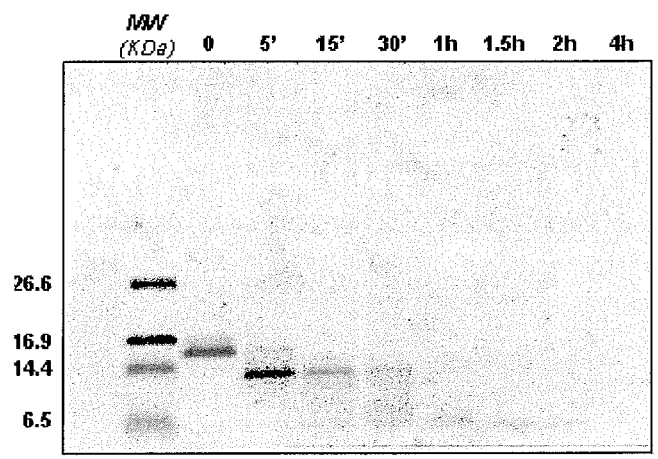

FIG. 57 shows the Tricine SDS-PAGE of the polypeptide variant of SEQ ID NO:81 (CT544) at different timepoints after protease digestion.

Figure 58:
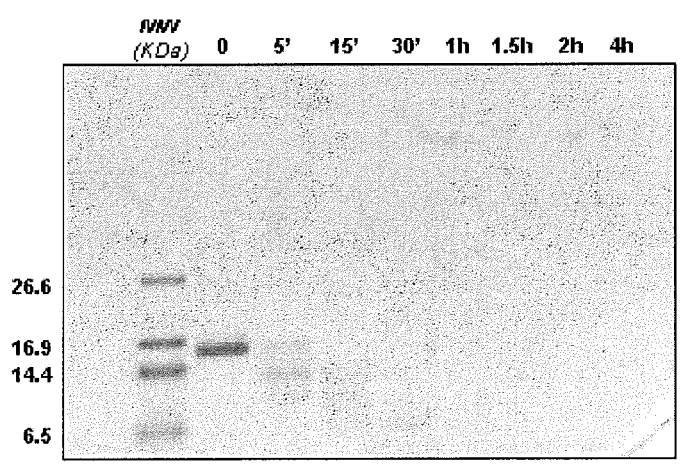

FIG. 58 shows the Tricine SDS-PAGE of the polypeptide variant of SEQ ID NO:82 (CT545) at different timepoints after protease digestion.

Figure 59:
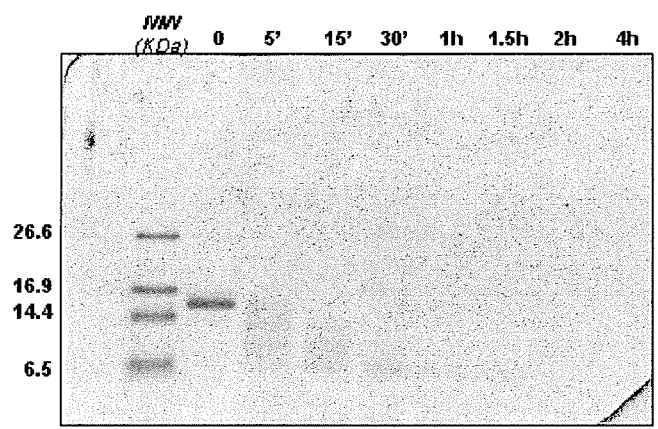

FIG. 59 shows the Tricine SDS-PAGE of the polypeptide variant of SEQ ID NO:83 (CT546) at different timepoints after protease digestion.

Figure 60:
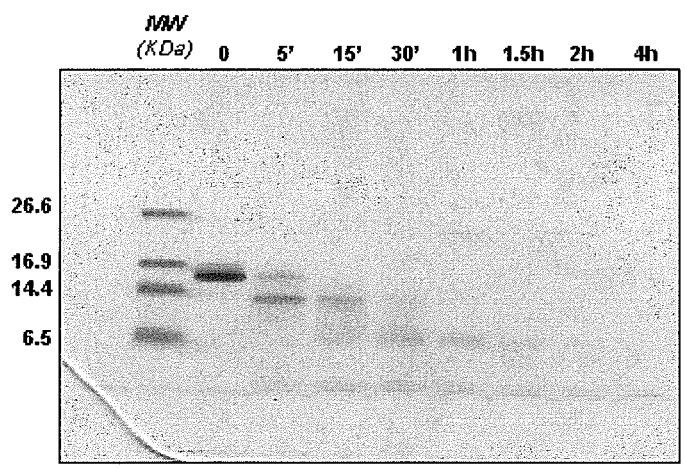

FIG. 60 shows the Tricine SDS-PAGE of the polypeptide variant of SEQ ID NO:84 (CT547) at different timepoints after protease digestion.

Figure 61:
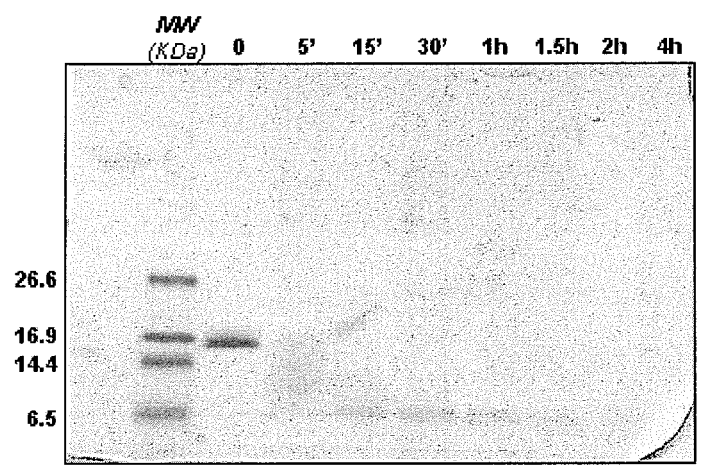

FIG. 61 shows the Tricine SDS-PAGE of the polypeptide variant of SEQ ID NO:86 (CT548) at different timepoints after protease digestion.

Figure 62:
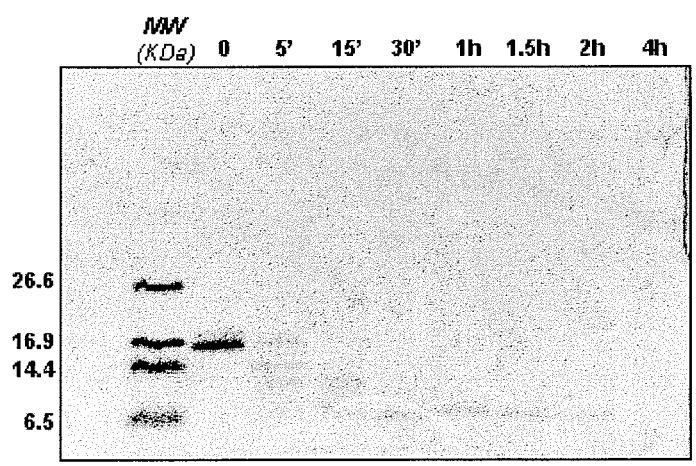

FIG. 62 shows the Tricine SDS-PAGE of the polypeptide variant of SEQ ID NO:87 (CT549) at different timepoints after protease digestion.

Figure 63:
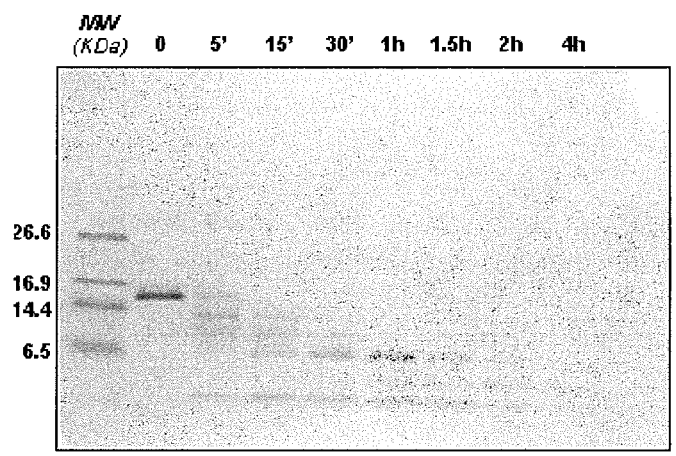

FIG. 63 shows the Tricine SDS-PAGE of the polypeptide variant of SEQ ID NO:94 (CT550) at different timepoints after protease digestion.

Figure 64:
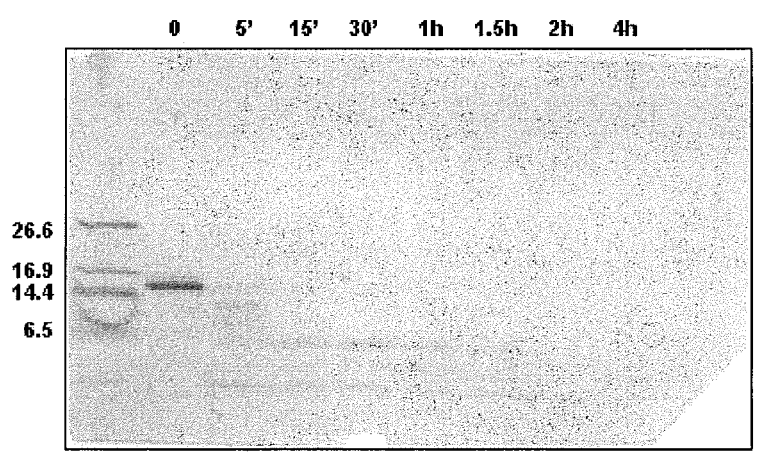

FIG. 64 shows the Tricine SDS-PAGE of the polypeptide variant of SEQ ID NO:95 (CT551) at different timepoints after protease digestion.

Figure 65:
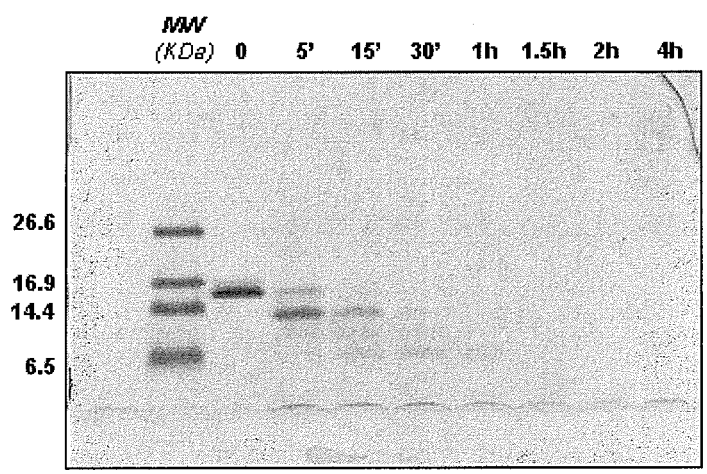

FIG. 65 shows the Tricine SDS-PAGE of the polypeptide variant of SEQ ID NO:97 (CT552) at different timepoints after protease digestion.

Figure 66:
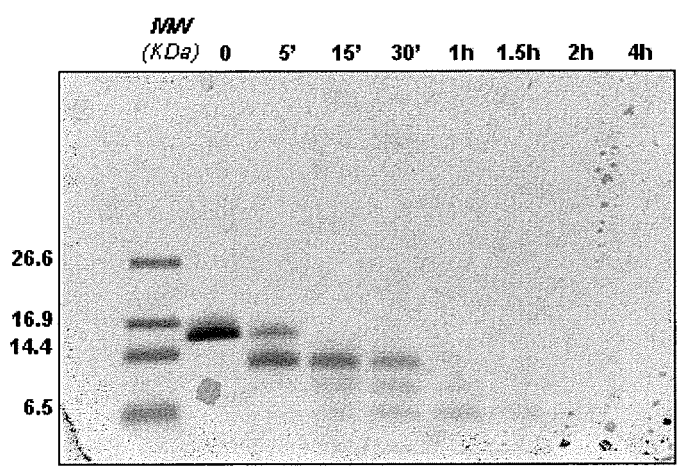

FIG. 66 shows the Tricine SDS-PAGE of the polypeptide variant of SEQ ID NO:98 (CT553) at different timepoints after protease digestion.

Figure 67:
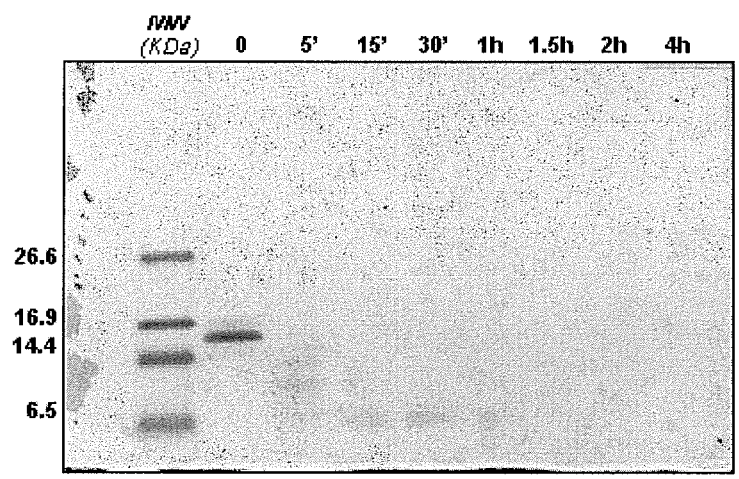

FIG. 67 shows the Tricine SDS-PAGE of the polypeptide variant of SEQ ID NO:99 (CT554) at different timepoints after protease digestion.

Figure 68:
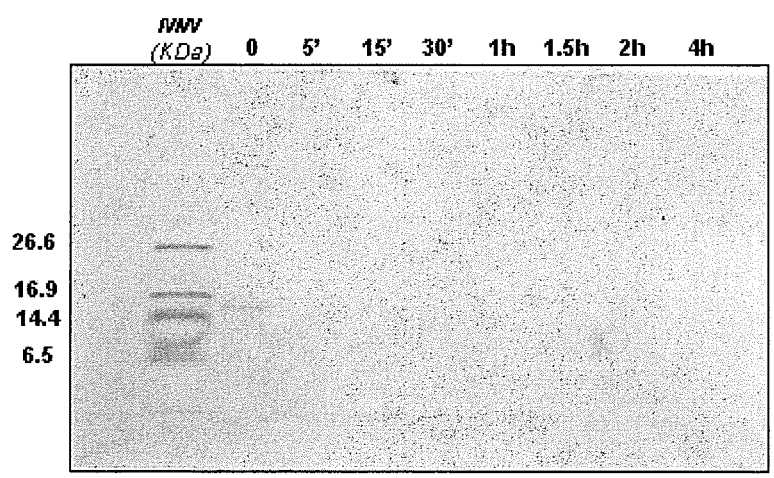

FIG. 68 shows the Tricine SDS-PAGE of the polypeptide variant of SEQ ID NO:100 (CT555) at different timepoints after protease digestion.

Figure 69:
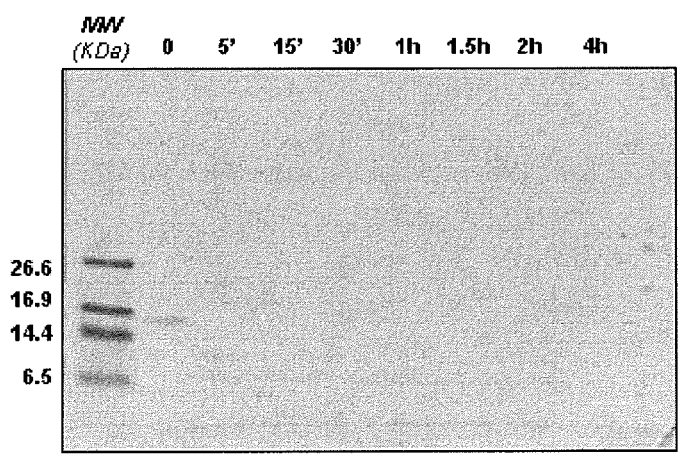

FIG. 69 shows the Tricine SDS-PAGE of the polypeptide variant of SEQ ID NO:101 (CT556) at different timepoints after protease digestion.

Figure 70:
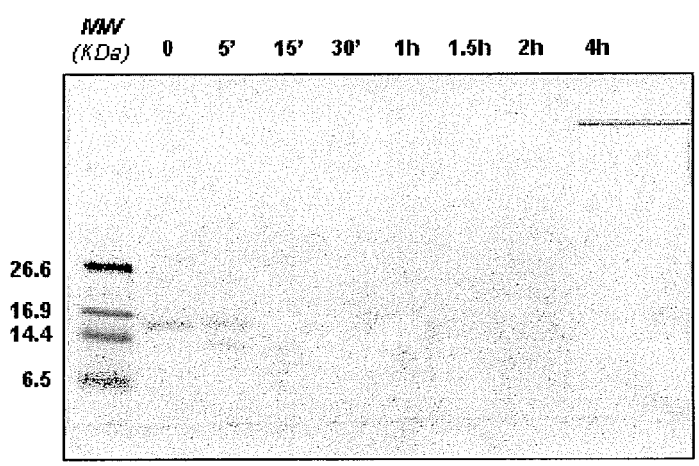

FIG. 70 shows the Tricine SDS-PAGE of the polypeptide variant of SEQ ID NO:102 (CT557) at different timepoints after protease digestion.

Figure 71:
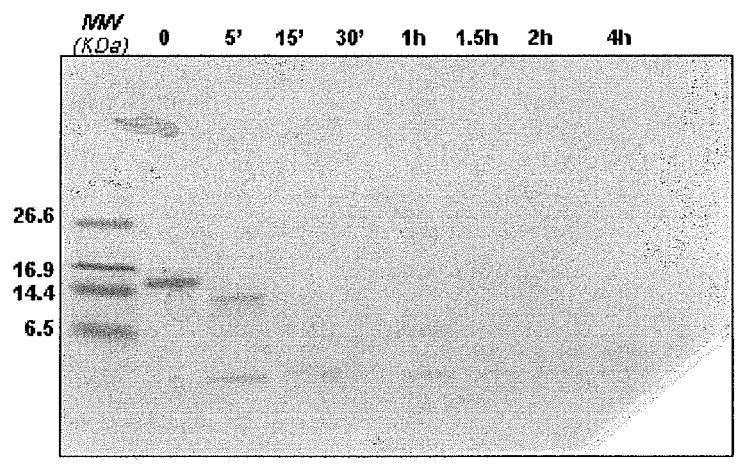

FIG. 71 shows the Tricine SDS-PAGE of the polypeptide variant of SEQ ID NO:103 (CT558) at different timepoints after protease digestion.

Figure 72:
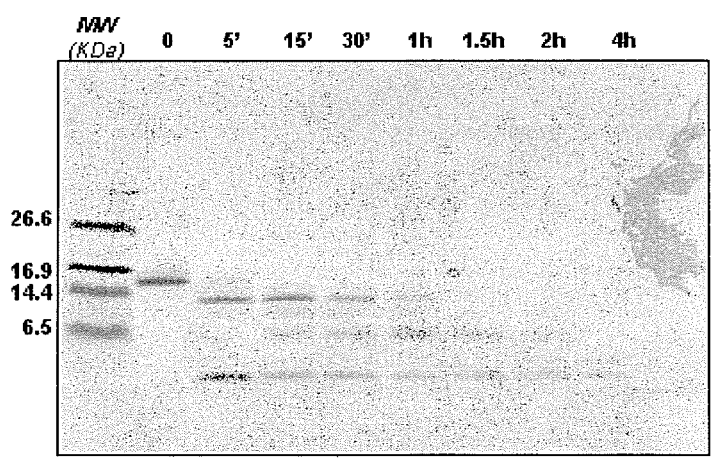

FIG. 72 shows the Tricine SDS-PAGE of the polypeptide variant of SEQ ID NO:104 (CT559) at different timepoints after protease digestion.

Figure 73:
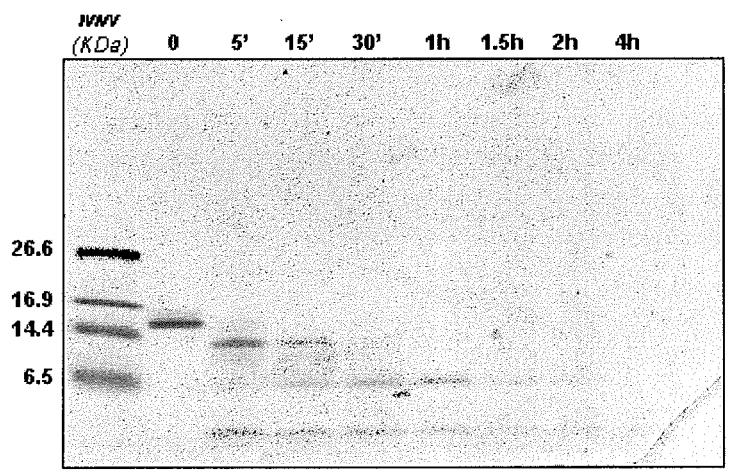

FIG. 73 shows the Tricine SDS-PAGE of the polypeptide variant of SEQ ID NO:106 (CT560) at different timepoints after protease digestion.

Figure 74:
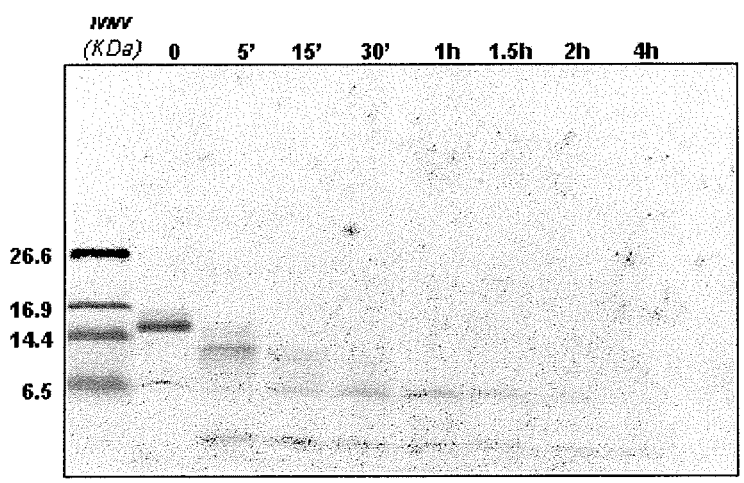

FIG. 74 shows the Tricine SDS-PAGE of the polypeptide variant of SEQ ID NO:107 (CT561) at different timepoints after protease digestion.

Figure 75:
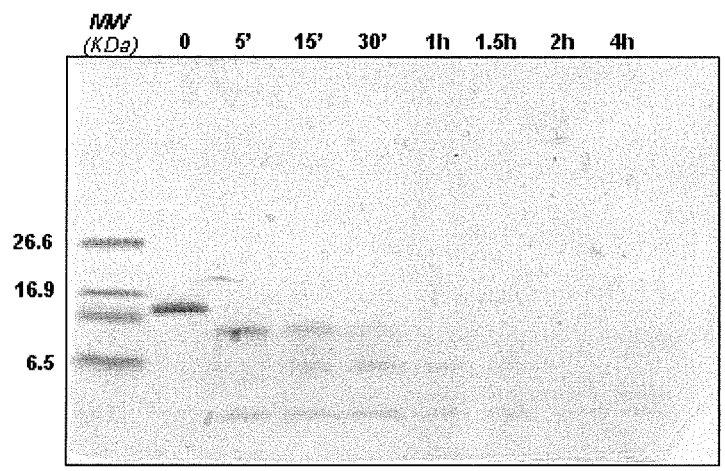

FIG. 75 shows the Tricine SDS-PAGE of the polypeptide variant of SEQ ID NO:109 (CT562) at different timepoints after protease digestion.

Figure 76:
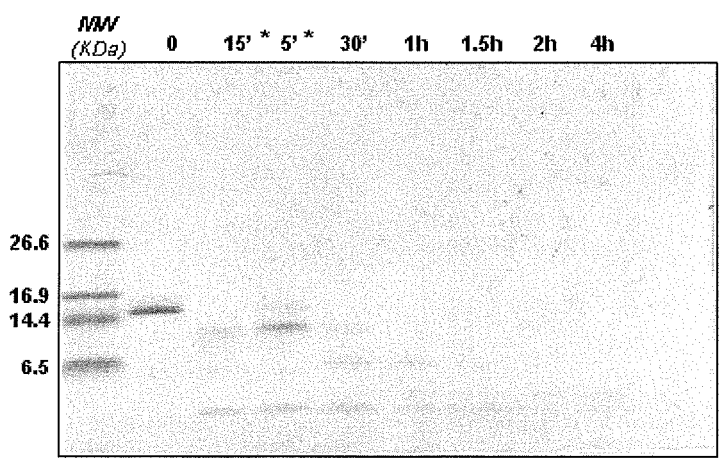

FIG. 76 shows the Tricine SDS-PAGE of the polypeptide variant of SEQ ID NO:110 (CT563) at different timepoints after protease digestion.

Figure 77:
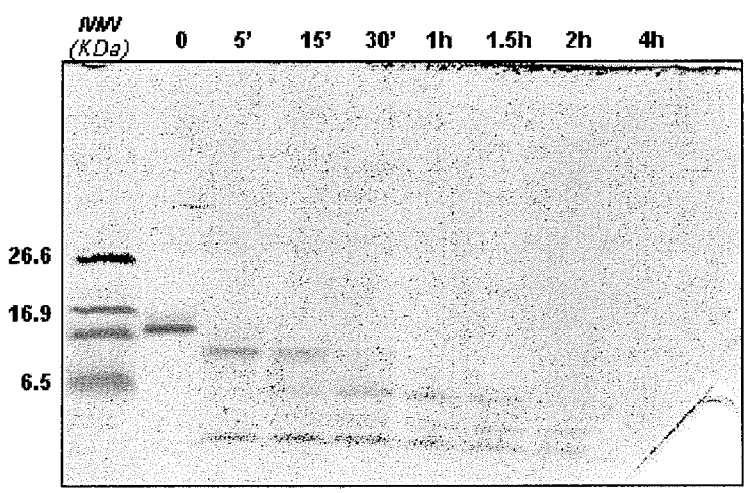

FIG. 77 shows the Tricine SDS-PAGE of the polypeptide variant of SEQ ID NO:111 (CT564) at different timepoints after protease digestion.

Figure 78:
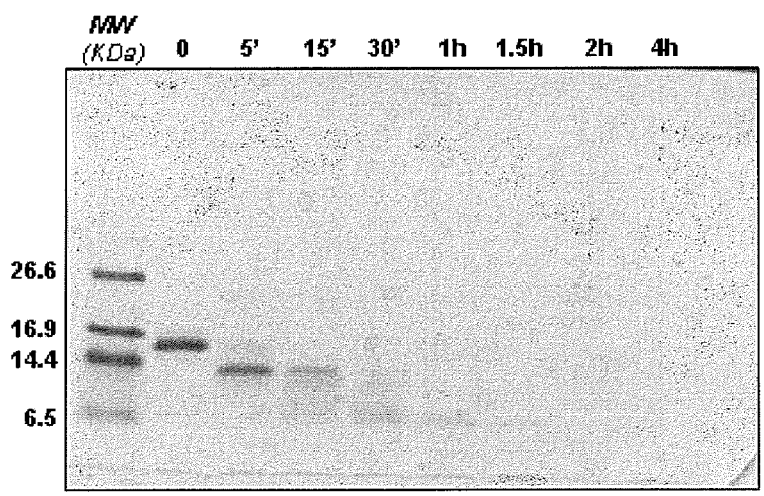

FIG. 78 shows the Tricine SDS-PAGE of the polypeptide variant of SEQ ID NO:112 (CT565) at different timepoints after protease digestion.

Figure 79:
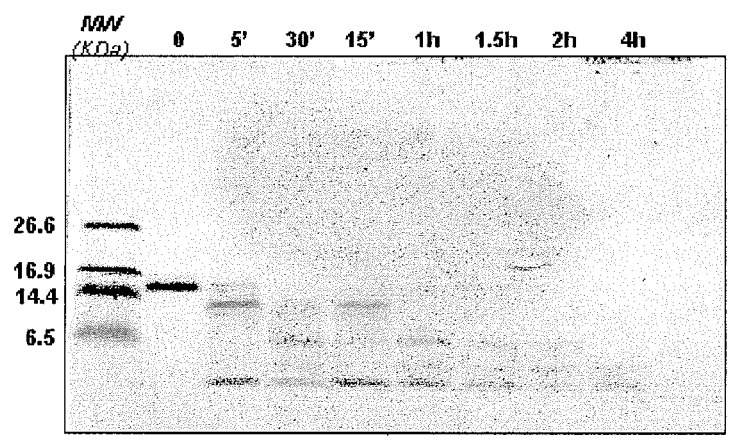

FIG. 79 shows the Tricine SDS-PAGE of the polypeptide variant of SEQ ID NO:113 (CT566) at different timepoints after protease digestion.

Figure 80:
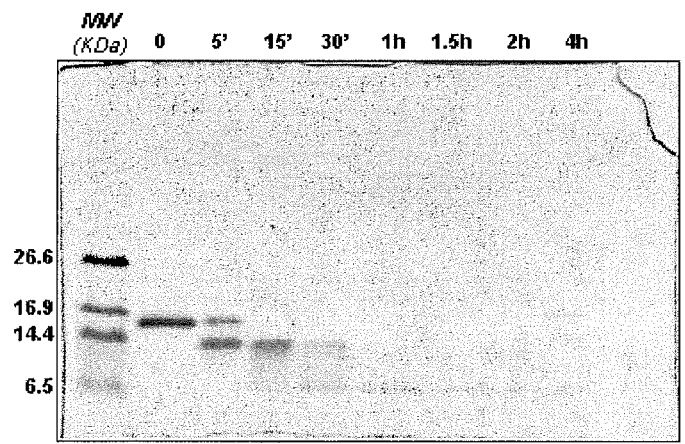

FIG. 80 shows the Tricine SDS-PAGE of the polypeptide variant of SEQ ID NO:114 (CT567) at different timepoints after protease digestion.

FIG. 81 shows a table in which the results of the Tricine SDS-PAGE are summarized. A cross indicates the presence on the gel of the band corresponding to the 84 amino acid long protein fragment of the HMGB1 Box-A wild-type or of the HMGB1 Box-A polypeptide variant.

EXAMPLES

1. Production of HMGB1 Box-A Native and Variants in Bacteria

Figure 9:
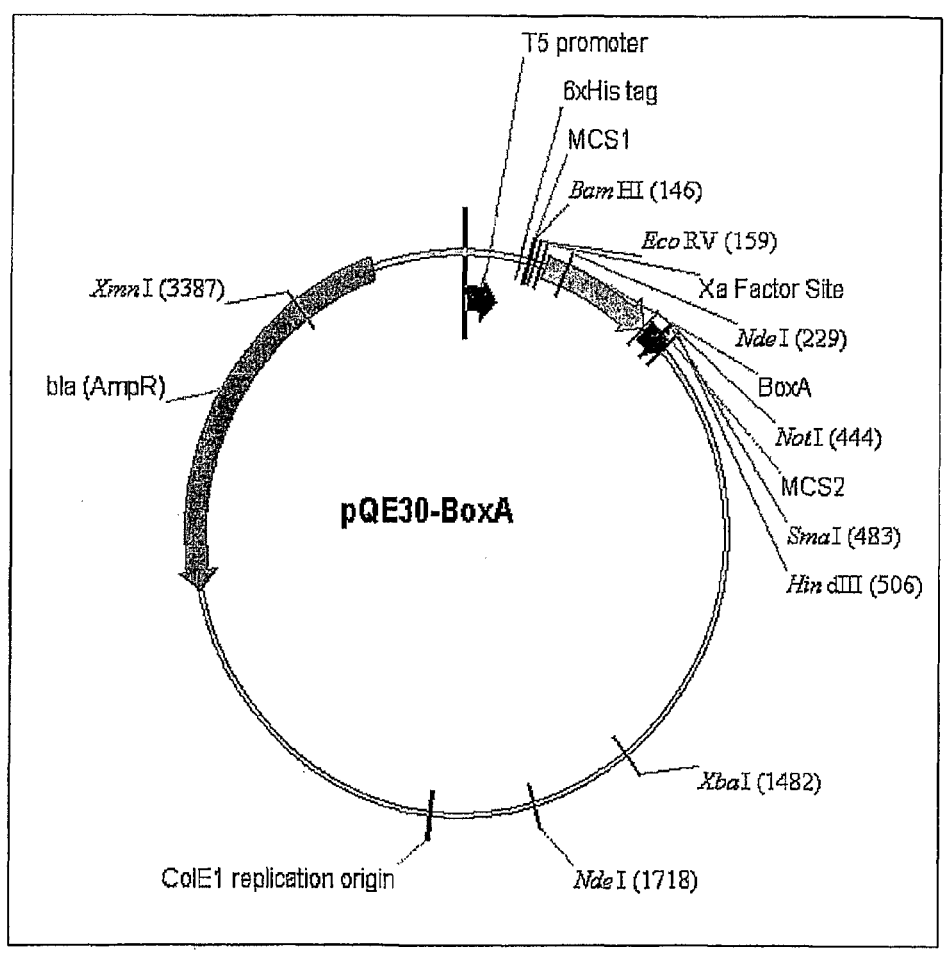

The in silico generated variants of HMGB1 Box-A were cloned from HMGB1 protein into an inducible plasmid vector (FIG. 9) used to transform *E. coli* M15 strain competent cells. M15 cells were grown overnight in 1 mL of LB medium containing Kanamicyn and Ampicillin in 96 deep-well plates under agitation (750 rpm). At $OD_{600\,nm}$ of 0.2-0.3 the cultures were diluted in 5 mL of LB medium in 24-well plates to reach an $OD_{600\,nm}$ of 0.07.

The M15 cells were incubated at 37° C. under constant agitation (200 rpm). The production of Box-A (native or variants) was induced by the addition of IPTG (1 mM final concentration) at $OD_{600\,nm}$ of 0.6. The culture was continued for three hours at 37° C. under agitation (200 rpm). M15 cells were then harvested by centrifugation at 1000 g for 15 minutes, the supernatant was discarded and the pellet stored at −80° C. at least for 1 hour before cells lysis and Box-A purification.

2. Purification of HMGB1 box-A Native and Variants

M15 cells pellet was thawed on ice for 15 min. The cells were resuspended in 1 mL NPI-10 buffer containing 1 mg/mL Lysozyme and incubated for 30 min at RT under agitation at 750 rpm on a plate shaker. After the equilibration of Ni-NTA QIAfilter with 200 μL of Superflow resin (QIAGEN catalog#969261) and 600 μL of NPI-10 buffer the bacterial lysate was loaded and 200 μL of absolute EtOH added. Four wash steps with 1 mL of NPI-20 were performed. The second and third washes were done with 1 mL NPI-20 added with 100 μg/mL Polymyxin (Fluka catalog#81271) in order to deplete LPS contaminants. After wash steps Box-A native and variants were eluted with 450 μL NPI-250. The samples were stored at 4° C.

Box-A native and variants were re-purified with a Detoxi-Gel polymyxin column (PIERCE) at 4° C. according to the supplier instructions. Finally the eluted proteins were filtered (0.22 μm) in PBS and stored at 4° C. to be tested.

3. Box-A Biological Activity Assay

HMGB1 stimulates the secretion of TNF-alpha and of other cytokines as well as the proliferation of macrophages and monocytes. Box-A acts as an antagonist by inhibiting the activity of HMGB1.

The activity of Box-A native and variants produced were measured by the level of inhibition on the stimulation produced by HMGB1 on RAW 264.7 cells (murine macrophages, ATCC).

HMGB1 Box-A native and variants produced as described above were tested in a two-step process of screening directed to test i) their inhibition of HMGB1 induced TNF-alpha release and ii) their resistance to proteolysis.

Figure 10:
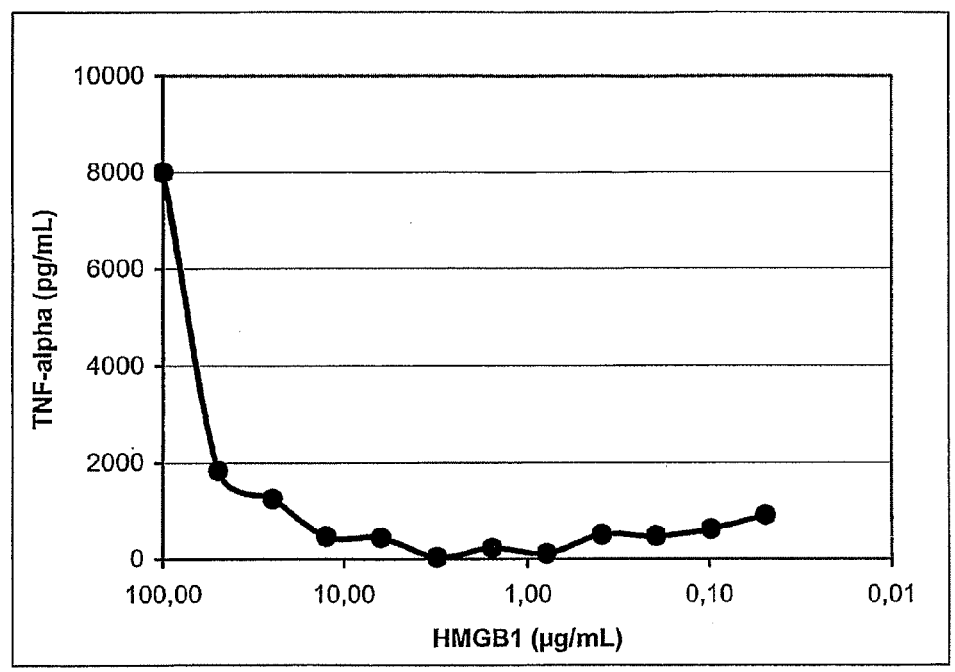

In order to determine the proper HMGB1 concentration to be used in inhibition assay RAW 264.7 cells were seeded in 96 well plates ($4\times10^5$ cells/well) and grown overnight in RPMI 1640 medium supplemented with 0.1% BSA. After overnight culture, cells were stimulated with HMGB1 (two times serial dilution concentrations between 100 μg/mL and 0.05 μg/mL) for 24 hours. The level of TNF-alpha produced was measured from cell media using ELISA (R&D systems), according to the manufacturer instructions. As presented in FIG. 10, HMGB1 significantly stimulated TNF-alpha release in macrophage cultures.

4. Box-A Inhibition of HMGB1 TNF-Alpha Release as Screening Test

Murine macrophage-like RAW 264.7 cells were seeded in 96 well plates ($4\times10^5$ cells/well) and grown overnight in RPMI 1640 medium supplemented with 0.1% BSA. After overnight culture, cells were stimulated with an adequate concentration of HMGB1 and Box-A native or variants or His-tagged (two times serial dilution between 20 μg/mL and 0.5 μg/mL) for 24 hours. The level of TNF-alpha was measured from cell media using ELISA (R&D systems), according to the manufacturer instructions.

Figure 11:
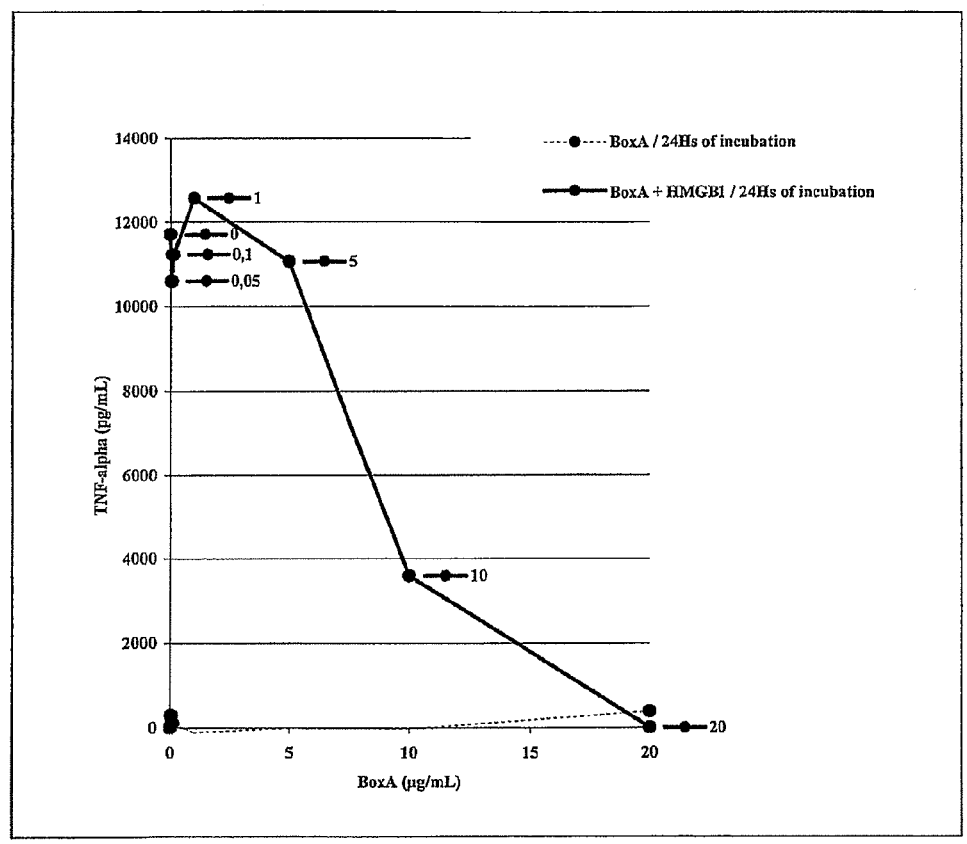

FIG. 11 shows an example of dose-dependent inhibition of HMGB1 induced TNF release by Box-A, with an EC50 of 7.5 μg/ml (solid line). 100% inhibition of TNF-alpha release is obtained with a concentration of 20 μg/ml of Box-A. In parallel, TNF-alpha levels are measured in Box-A stimulated cells without HMGB1 in order to determine the presence or absence of contaminating endotoxin in Box-A preparation and quantify any non-HMGB1 dependent release of TNF-alpha. No release of TNF-alpha is observed at all concentrations of Box-A used in the assay (dashed line).

5. Resistance to Proteolysis of Box-A Variants

Resistance of Box-A variants to proteolysis is determined as the residual biological activity (in the HMGB1/RAW cells system) following exposure to a mixture of selected proteases at increasing times of incubation.

20 μg of Box-A native or variants were treated with a mixture of proteases at 1% w/w of total proteins. The mixture of proteases was freshly prepared for each assay from stock solutions of endoproteinase Glu-C (SIGMA; 200 μg/ml), trypsin (SIGMA; 400 μg/ml) and α-chymotrypsin (SIGMA; 400 μg/ml).

Samples were collected at different time points between 5 minutes and 8 hours of incubation with proteases after stopping the reaction with the addition of 10 μl of anti-proteases solution (Roche). Biological activity of each sample was then evaluated by the screening test described above in order to assess the residual activity at each time point.

6. In Vitro Activity Testing

NIH/373 Cell Migration Assay

The purpose of the present study was to evaluate the activity of each of the HMGB1 Box-A polypeptide variants of the human HMGB1 Box-A full-length fragment as defined in SEQ ID NOs:2-116 and to compare their activity to that of human wild type HMGB1 Box-A full-length fragment of SEQ ID NO:1 in order to select all the variants with similar or better activity than wild type. HMGB1 Box-A activity is evaluated in vitro as inhibition of HMGB1-induced NIH/3T3 cells migration.

6.1 Materials

HMGB1 Box-A wild type and variants (Nautilus Biotech)
NIH/3T3 cells (ATCC n. CRL-1658)
D-MEM medium (GIBCO; cat. n. 31966-021)
Foetal Bovine Serum (GIBCO; cat. n. 10270-106)
Penicillin-Streptomycin 10,000 U/ml (GIBCO; cat. n. 15140-122)
L-Glutamine 200 mM (GIBCO; cat. n. 25030-024)
TrypLE Select (GIBCO; cat. n. 12563-011)
Phosphate Buffered Saline (0.138 M NaCl, 0.0027 M KCl, 0.01 M phosphate, pH 7.4)
PVP free filters (8 μm pore size; 13 mm total diameter) (Neuro Probe; cat. n. PFA8)
Human fibronectin (Roche; cat. n. 1080938)
Blind Well Chemotaxis Chambers (Neuro Probe; cat. n. BW25)
GIEMSA Stain Modified (Sigma; cat. n. GS1L)

6.2 Filters Preparation

Polycarbonate membranes PVP free filters (8 μm pore size, 13 mm total diameter) are prepared about one hour before performing the experiment by coating them with 30 μl/filter of a solution 50 μg/ml of fibronectin dispensed on the opaque side of the filter. The stock fibronectin solution is prepared by diluting the lyophilized fibronectin in ddH$_2$O to a final concentration of 1 mg/ml and by keeping the solution about 1 hour at 37° C. for complete dissolution. This stock solution can be stored at −20° C.

The filters are then left to dry under the laminar flux of the hood (about one hour).

6.3 Cells Preparation

NIH/3T3 cells are seeded the day before the experiment (approximately 22-24 hours before performing the experiment) $10^6$ cells/plate.

When the filters are ready to use, the cells are detached with Trypsin, counted and resuspended $10^6$ cells/ml in serum free culture medium.

6.4 Chemotaxis Assay

In each chemotaxis experiment 14 different polypeptide variants of the human HMGB1 Box-A full-length fragment of the invention are tested.

Growth cell medium without serum addition (w/o FBS) is used as negative control representing spontaneous migration.

1 nM HMGB1 is used as positive control. HMGB1 Box-A wild type or the tested polypeptide variants 0.5/1 nM are added to 1 nM HMGB1 to inhibit HMGB1-induced NIH/3T3 cell migration.

Negative control (w/o FBS) and positive control (1 nM HMGB1) are tested in triplicate in each experiment.

HMGB1 Box-A wild type (SEQ ID NO:1) activity in inhibiting HMGB1-induced cell migration is tested in triplicate in each experiment.

Each of the HMGB1 Box-A polypeptide (SEQ ID NO:2 to 116) variants is tested in duplicate.

Blind Well Chemotaxis Chambers are used. The clean, dry lower well of each chamber is filled with 50 μl of DMEM without FBS added with the appropriate chemotactic agent and inhibitors. A slight positive meniscus should form when the well is filled; this helps prevent air bubbles from being trapped when the filter is applied. With small forceps the filter is placed over the filled well (fibronectin treated side up), being careful not to trap air bubbles and not to touch the filter with fingers. The filter retainer is screwed in by hand. Cell suspension (50000 cells/50 μl) is pipetted into the upper well and 150 μl of serum free medium are added to fill the upper well of the chamber. The filled chamber is incubated for 3 hours (37° C., 5% CO$_2$) to allow cell migration. After incubation the fluid is removed from the filter. The retainer is unscrewed and immersed in cool distilled water. The filter is lifted out with forceps, placed on a clean surface (solid paraffin) (migrated cells side up) and fixed with a needle (placed on the border area).

6.5 GIEMSA Staining of Migrated Cells

The filters are fixed with ethanol once and then washed three times under running water. A working solution of GIEMSA Stain Modified diluted 1:10 in ddH$_2$O is prepared just before use. After washing of the filters, the staining is added and left to incubate for 20 minutes. Washing of the staining is performed under running water. The filters are then placed on slides with the migrated cells side down, and the non-migrated cells side is gently wiped off with a wet cotton swab (wipe twice, using two swabs or both ends of a double-tipped swab) being careful not to move the filter. After cleaning, a cover slide is placed on the filter and cells are counted under a microscope at 40× in 10 random fields/filter.

6.6 Data Representation and Statistical Analysis

The results of the NIH/3T3 migration assay performed are reported in the tables and bar graphs shown in FIGS. 12A-12R.

Data are represented in bar columns as MEAN±95% CI.

One-way ANOVA followed by Dunnett's post test (control column data: 1 nM HMGB1 sample+HMGB1 Box-A WT sample) is the statistical analysis performed.

When evaluating the results data, HMGB1 Box-A variants data having a post test p value <0.05 are considered significantly different from HMGB1 Box-A wild type. If the mean of the Box-A polypeptide variant is higher than that of Box-A wild type the column is coloured in red in the graph of the experiment shown in FIGS. 12A to 12R. Those red columns represent HMGB1 Box-A polypeptide variants showing less activity than wild type in inhibiting HMGB1-induced cell migration.

If the mean of the polypeptide variant results lower than that of wild type Box-A then the column is coloured in light blue in the graph of the experiment shown in FIGS. 12A to 12R. Those variants represent HMGB1 Box-A variants showing higher activity than HMGB1 Box-A wild type in inhibiting HMGB1-induced cell migration.

HMGB1 Box-A variants data having a post test p value >0.05 are considered not significantly different from HMGB1 Box-A wild type. The bar column of those variants are coloured in green. Those variants represent HMGB1 Box-A variants showing the same activity of wild type in inhibiting HMGB1-induced cell migration.

6.7 Results

The activity of polypeptide variants of the human HMGB1 high affinity binding domain Box-A of SEQ ID NOs:2 to 116 was evaluated in comparison to human HMGB1 Box-A wild-type of SEQ ID NO:1 as inhibition of HMGB1-induced cell migration.

The chemotaxis assays results revealed (FIGS. 12A to 12R) that for 26 polypeptide variants the mutation according to the present invention could lead to a higher activity in cell migration inhibition in comparison with the activity of the wild-type human HMGB1 Box-A. In particular, a higher activity in cell migration inhibition was shown for the polypeptide variants of SEQ ID NOs: 30-32, 35, 38, 40-41, 43, 48, 51, 57, 63-64, 69, 70, 94, 95, 100, 103-104, 106-107, 109-111 and 113.

Moreover, the chemotaxis assays results revealed (FIGS. 12A to 12R) that 41 polypeptide variants showed no changes in their activity in inhibiting HMGB1-induced cell migration compared to the activity of Box-A wild-type polypeptide. In particular, this is the case for the polypeptide variants of SEQ ID NOs: 2, 7, 9, 11, 15, 18, 22, 26-28, 33, 37, 39, 42, 44-47, 49, 52, 55, 59, 61, 62, 66-67, 71, 80-84, 86-87, 97-99, 101-102, 112 and 114.

All these Box-A polypeptide variants which exhibit a similar or a higher activity than the Box-A wild-type were tested for in vitro protease resistance, in order to choose the most resistant ones that are at least as active as Box-A wild-type (see protease resistance test in Example 7).

7. In Vitro Protease Resistance Testing

The purpose of the present study was to evaluate the in vitro protease resistance of to HMGB1 Box-A variants shown in Example 6 and to compare it to that of wild type HMGB1 Box-A of SEQ ID NO:1 in order to identify the variants with improved protease resistance with respect to wild type polypeptide.

7.1 Materials

- HMGB1 His-tagged Box-A wild type and selected variants (Nautilus biotech)
- Trypsine (Sigma; cat. n. T8658; lot.n. 045K5113)
- α-chymotrypsine (Sigma; cat. n. C6423; lot.n. 109H74858),
- Endoproteinase Asp-N (Sigma; cat. n. P3303; lot.n. 046K1049)
- Endoproteinase Glu-C(Sigma; cat. n. P6181; lot.n. 075K5100)
- Complete, Mini EDTA-free protease inhibitor cocktail (Roche; cat. n. 11836170 001)
- Trizma base (Sigma; cat. n. T6066)
- Acrilamide/bis solution 40% in water (Sigma; cat.n. 01709)
- SDS (Sigma; cat. n. 71729)
- Glycerol 99% (Sigma; cat. n. G9012)
- Temed (Sigma; cat. n. 87689)
- APS (Sigma; cat. n. A 3678)
- Polypeptide SDS-PAGE Molecular Weight Standards (Bio-Rad; cat. n. 161-0326)
- Premixed 10× Tris/tricine/SDS Buffer (Bio-Rad; cat. n. 161-0744)
- β-Mercaptoethanol (Sigma; cat. n. M7154)
- Methanol (VWR; cat. n. 20864.320)
- Acetic acid (VWR; cat. n. 20104.323)
- Brilliant Blue R (Sigma; cat. n. 80149)
- Bromophenol Blue (Sigma; cat. n. B0126)
- Hydrochloric acid (Merck; cat. n. 1.00319.2511)
- 3× sample loading buffer for Tricine gels (composition: 150 mM Tris-HCl, pH 6.8; 12% SDS; 36% glycerol; 6% 3-Mercaptoethanol; 0.04% of bromophenol blue)

7.2. Protease Mixture Preparation

A mixture of proteases containing trypsine, α-chymotrypsine, endoproteinase Asp-N and endoproteinase Glu-C is used.

Table 1 reports specificity of each of the proteases used in this study.

TABLE 1 protease specificity.

| Protease | Specificity |
|---|---|
| Tripsin | C-term of K, R<br>(not if P at C-term of cutting site; slower digestion if acidic residue on either side of cutting site) |
| α-chymotrypsin | C-term of T, P, W, L<br>(secondary hydrolysis: C-term of M, I, S, T, V, H, G, A) |
| Endoproteinase Asp-N | N-term of D, C |
| Endoproteinase Glu | C-term of E, D<br>(not if P is at C-term of cutting site) |

Each lyophilized protease is dissolved according to Manufacturer recommendations to obtain a stock solution that is aliquoted and stored at −80° C.

100 μg of trypsin are dissolved in 100 μl of $dH_2O$ to obtain a 1 μg/μl stock solution. 25 μg of α-chymotrypsine are dissolved in 50 μl of a solution 1 mM HCl, 2 mM $CaCl_2$ to obtain a 0.5 μg/μl stock solution. 2 μg of endoproteinase Asp-N are dissolved in 50 μl of $dH_2O$ to obtain a 0.04 μg/μl stock solution. 25 μg of endoproteinase Glu-C are dissolved in 50 μl of $dH_2O$ to obtain a 0.5 μg/μl stock solution.

Before performing the experiment one aliquot of each protease stock solution is left to thaw on ice.

Trypsin and endoproteinase Glu-C stock aliquots are diluted in $dH_2O$ to obtain a final working solution of 0.1 μg/μl. α-chymotrypsine stock aliquot is diluted in a solution 1 mM HCl, 2 mM $CaCl_2$ to obtain a final 0.1 μg/μl working solution. Endoproteinase Asp-N aliquot is used without dilution.

Just before performing the experiment a mixture of proteases containing 1% (in weight/weight of total Box-A contained in the sample) of each protease is freshly prepared and immediately added to HMGB1 Box-A to be digested.

7.3. HMGB1 Box-A Wild Type and Variants Protease Digestion

18 μg total of each HMGB1 Box-A (wild type or variants) are digested in each experiment.

HMGB1 Box-A to be tested is left to thaw on ice and the volume corresponding to 18 μg is taken. The volume of this solution is then brought with $dH_2O$ to a final volume of 90 μl in order to obtain the same final volume for each HMGB1 Box-A to be tested.

10 μl of this solution (corresponding to 2 μg of HMGB1 Box-A) are taken before adding the protease mixture. This sample corresponds to "time 0" not digested sample.

The remaining sample (16 μg of HMGB1 Box-A) is added with 8.8 μl (corresponding to 0.16 μg of each protease of the freshly prepared mixture; see 7.2) of protease mixture for digestion.

Protease digestion is performed at 25° C. and a volume corresponding to 2 μg of HMGB1 Box-A (originally present in the mixture) is sampled at defined time points. Digestion is stopped adding 4 μl of a solution of complete Mini EDTA-free protease inhibitor cocktail (1 tablet dissolved in 10 ml of $dH_2O$).

Timepoints for sampling are: 0, 5 minutes, 15 minutes, 30 minutes, 1 hour, 1.5 hours, 2 hours and 4 hours.

Soon after protease inhibition, samples are added with the appropriate amount of sample loading buffer 3× and incubated at 95° C. for about 3 minutes.

7.4. Tricine SDS-PAGE of Digested HMGB1 Box-A Wild Type and Variants

After protease digestion and samples preparation, time-points samples of each HMGB1 Box-A are loaded on a Tricine SDS PAGE gel (see for references: Schägger and von Jagow, "Tricine-sodium dodecyl sulphate-polyacrylamide gel electrophoresis for the separation of proteins in the range from 1 to 100 kDa", Anal. Biochem. 166, 368-379, 1987).

5 μl of Polypeptide SDS-PAGE Molecular Weight Standards (Bio-Rad) are loaded for reference on each gel.

Each well of the gel is loaded with 10 μl of sample (volume corresponding to 1 μg of HMGB1 Box-A before digestion).

Electrophoresis is performed at 30 V until the bromophenol blue has entered the separating portion of the gel, then at 120 V (Mini Protean 3 System; Bio-Rad) till the end of the run.

Gels are stained by soaking in a Coomassie Brilliant Blue R staining solution (0.1% w/v in 50% methanol, 10% acetic acid) for 1 hour and destained overnight in destaining solution (30% methanol, 10% acetic acid).

Gel images are acquired with Gel Doc 2000 (Bio-Rad) imaging system.

7.5 Results

In the above reported assay conditions HGMB1 wild-type protein resisted approximately 30 minutes to complete protease digestion. In FIG. 13 the band corresponding to the 84-amino acid full-length fragment of human HMGB1 Box-A wild-type of SEQ ID NO:1 protein is visible until 30 minutes of protease digestion.

21 Box-A polypeptide variants tested showed an increased resistance to protease (FIG. 15). In the reported assay conditions these variants resist from 1 hour to 2 hours to protease digestion. The polypeptide variants of SEQ ID NOs: 33, 35, 37, 38, 39, 42, 43, 44, 47, 48, 57, 62, 69 and 104 showed a resistance of 1 hour to protease digestion. FIGS. 27-31, 34-36, 39-40, 45, 48, 53 and 72 show a band corresponding to the not His-tagged protein of 84 amino acids which is visible until 1 hour of protease digestion.

The polypeptide variants of SEQ ID NOs: 45, 49, 52, 55 and 67 showed a resistance of 1.5 hours to protease digestion. FIGS. 37, 41, 43, 44 and 52 show a band corresponding to the not His-tagged protein of 84 amino acids which is clearly visible 1 hour and a half after protease digestion. The polypeptide variants of SEQ ID NOs: 59 and 64 even show a resistance of up to 2 hours to protease digestion. FIGS. 46 and 50 show a band of the not His-tagged protein of 84 amino acids which is clearly visible until 2 hours after protease digestion.

REFERENCES

Andersson, U., Erlandsson-Harris, H., Yang, H. and Tracey, K. J. (2002) *HMGB1 as a DNA-binding cytokine* J. Leucocyte Biol., 72: 1084-1091

Agresti, A. and Bianchi, M. E. (2003) *HMGB-proteins and gene expression* Current Opin. In Genetics and Develop., 13: 170-178

Degryse, B., de Virgilio, M. (2003) *The nuclear protein HMGB1, a new kind of chemokine?* FEBS Letters, 553: 11-17

Thomas, J. O. (2001) *HMGB1 and 2: architectural DNA-binding proteins* Biochemical Society Transactions, 29: 395-401

Ferrari, S., Harley, V. H., Pontiggia, A., Goodfellow, P. N., Lovell-Badge, R. and Bianchi, M. E. (1992) *SRY, like HMGB1, recognizes sharp angles in DNA* The EMBO J., 11: 4497-4506

Pontiggia, A., Negri, A., Beltrame, M. and Bianchi, M. E. (1993) *Protein HU binds specifically to kinked DNA* Mot. Biol., 7: 343-350

Scaffidi, P., Misteli, T. and Bianchi, M. E. (2002) *Release of chromatin protein HMGB1 by necrotic cells triggers inflammation* Nature, 418: 191-195

Bonaldi, T., Talamo, F., Scaffidi, P., Ferrera, D., Porto, A., Bachi, A., Rubartelli, A., Agresti, A. and Bianchi M. E. (2003) *Monocytic cells hyperacetylate chromatin protein HMGB1 to redirect it towards Secretion* The EMBO Journal, 22: 5551-5560

Taniguchi, N., Kawahara, K., Yone, K., Hashiguchi, T., Yamakuchi, M., Inoue, K., Yamada, S., Ijiri, K., Matsunaga, S., Nakajima, T., Komiya S. and Maruyama, I. (2003) *High mobility group box chromosomal protein 1 plays a role in the pathogenesis of arthritis as a novel cytokine* Arthritis and Rheumatism, 48:971-981

Palumbo, R., Sanpaolesi, M., De Marchis, F., Tonlorenzi, R., Colombetti, S., Mondino, A., Cossu, G. and Bianchi, M. E. (2004) *Extracellular HMGB1, a signal of tissue damage, induces nesoangioblast migration and proliferation* The J. of Cell Biology, 164: 441-449

Friedman, S. G., Czura, C., J. and Tracey, K. J. (2003) *The gesture life of high mobility group box* 1 Current Opinion in Clinical Nutrition and Metabolica Care, 6: 283-287

Yang, H., Wang, H., and Tracey, K. J. (2001) *HMGB1 rediscovered as a cytokine* Shock, 15: 247-253

Gardella, S., Andrei, C., Ferrera, D., Lotti, L. V., Torrisi, M. R., Bianchi, M. E. And Rubartelli, A. (2002) *The nuclear protein HMGB1 is secreted by monocytes via a non-classical, vesicle-mediated secretory pathway*. EMBO. Rep., 3: 995-1001

Schmidt, A. M., Yan, S. D., Yan, S. F. and Stern, D. M. (2001) *The multiligand receptor RAGE as a progression factor amplifying immune and inflammatory responses* J. Clin. Invest., 108: 949-955

Czura, C. J., Tracey, K. J. (2003) *Targeting high mobility group box* 1 *as a late acting mediator of inflammation* Crit. Care Med., 31: S46-S50

Lotze, M. T. and De Marco, R. A. (2003) *Editorial overview—Dealing with death: HMGB1 as a novel target for cancer therapy* Current Opinion in Investigational Drugs, 4: 1405-1409

Pullerits, R., Jonsson, I. M., Verdreng, M., Bokarewa, M., Andersson, U., Erlandsson-Harris, H. and Tarkowski, A. (2003) *High mobility group box chromosomal protein 1, a DNA binding cytokine, induces arthritis* Arthritis and Rheumatism, 48: 1693-1700

Kokkola, R., Li, J., Sundenberg, E., Aveberger, A. C., Palmblad, K., Yang, H., Tracey, K. J., Andersson, U. and Erlandsson-Harris, H. (2003) *Successful treatment of collagen-induced arthritis in mice and rats by targeting extracellular high mobility group box chromosomal protein* 1 *activity* Arthritis and Rheumatism, 48: 2052-2058

Yan, S. D., Chen, X., Fu, J., Chen, M., Zhu, H., Roher, A., Slattery, T., Zhao, L., Nagashima, M., Morser, J., Migheli, A., Nawroth, P., Stern, D., Schmidt, A. M. (1996) *RAGE and amyloid-beta peptide neurotoxicity in Alzheimer's disease* Nature, 382: 685-691

Yang, H., Ochani, M., Li, J., Qiang, X., Tanovic, M., Harris, H. E., Susarla, S. M., Ulloa, L., Wang, H., DiRaimo, R., Czura, C. J., Wang, H., Roth, J., Warren, H. S., Fink, M. P., Fenton, M. J., Andersson, U. and Tracey, K. J. (2004) *Reversing established sepsis with antagonists of endogenous high-mobility group box*-1 PNAS, 101:296-301

The invention claimed is:

1. An isolated polypeptide variant of HMGB1 high affinity binding domain Box-A (HMGB1 Box-A) having an amino acid sequence selected from the group consisting of SEQ ID NOs.: 33, 35, 37-39, 42-45, 47-49, 52, 55, 57, 62, 67, 69, and 104.

2. A medicament comprising the polypeptide variant of claim 1 as an active agent.

3. A pharmaceutical composition comprising an effective amount of at least one polypeptide variant of claim 1 as an active agent and a pharmaceutically acceptable carrier.

4. The composition of claim 3 wherein the at least one polypeptide variant is in combination with at least one further agent.

5. The composition of claim 3, further comprising ingredients suitable for therapeutic applications.

* * * * *

SEQUENCE LISTING

<160> NUMBER OF SEQ ID NOS: 610

<210> SEQ ID NO 1
<211> LENGTH: 84
<212> TYPE: PRT
<213> ORGANISM: homo sapiens

<400> SEQUENCE: 1

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 2
<211> LENGTH: 84
<212> TYPE: PRT
<213> ORGANISM: homo sapiens

<400> SEQUENCE: 2

Gly Asn Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 3
<211> LENGTH: 84
<212> TYPE: PRT
<213> ORGANISM: homo sapiens

<400> SEQUENCE: 3

Gly Gln Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

```
<210> SEQ ID NO 4
<211> LENGTH: 84
<212> TYPE: PRT
<213> ORGANISM: homo sapiens

<400> SEQUENCE: 4

Gly Lys Gly Asn Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 5
<211> LENGTH: 84
<212> TYPE: PRT
<213> ORGANISM: homo sapiens

<400> SEQUENCE: 5

Gly Lys Gly Gln Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 6
<211> LENGTH: 84
<212> TYPE: PRT
<213> ORGANISM: homo sapiens

<400> SEQUENCE: 6

Gly Lys Gly Asp Ala Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 7
<211> LENGTH: 84
<212> TYPE: PRT
<213> ORGANISM: homo sapiens
```

```
<400> SEQUENCE: 7

Gly Lys Gly Asp Ser Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 8
<211> LENGTH: 84
<212> TYPE: PRT
<213> ORGANISM: homo sapiens

<400> SEQUENCE: 8

Gly Lys Gly Asp Pro Asn Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 9
<211> LENGTH: 84
<212> TYPE: PRT
<213> ORGANISM: homo sapiens

<400> SEQUENCE: 9

Gly Lys Gly Asp Pro Gln Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 10
<211> LENGTH: 84
<212> TYPE: PRT
<213> ORGANISM: homo sapiens

<400> SEQUENCE: 10

Gly Lys Gly Asp Pro Lys Asn Pro Arg Gly Lys Met Ser Ser Tyr Ala
1               5                   10                  15
```

```
Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 11
<211> LENGTH: 84
<212> TYPE: PRT
<213> ORGANISM: homo sapiens

<400> SEQUENCE: 11

Gly Lys Gly Asp Pro Lys Gln Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 12
<211> LENGTH: 84
<212> TYPE: PRT
<213> ORGANISM: homo sapiens

<400> SEQUENCE: 12

Gly Lys Gly Asp Pro Lys Lys Ala Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 13
<211> LENGTH: 84
<212> TYPE: PRT
<213> ORGANISM: homo sapiens

<400> SEQUENCE: 13

Gly Lys Gly Asp Pro Lys Lys Ser Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45
```

```
Lys Thr Met Ser Ala Lys Glu Lys Gly Lys Phe Glu Asp Met Ala Lys
        50                  55                  60
Ala Asp Lys Ala Arg Tyr Glu Arg Glu Met Lys Thr Tyr Ile Pro Pro
 65                  70                  75                  80
Lys Gly Glu Thr

<210> SEQ ID NO 14
<211> LENGTH: 84
<212> TYPE: PRT
<213> ORGANISM: homo sapiens

<400> SEQUENCE: 14

Gly Lys Gly Asp Pro Lys Lys Pro His Gly Lys Met Ser Ser Tyr Ala
 1               5                  10                  15
Phe Phe Val Gln Thr Cys Arg Glu Glu His Lys Lys Lys His Pro Asp
                20                  25                  30
Ala Ser Val Asn Phe Ser Glu Phe Ser Lys Lys Cys Ser Glu Arg Trp
            35                  40                  45
Lys Thr Met Ser Ala Lys Glu Lys Gly Lys Phe Glu Asp Met Ala Lys
        50                  55                  60
Ala Asp Lys Ala Arg Tyr Glu Arg Glu Met Lys Thr Tyr Ile Pro Pro
 65                  70                  75                  80
Lys Gly Glu Thr

<210> SEQ ID NO 15
<211> LENGTH: 84
<212> TYPE: PRT
<213> ORGANISM: homo sapiens

<400> SEQUENCE: 15

Gly Lys Gly Asp Pro Lys Lys Pro Gln Gly Lys Met Ser Ser Tyr Ala
 1               5                  10                  15
Phe Phe Val Gln Thr Cys Arg Glu Glu His Lys Lys Lys His Pro Asp
                20                  25                  30
Ala Ser Val Asn Phe Ser Glu Phe Ser Lys Lys Cys Ser Glu Arg Trp
            35                  40                  45
Lys Thr Met Ser Ala Lys Glu Lys Gly Lys Phe Glu Asp Met Ala Lys
        50                  55                  60
Ala Asp Lys Ala Arg Tyr Glu Arg Glu Met Lys Thr Tyr Ile Pro Pro
 65                  70                  75                  80
Lys Gly Glu Thr

<210> SEQ ID NO 16
<211> LENGTH: 84
<212> TYPE: PRT
<213> ORGANISM: homo sapiens

<400> SEQUENCE: 16

Gly Lys Gly Asp Pro Lys Lys Pro Arg Gly Asn Met Ser Ser Tyr Ala
 1               5                  10                  15
Phe Phe Val Gln Thr Cys Arg Glu Glu His Lys Lys Lys His Pro Asp
                20                  25                  30
Ala Ser Val Asn Phe Ser Glu Phe Ser Lys Lys Cys Ser Glu Arg Trp
            35                  40                  45
Lys Thr Met Ser Ala Lys Glu Lys Gly Lys Phe Glu Asp Met Ala Lys
        50                  55                  60
Ala Asp Lys Ala Arg Tyr Glu Arg Glu Met Lys Thr Tyr Ile Pro Pro
```

65            70            75            80

Lys Gly Glu Thr

<210> SEQ ID NO 17
<211> LENGTH: 84
<212> TYPE: PRT
<213> ORGANISM: homo sapiens

<400> SEQUENCE: 17

Gly Lys Gly Asp Pro Lys Lys Pro Arg Gly Gln Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65              70                  75                  80

Lys Gly Glu Thr

<210> SEQ ID NO 18
<211> LENGTH: 84
<212> TYPE: PRT
<213> ORGANISM: homo sapiens

<400> SEQUENCE: 18

Gly Lys Gly Asp Pro Lys Lys Pro Arg Gly Lys Ile Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65              70                  75                  80

Lys Gly Glu Thr

<210> SEQ ID NO 19
<211> LENGTH: 84
<212> TYPE: PRT
<213> ORGANISM: homo sapiens

<400> SEQUENCE: 19

Gly Lys Gly Asp Pro Lys Lys Pro Arg Gly Lys Val Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65              70                  75                  80

Lys Gly Glu Thr

```
<210> SEQ ID NO 20
<211> LENGTH: 84
<212> TYPE: PRT
<213> ORGANISM: homo sapiens

<400> SEQUENCE: 20

Gly Lys Gly Asp Pro Lys Lys Pro Arg Gly Lys Met Ser Ser His Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 21
<211> LENGTH: 84
<212> TYPE: PRT
<213> ORGANISM: homo sapiens

<400> SEQUENCE: 21

Gly Lys Gly Asp Pro Lys Lys Pro Arg Gly Lys Met Ser Ser Ile Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 22
<211> LENGTH: 84
<212> TYPE: PRT
<213> ORGANISM: homo sapiens

<400> SEQUENCE: 22

Gly Lys Gly Asp Pro Lys Lys Pro Arg Gly Lys Met Ser Ser Tyr Ala
1               5                   10                  15

Ile Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 23
<211> LENGTH: 84
<212> TYPE: PRT
<213> ORGANISM: homo sapiens
```

-continued

```
<400> SEQUENCE: 23

Gly Lys Gly Asp Pro Lys Lys Pro Arg Gly Lys Met Ser Ser Tyr Ala
1               5                   10                  15

Val Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 24
<211> LENGTH: 84
<212> TYPE: PRT
<213> ORGANISM: homo sapiens

<400> SEQUENCE: 24

Gly Lys Gly Asp Pro Lys Lys Pro Arg Gly Lys Met Ser Ser Tyr Ala
1               5                   10                  15

Phe Ile Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 25
<211> LENGTH: 84
<212> TYPE: PRT
<213> ORGANISM: homo sapiens

<400> SEQUENCE: 25

Gly Lys Gly Asp Pro Lys Lys Pro Arg Gly Lys Met Ser Ser Tyr Ala
1               5                   10                  15

Phe Val Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 26
<211> LENGTH: 84
<212> TYPE: PRT
<213> ORGANISM: homo sapiens

<400> SEQUENCE: 26

Gly Lys Gly Asp Pro Lys Lys Pro Arg Gly Lys Met Ser Ser Tyr Ala
1               5                   10                  15
```

```
Phe Phe Val Gln Thr Cys His Glu Glu His Lys Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 27
<211> LENGTH: 83
<212> TYPE: PRT
<213> ORGANISM: homo sapiens

<400> SEQUENCE: 27

Gly Lys Gly Asp Pro Lys Lys Pro Arg Gly Lys Met Ser Ser Tyr Ala
 1               5                  10                  15

Phe Phe Val Gln Thr Cys Gln Glu Glu His Lys Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys Ala
        50                  55                  60

Asp Lys Ala Tyr Glu Arg Glu Met Lys Thr Tyr Ile Pro Pro Lys Lys
 65                  70                  75                  80

Gly Glu Thr

<210> SEQ ID NO 28
<211> LENGTH: 84
<212> TYPE: PRT
<213> ORGANISM: homo sapiens

<400> SEQUENCE: 28

Gly Lys Gly Asp Pro Lys Lys Pro Arg Gly Lys Met Ser Ser Tyr Ala
 1               5                  10                  15

Phe Phe Val Gln Thr Cys Arg Gln Glu His Lys Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 29
<211> LENGTH: 84
<212> TYPE: PRT
<213> ORGANISM: homo sapiens

<400> SEQUENCE: 29

Gly Lys Gly Asp Pro Lys Lys Pro Arg Gly Lys Met Ser Ser Tyr Ala
 1               5                  10                  15

Phe Phe Val Gln Thr Cys Arg His Glu His Lys Lys Lys His Pro Asp
            20                  25                  30

Ala Ser Val Asn Phe Ser Glu Phe Ser Lys Lys Cys Ser Glu Arg Trp
            35                  40                  45
```

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 30
<211> LENGTH: 84
<212> TYPE: PRT
<213> ORGANISM: homo sapiens

<400> SEQUENCE: 30

Gly Lys Gly Asp Pro Lys Lys Pro Arg Gly Lys Met Ser Ser Tyr Ala
  1               5                  10                  15

Phe Phe Val Gln Thr Cys Arg Asn Glu His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 31
<211> LENGTH: 84
<212> TYPE: PRT
<213> ORGANISM: homo sapiens

<400> SEQUENCE: 31

Gly Lys Gly Asp Pro Lys Lys Pro Arg Gly Lys Met Ser Ser Tyr Ala
  1               5                  10                  15

Phe Phe Val Gln Thr Cys Arg Glu Gln His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 32
<211> LENGTH: 84
<212> TYPE: PRT
<213> ORGANISM: homo sapiens

<400> SEQUENCE: 32

Gly Lys Gly Asp Pro Lys Lys Pro Arg Gly Lys Met Ser Ser Tyr Ala
  1               5                  10                  15

Phe Phe Val Gln Thr Cys Arg Glu His His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro

```
                65                  70                  75                  80
Lys Gly Glu Thr

<210> SEQ ID NO 33
<211> LENGTH: 84
<212> TYPE: PRT
<213> ORGANISM: homo sapiens

<400> SEQUENCE: 33

Gly Lys Gly Asp Pro Lys Lys Pro Arg Gly Lys Met Ser Ser Tyr Ala
1               5                   10                  15
Phe Phe Val Gln Thr Cys Arg Glu Asn His Lys Lys His Pro Asp
                20                  25                  30
Ala Ser Val Asn Phe Ser Glu Phe Ser Lys Lys Cys Ser Glu Arg Trp
            35                  40                  45
Lys Thr Met Ser Ala Lys Glu Lys Gly Lys Phe Glu Asp Met Ala Lys
        50                  55                  60
Ala Asp Lys Ala Arg Tyr Glu Arg Glu Met Lys Thr Tyr Ile Pro Pro
65                  70                  75                  80
Lys Gly Glu Thr

<210> SEQ ID NO 34
<211> LENGTH: 84
<212> TYPE: PRT
<213> ORGANISM: homo sapiens

<400> SEQUENCE: 34

Gly Lys Gly Asp Pro Lys Lys Pro Arg Gly Lys Met Ser Ser Tyr Ala
1               5                   10                  15
Phe Phe Val Gln Thr Cys Arg Glu Glu His Asn Lys Lys His Pro Asp
                20                  25                  30
Ala Ser Val Asn Phe Ser Glu Phe Ser Lys Lys Cys Ser Glu Arg Trp
            35                  40                  45
Lys Thr Met Ser Ala Lys Glu Lys Gly Lys Phe Glu Asp Met Ala Lys
        50                  55                  60
Ala Asp Lys Ala Arg Tyr Glu Arg Glu Met Lys Thr Tyr Ile Pro Pro
65                  70                  75                  80
Lys Gly Glu Thr

<210> SEQ ID NO 35
<211> LENGTH: 84
<212> TYPE: PRT
<213> ORGANISM: homo sapiens

<400> SEQUENCE: 35

Gly Lys Gly Asp Pro Lys Lys Pro Arg Gly Lys Met Ser Ser Tyr Ala
1               5                   10                  15
Phe Phe Val Gln Thr Cys Arg Glu Glu His Gln Lys Lys His Pro Asp
                20                  25                  30
Ala Ser Val Asn Phe Ser Glu Phe Ser Lys Lys Cys Ser Glu Arg Trp
            35                  40                  45
Lys Thr Met Ser Ala Lys Glu Lys Gly Lys Phe Glu Asp Met Ala Lys
        50                  55                  60
Ala Asp Lys Ala Arg Tyr Glu Arg Glu Met Lys Thr Tyr Ile Pro Pro
65                  70                  75                  80
Lys Gly Glu Thr
```

<210> SEQ ID NO 36
<211> LENGTH: 84
<212> TYPE: PRT
<213> ORGANISM: homo sapiens

<400> SEQUENCE: 36

Gly Lys Gly Asp Pro Lys Lys Pro Arg Gly Lys Met Ser Ser Tyr Ala
1               5                   10                  15

Phe Phe Val Gln Thr Cys Arg Glu Glu His Asn Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 37
<211> LENGTH: 84
<212> TYPE: PRT
<213> ORGANISM: homo sapiens

<400> SEQUENCE: 37

Gly Lys Gly Asp Pro Lys Lys Pro Arg Gly Lys Met Ser Ser Tyr Ala
1               5                   10                  15

Phe Phe Val Gln Thr Cys Arg Glu Glu His Gln Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 38
<211> LENGTH: 84
<212> TYPE: PRT
<213> ORGANISM: homo sapiens

<400> SEQUENCE: 38

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Asn His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 39
<211> LENGTH: 84
<212> TYPE: PRT
<213> ORGANISM: homo sapiens -continued

<400> SEQUENCE: 39

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Gln His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 40
<211> LENGTH: 84
<212> TYPE: PRT
<213> ORGANISM: homo sapiens

<400> SEQUENCE: 40

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Ala Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 41
<211> LENGTH: 84
<212> TYPE: PRT
<213> ORGANISM: homo sapiens

<400> SEQUENCE: 41

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Ser Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 42
<211> LENGTH: 84
<212> TYPE: PRT
<213> ORGANISM: homo sapiens

<400> SEQUENCE: 42

Gly Lys Gly Asp Pro Lys Lys Pro Arg Gly Lys Met Ser Ser Tyr Ala
1               5                   10                  15

```
Phe Phe Val Gln Thr Cys Arg Glu Glu His Lys Lys Lys His Pro Asn
             20                  25                  30
Ala Ser Val Asn Phe Ser Glu Phe Ser Lys Lys Cys Ser Glu Arg Trp
         35                  40                  45
Lys Thr Met Ser Ala Lys Glu Lys Gly Lys Phe Glu Asp Met Ala Lys
     50                  55                  60
Ala Asp Lys Ala Arg Tyr Glu Arg Glu Met Lys Thr Tyr Ile Pro Pro
 65                  70                  75                  80
Lys Gly Glu Thr

<210> SEQ ID NO 43
<211> LENGTH: 84
<212> TYPE: PRT
<213> ORGANISM: homo sapiens

<400> SEQUENCE: 43

Gly Lys Gly Asp Pro Lys Lys Pro Arg Gly Lys Met Ser Ser Tyr Ala
 1               5                  10                  15
Phe Phe Val Gln Thr Cys Arg Glu Glu His Lys Lys Lys His Pro Gln
             20                  25                  30
Ala Ser Val Asn Phe Ser Glu Phe Ser Lys Lys Cys Ser Glu Arg Trp
         35                  40                  45
Lys Thr Met Ser Ala Lys Glu Lys Gly Lys Phe Glu Asp Met Ala Lys
     50                  55                  60
Ala Asp Lys Ala Arg Tyr Glu Arg Glu Met Lys Thr Tyr Ile Pro Pro
 65                  70                  75                  80
Lys Gly Glu Thr

<210> SEQ ID NO 44
<211> LENGTH: 84
<212> TYPE: PRT
<213> ORGANISM: homo sapiens

<400> SEQUENCE: 44

Gly Lys Gly Asp Pro Lys Lys Pro Arg Gly Lys Met Ser Ser Tyr Ala
 1               5                  10                  15
Phe Phe Val Gln Thr Cys Arg Glu Glu His Lys Lys Lys His Pro Asp
             20                  25                  30
Ala Ser Val Asn Ile Ser Glu Phe Ser Lys Lys Cys Ser Glu Arg Trp
         35                  40                  45
Lys Thr Met Ser Ala Lys Glu Lys Gly Lys Phe Glu Asp Met Ala Lys
     50                  55                  60
Ala Asp Lys Ala Arg Tyr Glu Arg Glu Met Lys Thr Tyr Ile Pro Pro
 65                  70                  75                  80
Lys Gly Glu Thr

<210> SEQ ID NO 45
<211> LENGTH: 84
<212> TYPE: PRT
<213> ORGANISM: homo sapiens

<400> SEQUENCE: 45

Gly Lys Gly Asp Pro Lys Lys Pro Arg Gly Lys Met Ser Ser Tyr Ala
 1               5                  10                  15
Phe Phe Val Gln Thr Cys Arg Glu Glu His Lys Lys Lys His Pro Asp
             20                  25                  30
Ala Ser Val Asn Val Ser Glu Phe Ser Lys Lys Cys Ser Glu Arg Trp
         35                  40                  45
```

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 46
<211> LENGTH: 84
<212> TYPE: PRT
<213> ORGANISM: homo sapiens

<400> SEQUENCE: 46

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Gln Phe Ser Lys Lys Cys Ser Glu Arg Trp
            35                  40                  45

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 47
<211> LENGTH: 84
<212> TYPE: PRT
<213> ORGANISM: homo sapiens

<400> SEQUENCE: 47

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser His Phe Ser Lys Lys Cys Ser Glu Arg Trp
            35                  40                  45

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 48
<211> LENGTH: 84
<212> TYPE: PRT
<213> ORGANISM: homo sapiens

<400> SEQUENCE: 48

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Asn Phe Ser Lys Lys Cys Ser Glu Arg Trp
            35                  40                  45

Lys Thr Met Ser Ala Lys Glu Lys Gly Lys Phe Glu Asp Met Ala Lys
            50                  55                  60

Ala Asp Lys Ala Arg Tyr Glu Arg Glu Met Lys Thr Tyr Ile Pro Pro

```
                 65                  70                  75                  80
Lys Gly Glu Thr

<210> SEQ ID NO 49
<211> LENGTH: 84
<212> TYPE: PRT
<213> ORGANISM: homo sapiens

<400> SEQUENCE: 49

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Ile Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 50
<211> LENGTH: 84
<212> TYPE: PRT
<213> ORGANISM: homo sapiens

<400> SEQUENCE: 50

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Val Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 51
<211> LENGTH: 84
<212> TYPE: PRT
<213> ORGANISM: homo sapiens

<400> SEQUENCE: 51

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Asn Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr
```

```
<210> SEQ ID NO 52
<211> LENGTH: 84
<212> TYPE: PRT
<213> ORGANISM: homo sapiens

<400> SEQUENCE: 52

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Gln Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 53
<211> LENGTH: 84
<212> TYPE: PRT
<213> ORGANISM: homo sapiens

<400> SEQUENCE: 53

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Asn Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 54
<211> LENGTH: 84
<212> TYPE: PRT
<213> ORGANISM: homo sapiens

<400> SEQUENCE: 54

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Gln Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 55
<211> LENGTH: 84
<212> TYPE: PRT
<213> ORGANISM: homo sapiens
```

-continued

<400> SEQUENCE: 55

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Gln Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 56
<211> LENGTH: 84
<212> TYPE: PRT
<213> ORGANISM: homo sapiens

<400> SEQUENCE: 56

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser His Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 57
<211> LENGTH: 84
<212> TYPE: PRT
<213> ORGANISM: homo sapiens

<400> SEQUENCE: 57

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Asn Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 58
<211> LENGTH: 84
<212> TYPE: PRT
<213> ORGANISM: homo sapiens

<400> SEQUENCE: 58

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu His Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 59
<211> LENGTH: 84
<212> TYPE: PRT
<213> ORGANISM: homo sapiens

<400> SEQUENCE: 59

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Gln Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 60
<211> LENGTH: 84
<212> TYPE: PRT
<213> ORGANISM: homo sapiens

<400> SEQUENCE: 60

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Tyr
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 61
<211> LENGTH: 84
<212> TYPE: PRT
<213> ORGANISM: homo sapiens

<400> SEQUENCE: 61

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Ser
        35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 62
<211> LENGTH: 84
<212> TYPE: PRT
<213> ORGANISM: homo sapiens

<400> SEQUENCE: 62

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Asn Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 63
<211> LENGTH: 84
<212> TYPE: PRT
<213> ORGANISM: homo sapiens

<400> SEQUENCE: 63

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Gln Thr Met Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 64
<211> LENGTH: 84
<212> TYPE: PRT
<213> ORGANISM: homo sapiens

<400> SEQUENCE: 64

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Ile Ser Ala Lys Glu Lys Gly Lys Phe Glu Asp Met Ala Lys
        50                  55                  60

Ala Asp Lys Ala Arg Tyr Glu Arg Glu Met Lys Thr Tyr Ile Pro Pro

```
65                  70                  75                  80
Lys Gly Glu Thr

<210> SEQ ID NO 65
<211> LENGTH: 84
<212> TYPE: PRT
<213> ORGANISM: homo sapiens

<400> SEQUENCE: 65

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Val Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 66
<211> LENGTH: 84
<212> TYPE: PRT
<213> ORGANISM: homo sapiens

<400> SEQUENCE: 66

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Asn Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 67
<211> LENGTH: 84
<212> TYPE: PRT
<213> ORGANISM: homo sapiens

<400> SEQUENCE: 67

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Gln Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr
```

```
<210> SEQ ID NO 68
<211> LENGTH: 84
<212> TYPE: PRT
<213> ORGANISM: homo sapiens

<400> SEQUENCE: 68

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Gln Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 69
<211> LENGTH: 84
<212> TYPE: PRT
<213> ORGANISM: homo sapiens

<400> SEQUENCE: 69

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys His Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 70
<211> LENGTH: 84
<212> TYPE: PRT
<213> ORGANISM: homo sapiens

<400> SEQUENCE: 70

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Asn Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 71
<211> LENGTH: 84
<212> TYPE: PRT
<213> ORGANISM: homo sapiens
```

<400> SEQUENCE: 71

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Asn Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 72
<211> LENGTH: 84
<212> TYPE: PRT
<213> ORGANISM: homo sapiens

<400> SEQUENCE: 72

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Gln Gly Lys Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 73
<211> LENGTH: 84
<212> TYPE: PRT
<213> ORGANISM: homo sapiens

<400> SEQUENCE: 73

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Asn Phe Glu Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 74
<211> LENGTH: 84
<212> TYPE: PRT
<213> ORGANISM: homo sapiens

<400> SEQUENCE: 74

Gly Lys Gly Asp Pro Lys Lys Pro Arg Gly Lys Met Ser Ser Tyr Ala
1               5                   10                  15

```
Phe Phe Val Gln Thr Cys Arg Glu Glu His Lys Lys Lys His Pro Asp
             20                  25                  30

Ala Ser Val Asn Phe Ser Glu Phe Ser Lys Lys Cys Ser Glu Arg Trp
         35                  40                  45

Lys Thr Met Ser Ala Lys Glu Lys Gly Gln Phe Glu Asp Met Ala Lys
     50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 75
<211> LENGTH: 84
<212> TYPE: PRT
<213> ORGANISM: homo sapiens

<400> SEQUENCE: 75

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
             20                  25                  30

Ala Ser Val Asn Phe Ser Glu Phe Ser Lys Lys Cys Ser Glu Arg Trp
         35                  40                  45

Lys Thr Met Ser Ala Lys Glu Lys Gly Lys Ile Glu Asp Met Ala Lys
     50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 76
<211> LENGTH: 84
<212> TYPE: PRT
<213> ORGANISM: homo sapiens

<400> SEQUENCE: 76

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
             20                  25                  30

Ala Ser Val Asn Phe Ser Glu Phe Ser Lys Lys Cys Ser Glu Arg Trp
         35                  40                  45

Lys Thr Met Ser Ala Lys Glu Lys Gly Lys Val Glu Asp Met Ala Lys
     50                  55                  60

Ala Asp Lys Ala Arg Tyr Glu Arg Glu Met Lys Thr Tyr Ile Pro Pro
 65                  70                  75                  80

Lys Gly Glu Thr

<210> SEQ ID NO 77
<211> LENGTH: 84
<212> TYPE: PRT
<213> ORGANISM: homo sapiens

<400> SEQUENCE: 77

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
             20                  25                  30

Ala Ser Val Asn Phe Ser Glu Phe Ser Lys Lys Cys Ser Glu Arg Trp
         35                  40                  45
```

```
Lys Thr Met Ser Ala Lys Glu Lys Gly Lys Phe Gln Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 78
<211> LENGTH: 84
<212> TYPE: PRT
<213> ORGANISM: homo sapiens

<400> SEQUENCE: 78

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe His Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 79
<211> LENGTH: 84
<212> TYPE: PRT
<213> ORGANISM: homo sapiens

<400> SEQUENCE: 79

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Asn Asp Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 80
<211> LENGTH: 84
<212> TYPE: PRT
<213> ORGANISM: homo sapiens

<400> SEQUENCE: 80

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asn Met Ala Lys
        50                  55                  60

Ala Asp Lys Ala Arg Tyr Glu Arg Glu Met Lys Thr Tyr Ile Pro Pro
```

```
                65                  70                  75                  80
Lys Gly Glu Thr

<210> SEQ ID NO 81
<211> LENGTH: 84
<212> TYPE: PRT
<213> ORGANISM: homo sapiens

<400> SEQUENCE: 81

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Gln Met Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 82
<211> LENGTH: 84
<212> TYPE: PRT
<213> ORGANISM: homo sapiens

<400> SEQUENCE: 82

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Ile Ala Lys
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 83
<211> LENGTH: 84
<212> TYPE: PRT
<213> ORGANISM: homo sapiens

<400> SEQUENCE: 83

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Val Ala Lys
        50                  55                  60

Ala Asp Lys Ala Arg Tyr Glu Arg Glu Met Lys Thr Tyr Ile Pro Pro
65                  70                  75                  80

Lys Gly Glu Thr
```

<210> SEQ ID NO 84
<211> LENGTH: 84
<212> TYPE: PRT
<213> ORGANISM: homo sapiens

<400> SEQUENCE: 84

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Asn
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 85
<211> LENGTH: 84
<212> TYPE: PRT
<213> ORGANISM: homo sapiens

<400> SEQUENCE: 85

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Gln
        50                  55                  60

Ala Asp Lys Ala Arg Tyr Glu Arg Glu Met Lys Thr Tyr Ile Pro Pro
65                  70                  75                  80

Lys Gly Glu Thr

<210> SEQ ID NO 86
<211> LENGTH: 84
<212> TYPE: PRT
<213> ORGANISM: homo sapiens

<400> SEQUENCE: 86

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asn Lys Ala Arg Tyr Glu Arg Glu Met Lys Thr Tyr Ile Pro Pro
65                  70                  75                  80

Lys Gly Glu Thr

<210> SEQ ID NO 87
<211> LENGTH: 84
<212> TYPE: PRT
<213> ORGANISM: homo sapiens

```
<400> SEQUENCE: 87

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Gln Lys Ala Arg Tyr Glu Arg Glu Met Lys Thr Tyr Ile Pro Pro
65                  70                  75                  80

Lys Gly Glu Thr

<210> SEQ ID NO 88
<211> LENGTH: 84
<212> TYPE: PRT
<213> ORGANISM: homo sapiens

<400> SEQUENCE: 88

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Asn Ala Arg Tyr Glu Arg Glu Met Lys Thr Tyr Ile Pro Pro
65                  70                  75                  80

Lys Gly Glu Thr

<210> SEQ ID NO 89
<211> LENGTH: 84
<212> TYPE: PRT
<213> ORGANISM: homo sapiens

<400> SEQUENCE: 89

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Gln Ala Arg Tyr Glu Arg Glu Met Lys Thr Tyr Ile Pro Pro
65                  70                  75                  80

Lys Gly Glu Thr

<210> SEQ ID NO 90
<211> LENGTH: 84
<212> TYPE: PRT
<213> ORGANISM: homo sapiens

<400> SEQUENCE: 90

Gly Lys Gly Asp Pro Lys Lys Pro Arg Gly Lys Met Ser Ser Tyr Ala
1               5                   10                  15
```

Phe Phe Val Gln Thr Cys Arg Glu Glu His Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
 50                  55                  60

Ala Asp Lys Ala His Tyr Glu Arg Glu Met Lys Thr Tyr Ile Pro Pro
 65                  70                  75                  80

Lys Gly Glu Thr

<210> SEQ ID NO 91
<211> LENGTH: 84
<212> TYPE: PRT
<213> ORGANISM: homo sapiens

<400> SEQUENCE: 91

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
 50                  55                  60

Ala Asp Lys Ala Gln Tyr Glu Arg Glu Met Lys Thr Tyr Ile Pro Pro
 65                  70                  75                  80

Lys Gly Glu Thr

<210> SEQ ID NO 92
<211> LENGTH: 84
<212> TYPE: PRT
<213> ORGANISM: homo sapiens

<400> SEQUENCE: 92

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
 50                  55                  60

Ala Asp Lys Ala Arg His Glu Arg Glu Met Lys Thr Tyr Ile Pro Pro
 65                  70                  75                  80

Lys Gly Glu Thr

<210> SEQ ID NO 93
<211> LENGTH: 84
<212> TYPE: PRT
<213> ORGANISM: homo sapiens

<400> SEQUENCE: 93

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                 20                  25                  30

Ala Ser Val Asn Phe Ser Glu Phe Ser Lys Lys Cys Ser Glu Arg Trp
             35                  40                  45

Lys Thr Met Ser Ala Lys Glu Lys Gly Lys Phe Glu Asp Met Ala Lys
            50                  55                  60

Ala Asp Lys Ala Arg Ile Glu Arg Glu Met Lys Thr Tyr Ile Pro Pro
 65                  70                  75                  80

Lys Gly Glu Thr

<210> SEQ ID NO 94
<211> LENGTH: 84
<212> TYPE: PRT
<213> ORGANISM: homo sapiens

<400> SEQUENCE: 94

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
            50                  55                  60

Ala Asp Lys Ala Arg Tyr Gln Arg Glu Met Lys Thr Tyr Ile Pro Pro
 65                  70                  75                  80

Lys Gly Glu Thr

<210> SEQ ID NO 95
<211> LENGTH: 84
<212> TYPE: PRT
<213> ORGANISM: homo sapiens

<400> SEQUENCE: 95

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
            50                  55                  60

Ala Asp Lys Ala Arg Tyr His Arg Glu Met Lys Thr Tyr Ile Pro Pro
 65                  70                  75                  80

Lys Gly Glu Thr

<210> SEQ ID NO 96
<211> LENGTH: 84
<212> TYPE: PRT
<213> ORGANISM: homo sapiens

<400> SEQUENCE: 96

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
                20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
            50                  55                  60

Ala Asp Lys Ala Arg Tyr Asn Arg Glu Met Lys Thr Tyr Ile Pro Pro

Lys Gly Glu Thr

<210> SEQ ID NO 97
<211> LENGTH: 84
<212> TYPE: PRT
<213> ORGANISM: homo sapiens

<400> SEQUENCE: 97

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu His Glu Met Lys Thr Tyr Ile Pro Pro
65                  70                  75                  80

Lys Gly Glu Thr

<210> SEQ ID NO 98
<211> LENGTH: 84
<212> TYPE: PRT
<213> ORGANISM: homo sapiens

<400> SEQUENCE: 98

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Gln Glu Met Lys Thr Tyr Ile Pro Pro
65                  70                  75                  80

Lys Gly Glu Thr

<210> SEQ ID NO 99
<211> LENGTH: 84
<212> TYPE: PRT
<213> ORGANISM: homo sapiens

<400> SEQUENCE: 99

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Gln Met Lys Thr Tyr Ile Pro Pro
65                  70                  75                  80

Lys Gly Glu Thr

<210> SEQ ID NO 100
<211> LENGTH: 84
<212> TYPE: PRT
<213> ORGANISM: homo sapiens

<400> SEQUENCE: 100

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg His Met Lys Thr Tyr Ile Pro Pro
65                  70                  75                  80

Lys Gly Glu Thr

<210> SEQ ID NO 101
<211> LENGTH: 84
<212> TYPE: PRT
<213> ORGANISM: homo sapiens

<400> SEQUENCE: 101

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Asn Met Lys Thr Tyr Ile Pro Pro
65                  70                  75                  80

Lys Gly Glu Thr

<210> SEQ ID NO 102
<211> LENGTH: 84
<212> TYPE: PRT
<213> ORGANISM: homo sapiens

<400> SEQUENCE: 102

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
            35                  40                  45

Lys Thr Met Ser Ala Lys Glu Lys Gly Lys Phe Glu Asp Met Ala Lys
        50                  55                  60

Ala Asp Lys Ala Arg Tyr Glu Arg Glu Ile Lys Thr Tyr Ile Pro Pro
65                  70                  75                  80

Lys Gly Glu Thr

<210> SEQ ID NO 103
<211> LENGTH: 84
<212> TYPE: PRT
<213> ORGANISM: homo sapiens -continued

```
<400> SEQUENCE: 103

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Val Lys Thr Tyr Ile Pro Pro
65                  70                  75                  80

Lys Gly Glu Thr

<210> SEQ ID NO 104
<211> LENGTH: 84
<212> TYPE: PRT
<213> ORGANISM: homo sapiens

<400> SEQUENCE: 104

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Asn Thr Tyr Ile Pro Pro
65                  70                  75                  80

Lys Gly Glu Thr

<210> SEQ ID NO 105
<211> LENGTH: 84
<212> TYPE: PRT
<213> ORGANISM: homo sapiens

<400> SEQUENCE: 105

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Gln Thr Tyr Ile Pro Pro
65                  70                  75                  80

Lys Gly Glu Thr

<210> SEQ ID NO 106
<211> LENGTH: 84
<212> TYPE: PRT
<213> ORGANISM: homo sapiens

<400> SEQUENCE: 106

Gly Lys Gly Asp Pro Lys Lys Pro Arg Gly Lys Met Ser Ser Tyr Ala
1               5                   10                  15
```

```
Phe Phe Val Gln Thr Cys Arg Glu Glu His Lys Lys Lys His Pro Asp
             20                  25                  30

Ala Ser Val Asn Phe Ser Glu Phe Ser Lys Lys Cys Ser Glu Arg Trp
         35                  40                  45

Lys Thr Met Ser Ala Lys Glu Lys Gly Lys Phe Glu Asp Met Ala Lys
     50                  55                  60

Ala Asp Lys Ala Arg Tyr Glu Arg Glu Met Lys Thr His Ile Pro Pro
 65                  70                  75                  80

Lys Gly Glu Thr

<210> SEQ ID NO 107
<211> LENGTH: 84
<212> TYPE: PRT
<213> ORGANISM: homo sapiens

<400> SEQUENCE: 107

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
             20                  25                  30

Ala Ser Val Asn Phe Ser Glu Phe Ser Lys Lys Cys Ser Glu Arg Trp
         35                  40                  45

Lys Thr Met Ser Ala Lys Glu Lys Gly Lys Phe Glu Asp Met Ala Lys
     50                  55                  60

Ala Asp Lys Ala Arg Tyr Glu Arg Glu Met Lys Thr Ile Ile Pro Pro
 65                  70                  75                  80

Lys Gly Glu Thr

<210> SEQ ID NO 108
<211> LENGTH: 84
<212> TYPE: PRT
<213> ORGANISM: homo sapiens

<400> SEQUENCE: 108

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
             20                  25                  30

Ala Ser Val Asn Phe Ser Glu Phe Ser Lys Lys Cys Ser Glu Arg Trp
         35                  40                  45

Lys Thr Met Ser Ala Lys Glu Lys Gly Lys Phe Glu Asp Met Ala Lys
     50                  55                  60

Ala Asp Lys Ala Arg Tyr Glu Arg Glu Met Lys Thr Tyr Ile Ala Pro
 65                  70                  75                  80

Lys Gly Glu Thr

<210> SEQ ID NO 109
<211> LENGTH: 84
<212> TYPE: PRT
<213> ORGANISM: homo sapiens

<400> SEQUENCE: 109

Gly Lys Gly Asp Pro Lys Lys Pro Arg Gly Lys Met Ser Ser Tyr Ala
 1               5                  10                  15

Phe Phe Val Gln Thr Cys Arg Glu Glu His Lys Lys Lys His Pro Asp
             20                  25                  30

Ala Ser Val Asn Phe Ser Glu Phe Ser Lys Lys Cys Ser Glu Arg Trp
         35                  40                  45
```

```
Lys Thr Met Ser Ala Lys Glu Lys Gly Lys Phe Glu Asp Met Ala Lys
         50                  55                  60
Ala Asp Lys Ala Arg Tyr Glu Arg Glu Met Lys Thr Tyr Ile Ser Pro
 65                  70                  75                  80
Lys Gly Glu Thr

<210> SEQ ID NO 110
<211> LENGTH: 84
<212> TYPE: PRT
<213> ORGANISM: homo sapiens

<400> SEQUENCE: 110

Gly Lys Gly Asp Pro Lys Lys Pro Arg Gly Lys Met Ser Ser Tyr Ala
 1                5                  10                  15
Phe Phe Val Gln Thr Cys Arg Glu Glu His Lys Lys Lys His Pro Asp
                 20                  25                  30
Ala Ser Val Asn Phe Ser Glu Phe Ser Lys Lys Cys Ser Glu Arg Trp
             35                  40                  45
Lys Thr Met Ser Ala Lys Glu Lys Gly Lys Phe Glu Asp Met Ala Lys
         50                  55                  60
Ala Asp Lys Ala Arg Tyr Glu Arg Glu Met Lys Thr Tyr Ile Pro Ala
 65                  70                  75                  80
Lys Gly Glu Thr

<210> SEQ ID NO 111
<211> LENGTH: 84
<212> TYPE: PRT
<213> ORGANISM: homo sapiens

<400> SEQUENCE: 111

Gly Lys Gly Asp Pro Lys Lys Pro Arg Gly Lys Met Ser Ser Tyr Ala
 1                5                  10                  15
Phe Phe Val Gln Thr Cys Arg Glu Glu His Lys Lys Lys His Pro Asp
                 20                  25                  30
Ala Ser Val Asn Phe Ser Glu Phe Ser Lys Lys Cys Ser Glu Arg Trp
             35                  40                  45
Lys Thr Met Ser Ala Lys Glu Lys Gly Lys Phe Glu Asp Met Ala Lys
         50                  55                  60
Ala Asp Lys Ala Arg Tyr Glu Arg Glu Met Lys Thr Tyr Ile Pro Ser
 65                  70                  75                  80
Lys Gly Glu Thr

<210> SEQ ID NO 112
<211> LENGTH: 84
<212> TYPE: PRT
<213> ORGANISM: homo sapiens

<400> SEQUENCE: 112

Gly Lys Gly Asp Pro Lys Lys Pro Arg Gly Lys Met Ser Ser Tyr Ala
 1                5                  10                  15
Phe Phe Val Gln Thr Cys Arg Glu Glu His Lys Lys Lys His Pro Asp
                 20                  25                  30
Ala Ser Val Asn Phe Ser Glu Phe Ser Lys Lys Cys Ser Glu Arg Trp
             35                  40                  45
Lys Thr Met Ser Ala Lys Glu Lys Gly Lys Phe Glu Asp Met Ala Lys
         50                  55                  60
Ala Asp Lys Ala Arg Tyr Glu Arg Glu Met Lys Thr Tyr Ile Pro Pro
```

Asn Gly Glu Thr
            65              70              75              80

<210> SEQ ID NO 113
<211> LENGTH: 84
<212> TYPE: PRT
<213> ORGANISM: homo sapiens

<400> SEQUENCE: 113

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Gln Gly Glu Thr

<210> SEQ ID NO 114
<211> LENGTH: 84
<212> TYPE: PRT
<213> ORGANISM: homo sapiens

<400> SEQUENCE: 114

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Gln Thr

<210> SEQ ID NO 115
<211> LENGTH: 84
<212> TYPE: PRT
<213> ORGANISM: homo sapiens

<400> SEQUENCE: 115

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly His Thr

```
<210> SEQ ID NO 116
<211> LENGTH: 84
<212> TYPE: PRT
<213> ORGANISM: homo sapiens

<400> SEQUENCE: 116

Gly Lys Gly Asp Pro Lys Lys Pro Arg Gly Lys Met Ser Ser Tyr Ala
1               5                   10                  15

Phe Phe Val Gln Thr Cys Arg Glu Glu His Lys Lys His Pro Asp
            20                  25                  30

Ala Ser Val Asn Phe Ser Glu Phe Ser Lys Lys Cys Ser Glu Arg Trp
        35                  40                  45

Lys Thr Met Ser Ala Lys Glu Lys Gly Lys Phe Glu Asp Met Ala Lys
    50                  55                  60

Ala Asp Lys Ala Arg Tyr Glu Arg Glu Met Lys Thr Tyr Ile Pro Pro
65                  70                  75                  80

Lys Gly Asn Thr

<210> SEQ ID NO 117
<211> LENGTH: 77
<212> TYPE: PRT
<213> ORGANISM: homo sapiens

<400> SEQUENCE: 117

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 118
<211> LENGTH: 77
<212> TYPE: PRT
<213> ORGANISM: homo sapiens

<400> SEQUENCE: 118

Ala Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 119
<211> LENGTH: 77
<212> TYPE: PRT
<213> ORGANISM: homo sapiens

<400> SEQUENCE: 119

Ser Arg Gly Lys Met Ser Ser Tyr Ala Phe Phe Val Gln Thr Cys Arg
1               5                   10                  15
```

```
Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 120
<211> LENGTH: 77
<212> TYPE: PRT
<213> ORGANISM: homo sapiens

<400> SEQUENCE: 120

Pro His Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 121
<211> LENGTH: 77
<212> TYPE: PRT
<213> ORGANISM: homo sapiens

<400> SEQUENCE: 121

Pro Gln Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 122
<211> LENGTH: 77
<212> TYPE: PRT
<213> ORGANISM: homo sapiens

<400> SEQUENCE: 122

Pro Arg Gly Asn Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
```

```
65                  70                  75

<210> SEQ ID NO 123
<211> LENGTH: 77
<212> TYPE: PRT
<213> ORGANISM: homo sapiens

<400> SEQUENCE: 123

Pro Arg Gly Gln Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 124
<211> LENGTH: 77
<212> TYPE: PRT
<213> ORGANISM: homo sapiens

<400> SEQUENCE: 124

Pro Arg Gly Lys Ile Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 125
<211> LENGTH: 77
<212> TYPE: PRT
<213> ORGANISM: homo sapiens

<400> SEQUENCE: 125

Pro Arg Gly Lys Val Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 126
<211> LENGTH: 77
<212> TYPE: PRT
<213> ORGANISM: homo sapiens

<400> SEQUENCE: 126

Pro Arg Gly Lys Met Ser Ser His Ala Phe Phe Val Gln Thr Cys Arg
```

```
                1               5                   10                  15
Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 127
<211> LENGTH: 77
<212> TYPE: PRT
<213> ORGANISM: homo sapiens

<400> SEQUENCE: 127

Pro Arg Gly Lys Met Ser Ser Ile Ala Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 128
<211> LENGTH: 77
<212> TYPE: PRT
<213> ORGANISM: homo sapiens

<400> SEQUENCE: 128

Pro Arg Gly Lys Met Ser Ser Tyr Ala Ile Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 129
<211> LENGTH: 77
<212> TYPE: PRT
<213> ORGANISM: homo sapiens

<400> SEQUENCE: 129

Pro Arg Gly Lys Met Ser Ser Tyr Ala Val Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
    50                  55                  60
```

Arg Glu Met Lys Thr Tyr Ile Pro Pro Lys Gly Glu Thr
65                  70                  75

<210> SEQ ID NO 130
<211> LENGTH: 77
<212> TYPE: PRT
<213> ORGANISM: homo sapiens

<400> SEQUENCE: 130

Pro Arg Gly Lys Met Ser Ser Tyr Ala Phe Ile Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 131
<211> LENGTH: 77
<212> TYPE: PRT
<213> ORGANISM: homo sapiens

<400> SEQUENCE: 131

Pro Arg Gly Lys Met Ser Ser Tyr Ala Phe Val Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 132
<211> LENGTH: 77
<212> TYPE: PRT
<213> ORGANISM: homo sapiens

<400> SEQUENCE: 132

Pro Arg Gly Lys Met Ser Ser Tyr Ala Phe Phe Val Gln Thr Cys His
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 133
<211> LENGTH: 77
<212> TYPE: PRT
<213> ORGANISM: homo sapiens

<400> SEQUENCE: 133

Pro Arg Gly Lys Met Ser Ser Tyr Ala Phe Phe Val Gln Thr Cys Gln
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65              70                  75

<210> SEQ ID NO 134
<211> LENGTH: 77
<212> TYPE: PRT
<213> ORGANISM: homo sapiens

<400> SEQUENCE: 134

Pro Arg Gly Lys Met Ser Ser Tyr Ala Phe Phe Val Gln Thr Cys Arg
1               5                   10                  15

Gln Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65              70                  75

<210> SEQ ID NO 135
<211> LENGTH: 77
<212> TYPE: PRT
<213> ORGANISM: homo sapiens

<400> SEQUENCE: 135

Pro Arg Gly Lys Met Ser Ser Tyr Ala Phe Phe Val Gln Thr Cys Arg
1               5                   10                  15

His Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65              70                  75

<210> SEQ ID NO 136
<211> LENGTH: 77
<212> TYPE: PRT
<213> ORGANISM: homo sapiens

<400> SEQUENCE: 136

Pro Arg Gly Lys Met Ser Ser Tyr Ala Phe Phe Val Gln Thr Cys Arg
1               5                   10                  15

Asn Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

```
Arg Glu Met Lys Thr Tyr Ile Pro Pro Lys Gly Glu Thr
 65                  70                  75
```

<210> SEQ ID NO 137
<211> LENGTH: 77
<212> TYPE: PRT
<213> ORGANISM: homo sapiens

<400> SEQUENCE: 137

```
Pro Arg Gly Lys Met Ser Ser Tyr Ala Phe Phe Val Gln Thr Cys Arg
 1               5                  10                  15

Glu Gln His Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
             50                  55                  60

Arg Glu Met Lys Thr Tyr Ile Pro Pro Lys Gly Glu Thr
 65                  70                  75
```

<210> SEQ ID NO 138
<211> LENGTH: 77
<212> TYPE: PRT
<213> ORGANISM: homo sapiens

<400> SEQUENCE: 138

```
Pro Arg Gly Lys Met Ser Ser Tyr Ala Phe Phe Val Gln Thr Cys Arg
 1               5                  10                  15

Glu His His Lys Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
             50                  55                  60

Arg Glu Met Lys Thr Tyr Ile Pro Pro Lys Gly Glu Thr
 65                  70                  75
```

<210> SEQ ID NO 139
<211> LENGTH: 77
<212> TYPE: PRT
<213> ORGANISM: homo sapiens

<400> SEQUENCE: 139

```
Pro Arg Gly Lys Met Ser Ser Tyr Ala Phe Phe Val Gln Thr Cys Arg
 1               5                  10                  15

Glu Asn His Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
             50                  55                  60

Arg Glu Met Lys Thr Tyr Ile Pro Pro Lys Gly Glu Thr
 65                  70                  75
```

<210> SEQ ID NO 140
<211> LENGTH: 77
<212> TYPE: PRT
<213> ORGANISM: homo sapiens

<400> SEQUENCE: 140

```
Pro Arg Gly Lys Met Ser Ser Tyr Ala Phe Phe Val Gln Thr Cys Arg
1               5                   10                  15

Glu Glu His Asn Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 141
<211> LENGTH: 77
<212> TYPE: PRT
<213> ORGANISM: homo sapiens

<400> SEQUENCE: 141

Pro Arg Gly Lys Met Ser Ser Tyr Ala Phe Phe Val Gln Thr Cys Arg
1               5                   10                  15

Glu Glu His Gln Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 142
<211> LENGTH: 77
<212> TYPE: PRT
<213> ORGANISM: homo sapiens

<400> SEQUENCE: 142

Pro Arg Gly Lys Met Ser Ser Tyr Ala Phe Phe Val Gln Thr Cys Arg
1               5                   10                  15

Glu Glu His Lys Asn Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 143
<211> LENGTH: 77
<212> TYPE: PRT
<213> ORGANISM: homo sapiens

<400> SEQUENCE: 143

Pro Arg Gly Lys Met Ser Ser Tyr Ala Phe Phe Val Gln Thr Cys Arg
1               5                   10                  15

Glu Glu His Lys Gln Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
```

```
            50                  55                  60
Arg Glu Met Lys Thr Tyr Ile Pro Pro Lys Gly Glu Thr
 65                  70                  75

<210> SEQ ID NO 144
<211> LENGTH: 77
<212> TYPE: PRT
<213> ORGANISM: homo sapiens

<400> SEQUENCE: 144

Pro Arg Gly Lys Met Ser Ser Tyr Ala Phe Phe Val Gln Thr Cys Arg
  1               5                  10                  15

Glu Glu His Lys Lys Asn His Pro Asp Ala Ser Val Asn Phe Ser Glu
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75

<210> SEQ ID NO 145
<211> LENGTH: 77
<212> TYPE: PRT
<213> ORGANISM: homo sapiens

<400> SEQUENCE: 145

Pro Arg Gly Lys Met Ser Ser Tyr Ala Phe Phe Val Gln Thr Cys Arg
  1               5                  10                  15

Glu Glu His Lys Lys Gln His Pro Asp Ala Ser Val Asn Phe Ser Glu
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75

<210> SEQ ID NO 146
<211> LENGTH: 77
<212> TYPE: PRT
<213> ORGANISM: homo sapiens

<400> SEQUENCE: 146

Pro Arg Gly Lys Met Ser Ser Tyr Ala Phe Phe Val Gln Thr Cys Arg
  1               5                  10                  15

Glu Glu His Lys Lys Lys His Ala Asp Ala Ser Val Asn Phe Ser Glu
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
         50                  55                  60

Arg Glu Met Lys Thr Tyr Ile Pro Pro Lys Gly Glu Thr
 65                  70                  75

<210> SEQ ID NO 147
<211> LENGTH: 77
<212> TYPE: PRT
<213> ORGANISM: homo sapiens
```

<400> SEQUENCE: 147

Pro Arg Gly Lys Met Ser Ser Tyr Ala Phe Phe Val Gln Thr Cys Arg
1               5                   10                  15

Glu Glu His Lys Lys His Ser Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 148
<211> LENGTH: 77
<212> TYPE: PRT
<213> ORGANISM: homo sapiens

<400> SEQUENCE: 148

Pro Arg Gly Lys Met Ser Ser Tyr Ala Phe Phe Val Gln Thr Cys Arg
1               5                   10                  15

Glu Glu His Lys Lys His Pro Asn Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 149
<211> LENGTH: 77
<212> TYPE: PRT
<213> ORGANISM: homo sapiens

<400> SEQUENCE: 149

Pro Arg Gly Lys Met Ser Ser Tyr Ala Phe Phe Val Gln Thr Cys Arg
1               5                   10                  15

Glu Glu His Lys Lys His Pro Gln Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 150
<211> LENGTH: 77
<212> TYPE: PRT
<213> ORGANISM: homo sapiens

<400> SEQUENCE: 150

Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Ile Ser Glu
            20                  25                  30

Phe Ser Lys Lys Cys Ser Glu Arg Trp Lys Thr Met Ser Ala Lys Glu
        35                  40                  45

```
Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75
```

<210> SEQ ID NO 151
<211> LENGTH: 77
<212> TYPE: PRT
<213> ORGANISM: homo sapiens

<400> SEQUENCE: 151

```
Pro Arg Gly Lys Met Ser Ser Tyr Ala Phe Phe Val Gln Thr Cys Arg
  1               5                  10                  15

Glu Glu His Lys Lys Lys His Pro Asp Ala Ser Val Asn Val Ser Glu
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75
```

<210> SEQ ID NO 152
<211> LENGTH: 77
<212> TYPE: PRT
<213> ORGANISM: homo sapiens

<400> SEQUENCE: 152

```
Pro Arg Gly Lys Met Ser Ser Tyr Ala Phe Phe Val Gln Thr Cys Arg
  1               5                  10                  15

Glu Glu His Lys Lys Lys His Pro Asp Ala Ser Val Asn Phe Ser Gln
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75
```

<210> SEQ ID NO 153
<211> LENGTH: 77
<212> TYPE: PRT
<213> ORGANISM: homo sapiens

<400> SEQUENCE: 153

```
Pro Arg Gly Lys Met Ser Ser Tyr Ala Phe Phe Val Gln Thr Cys Arg
  1               5                  10                  15

Glu Glu His Lys Lys Lys His Pro Asp Ala Ser Val Asn Phe Ser His
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75
```

<210> SEQ ID NO 154
<211> LENGTH: 77
<212> TYPE: PRT
<213> ORGANISM: homo sapiens

```
<400> SEQUENCE: 154

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Asn
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 155
<211> LENGTH: 77
<212> TYPE: PRT
<213> ORGANISM: homo sapiens

<400> SEQUENCE: 155

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Ile Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 156
<211> LENGTH: 77
<212> TYPE: PRT
<213> ORGANISM: homo sapiens

<400> SEQUENCE: 156

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Val Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 157
<211> LENGTH: 77
<212> TYPE: PRT
<213> ORGANISM: homo sapiens

<400> SEQUENCE: 157

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Asn Lys Cys Ser Glu Arg Trp Lys Thr Met Ser Ala Lys Glu
        35                  40                  45
```

```
Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75
```

<210> SEQ ID NO 158
<211> LENGTH: 77
<212> TYPE: PRT
<213> ORGANISM: homo sapiens

<400> SEQUENCE: 158

```
Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
                20                  25                  30

Phe Ser Gln Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75
```

<210> SEQ ID NO 159
<211> LENGTH: 77
<212> TYPE: PRT
<213> ORGANISM: homo sapiens

<400> SEQUENCE: 159

```
Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
                20                  25                  30

Phe Ser Lys Asn Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75
```

<210> SEQ ID NO 160
<211> LENGTH: 77
<212> TYPE: PRT
<213> ORGANISM: homo sapiens

<400> SEQUENCE: 160

```
Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
                20                  25                  30

Phe Ser Lys Gln Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75
```

<210> SEQ ID NO 161
<211> LENGTH: 77
<212> TYPE: PRT

<213> ORGANISM: homo sapiens

<400> SEQUENCE: 161

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Gln Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 162
<211> LENGTH: 77
<212> TYPE: PRT
<213> ORGANISM: homo sapiens

<400> SEQUENCE: 162

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser His Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 163
<211> LENGTH: 77
<212> TYPE: PRT
<213> ORGANISM: homo sapiens

<400> SEQUENCE: 163

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Asn Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 164
<211> LENGTH: 77
<212> TYPE: PRT
<213> ORGANISM: homo sapiens

<400> SEQUENCE: 164

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu His Trp Lys Thr Met Ser Ala Lys Glu

```
                35                  40                  45
Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 165
<211> LENGTH: 77
<212> TYPE: PRT
<213> ORGANISM: homo sapiens

<400> SEQUENCE: 165

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
                20                  25                  30

Phe Ser Lys Lys Cys Ser Glu Gln Trp Lys Thr Met Ser Ala Lys Glu
            35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 166
<211> LENGTH: 77
<212> TYPE: PRT
<213> ORGANISM: homo sapiens

<400> SEQUENCE: 166

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
                20                  25                  30

Phe Ser Lys Lys Cys Ser Glu Arg Tyr Lys Thr Met Ser Ala Lys Glu
            35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 167
<211> LENGTH: 77
<212> TYPE: PRT
<213> ORGANISM: homo sapiens

<400> SEQUENCE: 167

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
                20                  25                  30

Phe Ser Lys Lys Cys Ser Glu Arg Ser Lys Thr Met Ser Ala Lys Glu
            35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 168
<211> LENGTH: 77
```

```
<212> TYPE: PRT
<213> ORGANISM: homo sapiens

<400> SEQUENCE: 168

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Asn Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 169
<211> LENGTH: 77
<212> TYPE: PRT
<213> ORGANISM: homo sapiens

<400> SEQUENCE: 169

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Gln Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 170
<211> LENGTH: 77
<212> TYPE: PRT
<213> ORGANISM: homo sapiens

<400> SEQUENCE: 170

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Ile Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 171
<211> LENGTH: 77
<212> TYPE: PRT
<213> ORGANISM: homo sapiens

<400> SEQUENCE: 171

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30
```

Phe Ser Lys Lys Cys Ser Glu Arg Trp Lys Thr Val Ser Ala Lys Glu
         35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 172
<211> LENGTH: 77
<212> TYPE: PRT
<213> ORGANISM: homo sapiens

<400> SEQUENCE: 172

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
                 20                  25                  30

Phe Ser Lys Lys Cys Ser Glu Arg Trp Lys Thr Met Ser Ala Asn Glu
         35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 173
<211> LENGTH: 77
<212> TYPE: PRT
<213> ORGANISM: homo sapiens

<400> SEQUENCE: 173

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
                 20                  25                  30

Phe Ser Lys Lys Cys Ser Glu Arg Trp Lys Thr Met Ser Ala Gln Glu
         35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 174
<211> LENGTH: 77
<212> TYPE: PRT
<213> ORGANISM: homo sapiens

<400> SEQUENCE: 174

Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
                 20                  25                  30

Phe Ser Lys Lys Cys Ser Glu Arg Trp Lys Thr Met Ser Ala Lys Gln
         35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 175

<211> LENGTH: 77
<212> TYPE: PRT
<213> ORGANISM: homo sapiens

<400> SEQUENCE: 175

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys His
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 176
<211> LENGTH: 77
<212> TYPE: PRT
<213> ORGANISM: homo sapiens

<400> SEQUENCE: 176

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Asn
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 177
<211> LENGTH: 77
<212> TYPE: PRT
<213> ORGANISM: homo sapiens

<400> SEQUENCE: 177

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Asn Gly Lys Phe Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 178
<211> LENGTH: 77
<212> TYPE: PRT
<213> ORGANISM: homo sapiens

<400> SEQUENCE: 178

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

```
Phe Ser Lys Lys Cys Ser Glu Arg Trp Lys Thr Met Ser Ala Lys Glu
            35                  40                  45

Gln Gly Lys Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75
```

<210> SEQ ID NO 179
<211> LENGTH: 77
<212> TYPE: PRT
<213> ORGANISM: homo sapiens

<400> SEQUENCE: 179

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Asn Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75
```

<210> SEQ ID NO 180
<211> LENGTH: 77
<212> TYPE: PRT
<213> ORGANISM: homo sapiens

<400> SEQUENCE: 180

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Gln Phe Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75
```

<210> SEQ ID NO 181
<211> LENGTH: 77
<212> TYPE: PRT
<213> ORGANISM: homo sapiens

<400> SEQUENCE: 181

```
Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Ile Glu Asp Met Ala Lys Ala Asp Lys Ala Arg Tyr Glu
        50                  55                  60

Arg Glu Met Lys Thr Tyr Ile Pro Pro Lys Gly Glu Thr
65                  70                  75
```

```
<210> SEQ ID NO 182
<211> LENGTH: 77
<212> TYPE: PRT
<213> ORGANISM: homo sapiens

<400> SEQUENCE: 182

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Val Glu Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 183
<211> LENGTH: 77
<212> TYPE: PRT
<213> ORGANISM: homo sapiens

<400> SEQUENCE: 183

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Gln Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 184
<211> LENGTH: 77
<212> TYPE: PRT
<213> ORGANISM: homo sapiens

<400> SEQUENCE: 184

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe His Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 185
<211> LENGTH: 77
<212> TYPE: PRT
<213> ORGANISM: homo sapiens

<400> SEQUENCE: 185

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
```

```
            20                  25                  30

Phe Ser Lys Lys Cys Ser Glu Arg Trp Lys Thr Met Ser Ala Lys Glu
        35                  40                  45

Lys Gly Lys Phe Asn Asp Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 186
<211> LENGTH: 77
<212> TYPE: PRT
<213> ORGANISM: homo sapiens

<400> SEQUENCE: 186

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asn Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 187
<211> LENGTH: 77
<212> TYPE: PRT
<213> ORGANISM: homo sapiens

<400> SEQUENCE: 187

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Gln Met Ala Lys Ala Asp Lys Ala Arg Tyr Glu
    50                  55                  60

Arg Glu Met Lys Thr Tyr Ile Pro Pro Lys Gly Glu Thr
65                  70                  75

<210> SEQ ID NO 188
<211> LENGTH: 77
<212> TYPE: PRT
<213> ORGANISM: homo sapiens

<400> SEQUENCE: 188

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Ile Ala Lys Ala Asp Lys Ala Arg Tyr Glu
    50                  55                  60

Arg Glu Met Lys Thr Tyr Ile Pro Pro Lys Gly Glu Thr
65                  70                  75
```

```
<210> SEQ ID NO 189
<211> LENGTH: 77
<212> TYPE: PRT
<213> ORGANISM: homo sapiens

<400> SEQUENCE: 189

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Val Ala Lys Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 190
<211> LENGTH: 77
<212> TYPE: PRT
<213> ORGANISM: homo sapiens

<400> SEQUENCE: 190

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Asn Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 191
<211> LENGTH: 77
<212> TYPE: PRT
<213> ORGANISM: homo sapiens

<400> SEQUENCE: 191

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
                20                  25                  30

Phe Ser Lys Lys Cys Ser Glu Arg Trp Lys Thr Met Ser Ala Lys Glu
            35                  40                  45

Lys Gly Lys Phe Glu Asp Met Ala Gln Ala Asp Lys Ala Arg Tyr Glu
        50                  55                  60

Arg Glu Met Lys Thr Tyr Ile Pro Pro Lys Gly Glu Thr
65                  70                  75

<210> SEQ ID NO 192
<211> LENGTH: 77
<212> TYPE: PRT
<213> ORGANISM: homo sapiens

<400> SEQUENCE: 192

Pro Arg Gly Lys Met Ser Ser Tyr Ala Phe Phe Val Gln Thr Cys Arg
1               5                   10                  15
```

-continued

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asn Lys Ala Arg Tyr Glu
    50                  55                  60

Arg Glu Met Lys Thr Tyr Ile Pro Pro Lys Gly Glu Thr
65                  70                  75

<210> SEQ ID NO 193
<211> LENGTH: 77
<212> TYPE: PRT
<213> ORGANISM: homo sapiens

<400> SEQUENCE: 193

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Gln Lys Ala Arg Tyr Glu
    50                  55                  60

Arg Glu Met Lys Thr Tyr Ile Pro Pro Lys Gly Glu Thr
65                  70                  75

<210> SEQ ID NO 194
<211> LENGTH: 77
<212> TYPE: PRT
<213> ORGANISM: homo sapiens

<400> SEQUENCE: 194

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Asn Ala Arg Tyr Glu
    50                  55                  60

Arg Glu Met Lys Thr Tyr Ile Pro Pro Lys Gly Glu Thr
65                  70                  75

<210> SEQ ID NO 195
<211> LENGTH: 77
<212> TYPE: PRT
<213> ORGANISM: homo sapiens

<400> SEQUENCE: 195

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Gln Ala Arg Tyr Glu
    50                  55                  60

Arg Glu Met Lys Thr Tyr Ile Pro Pro Lys Gly Glu Thr
65                  70                  75

<210> SEQ ID NO 196
<211> LENGTH: 77
<212> TYPE: PRT
<213> ORGANISM: homo sapiens

<400> SEQUENCE: 196

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala His Tyr Glu
    50                  55                  60

Arg Glu Met Lys Thr Tyr Ile Pro Pro Lys Gly Glu Thr
65                  70                  75

<210> SEQ ID NO 197
<211> LENGTH: 77
<212> TYPE: PRT
<213> ORGANISM: homo sapiens

<400> SEQUENCE: 197

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Gln Tyr Glu
    50                  55                  60

Arg Glu Met Lys Thr Tyr Ile Pro Pro Lys Gly Glu Thr
65                  70                  75

<210> SEQ ID NO 198
<211> LENGTH: 77
<212> TYPE: PRT
<213> ORGANISM: homo sapiens

<400> SEQUENCE: 198

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg His Glu
    50                  55                  60

Arg Glu Met Lys Thr Tyr Ile Pro Pro Lys Gly Glu Thr
65                  70                  75

<210> SEQ ID NO 199
<211> LENGTH: 77
<212> TYPE: PRT
<213> ORGANISM: homo sapiens

<400> SEQUENCE: 199

Pro Arg Gly Lys Met Ser Ser Tyr Ala Phe Phe Val Gln Thr Cys Arg
1               5                   10                  15

```
Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Ile Glu
        50                  55                  60

Arg Glu Met Lys Thr Tyr Ile Pro Pro Lys Gly Glu Thr
65                  70                  75

<210> SEQ ID NO 200
<211> LENGTH: 77
<212> TYPE: PRT
<213> ORGANISM: homo sapiens

<400> SEQUENCE: 200

Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Gln
        50                  55                  60

Arg Glu Met Lys Thr Tyr Ile Pro Pro Lys Gly Glu Thr
65                  70                  75

<210> SEQ ID NO 201
<211> LENGTH: 77
<212> TYPE: PRT
<213> ORGANISM: homo sapiens

<400> SEQUENCE: 201

Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr His
        50                  55                  60

Arg Glu Met Lys Thr Tyr Ile Pro Pro Lys Gly Glu Thr
65                  70                  75

<210> SEQ ID NO 202
<211> LENGTH: 77
<212> TYPE: PRT
<213> ORGANISM: homo sapiens

<400> SEQUENCE: 202

Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
            35                  40                  45

Lys Gly Lys Phe Glu Asp Met Ala Lys Ala Asp Lys Ala Arg Tyr Asn
        50                  55                  60

Arg Glu Met Lys Thr Tyr Ile Pro Pro Lys Gly Glu Thr
```

65                    70                    75

<210> SEQ ID NO 203
<211> LENGTH: 77
<212> TYPE: PRT
<213> ORGANISM: homo sapiens

<400> SEQUENCE: 203

Pro Arg Gly Lys Met Ser Ser Tyr Ala Phe Phe Val Gln Thr Cys Arg
1               5                   10                 15

Glu Glu His Lys Lys Lys His Pro Asp Ala Ser Val Asn Phe Ser Glu
              20                   25                   30

Phe Ser Lys Lys Cys Ser Glu Arg Trp Lys Thr Met Ser Ala Lys Glu
         35                   40                 45

Lys Gly Lys Phe Glu Asp Met Ala Lys Ala Asp Lys Ala Arg Tyr Glu
    50                   55                   60

His Glu Met Lys Thr Tyr Ile Pro Pro Lys Gly Glu Thr
65                    70                    75

<210> SEQ ID NO 204
<211> LENGTH: 77
<212> TYPE: PRT
<213> ORGANISM: homo sapiens

<400> SEQUENCE: 204

Pro Arg Gly Lys Met Ser Ser Tyr Ala Phe Phe Val Gln Thr Cys Arg
1               5                   10                 15

Glu Glu His Lys Lys Lys His Pro Asp Ala Ser Val Asn Phe Ser Glu
              20                   25                   30

Phe Ser Lys Lys Cys Ser Glu Arg Trp Lys Thr Met Ser Ala Lys Glu
         35                   40                 45

Lys Gly Lys Phe Glu Asp Met Ala Lys Ala Asp Lys Ala Arg Tyr Glu
    50                   55                   60

Gln Glu Met Lys Thr Tyr Ile Pro Pro Lys Gly Glu Thr
65                    70                    75

<210> SEQ ID NO 205
<211> LENGTH: 77
<212> TYPE: PRT
<213> ORGANISM: homo sapiens

<400> SEQUENCE: 205

Pro Arg Gly Lys Met Ser Ser Tyr Ala Phe Phe Val Gln Thr Cys Arg
1               5                   10                 15

Glu Glu His Lys Lys Lys His Pro Asp Ala Ser Val Asn Phe Ser Glu
              20                   25                   30

Phe Ser Lys Lys Cys Ser Glu Arg Trp Lys Thr Met Ser Ala Lys Glu
         35                   40                 45

Lys Gly Lys Phe Glu Asp Met Ala Lys Ala Asp Lys Ala Arg Tyr Glu
    50                   55                   60

Arg Gln Met Lys Thr Tyr Ile Pro Pro Lys Gly Glu Thr
65                    70                    75

<210> SEQ ID NO 206
<211> LENGTH: 77
<212> TYPE: PRT
<213> ORGANISM: homo sapiens

<400> SEQUENCE: 206

Pro Arg Gly Lys Met Ser Ser Tyr Ala Phe Phe Val Gln Thr Cys Arg

```
                1               5                  10                 15
Glu Glu His Lys Lys His Pro Asp Ala Ser Val Asn Phe Ser Glu
            20                  25                 30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg His Met Lys Thr Tyr Ile Pro Pro Lys Gly Glu Thr
65                  70                  75

<210> SEQ ID NO 207
<211> LENGTH: 77
<212> TYPE: PRT
<213> ORGANISM: homo sapiens

<400> SEQUENCE: 207

Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Asn Met Lys Thr Tyr Ile Pro Pro Lys Gly Glu Thr
65                  70                  75

<210> SEQ ID NO 208
<211> LENGTH: 77
<212> TYPE: PRT
<213> ORGANISM: homo sapiens

<400> SEQUENCE: 208

Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Ile Lys Thr Tyr Ile Pro Pro Lys Gly Glu Thr
65                  70                  75

<210> SEQ ID NO 209
<211> LENGTH: 77
<212> TYPE: PRT
<213> ORGANISM: homo sapiens

<400> SEQUENCE: 209

Pro Arg Gly Lys Met Ser Ser Tyr Ala Phe Phe Val Gln Thr Cys Arg
1               5                   10                  15

Glu Glu His Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60
```

```
Arg Glu Val Lys Thr Tyr Ile Pro Pro Lys Gly Glu Thr
 65                  70                  75
```

<210> SEQ ID NO 210
<211> LENGTH: 77
<212> TYPE: PRT
<213> ORGANISM: homo sapiens

<400> SEQUENCE: 210

```
Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
         35                  40                  45

Lys Gly Lys Phe Glu Asp Met Ala Lys Ala Asp Lys Ala Arg Tyr Glu
     50                  55                  60

Arg Glu Met Asn Thr Tyr Ile Pro Pro Lys Gly Glu Thr
 65                  70                  75
```

<210> SEQ ID NO 211
<211> LENGTH: 77
<212> TYPE: PRT
<213> ORGANISM: homo sapiens

<400> SEQUENCE: 211

```
Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
         35                  40                  45

Lys Gly Lys Phe Glu Asp Met Ala Lys Ala Asp Lys Ala Arg Tyr Glu
     50                  55                  60

Arg Glu Met Gln Thr Tyr Ile Pro Pro Lys Gly Glu Thr
 65                  70                  75
```

<210> SEQ ID NO 212
<211> LENGTH: 77
<212> TYPE: PRT
<213> ORGANISM: homo sapiens

<400> SEQUENCE: 212

```
Pro Arg Gly Lys Met Ser Ser Tyr Ala Phe Phe Val Gln Thr Cys Arg
 1               5                  10                  15

Glu Glu His Lys Lys Lys His Pro Asp Ala Ser Val Asn Phe Ser Glu
             20                  25                  30

Phe Ser Lys Lys Cys Ser Glu Arg Trp Lys Thr Met Ser Ala Lys Glu
         35                  40                  45

Lys Gly Lys Phe Glu Asp Met Ala Lys Ala Asp Lys Ala Arg Tyr Glu
     50                  55                  60

Arg Glu Met Lys Thr His Ile Pro Pro Lys Gly Glu Thr
 65                  70                  75
```

<210> SEQ ID NO 213
<211> LENGTH: 77
<212> TYPE: PRT
<213> ORGANISM: homo sapiens

<400> SEQUENCE: 213

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Ile Ile Pro Pro Lys Gly Glu Thr
65                  70                  75

<210> SEQ ID NO 214
<211> LENGTH: 77
<212> TYPE: PRT
<213> ORGANISM: homo sapiens

<400> SEQUENCE: 214

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Ala Pro Lys Gly Glu Thr
65                  70                  75

<210> SEQ ID NO 215
<211> LENGTH: 77
<212> TYPE: PRT
<213> ORGANISM: homo sapiens

<400> SEQUENCE: 215

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Ser Pro Lys Gly Glu Thr
65                  70                  75

<210> SEQ ID NO 216
<211> LENGTH: 77
<212> TYPE: PRT
<213> ORGANISM: homo sapiens

<400> SEQUENCE: 216

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Ala Lys Gly Glu Thr
65                  70                  75

<210> SEQ ID NO 217
<211> LENGTH: 77
<212> TYPE: PRT
<213> ORGANISM: homo sapiens

<400> SEQUENCE: 217

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Ser Lys Gly Glu Thr
65                  70                  75

<210> SEQ ID NO 218
<211> LENGTH: 77
<212> TYPE: PRT
<213> ORGANISM: homo sapiens

<400> SEQUENCE: 218

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Asn Gly Glu Thr
65                  70                  75

<210> SEQ ID NO 219
<211> LENGTH: 77
<212> TYPE: PRT
<213> ORGANISM: homo sapiens

<400> SEQUENCE: 219

Pro Arg Gly Lys Met Ser Ser Tyr Ala Phe Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Gln Gly Glu Thr
65                  70                  75

<210> SEQ ID NO 220
<211> LENGTH: 77
<212> TYPE: PRT
<213> ORGANISM: homo sapiens

<400> SEQUENCE: 220

```
Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Gln Thr
65                  70                  75

<210> SEQ ID NO 221
<211> LENGTH: 77
<212> TYPE: PRT
<213> ORGANISM: homo sapiens

<400> SEQUENCE: 221

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly His Thr
65                  70                  75

<210> SEQ ID NO 222
<211> LENGTH: 77
<212> TYPE: PRT
<213> ORGANISM: homo sapiens

<400> SEQUENCE: 222

Pro Arg Gly Lys Met Ser Ser Tyr Ala Phe Val Gln Thr Cys Arg
1               5                   10                  15

Glu Glu His Lys Lys Lys His Pro Asp Ala Ser Val Asn Phe Ser Glu
            20                  25                  30

Phe Ser Lys Lys Cys Ser Glu Arg Trp Lys Thr Met Ser Ala Lys Glu
        35                  40                  45

Lys Gly Lys Phe Glu Asp Met Ala Lys Ala Asp Lys Ala Arg Tyr Glu
    50                  55                  60

Arg Glu Met Lys Thr Tyr Ile Pro Pro Lys Gly Asn Thr
65                  70                  75

<210> SEQ ID NO 223
<211> LENGTH: 54
<212> TYPE: PRT
<213> ORGANISM: homo sapiens

<400> SEQUENCE: 223

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
```

<210> SEQ ID NO 224
<211> LENGTH: 54
<212> TYPE: PRT
<213> ORGANISM: homo sapiens

<400> SEQUENCE: 224

Ala Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 225
<211> LENGTH: 54
<212> TYPE: PRT
<213> ORGANISM: homo sapiens

<400> SEQUENCE: 225

Ser Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 226
<211> LENGTH: 54
<212> TYPE: PRT
<213> ORGANISM: homo sapiens

<400> SEQUENCE: 226

Pro Asn Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 227
<211> LENGTH: 54
<212> TYPE: PRT
<213> ORGANISM: homo sapiens

<400> SEQUENCE: 227

Pro Gln Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

<210> SEQ ID NO 228
<211> LENGTH: 54
<212> TYPE: PRT
<213> ORGANISM: homo sapiens

<400> SEQUENCE: 228

Pro Asp Ala Ser Val Asn Ile Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 229
<211> LENGTH: 54
<212> TYPE: PRT
<213> ORGANISM: homo sapiens

<400> SEQUENCE: 229

Pro Asp Ala Ser Val Asn Val Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 230
<211> LENGTH: 54
<212> TYPE: PRT
<213> ORGANISM: homo sapiens

<400> SEQUENCE: 230

Pro Asp Ala Ser Val Asn Phe Ser Gln Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 231
<211> LENGTH: 54
<212> TYPE: PRT
<213> ORGANISM: homo sapiens

<400> SEQUENCE: 231

Pro Asp Ala Ser Val Asn Phe Ser His Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

-continued

<210> SEQ ID NO 232
<211> LENGTH: 54
<212> TYPE: PRT
<213> ORGANISM: homo sapiens

<400> SEQUENCE: 232

Pro Asp Ala Ser Val Asn Phe Ser Asn Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 233
<211> LENGTH: 54
<212> TYPE: PRT
<213> ORGANISM: homo sapiens

<400> SEQUENCE: 233

Pro Asp Ala Ser Val Asn Phe Ser Glu Ile Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 234
<211> LENGTH: 54
<212> TYPE: PRT
<213> ORGANISM: homo sapiens

<400> SEQUENCE: 234

Pro Asp Ala Ser Val Asn Phe Ser Glu Val Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 235
<211> LENGTH: 54
<212> TYPE: PRT
<213> ORGANISM: homo sapiens

<400> SEQUENCE: 235

Pro Asp Ala Ser Val Asn Phe Ser Glu Phe Ser Asn Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

<210> SEQ ID NO 236
<211> LENGTH: 54
<212> TYPE: PRT
<213> ORGANISM: homo sapiens

<400> SEQUENCE: 236

Pro Asp Ala Ser Val Asn Phe Ser Glu Phe Ser Gln Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 237
<211> LENGTH: 54
<212> TYPE: PRT
<213> ORGANISM: homo sapiens

<400> SEQUENCE: 237

Pro Asp Ala Ser Val Asn Phe Ser Glu Phe Ser Lys Asn Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 238
<211> LENGTH: 54
<212> TYPE: PRT
<213> ORGANISM: homo sapiens

<400> SEQUENCE: 238

Pro Asp Ala Ser Val Asn Phe Ser Glu Phe Ser Lys Gln Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 239
<211> LENGTH: 54
<212> TYPE: PRT
<213> ORGANISM: homo sapiens

<400> SEQUENCE: 239

Pro Asp Ala Ser Val Asn Phe Ser Glu Phe Ser Lys Lys Cys Ser Gln
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

-continued

<210> SEQ ID NO 240
<211> LENGTH: 54
<212> TYPE: PRT
<213> ORGANISM: homo sapiens

<400> SEQUENCE: 240

Pro Asp Ala Ser Val Asn Phe Ser Glu Phe Ser Lys Lys Cys Ser His
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 241
<211> LENGTH: 54
<212> TYPE: PRT
<213> ORGANISM: homo sapiens

<400> SEQUENCE: 241

Pro Asp Ala Ser Val Asn Phe Ser Glu Phe Ser Lys Lys Cys Ser Asn
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 242
<211> LENGTH: 54
<212> TYPE: PRT
<213> ORGANISM: homo sapiens

<400> SEQUENCE: 242

Pro Asp Ala Ser Val Asn Phe Ser Glu Phe Ser Lys Lys Cys Ser Glu
1               5                   10                  15

His Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 243
<211> LENGTH: 54
<212> TYPE: PRT
<213> ORGANISM: homo sapiens

<400> SEQUENCE: 243

Pro Asp Ala Ser Val Asn Phe Ser Glu Phe Ser Lys Lys Cys Ser Glu
1               5                   10                  15

Gln Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

50

<210> SEQ ID NO 244
<211> LENGTH: 54
<212> TYPE: PRT
<213> ORGANISM: homo sapiens

<400> SEQUENCE: 244

Pro Asp Ala Ser Val Asn Phe Ser Glu Phe Ser Lys Lys Cys Ser Glu
1               5                   10                  15

Arg Tyr Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 245
<211> LENGTH: 54
<212> TYPE: PRT
<213> ORGANISM: homo sapiens

<400> SEQUENCE: 245

Pro Asp Ala Ser Val Asn Phe Ser Glu Phe Ser Lys Lys Cys Ser Glu
1               5                   10                  15

Arg Ser Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 246
<211> LENGTH: 54
<212> TYPE: PRT
<213> ORGANISM: homo sapiens

<400> SEQUENCE: 246

Pro Asp Ala Ser Val Asn Phe Ser Glu Phe Ser Lys Lys Cys Ser Glu
1               5                   10                  15

Arg Trp Asn Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 247
<211> LENGTH: 54
<212> TYPE: PRT
<213> ORGANISM: homo sapiens

<400> SEQUENCE: 247

Pro Asp Ala Ser Val Asn Phe Ser Glu Phe Ser Lys Lys Cys Ser Glu
1               5                   10                  15

Arg Trp Gln Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

-continued

<210> SEQ ID NO 248
<211> LENGTH: 54
<212> TYPE: PRT
<213> ORGANISM: homo sapiens

<400> SEQUENCE: 248

Pro Asp Ala Ser Val Asn Phe Ser Glu Phe Ser Lys Lys Cys Ser Glu
1               5                   10                  15

Arg Trp Lys Thr Ile Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 249
<211> LENGTH: 54
<212> TYPE: PRT
<213> ORGANISM: homo sapiens

<400> SEQUENCE: 249

Pro Asp Ala Ser Val Asn Phe Ser Glu Phe Ser Lys Lys Cys Ser Glu
1               5                   10                  15

Arg Trp Lys Thr Val Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 250
<211> LENGTH: 54
<212> TYPE: PRT
<213> ORGANISM: homo sapiens

<400> SEQUENCE: 250

Pro Asp Ala Ser Val Asn Phe Ser Glu Phe Ser Lys Lys Cys Ser Glu
1               5                   10                  15

Arg Trp Lys Thr Met Ser Ala Asn Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 251
<211> LENGTH: 54
<212> TYPE: PRT
<213> ORGANISM: homo sapiens

<400> SEQUENCE: 251

Pro Asp Ala Ser Val Asn Phe Ser Glu Phe Ser Lys Lys Cys Ser Glu
1               5                   10                  15

Arg Trp Lys Thr Met Ser Ala Gln Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

-continued

50

<210> SEQ ID NO 252
<211> LENGTH: 54
<212> TYPE: PRT
<213> ORGANISM: homo sapiens

<400> SEQUENCE: 252

Pro Asp Ala Ser Val Asn Phe Ser Glu Phe Ser Lys Lys Cys Ser Glu
1               5                   10                  15

Arg Trp Lys Thr Met Ser Ala Lys Gln Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 253
<211> LENGTH: 54
<212> TYPE: PRT
<213> ORGANISM: homo sapiens

<400> SEQUENCE: 253

Pro Asp Ala Ser Val Asn Phe Ser Glu Phe Ser Lys Lys Cys Ser Glu
1               5                   10                  15

Arg Trp Lys Thr Met Ser Ala Lys His Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 254
<211> LENGTH: 54
<212> TYPE: PRT
<213> ORGANISM: homo sapiens

<400> SEQUENCE: 254

Pro Asp Ala Ser Val Asn Phe Ser Glu Phe Ser Lys Lys Cys Ser Glu
1               5                   10                  15

Arg Trp Lys Thr Met Ser Ala Lys Asn Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 255
<211> LENGTH: 54
<212> TYPE: PRT
<213> ORGANISM: homo sapiens

<400> SEQUENCE: 255

Pro Asp Ala Ser Val Asn Phe Ser Glu Phe Ser Lys Lys Cys Ser Glu
1               5                   10                  15

Arg Trp Lys Thr Met Ser Ala Lys Glu Asn Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

```
<210> SEQ ID NO 256
<211> LENGTH: 54
<212> TYPE: PRT
<213> ORGANISM: homo sapiens

<400> SEQUENCE: 256

Pro Asp Ala Ser Val Asn Phe Ser Glu Phe Ser Lys Lys Cys Ser Glu
1               5                   10                  15
Arg Trp Lys Thr Met Ser Ala Lys Glu Gln Gly Lys Phe Glu Asp Met
            20                  25                  30
Ala Lys Ala Asp Lys Ala Arg Tyr Glu Arg Glu Met Lys Thr Tyr Ile
        35                  40                  45
Pro Pro Lys Gly Glu Thr
    50

<210> SEQ ID NO 257
<211> LENGTH: 54
<212> TYPE: PRT
<213> ORGANISM: homo sapiens

<400> SEQUENCE: 257

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Asn Phe Glu Asp Met
            20                  25                  30
Ala Lys Ala Asp Lys Ala Arg Tyr Glu Arg Glu Met Lys Thr Tyr Ile
        35                  40                  45
Pro Pro Lys Gly Glu Thr
    50

<210> SEQ ID NO 258
<211> LENGTH: 54
<212> TYPE: PRT
<213> ORGANISM: homo sapiens

<400> SEQUENCE: 258

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Gln Phe Glu Asp Met
            20                  25                  30
Ala Lys Ala Asp Lys Ala Arg Tyr Glu Arg Glu Met Lys Thr Tyr Ile
        35                  40                  45
Pro Pro Lys Gly Glu Thr
    50

<210> SEQ ID NO 259
<211> LENGTH: 54
<212> TYPE: PRT
<213> ORGANISM: homo sapiens

<400> SEQUENCE: 259

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Ile Glu Asp Met
            20                  25                  30
Ala Lys Ala Asp Lys Ala Arg Tyr Glu Arg Glu Met Lys Thr Tyr Ile
        35                  40                  45
Pro Pro Lys Gly Glu Thr
```

<210> SEQ ID NO 260
<211> LENGTH: 54
<212> TYPE: PRT
<213> ORGANISM: homo sapiens

<400> SEQUENCE: 260

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Val Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 261
<211> LENGTH: 54
<212> TYPE: PRT
<213> ORGANISM: homo sapiens

<400> SEQUENCE: 261

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Gln Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 262
<211> LENGTH: 54
<212> TYPE: PRT
<213> ORGANISM: homo sapiens

<400> SEQUENCE: 262

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe His Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 263
<211> LENGTH: 54
<212> TYPE: PRT
<213> ORGANISM: homo sapiens

<400> SEQUENCE: 263

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Asn Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr

<210> SEQ ID NO 264
<211> LENGTH: 54
<212> TYPE: PRT
<213> ORGANISM: homo sapiens

<400> SEQUENCE: 264

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asn Met
            20                  25                  30
Ala Lys Ala Asp Lys Ala Arg Tyr Glu Arg Glu Met Lys Thr Tyr Ile
        35                  40                  45
Pro Pro Lys Gly Glu Thr
    50

<210> SEQ ID NO 265
<211> LENGTH: 54
<212> TYPE: PRT
<213> ORGANISM: homo sapiens

<400> SEQUENCE: 265

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Gln Met
            20                  25                  30
Ala Lys Ala Asp Lys Ala Arg Tyr Glu Arg Glu Met Lys Thr Tyr Ile
        35                  40                  45
Pro Pro Lys Gly Glu Thr
    50

<210> SEQ ID NO 266
<211> LENGTH: 54
<212> TYPE: PRT
<213> ORGANISM: homo sapiens

<400> SEQUENCE: 266

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Ile
            20                  25                  30
Ala Lys Ala Asp Lys Ala Arg Tyr Glu Arg Glu Met Lys Thr Tyr Ile
        35                  40                  45
Pro Pro Lys Gly Glu Thr
    50

<210> SEQ ID NO 267
<211> LENGTH: 54
<212> TYPE: PRT
<213> ORGANISM: homo sapiens

<400> SEQUENCE: 267

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Val
            20                  25                  30
Ala Lys Ala Asp Lys Ala Arg Tyr Glu Arg Glu Met Lys Thr Tyr Ile
        35                  40                  45
Pro Pro Lys Gly Glu Thr

<210> SEQ ID NO 268
<211> LENGTH: 54
<212> TYPE: PRT
<213> ORGANISM: homo sapiens

<400> SEQUENCE: 268

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Asn Ala Asp Lys Ala Arg Tyr Glu Arg Glu Met Lys Thr Tyr Ile
        35                  40                  45

Pro Pro Lys Gly Glu Thr
    50

<210> SEQ ID NO 269
<211> LENGTH: 54
<212> TYPE: PRT
<213> ORGANISM: homo sapiens

<400> SEQUENCE: 269

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Gln Ala Asp Lys Ala Arg Tyr Glu Arg Glu Met Lys Thr Tyr Ile
        35                  40                  45

Pro Pro Lys Gly Glu Thr
    50

<210> SEQ ID NO 270
<211> LENGTH: 54
<212> TYPE: PRT
<213> ORGANISM: homo sapiens

<400> SEQUENCE: 270

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asn Lys Ala Arg Tyr Glu Arg Glu Met Lys Thr Tyr Ile
        35                  40                  45

Pro Pro Lys Gly Glu Thr
    50

<210> SEQ ID NO 271
<211> LENGTH: 54
<212> TYPE: PRT
<213> ORGANISM: homo sapiens

<400> SEQUENCE: 271

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Gln Lys Ala Arg Tyr Glu Arg Glu Met Lys Thr Tyr Ile
        35                  40                  45

Pro Pro Lys Gly Glu Thr

<210> SEQ ID NO 272
<211> LENGTH: 54
<212> TYPE: PRT
<213> ORGANISM: homo sapiens

<400> SEQUENCE: 272

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Met
            20                  25                  30
Ala Lys Ala Asp Asn Ala Arg Tyr Glu Arg Glu Met Lys Thr Tyr Ile
        35                  40                  45
Pro Pro Lys Gly Glu Thr
    50

<210> SEQ ID NO 273
<211> LENGTH: 54
<212> TYPE: PRT
<213> ORGANISM: homo sapiens

<400> SEQUENCE: 273

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Met
            20                  25                  30
Ala Lys Ala Asp Gln Ala Arg Tyr Glu Arg Glu Met Lys Thr Tyr Ile
        35                  40                  45
Pro Pro Lys Gly Glu Thr
    50

<210> SEQ ID NO 274
<211> LENGTH: 54
<212> TYPE: PRT
<213> ORGANISM: homo sapiens

<400> SEQUENCE: 274

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Met
            20                  25                  30
Ala Lys Ala Asp Lys Ala His Tyr Glu Arg Glu Met Lys Thr Tyr Ile
        35                  40                  45
Pro Pro Lys Gly Glu Thr
    50

<210> SEQ ID NO 275
<211> LENGTH: 54
<212> TYPE: PRT
<213> ORGANISM: homo sapiens

<400> SEQUENCE: 275

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Met
            20                  25                  30
Ala Lys Ala Asp Lys Ala Gln Tyr Glu Arg Glu Met Lys Thr Tyr Ile
        35                  40                  45
Pro Pro Lys Gly Glu Thr

<210> SEQ ID NO 276
<211> LENGTH: 54
<212> TYPE: PRT
<213> ORGANISM: homo sapiens

<400> SEQUENCE: 276

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg His Glu Arg Glu Met Lys Thr Tyr Ile
        35                  40                  45

Pro Pro Lys Gly Glu Thr
    50

<210> SEQ ID NO 277
<211> LENGTH: 54
<212> TYPE: PRT
<213> ORGANISM: homo sapiens

<400> SEQUENCE: 277

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Ile Glu Arg Glu Met Lys Thr Tyr Ile
        35                  40                  45

Pro Pro Lys Gly Glu Thr
    50

<210> SEQ ID NO 278
<211> LENGTH: 54
<212> TYPE: PRT
<213> ORGANISM: homo sapiens

<400> SEQUENCE: 278

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Gln Arg Glu Met Lys Thr Tyr Ile
        35                  40                  45

Pro Pro Lys Gly Glu Thr
    50

<210> SEQ ID NO 279
<211> LENGTH: 54
<212> TYPE: PRT
<213> ORGANISM: homo sapiens

<400> SEQUENCE: 279

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr His Arg Glu Met Lys Thr Tyr Ile
        35                  40                  45

Pro Pro Lys Gly Glu Thr

<210> SEQ ID NO 280
<211> LENGTH: 54
<212> TYPE: PRT
<213> ORGANISM: homo sapiens

<400> SEQUENCE: 280

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Met
            20                  25                  30
Ala Lys Ala Asp Lys Ala Arg Tyr Asn Arg Glu Met Lys Thr Tyr Ile
        35                  40                  45
Pro Pro Lys Gly Glu Thr
    50

<210> SEQ ID NO 281
<211> LENGTH: 54
<212> TYPE: PRT
<213> ORGANISM: homo sapiens

<400> SEQUENCE: 281

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Met
            20                  25                  30
Ala Lys Ala Asp Lys Ala Arg Tyr Glu His Glu Met Lys Thr Tyr Ile
        35                  40                  45
Pro Pro Lys Gly Glu Thr
    50

<210> SEQ ID NO 282
<211> LENGTH: 54
<212> TYPE: PRT
<213> ORGANISM: homo sapiens

<400> SEQUENCE: 282

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Met
            20                  25                  30
Ala Lys Ala Asp Lys Ala Arg Tyr Glu Gln Glu Met Lys Thr Tyr Ile
        35                  40                  45
Pro Pro Lys Gly Glu Thr
    50

<210> SEQ ID NO 283
<211> LENGTH: 54
<212> TYPE: PRT
<213> ORGANISM: homo sapiens

<400> SEQUENCE: 283

Pro Asp Ala Ser Val Asn Phe Ser Glu Phe Ser Lys Lys Cys Ser Glu
1               5                   10                  15
Arg Trp Lys Thr Met Ser Ala Lys Glu Lys Gly Lys Phe Glu Asp Met
            20                  25                  30
Ala Lys Ala Asp Lys Ala Arg Tyr Glu Arg Gln Met Lys Thr Tyr Ile
        35                  40                  45
Pro Pro Lys Gly Glu Thr

```
<210> SEQ ID NO 284
<211> LENGTH: 54
<212> TYPE: PRT
<213> ORGANISM: homo sapiens

<400> SEQUENCE: 284

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg His Met Lys Thr Tyr Ile
        35                  40                  45

Pro Pro Lys Gly Glu Thr
    50

<210> SEQ ID NO 285
<211> LENGTH: 54
<212> TYPE: PRT
<213> ORGANISM: homo sapiens

<400> SEQUENCE: 285

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Asn Met Lys Thr Tyr Ile
        35                  40                  45

Pro Pro Lys Gly Glu Thr
    50

<210> SEQ ID NO 286
<211> LENGTH: 54
<212> TYPE: PRT
<213> ORGANISM: homo sapiens

<400> SEQUENCE: 286

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Ile Lys Thr Tyr Ile
        35                  40                  45

Pro Pro Lys Gly Glu Thr
    50

<210> SEQ ID NO 287
<211> LENGTH: 54
<212> TYPE: PRT
<213> ORGANISM: homo sapiens

<400> SEQUENCE: 287

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Val Lys Thr Tyr Ile
        35                  40                  45

Pro Pro Lys Gly Glu Thr
```

-continued

<210> SEQ ID NO 288
<211> LENGTH: 54
<212> TYPE: PRT
<213> ORGANISM: homo sapiens

<400> SEQUENCE: 288

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Asn Thr Tyr Ile
        35                  40                  45

Pro Pro Lys Gly Glu Thr
    50

<210> SEQ ID NO 289
<211> LENGTH: 54
<212> TYPE: PRT
<213> ORGANISM: homo sapiens

<400> SEQUENCE: 289

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Gln Thr Tyr Ile
        35                  40                  45

Pro Pro Lys Gly Glu Thr
    50

<210> SEQ ID NO 290
<211> LENGTH: 54
<212> TYPE: PRT
<213> ORGANISM: homo sapiens

<400> SEQUENCE: 290

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr His Ile
        35                  40                  45

Pro Pro Lys Gly Glu Thr
    50

<210> SEQ ID NO 291
<211> LENGTH: 54
<212> TYPE: PRT
<213> ORGANISM: homo sapiens

<400> SEQUENCE: 291

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Ile Ile
        35                  40                  45

Pro Pro Lys Gly Glu Thr

<210> SEQ ID NO 292
<211> LENGTH: 54
<212> TYPE: PRT
<213> ORGANISM: homo sapiens

<400> SEQUENCE: 292

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Ala Pro Lys Gly Glu Thr
    50

<210> SEQ ID NO 293
<211> LENGTH: 54
<212> TYPE: PRT
<213> ORGANISM: homo sapiens

<400> SEQUENCE: 293

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Ser Pro Lys Gly Glu Thr
    50

<210> SEQ ID NO 294
<211> LENGTH: 54
<212> TYPE: PRT
<213> ORGANISM: homo sapiens

<400> SEQUENCE: 294

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Ala Lys Gly Glu Thr
    50

<210> SEQ ID NO 295
<211> LENGTH: 54
<212> TYPE: PRT
<213> ORGANISM: homo sapiens

<400> SEQUENCE: 295

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Ser Lys Gly Glu Thr

<210> SEQ ID NO 296
<211> LENGTH: 54
<212> TYPE: PRT
<213> ORGANISM: homo sapiens

<400> SEQUENCE: 296

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Asn Gly Glu Thr
    50

<210> SEQ ID NO 297
<211> LENGTH: 54
<212> TYPE: PRT
<213> ORGANISM: homo sapiens

<400> SEQUENCE: 297

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Gln Gly Glu Thr
    50

<210> SEQ ID NO 298
<211> LENGTH: 54
<212> TYPE: PRT
<213> ORGANISM: homo sapiens

<400> SEQUENCE: 298

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Gln Thr
    50

<210> SEQ ID NO 299
<211> LENGTH: 54
<212> TYPE: PRT
<213> ORGANISM: homo sapiens

<400> SEQUENCE: 299

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly His Thr

-continued

<210> SEQ ID NO 300
<211> LENGTH: 54
<212> TYPE: PRT
<213> ORGANISM: homo sapiens

<400> SEQUENCE: 300

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Asn Thr
    50

<210> SEQ ID NO 301
<211> LENGTH: 84
<212> TYPE: PRT
<213> ORGANISM: Anopheles gambia

<400> SEQUENCE: 301

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 302
<211> LENGTH: 84
<212> TYPE: PRT
<213> ORGANISM: Anopheles gambia

<400> SEQUENCE: 302

Gly Asn Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 303
<211> LENGTH: 84
<212> TYPE: PRT
<213> ORGANISM: Anopheles gambia

<400> SEQUENCE: 303

```
Gly Gln Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65              70                  75                  80

Lys Gly Ala Val
```

<210> SEQ ID NO 304
<211> LENGTH: 84
<212> TYPE: PRT
<213> ORGANISM: Anopheles gambia

<400> SEQUENCE: 304

```
Gly Lys Val Asn Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65              70                  75                  80

Lys Gly Ala Val
```

<210> SEQ ID NO 305
<211> LENGTH: 84
<212> TYPE: PRT
<213> ORGANISM: Anopheles gambia

<400> SEQUENCE: 305

```
Gly Lys Val Gln Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Tyr Glu Leu Glu Met Gln Ser Tyr Val Pro Pro
65              70                  75                  80

Lys Gly Ala Val
```

<210> SEQ ID NO 306
<211> LENGTH: 84
<212> TYPE: PRT
<213> ORGANISM: Anopheles gambia

<400> SEQUENCE: 306

```
Gly Lys Val Lys Asn Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30
```

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 307
<211> LENGTH: 84
<212> TYPE: PRT
<213> ORGANISM: Anopheles gambia

<400> SEQUENCE: 307

Gly Lys Val Lys Gln Asn Lys Pro Arg Gly Arg Met Thr Ala Tyr Ala
 1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 308
<211> LENGTH: 84
<212> TYPE: PRT
<213> ORGANISM: Anopheles gambia

<400> SEQUENCE: 308

Gly Lys Val Lys Asp Asn Pro Arg Gly Arg Met Thr Ala Tyr Ala
 1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 309
<211> LENGTH: 84
<212> TYPE: PRT
<213> ORGANISM: Anopheles gambia

<400> SEQUENCE: 309

Gly Lys Val Lys Asp Asn Gln Pro Arg Gly Arg Met Thr Ala Tyr Ala
 1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu

```
            50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 310
<211> LENGTH: 84
<212> TYPE: PRT
<213> ORGANISM: Anopheles gambia

<400> SEQUENCE: 310

Gly Lys Val Lys Asp Asn Lys Ala Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 311
<211> LENGTH: 84
<212> TYPE: PRT
<213> ORGANISM: Anopheles gambia

<400> SEQUENCE: 311

Gly Lys Val Lys Asp Asn Lys Ser Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 312
<211> LENGTH: 84
<212> TYPE: PRT
<213> ORGANISM: Anopheles gambia

<400> SEQUENCE: 312

Gly Lys Val Lys Asp Asn Lys Pro His Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 313
<211> LENGTH: 84
<212> TYPE: PRT
<213> ORGANISM: Anopheles gambia

<400> SEQUENCE: 313

```
Gly Lys Val Lys Asp Asn Lys Pro Gln Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val
```

<210> SEQ ID NO 314
<211> LENGTH: 84
<212> TYPE: PRT
<213> ORGANISM: Anopheles gambia

<400> SEQUENCE: 314

```
Gly Lys Val Lys Asp Asn Lys Pro Arg Gly His Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val
```

<210> SEQ ID NO 315
<211> LENGTH: 84
<212> TYPE: PRT
<213> ORGANISM: Anopheles gambia

<400> SEQUENCE: 315

```
Gly Lys Val Lys Asp Asn Lys Pro Arg Gly Gln Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val
```

<210> SEQ ID NO 316
<211> LENGTH: 84

```
<212> TYPE: PRT
<213> ORGANISM: Anopheles gambia

<400> SEQUENCE: 316

Gly Lys Val Lys Asp Asn Lys Pro Arg Gly Arg Ile Thr Ala Tyr Ala
1               5                   10                  15

Phe Phe Val Gln Thr Cys Arg Glu Glu His Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu
                50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 317
<211> LENGTH: 84
<212> TYPE: PRT
<213> ORGANISM: Anopheles gambia

<400> SEQUENCE: 317

Gly Lys Val Lys Asp Asn Lys Pro Arg Gly Arg Val Thr Ala Tyr Ala
1               5                   10                  15

Phe Phe Val Gln Thr Cys Arg Glu Glu His Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu
                50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 318
<211> LENGTH: 84
<212> TYPE: PRT
<213> ORGANISM: Anopheles gambia

<400> SEQUENCE: 318

Gly Lys Val Lys Asp Asn Lys Pro Arg Gly Arg Met Thr Ala His Ala
1               5                   10                  15

Phe Phe Val Gln Thr Cys Arg Glu Glu His Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu
                50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 319
<211> LENGTH: 84
<212> TYPE: PRT
<213> ORGANISM: Anopheles gambia

<400> SEQUENCE: 319
```

-continued

Gly Lys Val Lys Asp Asn Lys Pro Arg Gly Arg Met Thr Ala Ile Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 320
<211> LENGTH: 84
<212> TYPE: PRT
<213> ORGANISM: Anopheles gambia

<400> SEQUENCE: 320

Gly Lys Val Lys Asp Asn Lys Pro Arg Gly Arg Met Thr Ala Tyr Ala
1               5                   10                  15

Ile Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 321
<211> LENGTH: 84
<212> TYPE: PRT
<213> ORGANISM: Anopheles gambia

<400> SEQUENCE: 321

Gly Lys Val Lys Asp Asn Lys Pro Arg Gly Arg Met Thr Ala Tyr Ala
1               5                   10                  15

Val Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 322
<211> LENGTH: 84
<212> TYPE: PRT
<213> ORGANISM: Anopheles gambia

<400> SEQUENCE: 322

Gly Lys Val Lys Asp Asn Lys Pro Arg Gly Arg Met Thr Ala Tyr Ala
1               5                   10                  15

Phe Ile Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 323
<211> LENGTH: 84
<212> TYPE: PRT
<213> ORGANISM: Anopheles gambia

<400> SEQUENCE: 323

Gly Lys Val Lys Asp Asn Lys Pro Arg Gly Arg Met Thr Ala Tyr Ala
 1               5                  10                  15

Phe Val Val Gln Thr Cys Arg Glu Glu His Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 324
<211> LENGTH: 84
<212> TYPE: PRT
<213> ORGANISM: Anopheles gambia

<400> SEQUENCE: 324

Gly Lys Val Lys Asp Asn Lys Pro Arg Gly Arg Met Thr Ala Tyr Ala
 1               5                  10                  15

Phe Phe Val Gln Thr Cys His Glu Glu His Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 325
<211> LENGTH: 84
<212> TYPE: PRT
<213> ORGANISM: Anopheles gambia

<400> SEQUENCE: 325

Gly Lys Val Lys Asp Asn Lys Pro Arg Gly Arg Met Thr Ala Tyr Ala
 1               5                  10                  15

Phe Phe Val Gln Thr Cys Gln Glu Glu His Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu

```
                    50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 326
<211> LENGTH: 84
<212> TYPE: PRT
<213> ORGANISM: Anopheles gambia

<400> SEQUENCE: 326

Gly Lys Val Lys Asp Asn Lys Pro Arg Gly Arg Met Thr Ala Tyr Ala
 1                5                  10                  15

Phe Phe Val Gln Thr Cys Arg Gln Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
     50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 327
<211> LENGTH: 84
<212> TYPE: PRT
<213> ORGANISM: Anopheles gambia

<400> SEQUENCE: 327

Gly Lys Val Lys Asp Asn Lys Pro Arg Gly Arg Met Thr Ala Tyr Ala
 1                5                  10                  15

Phe Phe Val Gln Thr Cys Arg His Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
     50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 328
<211> LENGTH: 84
<212> TYPE: PRT
<213> ORGANISM: Anopheles gambia

<400> SEQUENCE: 328

Gly Lys Val Lys Asp Asn Lys Pro Arg Gly Arg Met Thr Ala Tyr Ala
 1                5                  10                  15

Phe Phe Val Gln Thr Cys Arg Asn Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
     50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 329
<211> LENGTH: 84
<212> TYPE: PRT
<213> ORGANISM: Anopheles gambia

<400> SEQUENCE: 329

Gly Lys Val Lys Asp Asn Lys Pro Arg Gly Arg Met Thr Ala Tyr Ala
1               5                   10                  15

Phe Phe Val Gln Thr Cys Arg Glu Gln His Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 330
<211> LENGTH: 84
<212> TYPE: PRT
<213> ORGANISM: Anopheles gambia

<400> SEQUENCE: 330

Gly Lys Val Lys Asp Asn Lys Pro Arg Gly Arg Met Thr Ala Tyr Ala
1               5                   10                  15

Phe Phe Val Gln Thr Cys Arg Glu His His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 331
<211> LENGTH: 84
<212> TYPE: PRT
<213> ORGANISM: Anopheles gambia

<400> SEQUENCE: 331

Gly Lys Val Lys Asp Asn Lys Pro Arg Gly Arg Met Thr Ala Tyr Ala
1               5                   10                  15

Phe Phe Val Gln Thr Cys Arg Glu Asn His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 332
<211> LENGTH: 84

```
<212> TYPE: PRT
<213> ORGANISM: Anopheles gambia

<400> SEQUENCE: 332

Gly Lys Val Lys Asp Asn Lys Pro Arg Gly Arg Met Thr Ala Tyr Ala
1               5                   10                  15

Phe Phe Val Gln Thr Cys Arg Glu Glu His Asn Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 333
<211> LENGTH: 84
<212> TYPE: PRT
<213> ORGANISM: Anopheles gambia

<400> SEQUENCE: 333

Gly Lys Val Lys Asp Asn Lys Pro Arg Gly Arg Met Thr Ala Tyr Ala
1               5                   10                  15

Phe Phe Val Gln Thr Cys Arg Glu Glu His Gln Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 334
<211> LENGTH: 84
<212> TYPE: PRT
<213> ORGANISM: Anopheles gambia

<400> SEQUENCE: 334

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Asn Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 335
<211> LENGTH: 84
<212> TYPE: PRT
<213> ORGANISM: Anopheles gambia

<400> SEQUENCE: 335
```

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Gln Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val
```

<210> SEQ ID NO 336
<211> LENGTH: 84
<212> TYPE: PRT
<213> ORGANISM: Anopheles gambia

<400> SEQUENCE: 336

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Asn His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val
```

<210> SEQ ID NO 337
<211> LENGTH: 84
<212> TYPE: PRT
<213> ORGANISM: Anopheles gambia

<400> SEQUENCE: 337

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Gln His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val
```

<210> SEQ ID NO 338
<211> LENGTH: 84
<212> TYPE: PRT
<213> ORGANISM: Anopheles gambia

<400> SEQUENCE: 338

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Ala Glu
            20                  25                  30
```

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 339
<211> LENGTH: 84
<212> TYPE: PRT
<213> ORGANISM: Anopheles gambia

<400> SEQUENCE: 339

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys His Ser Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 340
<211> LENGTH: 84
<212> TYPE: PRT
<213> ORGANISM: Anopheles gambia

<400> SEQUENCE: 340

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys His Pro Gln
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 341
<211> LENGTH: 84
<212> TYPE: PRT
<213> ORGANISM: Anopheles gambia

<400> SEQUENCE: 341

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys His Pro His
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Glu

```
                50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 342
<211> LENGTH: 84
<212> TYPE: PRT
<213> ORGANISM: Anopheles gambia

<400> SEQUENCE: 342

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Asn
                 20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 343
<211> LENGTH: 84
<212> TYPE: PRT
<213> ORGANISM: Anopheles gambia

<400> SEQUENCE: 343

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Gln Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 344
<211> LENGTH: 84
<212> TYPE: PRT
<213> ORGANISM: Anopheles gambia

<400> SEQUENCE: 344

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

His Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 345
<211> LENGTH: 84
<212> TYPE: PRT
<213> ORGANISM: Anopheles gambia

<400> SEQUENCE: 345

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Asn Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 346
<211> LENGTH: 84
<212> TYPE: PRT
<213> ORGANISM: Anopheles gambia

<400> SEQUENCE: 346

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Ile Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 347
<211> LENGTH: 84
<212> TYPE: PRT
<213> ORGANISM: Anopheles gambia

<400> SEQUENCE: 347

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Val Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 348
<211> LENGTH: 84

```
<212> TYPE: PRT
<213> ORGANISM: Anopheles gambia

<400> SEQUENCE: 348

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Gln Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 349
<211> LENGTH: 84
<212> TYPE: PRT
<213> ORGANISM: Anopheles gambia

<400> SEQUENCE: 349

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala His Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 350
<211> LENGTH: 84
<212> TYPE: PRT
<213> ORGANISM: Anopheles gambia

<400> SEQUENCE: 350

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Asn Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 351
<211> LENGTH: 84
<212> TYPE: PRT
<213> ORGANISM: Anopheles gambia

<400> SEQUENCE: 351
```

-continued

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Ile Ser Arg Lys Cys Ala Glu Arg Trp
                35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 352
<211> LENGTH: 84
<212> TYPE: PRT
<213> ORGANISM: Anopheles gambia

<400> SEQUENCE: 352

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Val Ser Arg Lys Cys Ala Glu Arg Trp
                35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 353
<211> LENGTH: 84
<212> TYPE: PRT
<213> ORGANISM: Anopheles gambia

<400> SEQUENCE: 353

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser His Lys Cys Ala Glu Arg Trp
                35                  40                  45

Lys Thr Met Leu Asp Lys Glu Lys Gln Arg Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 354
<211> LENGTH: 84
<212> TYPE: PRT
<213> ORGANISM: Anopheles gambia

<400> SEQUENCE: 354

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Gln Lys Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 355
<211> LENGTH: 84
<212> TYPE: PRT
<213> ORGANISM: Anopheles gambia

<400> SEQUENCE: 355

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys His Pro Glu
                20                  25                  30

Glu Gln Val Ile Phe Ala Glu Phe Ser Arg Asn Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 356
<211> LENGTH: 84
<212> TYPE: PRT
<213> ORGANISM: Anopheles gambia

<400> SEQUENCE: 356

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys His Pro Glu
                20                  25                  30

Glu Gln Val Ile Phe Ala Glu Phe Ser Arg Gln Cys Ala Glu Arg Trp
            35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 357
<211> LENGTH: 84
<212> TYPE: PRT
<213> ORGANISM: Anopheles gambia

<400> SEQUENCE: 357

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys His Pro Glu
                20                  25                  30

Glu Gln Val Ile Phe Ala Glu Phe Ser Arg Lys Cys Ala Gln Arg Trp
            35                  40                  45

Lys Thr Met Leu Asp Lys Glu Lys Gln Arg Phe His Glu Met Ala Glu

```
            50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 358
<211> LENGTH: 84
<212> TYPE: PRT
<213> ORGANISM: Anopheles gambia

<400> SEQUENCE: 358

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Glu Gln Val Ile Phe Ala Glu Phe Ser Arg Lys Cys Ala His Arg Trp
             35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 359
<211> LENGTH: 84
<212> TYPE: PRT
<213> ORGANISM: Anopheles gambia

<400> SEQUENCE: 359

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Glu Gln Val Ile Phe Ala Glu Phe Ser Arg Lys Cys Ala Asn Arg Trp
             35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 360
<211> LENGTH: 84
<212> TYPE: PRT
<213> ORGANISM: Anopheles gambia

<400> SEQUENCE: 360

Gly Lys Val Lys Asp Asn Lys Pro Arg Gly Arg Met Thr Ala Tyr Ala
  1               5                  10                  15

Phe Phe Val Gln Thr Cys Arg Glu Glu His Lys Lys Lys His Pro Glu
                 20                  25                  30

Glu Gln Val Ile Phe Ala Glu Phe Ser Arg Lys Cys Ala Glu His Trp
             35                  40                  45

Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 361
<211> LENGTH: 84
<212> TYPE: PRT
<213> ORGANISM: Anopheles gambia

<400> SEQUENCE: 361

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Gln Trp
            35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 362
<211> LENGTH: 84
<212> TYPE: PRT
<213> ORGANISM: Anopheles gambia

<400> SEQUENCE: 362

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Tyr
            35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 363
<211> LENGTH: 84
<212> TYPE: PRT
<213> ORGANISM: Anopheles gambia

<400> SEQUENCE: 363

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Ser
            35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 364
<211> LENGTH: 84

```
<212> TYPE: PRT
<213> ORGANISM: Anopheles gambia

<400> SEQUENCE: 364

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Asn Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 365
<211> LENGTH: 84
<212> TYPE: PRT
<213> ORGANISM: Anopheles gambia

<400> SEQUENCE: 365

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Gln Thr Met Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 366
<211> LENGTH: 84
<212> TYPE: PRT
<213> ORGANISM: Anopheles gambia

<400> SEQUENCE: 366

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Ile Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 367
<211> LENGTH: 84
<212> TYPE: PRT
<213> ORGANISM: Anopheles gambia

<400> SEQUENCE: 367
```

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Val Leu Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65              70                  75                  80

Lys Gly Ala Val

<210> SEQ ID NO 368
<211> LENGTH: 84
<212> TYPE: PRT
<213> ORGANISM: Anopheles gambia

<400> SEQUENCE: 368

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Ile Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65              70                  75                  80

Lys Gly Ala Val

<210> SEQ ID NO 369
<211> LENGTH: 84
<212> TYPE: PRT
<213> ORGANISM: Anopheles gambia

<400> SEQUENCE: 369

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Val Asp Lys Glu Lys Gln Arg Phe His Glu Met Ala Glu
    50                  55                  60

Lys Asp Lys Ala Arg Tyr Glu Leu Glu Met Gln Ser Tyr Val Pro Pro
65              70                  75                  80

Lys Gly Ala Val

<210> SEQ ID NO 370
<211> LENGTH: 84
<212> TYPE: PRT
<213> ORGANISM: Anopheles gambia

<400> SEQUENCE: 370

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
          35                  40                  45

Lys Thr Met Leu Asn Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 371
<211> LENGTH: 84
<212> TYPE: PRT
<213> ORGANISM: Anopheles gambia

<400> SEQUENCE: 371

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
             20                  25                  30

Glu Gln Val Ile Phe Ala Glu Phe Ser Arg Lys Cys Ala Glu Arg Trp
          35                  40                  45

Lys Thr Met Leu Gln Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 372
<211> LENGTH: 84
<212> TYPE: PRT
<213> ORGANISM: Anopheles gambia

<400> SEQUENCE: 372

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
             20                  25                  30

Glu Gln Val Ile Phe Ala Glu Phe Ser Arg Lys Cys Ala Glu Arg Trp
          35                  40                  45

Lys Thr Met Leu Asp Asn Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 373
<211> LENGTH: 84
<212> TYPE: PRT
<213> ORGANISM: Anopheles gambia

<400> SEQUENCE: 373

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
             20                  25                  30

Glu Gln Val Ile Phe Ala Glu Phe Ser Arg Lys Cys Ala Glu Arg Trp
          35                  40                  45

Lys Thr Met Leu Asp Gln Glu Lys Gln Arg Phe His Glu Met Ala Glu

```
                    50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 374
<211> LENGTH: 84
<212> TYPE: PRT
<213> ORGANISM: Anopheles gambia

<400> SEQUENCE: 374

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Gln Lys Gln Arg Phe His Glu Met Ala Glu
        50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 375
<211> LENGTH: 84
<212> TYPE: PRT
<213> ORGANISM: Anopheles gambia

<400> SEQUENCE: 375

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys His Lys Gln Arg Phe His Glu Met Ala Glu
        50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 376
<211> LENGTH: 84
<212> TYPE: PRT
<213> ORGANISM: Anopheles gambia

<400> SEQUENCE: 376

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Asn Lys Gln Arg Phe His Glu Met Ala Glu
        50                  55                  60

Lys Asp Lys Ala Arg Tyr Glu Leu Glu Met Gln Ser Tyr Val Pro Pro
 65                  70                  75                  80
```

Lys Gly Ala Val

<210> SEQ ID NO 377
<211> LENGTH: 84
<212> TYPE: PRT
<213> ORGANISM: Anopheles gambia

<400> SEQUENCE: 377

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Asn Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 378
<211> LENGTH: 84
<212> TYPE: PRT
<213> ORGANISM: Anopheles gambia

<400> SEQUENCE: 378

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Gln Gln Arg Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 379
<211> LENGTH: 84
<212> TYPE: PRT
<213> ORGANISM: Anopheles gambia

<400> SEQUENCE: 379

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln His Phe His Glu Met Ala Glu
    50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 380
<211> LENGTH: 84

```
<212> TYPE: PRT
<213> ORGANISM: Anopheles gambia

<400> SEQUENCE: 380

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Gln Phe His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 381
<211> LENGTH: 84
<212> TYPE: PRT
<213> ORGANISM: Anopheles gambia

<400> SEQUENCE: 381

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Ile His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 382
<211> LENGTH: 84
<212> TYPE: PRT
<213> ORGANISM: Anopheles gambia

<400> SEQUENCE: 382

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Val His Glu Met Ala Glu
        50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 383
<211> LENGTH: 84
<212> TYPE: PRT
<213> ORGANISM: Anopheles gambia

<400> SEQUENCE: 383
```

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Gln Met Ala Glu
50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 384
<211> LENGTH: 84
<212> TYPE: PRT
<213> ORGANISM: Anopheles gambia

<400> SEQUENCE: 384

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His His Met Ala Glu
50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 385
<211> LENGTH: 84
<212> TYPE: PRT
<213> ORGANISM: Anopheles gambia

<400> SEQUENCE: 385

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Asn Met Ala Glu
50                  55                  60

Lys Asp Lys Ala Arg Tyr Glu Leu Glu Met Gln Ser Tyr Val Pro Pro
65                  70                  75                  80

Lys Gly Ala Val

<210> SEQ ID NO 386
<211> LENGTH: 84
<212> TYPE: PRT
<213> ORGANISM: Anopheles gambia

<400> SEQUENCE: 386

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Ile Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 387
<211> LENGTH: 84
<212> TYPE: PRT
<213> ORGANISM: Anopheles gambia

<400> SEQUENCE: 387

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Val Ala Glu
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 388
<211> LENGTH: 84
<212> TYPE: PRT
<213> ORGANISM: Anopheles gambia

<400> SEQUENCE: 388

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala Gln
 50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 389
<211> LENGTH: 84
<212> TYPE: PRT
<213> ORGANISM: Anopheles gambia

<400> SEQUENCE: 389

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
                35                  40                  45

Lys Thr Met Leu Asp Lys Glu Lys Gln Arg Phe His Glu Met Ala His

```
                    50                  55                  60
Lys Asp Lys Ala Arg Tyr Glu Leu Glu Met Gln Ser Tyr Val Pro Pro
 65                  70                  75                  80

Lys Gly Ala Val

<210> SEQ ID NO 390
<211> LENGTH: 84
<212> TYPE: PRT
<213> ORGANISM: Anopheles gambia

<400> SEQUENCE: 390

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Asn
         50                  55                  60

Lys Asp Lys Ala Arg Tyr Glu Leu Glu Met Gln Ser Tyr Val Pro Pro
 65                  70                  75                  80

Lys Gly Ala Val

<210> SEQ ID NO 391
<211> LENGTH: 84
<212> TYPE: PRT
<213> ORGANISM: Anopheles gambia

<400> SEQUENCE: 391

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Asn Asp Lys Ala Arg Tyr Glu Leu Glu Met Gln Ser Tyr Val Pro Pro
 65                  70                  75                  80

Lys Gly Ala Val

<210> SEQ ID NO 392
<211> LENGTH: 84
<212> TYPE: PRT
<213> ORGANISM: Anopheles gambia

<400> SEQUENCE: 392

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
         50                  55                  60

Gln Asp Lys Ala Arg Tyr Glu Leu Glu Met Gln Ser Tyr Val Pro Pro
 65                  70                  75                  80
```

```
<210> SEQ ID NO 393
<211> LENGTH: 84
<212> TYPE: PRT
<213> ORGANISM: Anopheles gambia

<400> SEQUENCE: 393

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asn Lys Ala Arg Tyr Glu Leu Glu Met Gln Ser Tyr Val Pro Pro
65                  70                  75                  80

Lys Gly Ala Val

<210> SEQ ID NO 394
<211> LENGTH: 84
<212> TYPE: PRT
<213> ORGANISM: Anopheles gambia

<400> SEQUENCE: 394

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Gln Lys Ala Arg Tyr Glu Leu Glu Met Gln Ser Tyr Val Pro Pro
65                  70                  75                  80

Lys Gly Ala Val

<210> SEQ ID NO 395
<211> LENGTH: 84
<212> TYPE: PRT
<213> ORGANISM: Anopheles gambia

<400> SEQUENCE: 395

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Asn Ala Arg Tyr Glu Leu Glu Met Gln Ser Tyr Val Pro Pro
65                  70                  75                  80

Lys Gly Ala Val

<210> SEQ ID NO 396
<211> LENGTH: 84
```

```
<212> TYPE: PRT
<213> ORGANISM: Anopheles gambia

<400> SEQUENCE: 396

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Gln Ala Arg Tyr Glu Leu Glu Met Gln Ser Tyr Val Pro Pro
65                  70                  75                  80

Lys Gly Ala Val

<210> SEQ ID NO 397
<211> LENGTH: 84
<212> TYPE: PRT
<213> ORGANISM: Anopheles gambia

<400> SEQUENCE: 397

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala His Tyr Glu Leu Glu Met Gln Ser Tyr Val Pro Pro
65                  70                  75                  80

Lys Gly Ala Val

<210> SEQ ID NO 398
<211> LENGTH: 84
<212> TYPE: PRT
<213> ORGANISM: Anopheles gambia

<400> SEQUENCE: 398

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Gln Tyr Glu Leu Glu Met Gln Ser Tyr Val Pro Pro
65                  70                  75                  80

Lys Gly Ala Val

<210> SEQ ID NO 399
<211> LENGTH: 84
<212> TYPE: PRT
<213> ORGANISM: Anopheles gambia

<400> SEQUENCE: 399
```

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg His Glu Leu Glu Met Gln Ser Tyr Val Pro Pro
65                  70                  75                  80

Lys Gly Ala Val
```

<210> SEQ ID NO 400
<211> LENGTH: 78
<212> TYPE: PRT
<213> ORGANISM: Anopheles gambia

<400> SEQUENCE: 400

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
            50                  55                  60

Lys Asp Lys Ala Arg Ile Glu Leu Glu Met Gln Ser Tyr Val
65                  70                  75
```

<210> SEQ ID NO 401
<211> LENGTH: 84
<212> TYPE: PRT
<213> ORGANISM: Anopheles gambia

<400> SEQUENCE: 401

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Lys Gln Arg Phe His Glu Met Ala Glu
            50                  55                  60

Lys Asp Lys Ala Arg Tyr Gln Leu Glu Met Gln Ser Tyr Val Pro Pro
65                  70                  75                  80

Lys Gly Ala Val
```

<210> SEQ ID NO 402
<211> LENGTH: 84
<212> TYPE: PRT
<213> ORGANISM: Anopheles gambia

<400> SEQUENCE: 402

```
Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
```

```
                35                  40                  45
Lys Thr Met Leu Asp Lys Glu Lys Gln Arg Phe His Glu Met Ala Glu
     50                  55                  60

Lys Asp Lys Ala Arg Tyr His Leu Glu Met Gln Ser Tyr Val Pro Pro
 65                  70                  75                  80

Lys Gly Ala Val

<210> SEQ ID NO 403
<211> LENGTH: 84
<212> TYPE: PRT
<213> ORGANISM: Anopheles gambia

<400> SEQUENCE: 403

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
 50                  55                  60

Lys Asp Lys Ala Arg Tyr Asn Leu Glu Met Gln Ser Tyr Val Pro Pro
 65                  70                  75                  80

Lys Gly Ala Val

<210> SEQ ID NO 404
<211> LENGTH: 84
<212> TYPE: PRT
<213> ORGANISM: Anopheles gambia

<400> SEQUENCE: 404

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
 50                  55                  60

Lys Asp Lys Ala Arg Tyr Glu Ile Glu Met Gln Ser Tyr Val Pro Pro
 65                  70                  75                  80

Lys Gly Ala Val

<210> SEQ ID NO 405
<211> LENGTH: 84
<212> TYPE: PRT
<213> ORGANISM: Anopheles gambia

<400> SEQUENCE: 405

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
             35                  40                  45

Lys Thr Met Leu Asp Lys Glu Lys Gln Arg Phe His Glu Met Ala Glu
 50                  55                  60
```

```
Lys Asp Lys Ala Arg Tyr Glu Val Glu Met Gln Ser Tyr Val Pro Pro
 65                  70                  75                  80

Lys Gly Ala Val
```

<210> SEQ ID NO 406
<211> LENGTH: 84
<212> TYPE: PRT
<213> ORGANISM: Anopheles gambia

<400> SEQUENCE: 406

```
Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Gln Met Gln Ser Tyr Val Pro Pro
 65                  70                  75                  80

Lys Gly Ala Val
```

<210> SEQ ID NO 407
<211> LENGTH: 84
<212> TYPE: PRT
<213> ORGANISM: Anopheles gambia

<400> SEQUENCE: 407

```
Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu His Met Gln Ser Tyr Val Pro Pro
 65                  70                  75                  80

Lys Gly Ala Val
```

<210> SEQ ID NO 408
<211> LENGTH: 84
<212> TYPE: PRT
<213> ORGANISM: Anopheles gambia

<400> SEQUENCE: 408

```
Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
                20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
        50                  55                  60

Lys Asp Lys Ala Arg Tyr Glu Leu Asn Met Gln Ser Tyr Val Pro Pro
 65                  70                  75                  80

Lys Gly Ala Val
```

```
<210> SEQ ID NO 409
<211> LENGTH: 84
<212> TYPE: PRT
<213> ORGANISM: Anopheles gambia

<400> SEQUENCE: 409

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Ile Gln Ser Tyr Val Pro Pro
65                  70                  75                  80

Lys Gly Ala Val

<210> SEQ ID NO 410
<211> LENGTH: 84
<212> TYPE: PRT
<213> ORGANISM: Anopheles gambia

<400> SEQUENCE: 410

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Val Gln Ser Tyr Val Pro Pro
65                  70                  75                  80

Lys Gly Ala Val

<210> SEQ ID NO 411
<211> LENGTH: 84
<212> TYPE: PRT
<213> ORGANISM: Anopheles gambia

<400> SEQUENCE: 411

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Glu Lys Gln Arg Phe His Glu Met Ala Glu
    50                  55                  60

Lys Asp Lys Ala Arg Tyr Glu Leu Glu Met Gln Ser His Val Pro Pro
65                  70                  75                  80

Lys Gly Ala Val

<210> SEQ ID NO 412
<211> LENGTH: 84
<212> TYPE: PRT
<213> ORGANISM: Anopheles gambia
```

<400> SEQUENCE: 412

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
50                  55                  60

Lys Asp Lys Ala Arg Tyr Glu Leu Glu Met Gln Ser Ile Val Pro Pro
65                  70                  75                  80

Lys Gly Ala Val

<210> SEQ ID NO 413
<211> LENGTH: 84
<212> TYPE: PRT
<213> ORGANISM: Anopheles gambia

<400> SEQUENCE: 413

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
50                  55                  60

Lys Asp Lys Ala Arg Tyr Glu Leu Glu Met Gln Ser Tyr Val Ala Pro
65                  70                  75                  80

Lys Gly Ala Val

<210> SEQ ID NO 414
<211> LENGTH: 84
<212> TYPE: PRT
<213> ORGANISM: Anopheles gambia

<400> SEQUENCE: 414

Gly Lys Val Lys Asp Asn Lys Pro Arg Gly Arg Met Thr Ala Tyr Ala
1               5                   10                  15

Phe Phe Val Gln Thr Cys Arg Glu Glu His Lys Lys His Pro Glu
            20                  25                  30

Glu Gln Val Ile Phe Ala Glu Phe Ser Arg Lys Cys Ala Glu Arg Trp
            35                  40                  45

Lys Thr Met Leu Asp Lys Glu Lys Gln Arg Phe His Glu Met Ala Glu
50                  55                  60

Lys Asp Lys Ala Arg Tyr Glu Leu Glu Met Gln Ser Tyr Val Ser Pro
65                  70                  75                  80

Lys Gly Ala Val

<210> SEQ ID NO 415
<211> LENGTH: 84
<212> TYPE: PRT
<213> ORGANISM: Anopheles gambia

<400> SEQUENCE: 415

Gly Lys Val Lys Asp Asn Lys Pro Arg Gly Arg Met Thr Ala Tyr Ala
1               5                   10                  15

```
Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Lys Gln Arg Phe His Glu Met Ala Glu
 50                  55                  60

Lys Asp Lys Ala Arg Tyr Glu Leu Glu Met Gln Ser Tyr Val Pro Ala
 65                  70                  75                  80

Lys Gly Ala Val

<210> SEQ ID NO 416
<211> LENGTH: 84
<212> TYPE: PRT
<213> ORGANISM: Anopheles gambia

<400> SEQUENCE: 416

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Lys Gln Arg Phe His Glu Met Ala Glu
 50                  55                  60

Lys Asp Lys Ala Arg Tyr Glu Leu Glu Met Gln Ser Tyr Val Pro Ser
 65                  70                  75                  80

Lys Gly Ala Val

<210> SEQ ID NO 417
<211> LENGTH: 84
<212> TYPE: PRT
<213> ORGANISM: Anopheles gambia

<400> SEQUENCE: 417

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
        35                  40                  45

Lys Thr Met Leu Asp Lys Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Asn Gly Ala Val

<210> SEQ ID NO 418
<211> LENGTH: 84
<212> TYPE: PRT
<213> ORGANISM: Anopheles gambia

<400> SEQUENCE: 418

Gly Lys Val Lys Asp Asn Lys Pro Arg Gly Arg Met Thr Ala Tyr Ala
 1               5                  10                  15

Phe Phe Val Gln Thr Cys Arg Glu Glu His Lys Lys Lys His Pro Glu
            20                  25                  30

Glu Gln Val Ile Phe Ala Glu Phe Ser Arg Lys Cys Ala Glu Arg Trp
```

```
                35                  40                  45
Lys Thr Met Leu Asp Lys Glu Lys Gln Arg Phe His Glu Met Ala Glu
 50                  55                  60

Lys Asp Lys Ala Arg Tyr Glu Leu Glu Met Gln Ser Tyr Val Pro Pro
 65                  70                  75                  80

Gln Gly Ala Val

<210> SEQ ID NO 419
<211> LENGTH: 77
<212> TYPE: PRT
<213> ORGANISM: Anopheles gambia

<400> SEQUENCE: 419

Pro Arg Gly Arg Met Thr Ala Tyr Ala Phe Phe Val Gln Thr Cys Arg
 1               5                  10                  15

Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 420
<211> LENGTH: 77
<212> TYPE: PRT
<213> ORGANISM: Anopheles gambia

<400> SEQUENCE: 420

Ala Arg Gly Arg Met Thr Ala Tyr Ala Phe Phe Val Gln Thr Cys Arg
 1               5                  10                  15

Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 421
<211> LENGTH: 77
<212> TYPE: PRT
<213> ORGANISM: Anopheles gambia

<400> SEQUENCE: 421

Ser Arg Gly Arg Met Thr Ala Tyr Ala Phe Phe Val Gln Thr Cys Arg
 1               5                  10                  15

Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75
```

```
<210> SEQ ID NO 422
<211> LENGTH: 77
<212> TYPE: PRT
<213> ORGANISM: Anopheles gambia

<400> SEQUENCE: 422

Pro His Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 423
<211> LENGTH: 77
<212> TYPE: PRT
<213> ORGANISM: Anopheles gambia

<400> SEQUENCE: 423

Pro Gln Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 424
<211> LENGTH: 77
<212> TYPE: PRT
<213> ORGANISM: Anopheles gambia

<400> SEQUENCE: 424

Pro Arg Gly His Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 425
<211> LENGTH: 77
<212> TYPE: PRT
<213> ORGANISM: Anopheles gambia

<400> SEQUENCE: 425

Pro Arg Gly Gln Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
```

```
                    20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 426
<211> LENGTH: 77
<212> TYPE: PRT
<213> ORGANISM: Anopheles gambia

<400> SEQUENCE: 426

Pro Arg Gly Arg Ile Thr Ala Tyr Ala Phe Phe Val Gln Thr Cys Arg
1               5                   10                  15

Glu Glu His Lys Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 427
<211> LENGTH: 77
<212> TYPE: PRT
<213> ORGANISM: Anopheles gambia

<400> SEQUENCE: 427

Pro Arg Gly Arg Val Thr Ala Tyr Ala Phe Phe Val Gln Thr Cys Arg
1               5                   10                  15

Glu Glu His Lys Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 428
<211> LENGTH: 77
<212> TYPE: PRT
<213> ORGANISM: Anopheles gambia

<400> SEQUENCE: 428

Pro Arg Gly Arg Met Thr Ala His Ala Phe Phe Val Gln Thr Cys Arg
1               5                   10                  15

Glu Glu His Lys Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75
```

<210> SEQ ID NO 429
<211> LENGTH: 77
<212> TYPE: PRT
<213> ORGANISM: Anopheles gambia

<400> SEQUENCE: 429

Pro Arg Gly Arg Met Thr Ala Ile Ala Phe Val Gln Thr Cys Arg
1               5                   10                  15

Glu Glu His Lys Lys His Pro Glu Gln Val Ile Phe Ala Glu
            20                  25                  30

Phe Ser Arg Lys Cys Ala Glu Arg Trp Lys Thr Met Leu Asp Lys Glu
                35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Lys Gly Ala Val
65                  70                  75

<210> SEQ ID NO 430
<211> LENGTH: 77
<212> TYPE: PRT
<213> ORGANISM: Anopheles gambia

<400> SEQUENCE: 430

Pro Arg Gly Arg Met Thr Ala Tyr Ala Ile Phe Val Gln Thr Cys Arg
1               5                   10                  15

Glu Glu His Lys Lys Lys His Pro Glu Gln Val Ile Phe Ala Glu
            20                  25                  30

Phe Ser Arg Lys Cys Ala Glu Arg Trp Lys Thr Met Leu Asp Lys Glu
                35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Lys Gly Ala Val
65                  70                  75

<210> SEQ ID NO 431
<211> LENGTH: 77
<212> TYPE: PRT
<213> ORGANISM: Anopheles gambia

<400> SEQUENCE: 431

Pro Arg Gly Arg Met Thr Ala Tyr Ala Val Phe Val Gln Thr Cys Arg
1               5                   10                  15

Glu Glu His Lys Lys Lys His Pro Glu Gln Val Ile Phe Ala Glu
            20                  25                  30

Phe Ser Arg Lys Cys Ala Glu Arg Trp Lys Thr Met Leu Asp Lys Glu
                35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Lys Gly Ala Val
65                  70                  75

<210> SEQ ID NO 432
<211> LENGTH: 77
<212> TYPE: PRT
<213> ORGANISM: Anopheles gambia

<400> SEQUENCE: 432

Pro Arg Gly Arg Met Thr Ala Tyr Ala Phe Ile Val Gln Thr Cys Arg
1               5                   10                  15

```
Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 433
<211> LENGTH: 77
<212> TYPE: PRT
<213> ORGANISM: Anopheles gambia

<400> SEQUENCE: 433

Pro Arg Gly Arg Met Thr Ala Tyr Ala Phe Val Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 434
<211> LENGTH: 77
<212> TYPE: PRT
<213> ORGANISM: Anopheles gambia

<400> SEQUENCE: 434

Pro Arg Gly Arg Met Thr Ala Tyr Ala Phe Phe Val Gln Thr Cys His
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 435
<211> LENGTH: 77
<212> TYPE: PRT
<213> ORGANISM: Anopheles gambia

<400> SEQUENCE: 435

Pro Arg Gly Arg Met Thr Ala Tyr Ala Phe Val Val Gln Thr Cys Gln
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75
```

<210> SEQ ID NO 436
<211> LENGTH: 77
<212> TYPE: PRT
<213> ORGANISM: Anopheles gambia

<400> SEQUENCE: 436

Pro Arg Gly Arg Met Thr Ala Tyr Ala Phe Phe Val Gln Thr Cys Arg
1               5                   10                  15

Gln Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 437
<211> LENGTH: 77
<212> TYPE: PRT
<213> ORGANISM: Anopheles gambia

<400> SEQUENCE: 437

Pro Arg Gly Arg Met Thr Ala Tyr Ala Phe Phe Val Gln Thr Cys Arg
1               5                   10                  15

His Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 438
<211> LENGTH: 77
<212> TYPE: PRT
<213> ORGANISM: Anopheles gambia

<400> SEQUENCE: 438

Pro Arg Gly Arg Met Thr Ala Tyr Ala Phe Phe Val Gln Thr Cys Arg
1               5                   10                  15

Asn Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 439
<211> LENGTH: 77
<212> TYPE: PRT
<213> ORGANISM: Anopheles gambia

<400> SEQUENCE: 439

Pro Arg Gly Arg Met Thr Ala Tyr Ala Phe Phe Val Gln Thr Cys Arg
1               5                   10                  15

Glu Gln His Lys Lys His Pro Glu Glu Gln Val Ile Phe Ala Glu
        20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 440
<211> LENGTH: 77
<212> TYPE: PRT
<213> ORGANISM: Anopheles gambia

<400> SEQUENCE: 440

Pro Arg Gly Arg Met Thr Ala Tyr Ala Phe Phe Val Gln Thr Cys Arg
1               5                   10                  15

Glu His His Lys Lys His Pro Glu Glu Gln Val Ile Phe Ala Glu
        20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 441
<211> LENGTH: 77
<212> TYPE: PRT
<213> ORGANISM: Anopheles gambia

<400> SEQUENCE: 441

Pro Arg Gly Arg Met Thr Ala Tyr Ala Phe Phe Val Gln Thr Cys Arg
1               5                   10                  15

Glu Asn His Lys Lys His Pro Glu Glu Gln Val Ile Phe Ala Glu
        20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 442
<211> LENGTH: 77
<212> TYPE: PRT
<213> ORGANISM: Anopheles gambia

<400> SEQUENCE: 442

Pro Arg Gly Arg Met Thr Ala Tyr Ala Phe Phe Val Gln Thr Cys Arg
1               5                   10                  15

Glu Glu His Asn Lys Lys His Pro Glu Glu Gln Val Ile Phe Ala Glu
        20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val 65              70              75

<210> SEQ ID NO 443
<211> LENGTH: 77
<212> TYPE: PRT
<213> ORGANISM: Anopheles gambia

<400> SEQUENCE: 443

Pro Arg Gly Arg Met Thr Ala Tyr Ala Phe Phe Val Gln Thr Cys Arg
1               5                   10                  15

Glu Glu His Gln Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65              70              75

<210> SEQ ID NO 444
<211> LENGTH: 77
<212> TYPE: PRT
<213> ORGANISM: Anopheles gambia

<400> SEQUENCE: 444

Pro Arg Gly Arg Met Thr Ala Tyr Ala Phe Phe Val Gln Thr Cys Arg
1               5                   10                  15

Glu Glu His Lys Asn Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65              70              75

<210> SEQ ID NO 445
<211> LENGTH: 77
<212> TYPE: PRT
<213> ORGANISM: Anopheles gambia

<400> SEQUENCE: 445

Pro Arg Gly Arg Met Thr Ala Tyr Ala Phe Phe Val Gln Thr Cys Arg
1               5                   10                  15

Glu Glu His Lys Gln Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65              70              75

<210> SEQ ID NO 446
<211> LENGTH: 77
<212> TYPE: PRT
<213> ORGANISM: Anopheles gambia

<400> SEQUENCE: 446

Pro Arg Gly Arg Met Thr Ala Tyr Ala Phe Phe Val Gln Thr Cys Arg

```
                1               5                  10                  15
Glu Glu His Lys Lys Asn His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 447
<211> LENGTH: 77
<212> TYPE: PRT
<213> ORGANISM: Anopheles gambia

<400> SEQUENCE: 447

Pro Arg Gly Arg Met Thr Ala Tyr Ala Phe Phe Val Gln Thr Cys Arg
1               5                  10                  15

Glu Glu His Lys Lys Gln His Pro Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 448
<211> LENGTH: 77
<212> TYPE: PRT
<213> ORGANISM: Anopheles gambia

<400> SEQUENCE: 448

Pro Arg Gly Arg Met Thr Ala Tyr Ala Phe Phe Val Gln Thr Cys Arg
1               5                  10                  15

Glu Glu His Lys Lys Lys His Ala Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 449
<211> LENGTH: 77
<212> TYPE: PRT
<213> ORGANISM: Anopheles gambia

<400> SEQUENCE: 449

Pro Arg Gly Arg Met Thr Ala Tyr Ala Phe Phe Val Gln Thr Cys Arg
1               5                  10                  15

Glu Glu His Lys Lys Lys His Ser Glu Glu Gln Val Ile Phe Ala Glu
                20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60
```

```
Leu Glu Met Gln Ser Tyr Val Pro Pro Lys Gly Ala Val
 65                  70                  75
```

<210> SEQ ID NO 450
<211> LENGTH: 77
<212> TYPE: PRT
<213> ORGANISM: Anopheles gambia

<400> SEQUENCE: 450

```
Pro Arg Gly Arg Met Thr Ala Tyr Ala Phe Phe Val Gln Thr Cys Arg
  1               5                  10                  15

Glu Glu His Lys Lys Lys His Pro Gln Glu Gln Val Ile Phe Ala Glu
             20                  25                  30

Phe Ser Arg Lys Cys Ala Glu Arg Trp Lys Thr Met Leu Asp Lys Glu
         35                  40                  45

Lys Gln Arg Phe His Glu Met Ala Glu Lys Asp Lys Ala Arg Tyr Glu
     50                  55                  60

Leu Glu Met Gln Ser Tyr Val Pro Pro Lys Gly Ala Val
 65                  70                  75
```

<210> SEQ ID NO 451
<211> LENGTH: 77
<212> TYPE: PRT
<213> ORGANISM: Anopheles gambia

<400> SEQUENCE: 451

```
Pro Arg Gly Arg Met Thr Ala Tyr Ala Phe Phe Val Gln Thr Cys Arg
  1               5                  10                  15

Glu Glu His Lys Lys Lys His Pro His Glu Gln Val Ile Phe Ala Glu
             20                  25                  30

Phe Ser Arg Lys Cys Ala Glu Arg Trp Lys Thr Met Leu Asp Lys Glu
         35                  40                  45

Lys Gln Arg Phe His Glu Met Ala Glu Lys Asp Lys Ala Arg Tyr Glu
     50                  55                  60

Leu Glu Met Gln Ser Tyr Val Pro Pro Lys Gly Ala Val
 65                  70                  75
```

<210> SEQ ID NO 452
<211> LENGTH: 77
<212> TYPE: PRT
<213> ORGANISM: Anopheles gambia

<400> SEQUENCE: 452

```
Pro Arg Gly Arg Met Thr Ala Tyr Ala Phe Phe Val Gln Thr Cys Arg
  1               5                  10                  15

Glu Glu His Lys Lys Lys His Pro Asn Glu Gln Val Ile Phe Ala Glu
             20                  25                  30

Phe Ser Arg Lys Cys Ala Glu Arg Trp Lys Thr Met Leu Asp Lys Glu
         35                  40                  45

Lys Gln Arg Phe His Glu Met Ala Glu Lys Asp Lys Ala Arg Tyr Glu
     50                  55                  60

Leu Glu Met Gln Ser Tyr Val Pro Pro Lys Gly Ala Val
 65                  70                  75
```

<210> SEQ ID NO 453
<211> LENGTH: 77
<212> TYPE: PRT
<213> ORGANISM: Anopheles gambia

<400> SEQUENCE: 453

```
Pro Arg Gly Arg Met Thr Ala Tyr Ala Phe Phe Val Gln Thr Cys Arg
1               5                   10                  15

Glu Glu His Lys Lys His Pro Glu Gln Val Ile Phe Ala Glu
            20              25              30

Phe Ser Arg Lys Cys Ala Glu Arg Trp Lys Thr Met Leu Asp Lys Glu
        35              40                  45

Lys Gln Arg Phe His Glu Met Ala Glu Lys Asp Lys Ala Arg Tyr Glu
        50              55              60

Leu Glu Met Gln Ser Tyr Val Pro Pro Lys Gly Ala Val
65              70              75

<210> SEQ ID NO 454
<211> LENGTH: 77
<212> TYPE: PRT
<213> ORGANISM: Anopheles gambia

<400> SEQUENCE: 454

Pro Arg Gly Arg Met Thr Ala Tyr Ala Phe Phe Val Gln Thr Cys Arg
1               5                   10                  15

Glu Glu His Lys Lys His Pro Glu His Gln Val Ile Phe Ala Glu
            20              25              30

Phe Ser Arg Lys Cys Ala Glu Arg Trp Lys Thr Met Leu Asp Lys Glu
        35              40                  45

Lys Gln Arg Phe His Glu Met Ala Glu Lys Asp Lys Ala Arg Tyr Glu
        50              55              60

Leu Glu Met Gln Ser Tyr Val Pro Pro Lys Gly Ala Val
65              70              75

<210> SEQ ID NO 455
<211> LENGTH: 77
<212> TYPE: PRT
<213> ORGANISM: Anopheles gambia

<400> SEQUENCE: 455

Pro Arg Gly Arg Met Thr Ala Tyr Ala Phe Phe Val Gln Thr Cys Arg
1               5                   10                  15

Glu Glu His Lys Lys His Pro Glu Asn Gln Val Ile Phe Ala Glu
            20              25              30

Phe Ser Arg Lys Cys Ala Glu Arg Trp Lys Thr Met Leu Asp Lys Glu
        35              40                  45

Lys Gln Arg Phe His Glu Met Ala Glu Lys Asp Lys Ala Arg Tyr Glu
        50              55              60

Leu Glu Met Gln Ser Tyr Val Pro Pro Lys Gly Ala Val
65              70              75

<210> SEQ ID NO 456
<211> LENGTH: 77
<212> TYPE: PRT
<213> ORGANISM: Anopheles gambia

<400> SEQUENCE: 456

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Ile Ala Glu
            20              25              30

Phe Ser Arg Lys Cys Ala Glu Arg Trp Lys Thr Met Leu Asp Lys Glu
        35              40                  45

Lys Gln Arg Phe His Glu Met Ala Glu Lys Asp Lys Ala Arg Tyr Glu
        50              55              60
```

Leu Glu Met Gln Ser Tyr Val Pro Pro Lys Gly Ala Val
65                  70                  75

<210> SEQ ID NO 457
<211> LENGTH: 77
<212> TYPE: PRT
<213> ORGANISM: Anopheles gambia

<400> SEQUENCE: 457

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Val Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Lys Gly Ala Val
65                  70                  75

<210> SEQ ID NO 458
<211> LENGTH: 77
<212> TYPE: PRT
<213> ORGANISM: Anopheles gambia

<400> SEQUENCE: 458

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Gln
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Lys Gly Ala Val
65                  70                  75

<210> SEQ ID NO 459
<211> LENGTH: 77
<212> TYPE: PRT
<213> ORGANISM: Anopheles gambia

<400> SEQUENCE: 459

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala His
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
            50                  55                  60

Leu Glu Met Gln Ser Tyr Val Pro Pro Lys Gly Ala Val
65                  70                  75

<210> SEQ ID NO 460
<211> LENGTH: 77
<212> TYPE: PRT
<213> ORGANISM: Anopheles gambia

<400> SEQUENCE: 460

Pro Arg Gly Arg Met Thr Ala Tyr Ala Phe Val Gln Thr Cys Arg
1               5                   10                  15

Glu Glu His Lys Lys Lys His Pro Glu Glu Gln Val Ile Phe Ala Asn
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 461
<211> LENGTH: 77
<212> TYPE: PRT
<213> ORGANISM: Anopheles gambia

<400> SEQUENCE: 461

Pro Arg Gly Arg Met Thr Ala Tyr Ala Phe Val Gln Thr Cys Arg
1               5                   10                  15

Glu Glu His Lys Lys Lys His Pro Glu Glu Gln Val Ile Phe Ala Glu
            20                  25                  30

Ile Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 462
<211> LENGTH: 77
<212> TYPE: PRT
<213> ORGANISM: Anopheles gambia

<400> SEQUENCE: 462

Pro Arg Gly Arg Met Thr Ala Tyr Ala Phe Val Gln Thr Cys Arg
1               5                   10                  15

Glu Glu His Lys Lys Lys His Pro Glu Glu Gln Val Ile Phe Ala Glu
            20                  25                  30

Val Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 463
<211> LENGTH: 77
<212> TYPE: PRT
<213> ORGANISM: Anopheles gambia

<400> SEQUENCE: 463

Pro Arg Gly Arg Met Thr Ala Tyr Ala Phe Val Gln Thr Cys Arg
1               5                   10                  15

Glu Glu His Lys Lys Lys His Pro Glu Glu Gln Val Ile Phe Ala Glu
            20                  25                  30

Phe Ser His Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu

```
                50                  55                  60
Leu Glu Met Gln Ser Tyr Val Pro Pro Lys Gly Ala Val
 65                  70                  75

<210> SEQ ID NO 464
<211> LENGTH: 77
<212> TYPE: PRT
<213> ORGANISM: Anopheles gambia

<400> SEQUENCE: 464

Pro Arg Gly Arg Met Thr Ala Tyr Ala Phe Phe Val Gln Thr Cys Arg
 1               5                  10                  15

Glu Glu His Lys Lys Lys His Pro Glu Glu Gln Val Ile Phe Ala Glu
                20                  25                  30

Phe Ser Gln Lys Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75

<210> SEQ ID NO 465
<211> LENGTH: 77
<212> TYPE: PRT
<213> ORGANISM: Anopheles gambia

<400> SEQUENCE: 465

Pro Arg Gly Arg Met Thr Ala Tyr Ala Phe Phe Val Gln Thr Cys Arg
 1               5                  10                  15

Glu Glu His Lys Lys Lys His Pro Glu Glu Gln Val Ile Phe Ala Glu
                20                  25                  30

Phe Ser Arg Asn Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75

<210> SEQ ID NO 466
<211> LENGTH: 77
<212> TYPE: PRT
<213> ORGANISM: Anopheles gambia

<400> SEQUENCE: 466

Pro Arg Gly Arg Met Thr Ala Tyr Ala Phe Phe Val Gln Thr Cys Arg
 1               5                  10                  15

Glu Glu His Lys Lys Lys His Pro Glu Glu Gln Val Ile Phe Ala Glu
                20                  25                  30

Phe Ser Arg Gln Cys Ala Glu Arg Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75

<210> SEQ ID NO 467
<211> LENGTH: 77
<212> TYPE: PRT
<213> ORGANISM: Anopheles gambia
```

-continued

<400> SEQUENCE: 467

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Gln Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 468
<211> LENGTH: 77
<212> TYPE: PRT
<213> ORGANISM: Anopheles gambia

<400> SEQUENCE: 468

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala His Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 469
<211> LENGTH: 77
<212> TYPE: PRT
<213> ORGANISM: Anopheles gambia

<400> SEQUENCE: 469

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Asn Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 470
<211> LENGTH: 77
<212> TYPE: PRT
<213> ORGANISM: Anopheles gambia

<400> SEQUENCE: 470

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu His Trp Lys Thr Met Leu Asp Lys Glu
        35                  40                  45

Lys Gln Arg Phe His Glu Met Ala Glu Lys Asp Lys Ala Arg Tyr Glu
                50                  55                  60

Leu Glu Met Gln Ser Tyr Val Pro Pro Lys Gly Ala Val
 65                  70                  75

<210> SEQ ID NO 471
<211> LENGTH: 77
<212> TYPE: PRT
<213> ORGANISM: Anopheles gambia

<400> SEQUENCE: 471

Pro Arg Gly Arg Met Thr Ala Tyr Ala Phe Phe Val Gln Thr Cys Arg
 1               5                  10                  15

Glu Glu His Lys Lys Lys His Pro Glu Glu Gln Val Ile Phe Ala Glu
                20                  25                  30

Phe Ser Arg Lys Cys Ala Glu Gln Trp Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75

<210> SEQ ID NO 472
<211> LENGTH: 77
<212> TYPE: PRT
<213> ORGANISM: Anopheles gambia

<400> SEQUENCE: 472

Pro Arg Gly Arg Met Thr Ala Tyr Ala Phe Phe Val Gln Thr Cys Arg
 1               5                  10                  15

Glu Glu His Lys Lys Lys His Pro Glu Glu Gln Val Ile Phe Ala Glu
                20                  25                  30

Phe Ser Arg Lys Cys Ala Glu Arg Tyr Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75

<210> SEQ ID NO 473
<211> LENGTH: 77
<212> TYPE: PRT
<213> ORGANISM: Anopheles gambia

<400> SEQUENCE: 473

Pro Arg Gly Arg Met Thr Ala Tyr Ala Phe Phe Val Gln Thr Cys Arg
 1               5                  10                  15

Glu Glu His Lys Lys Lys His Pro Glu Glu Gln Val Ile Phe Ala Glu
                20                  25                  30

Phe Ser Arg Lys Cys Ala Glu Arg Ser Lys Thr Met Leu Asp Lys Glu
            35                  40                  45

Lys Gln Arg Phe His Glu Met Ala Glu Lys Asp Lys Ala Arg Tyr Glu
        50                  55                  60

Leu Glu Met Gln Ser Tyr Val Pro Pro Lys Gly Ala Val
 65                  70                  75

<210> SEQ ID NO 474
<211> LENGTH: 77
<212> TYPE: PRT
<213> ORGANISM: Anopheles gambia -continued

<400> SEQUENCE: 474

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Asn Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 475
<211> LENGTH: 77
<212> TYPE: PRT
<213> ORGANISM: Anopheles gambia

<400> SEQUENCE: 475

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Gln Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 476
<211> LENGTH: 77
<212> TYPE: PRT
<213> ORGANISM: Anopheles gambia

<400> SEQUENCE: 476

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Ile Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 477
<211> LENGTH: 77
<212> TYPE: PRT
<213> ORGANISM: Anopheles gambia

<400> SEQUENCE: 477

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Val Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 478
<211> LENGTH: 77
<212> TYPE: PRT
<213> ORGANISM: Anopheles gambia

<400> SEQUENCE: 478

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
                20                  25                  30

Phe Ser Arg Lys Cys Ala Glu Arg Trp Lys Thr Met Ile Asp Lys Glu
            35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 479
<211> LENGTH: 77
<212> TYPE: PRT
<213> ORGANISM: Anopheles gambia

<400> SEQUENCE: 479

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
                20                  25                  30

Phe Ser Arg Lys Cys Ala Glu Arg Trp Lys Thr Met Val Asp Lys Glu
            35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 480
<211> LENGTH: 77
<212> TYPE: PRT
<213> ORGANISM: Anopheles gambia

<400> SEQUENCE: 480

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
                20                  25                  30

Phe Ser Arg Lys Cys Ala Glu Arg Trp Lys Thr Met Leu Asn Lys Glu
            35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 481
<211> LENGTH: 77
<212> TYPE: PRT

```
<213> ORGANISM: Anopheles gambia

<400> SEQUENCE: 481

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Gln Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 482
<211> LENGTH: 77
<212> TYPE: PRT
<213> ORGANISM: Anopheles gambia

<400> SEQUENCE: 482

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Asn Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 483
<211> LENGTH: 77
<212> TYPE: PRT
<213> ORGANISM: Anopheles gambia

<400> SEQUENCE: 483

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Gln Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 484
<211> LENGTH: 77
<212> TYPE: PRT
<213> ORGANISM: Anopheles gambia

<400> SEQUENCE: 484

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Gln
```

-continued

```
                35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 485
<211> LENGTH: 77
<212> TYPE: PRT
<213> ORGANISM: Anopheles gambia

<400> SEQUENCE: 485

Pro Arg Gly Arg Met Thr Ala Tyr Ala Phe Val Gln Thr Cys Arg
 1               5                  10                  15

Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys His
                35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 486
<211> LENGTH: 77
<212> TYPE: PRT
<213> ORGANISM: Anopheles gambia

<400> SEQUENCE: 486

Pro Arg Gly Arg Met Thr Ala Tyr Ala Phe Val Gln Thr Cys Arg
 1               5                  10                  15

Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys Asn
                35                  40                  45

Lys Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 487
<211> LENGTH: 77
<212> TYPE: PRT
<213> ORGANISM: Anopheles gambia

<400> SEQUENCE: 487

Pro Arg Gly Arg Met Thr Ala Tyr Ala Phe Val Gln Thr Cys Arg
 1               5                  10                  15

Glu Glu His Lys Lys His Pro Glu Glu Gln Val Ile Phe Ala Glu
                20                  25                  30

Phe Ser Arg Lys Cys Ala Glu Arg Trp Lys Thr Met Leu Asp Lys Glu
                35                  40                  45

Asn Gln Arg Phe His Glu Met Ala Glu Lys Asp Lys Ala Arg Tyr Glu
 50                  55                  60

Leu Glu Met Gln Ser Tyr Val Pro Pro Lys Gly Ala Val
 65                  70                  75

<210> SEQ ID NO 488
<211> LENGTH: 77
```

```
<212> TYPE: PRT
<213> ORGANISM: Anopheles gambia

<400> SEQUENCE: 488

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Gln Gln Arg Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 489
<211> LENGTH: 77
<212> TYPE: PRT
<213> ORGANISM: Anopheles gambia

<400> SEQUENCE: 489

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln His Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 490
<211> LENGTH: 77
<212> TYPE: PRT
<213> ORGANISM: Anopheles gambia

<400> SEQUENCE: 490

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Gln Phe His Glu Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 491
<211> LENGTH: 77
<212> TYPE: PRT
<213> ORGANISM: Anopheles gambia

<400> SEQUENCE: 491

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30
```

Phe Ser Arg Lys Cys Ala Glu Arg Trp Lys Thr Met Leu Asp Lys Glu
            35                  40                  45

Lys Gln Arg Ile His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 492
<211> LENGTH: 77
<212> TYPE: PRT
<213> ORGANISM: Anopheles gambia

<400> SEQUENCE: 492

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Val His Glu Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 493
<211> LENGTH: 77
<212> TYPE: PRT
<213> ORGANISM: Anopheles gambia

<400> SEQUENCE: 493

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Gln Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 494
<211> LENGTH: 77
<212> TYPE: PRT
<213> ORGANISM: Anopheles gambia

<400> SEQUENCE: 494

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His His Met Ala Glu Lys Asp Lys Ala Arg Tyr Glu
        50                  55                  60

Leu Glu Met Gln Ser Tyr Val Pro Pro Lys Gly Ala Val
65                  70                  75

<210> SEQ ID NO 495

<211> LENGTH: 77
<212> TYPE: PRT
<213> ORGANISM: Anopheles gambia

<400> SEQUENCE: 495

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Asn Met Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 496
<211> LENGTH: 77
<212> TYPE: PRT
<213> ORGANISM: Anopheles gambia

<400> SEQUENCE: 496

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Ile Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 497
<211> LENGTH: 77
<212> TYPE: PRT
<213> ORGANISM: Anopheles gambia

<400> SEQUENCE: 497

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Val Ala Glu Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 498
<211> LENGTH: 77
<212> TYPE: PRT
<213> ORGANISM: Anopheles gambia

<400> SEQUENCE: 498

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

```
Phe Ser Arg Lys Cys Ala Glu Arg Trp Lys Thr Met Leu Asp Lys Glu
            35                  40                  45

Lys Gln Arg Phe His Glu Met Ala Gln Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 499
<211> LENGTH: 77
<212> TYPE: PRT
<213> ORGANISM: Anopheles gambia

<400> SEQUENCE: 499

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala His Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 500
<211> LENGTH: 77
<212> TYPE: PRT
<213> ORGANISM: Anopheles gambia

<400> SEQUENCE: 500

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Asn Lys Asp Lys Ala Arg Tyr Glu
    50                  55                  60

Leu Glu Met Gln Ser Tyr Val Pro Pro Lys Gly Ala Val
65                  70                  75

<210> SEQ ID NO 501
<211> LENGTH: 77
<212> TYPE: PRT
<213> ORGANISM: Anopheles gambia

<400> SEQUENCE: 501

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
            35                  40                  45

Lys Gln Arg Phe His Glu Met Ala Glu Asn Asp Lys Ala Arg Tyr Glu
    50                  55                  60

Leu Glu Met Gln Ser Tyr Val Pro Pro Lys Gly Ala Val
65                  70                  75
```

```
<210> SEQ ID NO 502
<211> LENGTH: 77
<212> TYPE: PRT
<213> ORGANISM: Anopheles gambia

<400> SEQUENCE: 502

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Gln Asp Lys Ala Arg Tyr Glu
    50                  55                  60

Leu Glu Met Gln Ser Tyr Val Pro Pro Lys Gly Ala Val
65                  70                  75

<210> SEQ ID NO 503
<211> LENGTH: 77
<212> TYPE: PRT
<213> ORGANISM: Anopheles gambia

<400> SEQUENCE: 503

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asn Lys Ala Arg Tyr Glu
    50                  55                  60

Leu Glu Met Gln Ser Tyr Val Pro Pro Lys Gly Ala Val
65                  70                  75

<210> SEQ ID NO 504
<211> LENGTH: 77
<212> TYPE: PRT
<213> ORGANISM: Anopheles gambia

<400> SEQUENCE: 504

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Lys Lys Ala Arg Tyr Glu
    50                  55                  60

Leu Glu Met Gln Ser Tyr Val Pro Pro Lys Gly Ala Val
65                  70                  75

<210> SEQ ID NO 505
<211> LENGTH: 77
<212> TYPE: PRT
<213> ORGANISM: Anopheles gambia

<400> SEQUENCE: 505

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
```

```
            20                  25                  30
Phe Ser Arg Lys Cys Ala Glu Arg Trp Lys Thr Met Leu Asp Lys Glu
        35                  40                  45
Lys Gln Arg Phe His Glu Met Ala Glu Lys Asp Asn Ala Arg Tyr Glu
    50                  55                  60
Leu Glu Met Gln Ser Tyr Val Pro Pro Lys Gly Ala Val
65                  70                  75
```

<210> SEQ ID NO 506
<211> LENGTH: 77
<212> TYPE: PRT
<213> ORGANISM: Anopheles gambia

<400> SEQUENCE: 506

```
Pro Arg Gly Arg Met Thr Ala Tyr Ala Phe Phe Val Gln Thr Cys Arg
1               5                   10                  15
Glu Glu His Lys Lys Lys His Pro Glu Glu Gln Val Ile Phe Ala Glu
            20                  25                  30
Phe Ser Arg Lys Cys Ala Glu Arg Trp Lys Thr Met Leu Asp Lys Glu
        35                  40                  45
Lys Gln Arg Phe His Glu Met Ala Glu Lys Asp Gln Ala Arg Tyr Glu
    50                  55                  60
Leu Glu Met Gln Ser Tyr Val Pro Pro Lys Gly Ala Val
65                  70                  75
```

<210> SEQ ID NO 507
<211> LENGTH: 77
<212> TYPE: PRT
<213> ORGANISM: Anopheles gambia

<400> SEQUENCE: 507

```
Pro Arg Gly Arg Met Thr Ala Tyr Ala Phe Phe Val Gln Thr Cys Arg
1               5                   10                  15
Glu Glu His Lys Lys Lys His Pro Glu Glu Gln Val Ile Phe Ala Glu
            20                  25                  30
Phe Ser Arg Lys Cys Ala Glu Arg Trp Lys Thr Met Leu Asp Lys Glu
        35                  40                  45
Lys Gln Arg Phe His Glu Met Ala Glu Lys Asp Lys Ala His Tyr Glu
    50                  55                  60
Leu Glu Met Gln Ser Tyr Val Pro Pro Lys Gly Ala Val
65                  70                  75
```

<210> SEQ ID NO 508
<211> LENGTH: 77
<212> TYPE: PRT
<213> ORGANISM: Anopheles gambia

<400> SEQUENCE: 508

```
Pro Arg Gly Arg Met Thr Ala Tyr Ala Phe Phe Val Gln Thr Cys Arg
1               5                   10                  15
Glu Glu His Lys Lys Lys His Pro Glu Glu Gln Val Ile Phe Ala Glu
            20                  25                  30
Phe Ser Arg Lys Cys Ala Glu Arg Trp Lys Thr Met Leu Asp Lys Glu
        35                  40                  45
Lys Gln Arg Phe His Glu Met Ala Glu Lys Asp Lys Ala Gln Tyr Glu
    50                  55                  60
Leu Glu Met Gln Ser Tyr Val Pro Pro Lys Gly Ala Val
65                  70                  75
```

<210> SEQ ID NO 509
<211> LENGTH: 77
<212> TYPE: PRT
<213> ORGANISM: Anopheles gambia

<400> SEQUENCE: 509

Pro Arg Gly Arg Met Thr Ala Tyr Ala Phe Phe Val Gln Thr Cys Arg
1               5                   10                  15

Glu Glu His Lys Lys His Pro Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg His Glu
    50                  55                  60

Leu Glu Met Gln Ser Tyr Val Pro Pro Lys Gly Ala Val
65                  70                  75

<210> SEQ ID NO 510
<211> LENGTH: 77
<212> TYPE: PRT
<213> ORGANISM: Anopheles gambia

<400> SEQUENCE: 510

Pro Arg Gly Arg Met Thr Ala Tyr Ala Phe Phe Val Gln Thr Cys Arg
1               5                   10                  15

Glu Glu His Lys Lys His Pro Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Ile Glu
    50                  55                  60

Leu Glu Met Gln Ser Tyr Val Pro Pro Lys Gly Ala Val
65                  70                  75

<210> SEQ ID NO 511
<211> LENGTH: 77
<212> TYPE: PRT
<213> ORGANISM: Anopheles gambia

<400> SEQUENCE: 511

Pro Arg Gly Arg Met Thr Ala Tyr Ala Phe Phe Val Gln Thr Cys Arg
1               5                   10                  15

Glu Glu His Lys Lys His Pro Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Gln
    50                  55                  60

Leu Glu Met Gln Ser Tyr Val Pro Pro Lys Gly Ala Val
65                  70                  75

<210> SEQ ID NO 512
<211> LENGTH: 77
<212> TYPE: PRT
<213> ORGANISM: Anopheles gambia

<400> SEQUENCE: 512

Pro Arg Gly Arg Met Thr Ala Tyr Ala Phe Phe Val Gln Thr Cys Arg
1               5                   10                  15

```
Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr His
    50                  55                  60

Leu Glu Met Gln Ser Tyr Val Pro Pro Lys Gly Ala Val
65                  70                  75
```

<210> SEQ ID NO 513
<211> LENGTH: 77
<212> TYPE: PRT
<213> ORGANISM: Anopheles gambia

<400> SEQUENCE: 513

```
Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Asn
    50                  55                  60

Leu Glu Met Gln Ser Tyr Val Pro Pro Lys Gly Ala Val
65                  70                  75
```

<210> SEQ ID NO 514
<211> LENGTH: 77
<212> TYPE: PRT
<213> ORGANISM: Anopheles gambia

<400> SEQUENCE: 514

```
Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Ile Glu Met Gln Ser Tyr Val Pro Pro Lys Gly Ala Val
65                  70                  75
```

<210> SEQ ID NO 515
<211> LENGTH: 77
<212> TYPE: PRT
<213> ORGANISM: Anopheles gambia

<400> SEQUENCE: 515

```
Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Val Glu Met Gln Ser Tyr Val Pro Pro Lys Gly Ala Val
65                  70                  75
```

<210> SEQ ID NO 516
<211> LENGTH: 77
<212> TYPE: PRT
<213> ORGANISM: Anopheles gambia

<400> SEQUENCE: 516

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Gln Met Gln Ser Tyr Val Pro Pro Lys Gly Ala Val
65                  70                  75

<210> SEQ ID NO 517
<211> LENGTH: 77
<212> TYPE: PRT
<213> ORGANISM: Anopheles gambia

<400> SEQUENCE: 517

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu His Met Gln Ser Tyr Val Pro Pro Lys Gly Ala Val
65                  70                  75

<210> SEQ ID NO 518
<211> LENGTH: 77
<212> TYPE: PRT
<213> ORGANISM: Anopheles gambia

<400> SEQUENCE: 518

Pro Arg Gly Arg Met Thr Ala Tyr Ala Phe Phe Val Gln Thr Cys Arg
1               5                   10                  15

Glu Glu His Lys Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Asn Met Gln Ser Tyr Val Pro Pro Lys Gly Ala Val
65                  70                  75

<210> SEQ ID NO 519
<211> LENGTH: 77
<212> TYPE: PRT
<213> ORGANISM: Anopheles gambia

<400> SEQUENCE: 519

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Ile Gln Ser Tyr Val Pro Pro Lys Gly Ala Val
65                  70                  75

<210> SEQ ID NO 520
<211> LENGTH: 77
<212> TYPE: PRT
<213> ORGANISM: Anopheles gambia

<400> SEQUENCE: 520

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Val Gln Ser Tyr Val Pro Pro Lys Gly Ala Val
65                  70                  75

<210> SEQ ID NO 521
<211> LENGTH: 77
<212> TYPE: PRT
<213> ORGANISM: Anopheles gambia

<400> SEQUENCE: 521

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser His Val Pro Pro Lys Gly Ala Val
65                  70                  75

<210> SEQ ID NO 522
<211> LENGTH: 77
<212> TYPE: PRT
<213> ORGANISM: Anopheles gambia

<400> SEQUENCE: 522

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Ile Val Pro Pro Lys Gly Ala Val

<210> SEQ ID NO 523
<211> LENGTH: 77
<212> TYPE: PRT
<213> ORGANISM: Anopheles gambia

<400> SEQUENCE: 523

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Ala Pro Lys Gly Ala Val
65                  70                  75

<210> SEQ ID NO 524
<211> LENGTH: 77
<212> TYPE: PRT
<213> ORGANISM: Anopheles gambia

<400> SEQUENCE: 524

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Ser Pro Lys Gly Ala Val
65                  70                  75

<210> SEQ ID NO 525
<211> LENGTH: 77
<212> TYPE: PRT
<213> ORGANISM: Anopheles gambia

<400> SEQUENCE: 525

Pro Arg Gly Arg Met Thr Ala Tyr Ala Phe Phe Val Gln Thr Cys Arg
1               5                   10                  15

Glu Glu His Lys Lys His Pro Glu Glu Gln Val Ile Phe Ala Glu
            20                  25                  30

Phe Ser Arg Lys Cys Ala Glu Arg Trp Lys Thr Met Leu Asp Lys Glu
        35                  40                  45

Lys Gln Arg Phe His Glu Met Ala Glu Lys Asp Lys Ala Arg Tyr Glu
    50                  55                  60

Leu Glu Met Gln Ser Tyr Val Pro Ala Lys Gly Ala Val
65                  70                  75

<210> SEQ ID NO 526
<211> LENGTH: 77
<212> TYPE: PRT
<213> ORGANISM: Anopheles gambia

<400> SEQUENCE: 526

Pro Arg Gly Arg Met Thr Ala Tyr Ala Phe Phe Val Gln Thr Cys Arg

```
                1               5                  10                 15
Glu Glu His Lys Lys His Pro Glu Glu Gln Val Ile Phe Ala Glu
                20                 25                 30

Phe Ser Arg Lys Cys Ala Glu Arg Trp Lys Thr Met Leu Asp Lys Glu
            35                  40                 45

Lys Gln Arg Phe His Glu Met Ala Glu Lys Asp Lys Ala Arg Tyr Glu
        50                  55                 60

Leu Glu Met Gln Ser Tyr Val Pro Ser Lys Gly Ala Val
65                  70                  75
```

<210> SEQ ID NO 527
<211> LENGTH: 77
<212> TYPE: PRT
<213> ORGANISM: Anopheles gambia

<400> SEQUENCE: 527

```
Pro Arg Gly Arg Met Thr Ala Tyr Ala Phe Phe Val Gln Thr Cys Arg
1               5                  10                 15

Glu Glu His Lys Lys His Pro Glu Glu Gln Val Ile Phe Ala Glu
                20                 25                 30

Phe Ser Arg Lys Cys Ala Glu Arg Trp Lys Thr Met Leu Asp Lys Glu
            35                  40                 45

Lys Gln Arg Phe His Glu Met Ala Glu Lys Asp Lys Ala Arg Tyr Glu
        50                  55                 60

Leu Glu Met Gln Ser Tyr Val Pro Pro Asn Gly Ala Val
65                  70                  75
```

<210> SEQ ID NO 528
<211> LENGTH: 77
<212> TYPE: PRT
<213> ORGANISM: Anopheles gambia

<400> SEQUENCE: 528

```
Pro Arg Gly Arg Met Thr Ala Tyr Ala Phe Phe Val Gln Thr Cys Arg
1               5                  10                 15

Glu Glu His Lys Lys His Pro Glu Glu Gln Val Ile Phe Ala Glu
                20                 25                 30

Phe Ser Arg Lys Cys Ala Glu Arg Trp Lys Thr Met Leu Asp Lys Glu
            35                  40                 45

Lys Gln Arg Phe His Glu Met Ala Glu Lys Asp Lys Ala Arg Tyr Glu
        50                  55                 60

Leu Glu Met Gln Ser Tyr Val Pro Pro Gln Gly Ala Val
65                  70                  75
```

<210> SEQ ID NO 529
<211> LENGTH: 54
<212> TYPE: PRT
<213> ORGANISM: Anopheles gambia

<400> SEQUENCE: 529

```
Pro Glu Glu Gln Val Ile Phe Ala Glu Phe Ser Arg Lys Cys Ala Glu
1               5                  10                 15

Arg Trp Lys Thr Met Leu Asp Lys Glu Lys Gln Arg Phe His Glu Met
            20                  25                 30

Ala Glu Lys Asp Lys Ala Arg Tyr Glu Leu Glu Met Gln Ser Tyr Val
        35                  40                 45

Pro Pro Lys Gly Ala Val
    50
```

```
<210> SEQ ID NO 530
<211> LENGTH: 54
<212> TYPE: PRT
<213> ORGANISM: Anopheles gambia

<400> SEQUENCE: 530

Ala Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 531
<211> LENGTH: 54
<212> TYPE: PRT
<213> ORGANISM: Anopheles gambia

<400> SEQUENCE: 531

Ser Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 532
<211> LENGTH: 54
<212> TYPE: PRT
<213> ORGANISM: Anopheles gambia

<400> SEQUENCE: 532

Pro Gln Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 533
<211> LENGTH: 54
<212> TYPE: PRT
<213> ORGANISM: Anopheles gambia

<400> SEQUENCE: 533

Pro His Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50
```

<210> SEQ ID NO 534
<211> LENGTH: 54
<212> TYPE: PRT
<213> ORGANISM: Anopheles gambia

<400> SEQUENCE: 534

Pro Asn Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 535
<211> LENGTH: 54
<212> TYPE: PRT
<213> ORGANISM: Anopheles gambia

<400> SEQUENCE: 535

Pro Glu Gln Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 536
<211> LENGTH: 54
<212> TYPE: PRT
<213> ORGANISM: Anopheles gambia

<400> SEQUENCE: 536

Pro Glu His Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 537
<211> LENGTH: 54
<212> TYPE: PRT
<213> ORGANISM: Anopheles gambia

<400> SEQUENCE: 537

Pro Glu Asn Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 538
<211> LENGTH: 54
<212> TYPE: PRT
<213> ORGANISM: Anopheles gambia

<400> SEQUENCE: 538

Pro Glu Glu Gln Val Ile Ile Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 539
<211> LENGTH: 54
<212> TYPE: PRT
<213> ORGANISM: Anopheles gambia

<400> SEQUENCE: 539

Pro Glu Glu Gln Val Ile Val Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 540
<211> LENGTH: 54
<212> TYPE: PRT
<213> ORGANISM: Anopheles gambia

<400> SEQUENCE: 540

Pro Glu Glu Gln Val Ile Phe Ala Gln Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 541
<211> LENGTH: 54
<212> TYPE: PRT
<213> ORGANISM: Anopheles gambia

<400> SEQUENCE: 541

Pro Glu Glu Gln Val Ile Phe Ala His Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

-continued

<210> SEQ ID NO 542
<211> LENGTH: 54
<212> TYPE: PRT
<213> ORGANISM: Anopheles gambia

<400> SEQUENCE: 542

Pro Glu Glu Gln Val Ile Phe Ala Asn Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
        50

<210> SEQ ID NO 543
<211> LENGTH: 54
<212> TYPE: PRT
<213> ORGANISM: Anopheles gambia

<400> SEQUENCE: 543

Pro Glu Glu Gln Val Ile Phe Ala Glu Ile Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
        50

<210> SEQ ID NO 544
<211> LENGTH: 54
<212> TYPE: PRT
<213> ORGANISM: Anopheles gambia

<400> SEQUENCE: 544

Pro Glu Glu Gln Val Ile Phe Ala Glu Val Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
        50

<210> SEQ ID NO 545
<211> LENGTH: 54
<212> TYPE: PRT
<213> ORGANISM: Anopheles gambia

<400> SEQUENCE: 545

Pro Glu Glu Gln Val Ile Phe Ala Glu Phe Ser His Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
        50

```
<210> SEQ ID NO 546
<211> LENGTH: 54
<212> TYPE: PRT
<213> ORGANISM: Anopheles gambia

<400> SEQUENCE: 546

Pro Glu Glu Gln Val Ile Phe Ala Glu Phe Ser Gln Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 547
<211> LENGTH: 54
<212> TYPE: PRT
<213> ORGANISM: Anopheles gambia

<400> SEQUENCE: 547

Pro Glu Glu Gln Val Ile Phe Ala Glu Phe Ser Arg Asn Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 548
<211> LENGTH: 54
<212> TYPE: PRT
<213> ORGANISM: Anopheles gambia

<400> SEQUENCE: 548

Pro Glu Glu Gln Val Ile Phe Ala Glu Phe Ser Arg Gln Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 549
<211> LENGTH: 54
<212> TYPE: PRT
<213> ORGANISM: Anopheles gambia

<400> SEQUENCE: 549

Pro Glu Glu Gln Val Ile Phe Ala Glu Phe Ser Arg Lys Cys Ala Gln
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50
```

<210> SEQ ID NO 550
<211> LENGTH: 54
<212> TYPE: PRT
<213> ORGANISM: Anopheles gambia

<400> SEQUENCE: 550

Pro Glu Glu Gln Val Ile Phe Ala Glu Phe Ser Arg Lys Cys Ala His
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 551
<211> LENGTH: 54
<212> TYPE: PRT
<213> ORGANISM: Anopheles gambia

<400> SEQUENCE: 551

Pro Glu Glu Gln Val Ile Phe Ala Glu Phe Ser Arg Lys Cys Ala Asn
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 552
<211> LENGTH: 54
<212> TYPE: PRT
<213> ORGANISM: Anopheles gambia

<400> SEQUENCE: 552

Pro Glu Glu Gln Val Ile Phe Ala Glu Phe Ser Arg Lys Cys Ala Glu
1               5                   10                  15

His Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 553
<211> LENGTH: 54
<212> TYPE: PRT
<213> ORGANISM: Anopheles gambia

<400> SEQUENCE: 553

Pro Glu Glu Gln Val Ile Phe Ala Glu Phe Ser Arg Lys Cys Ala Glu
1               5                   10                  15

Gln Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 554
<211> LENGTH: 54
<212> TYPE: PRT
<213> ORGANISM: Anopheles gambia

<400> SEQUENCE: 554

Pro Glu Glu Gln Val Ile Phe Ala Glu Phe Ser Arg Lys Cys Ala Glu
1               5                   10                  15

Arg Tyr Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 555
<211> LENGTH: 54
<212> TYPE: PRT
<213> ORGANISM: Anopheles gambia

<400> SEQUENCE: 555

Pro Glu Glu Gln Val Ile Phe Ala Glu Phe Ser Arg Lys Cys Ala Glu
1               5                   10                  15

Arg Ser Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 556
<211> LENGTH: 54
<212> TYPE: PRT
<213> ORGANISM: Anopheles gambia

<400> SEQUENCE: 556

Pro Glu Glu Gln Val Ile Phe Ala Glu Phe Ser Arg Lys Cys Ala Glu
1               5                   10                  15

Arg Trp Asn Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 557
<211> LENGTH: 54
<212> TYPE: PRT
<213> ORGANISM: Anopheles gambia

<400> SEQUENCE: 557

Pro Glu Glu Gln Val Ile Phe Ala Glu Phe Ser Arg Lys Cys Ala Glu
1               5                   10                  15

Arg Trp Gln Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 558
<211> LENGTH: 54
<212> TYPE: PRT
<213> ORGANISM: Anopheles gambia

<400> SEQUENCE: 558

Pro Glu Glu Gln Val Ile Phe Ala Glu Phe Ser Arg Lys Cys Ala Glu
1               5                   10                  15

Arg Trp Lys Thr Ile Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 559
<211> LENGTH: 54
<212> TYPE: PRT
<213> ORGANISM: Anopheles gambia

<400> SEQUENCE: 559

Pro Glu Glu Gln Val Ile Phe Ala Glu Phe Ser Arg Lys Cys Ala Glu
1               5                   10                  15

Arg Trp Lys Thr Val Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 560
<211> LENGTH: 54
<212> TYPE: PRT
<213> ORGANISM: Anopheles gambia

<400> SEQUENCE: 560

Pro Glu Glu Gln Val Ile Phe Ala Glu Phe Ser Arg Lys Cys Ala Glu
1               5                   10                  15

Arg Trp Lys Thr Met Ile Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 561
<211> LENGTH: 54
<212> TYPE: PRT
<213> ORGANISM: Anopheles gambia

<400> SEQUENCE: 561

Pro Glu Glu Gln Val Ile Phe Ala Glu Phe Ser Arg Lys Cys Ala Glu
1               5                   10                  15

Arg Trp Lys Thr Met Val Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 562
<211> LENGTH: 54
<212> TYPE: PRT
<213> ORGANISM: Anopheles gambia

<400> SEQUENCE: 562

Pro Glu Glu Gln Val Ile Phe Ala Glu Phe Ser Arg Lys Cys Ala Glu
1               5                   10                  15

Arg Trp Lys Thr Met Leu Asn Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 563
<211> LENGTH: 54
<212> TYPE: PRT
<213> ORGANISM: Anopheles gambia

<400> SEQUENCE: 563

Pro Glu Glu Gln Val Ile Phe Ala Glu Phe Ser Arg Lys Cys Ala Glu
1               5                   10                  15

Arg Trp Lys Thr Met Leu Gln Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 564
<211> LENGTH: 54
<212> TYPE: PRT
<213> ORGANISM: Anopheles gambia

<400> SEQUENCE: 564

Pro Glu Glu Gln Val Ile Phe Ala Glu Phe Ser Arg Lys Cys Ala Glu
1               5                   10                  15

Arg Trp Lys Thr Met Leu Asp Asn Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 565
<211> LENGTH: 54
<212> TYPE: PRT
<213> ORGANISM: Anopheles gambia

<400> SEQUENCE: 565

Pro Glu Glu Gln Val Ile Phe Ala Glu Phe Ser Arg Lys Cys Ala Glu
1               5                   10                  15

Arg Trp Lys Thr Met Leu Asp Gln Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 566
<211> LENGTH: 54
<212> TYPE: PRT
<213> ORGANISM: Anopheles gambia

<400> SEQUENCE: 566

Pro Glu Glu Gln Val Ile Phe Ala Glu Phe Ser Arg Lys Cys Ala Glu
1               5                   10                  15

Arg Trp Lys Thr Met Leu Asp Lys Gln Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 567
<211> LENGTH: 54
<212> TYPE: PRT
<213> ORGANISM: Anopheles gambia

<400> SEQUENCE: 567

Pro Glu Glu Gln Val Ile Phe Ala Glu Phe Ser Arg Lys Cys Ala Glu
1               5                   10                  15

Arg Trp Lys Thr Met Leu Asp Lys His Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 568
<211> LENGTH: 54
<212> TYPE: PRT
<213> ORGANISM: Anopheles gambia

<400> SEQUENCE: 568

Pro Glu Glu Gln Val Ile Phe Ala Glu Phe Ser Arg Lys Cys Ala Glu
1               5                   10                  15

Arg Trp Lys Thr Met Leu Asp Lys Asn Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 569
<211> LENGTH: 54
<212> TYPE: PRT
<213> ORGANISM: Anopheles gambia

<400> SEQUENCE: 569

Pro Glu Glu Gln Val Ile Phe Ala Glu Phe Ser Arg Lys Cys Ala Glu
1               5                   10                  15

Arg Trp Lys Thr Met Leu Asp Lys Glu Asn Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 570
<211> LENGTH: 54
<212> TYPE: PRT
<213> ORGANISM: Anopheles gambia

<400> SEQUENCE: 570

Pro Glu Glu Gln Val Ile Phe Ala Glu Phe Ser Arg Lys Cys Ala Glu
1               5                   10                  15

Arg Trp Lys Thr Met Leu Asp Lys Glu Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 571
<211> LENGTH: 54
<212> TYPE: PRT
<213> ORGANISM: Anopheles gambia

<400> SEQUENCE: 571

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln His Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 572
<211> LENGTH: 54
<212> TYPE: PRT
<213> ORGANISM: Anopheles gambia

<400> SEQUENCE: 572

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Gln Phe His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 573
<211> LENGTH: 54
<212> TYPE: PRT
<213> ORGANISM: Anopheles gambia

<400> SEQUENCE: 573

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Ile His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 574
<211> LENGTH: 54
<212> TYPE: PRT
<213> ORGANISM: Anopheles gambia

<400> SEQUENCE: 574

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Val His Glu Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 575
<211> LENGTH: 54
<212> TYPE: PRT
<213> ORGANISM: Anopheles gambia

<400> SEQUENCE: 575

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Gln Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 576
<211> LENGTH: 54
<212> TYPE: PRT
<213> ORGANISM: Anopheles gambia

<400> SEQUENCE: 576

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His His Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 577
<211> LENGTH: 54
<212> TYPE: PRT
<213> ORGANISM: Anopheles gambia

<400> SEQUENCE: 577

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Asn Met
            20                  25                  30

Ala Glu Lys Asp Lys Ala Arg Tyr Glu Leu Glu Met Gln Ser Tyr Val
        35                  40                  45

Pro Pro Lys Gly Ala Val
    50

-continued

<210> SEQ ID NO 578
<211> LENGTH: 54
<212> TYPE: PRT
<213> ORGANISM: Anopheles gambia

<400> SEQUENCE: 578

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Ile
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 579
<211> LENGTH: 54
<212> TYPE: PRT
<213> ORGANISM: Anopheles gambia

<400> SEQUENCE: 579

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Val
            20                  25                  30

Ala Glu Lys Asp Lys Ala Arg Tyr Glu Leu Glu Met Gln Ser Tyr Val
        35                  40                  45

Pro Pro Lys Gly Ala Val
    50

<210> SEQ ID NO 580
<211> LENGTH: 54
<212> TYPE: PRT
<213> ORGANISM: Anopheles gambia

<400> SEQUENCE: 580

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Gln Lys Asp Lys Ala Arg Tyr Glu Leu Glu Met Gln Ser Tyr Val
        35                  40                  45

Pro Pro Lys Gly Ala Val
    50

<210> SEQ ID NO 581
<211> LENGTH: 54
<212> TYPE: PRT
<213> ORGANISM: Anopheles gambia

<400> SEQUENCE: 581

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala His Lys Asp Lys Ala Arg Tyr Glu Leu Glu Met Gln Ser Tyr Val
        35                  40                  45

Pro Pro Lys Gly Ala Val
    50

<210> SEQ ID NO 582
<211> LENGTH: 54
<212> TYPE: PRT
<213> ORGANISM: Anopheles gambia

<400> SEQUENCE: 582

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Asn Lys Asp Lys Ala Arg Tyr Glu Leu Glu Met Gln Ser Tyr Val
        35                  40                  45

Pro Pro Lys Gly Ala Val
    50

<210> SEQ ID NO 583
<211> LENGTH: 54
<212> TYPE: PRT
<213> ORGANISM: Anopheles gambia

<400> SEQUENCE: 583

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Asn Asp Lys Ala Arg Tyr Glu Leu Glu Met Gln Ser Tyr Val
        35                  40                  45

Pro Pro Lys Gly Ala Val
    50

<210> SEQ ID NO 584
<211> LENGTH: 54
<212> TYPE: PRT
<213> ORGANISM: Anopheles gambia

<400> SEQUENCE: 584

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Gln Asp Lys Ala Arg Tyr Glu Leu Glu Met Gln Ser Tyr Val
        35                  40                  45

Pro Pro Lys Gly Ala Val
    50

<210> SEQ ID NO 585
<211> LENGTH: 54
<212> TYPE: PRT
<213> ORGANISM: Anopheles gambia

<400> SEQUENCE: 585

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asn Lys Ala Arg Tyr Glu Leu Glu Met Gln Ser Tyr Val
        35                  40                  45

Pro Pro Lys Gly Ala Val
    50

<210> SEQ ID NO 586
<211> LENGTH: 54
<212> TYPE: PRT
<213> ORGANISM: Anopheles gambia

<400> SEQUENCE: 586

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Gln Lys Ala Arg Tyr Glu Leu Glu Met Gln Ser Tyr Val
        35                  40                  45

Pro Pro Lys Gly Ala Val
    50

<210> SEQ ID NO 587
<211> LENGTH: 54
<212> TYPE: PRT
<213> ORGANISM: Anopheles gambia

<400> SEQUENCE: 587

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Asn Ala Arg Tyr Glu Leu Glu Met Gln Ser Tyr Val
        35                  40                  45

Pro Pro Lys Gly Ala Val
    50

<210> SEQ ID NO 588
<211> LENGTH: 54
<212> TYPE: PRT
<213> ORGANISM: Anopheles gambia

<400> SEQUENCE: 588

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Gln Ala Arg Tyr Glu Leu Glu Met Gln Ser Tyr Val
        35                  40                  45

Pro Pro Lys Gly Ala Val
    50

<210> SEQ ID NO 589
<211> LENGTH: 54
<212> TYPE: PRT
<213> ORGANISM: Anopheles gambia

<400> SEQUENCE: 589

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala His Tyr Glu Leu Glu Met Gln Ser Tyr Val
        35                  40                  45

Pro Pro Lys Gly Ala Val
    50

<210> SEQ ID NO 590
<211> LENGTH: 54
<212> TYPE: PRT
<213> ORGANISM: Anopheles gambia

<400> SEQUENCE: 590

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Gln Tyr Glu Leu Glu Met Gln Ser Tyr Val
        35                  40                  45

Pro Pro Lys Gly Ala Val
    50

<210> SEQ ID NO 591
<211> LENGTH: 54
<212> TYPE: PRT
<213> ORGANISM: Anopheles gambia

<400> SEQUENCE: 591

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg His Glu Leu Glu Met Gln Ser Tyr Val
        35                  40                  45

Pro Pro Lys Gly Ala Val
    50

<210> SEQ ID NO 592
<211> LENGTH: 54
<212> TYPE: PRT
<213> ORGANISM: Anopheles gambia

<400> SEQUENCE: 592

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Ile Glu Leu Glu Met Gln Ser Tyr Val
        35                  40                  45

Pro Pro Lys Gly Ala Val
    50

<210> SEQ ID NO 593
<211> LENGTH: 54
<212> TYPE: PRT
<213> ORGANISM: Anopheles gambia

<400> SEQUENCE: 593

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Gln Leu Glu Met Gln Ser Tyr Val
        35                  40                  45

Pro Pro Lys Gly Ala Val
    50

<210> SEQ ID NO 594
<211> LENGTH: 54
<212> TYPE: PRT
<213> ORGANISM: Anopheles gambia

<400> SEQUENCE: 594

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr His Leu Glu Met Gln Ser Tyr Val
        35                  40                  45

Pro Pro Lys Gly Ala Val
    50

<210> SEQ ID NO 595
<211> LENGTH: 54
<212> TYPE: PRT
<213> ORGANISM: Anopheles gambia

<400> SEQUENCE: 595

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Asn Leu Glu Met Gln Ser Tyr Val
        35                  40                  45

Pro Pro Lys Gly Ala Val
    50

<210> SEQ ID NO 596
<211> LENGTH: 54
<212> TYPE: PRT
<213> ORGANISM: Anopheles gambia

<400> SEQUENCE: 596

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Ile Glu Met Gln Ser Tyr Val
        35                  40                  45

Pro Pro Lys Gly Ala Val
    50

<210> SEQ ID NO 597
<211> LENGTH: 54
<212> TYPE: PRT
<213> ORGANISM: Anopheles gambia

<400> SEQUENCE: 597

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Val Glu Met Gln Ser Tyr Val
        35                  40                  45

Pro Pro Lys Gly Ala Val
    50

```
<210> SEQ ID NO 598
<211> LENGTH: 54
<212> TYPE: PRT
<213> ORGANISM: Anopheles gambia

<400> SEQUENCE: 598

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Gln Met Gln Ser Tyr Val
        35                  40                  45

Pro Pro Lys Gly Ala Val
    50

<210> SEQ ID NO 599
<211> LENGTH: 54
<212> TYPE: PRT
<213> ORGANISM: Anopheles gambia

<400> SEQUENCE: 599

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu His Met Gln Ser Tyr Val
        35                  40                  45

Pro Pro Lys Gly Ala Val
    50

<210> SEQ ID NO 600
<211> LENGTH: 54
<212> TYPE: PRT
<213> ORGANISM: Anopheles gambia

<400> SEQUENCE: 600

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Asn Met Gln Ser Tyr Val
        35                  40                  45

Pro Pro Lys Gly Ala Val
    50

<210> SEQ ID NO 601
<211> LENGTH: 54
<212> TYPE: PRT
<213> ORGANISM: Anopheles gambia

<400> SEQUENCE: 601

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Ile Gln Ser Tyr Val
        35                  40                  45

Pro Pro Lys Gly Ala Val
    50
```

```
<210> SEQ ID NO 602
<211> LENGTH: 54
<212> TYPE: PRT
<213> ORGANISM: Anopheles gambia

<400> SEQUENCE: 602

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Val Gln Ser Tyr Val
        35                  40                  45

Pro Pro Lys Gly Ala Val
    50

<210> SEQ ID NO 603
<211> LENGTH: 54
<212> TYPE: PRT
<213> ORGANISM: Anopheles gambia

<400> SEQUENCE: 603

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser His Val
        35                  40                  45

Pro Pro Lys Gly Ala Val
    50

<210> SEQ ID NO 604
<211> LENGTH: 54
<212> TYPE: PRT
<213> ORGANISM: Anopheles gambia

<400> SEQUENCE: 604

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Ile Val
        35                  40                  45

Pro Pro Lys Gly Ala Val
    50

<210> SEQ ID NO 605
<211> LENGTH: 54
<212> TYPE: PRT
<213> ORGANISM: Anopheles gambia

<400> SEQUENCE: 605

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Ala Pro Lys Gly Ala Val
    50
```

<210> SEQ ID NO 606
<211> LENGTH: 54
<212> TYPE: PRT
<213> ORGANISM: Anopheles gambia

<400> SEQUENCE: 606

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Ser Pro Lys Gly Ala Val
    50

<210> SEQ ID NO 607
<211> LENGTH: 54
<212> TYPE: PRT
<213> ORGANISM: Anopheles gambia

<400> SEQUENCE: 607

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Ala Lys Gly Ala Val
    50

<210> SEQ ID NO 608
<211> LENGTH: 54
<212> TYPE: PRT
<213> ORGANISM: Anopheles gambia

<400> SEQUENCE: 608

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Ser Lys Gly Ala Val
    50

<210> SEQ ID NO 609
<211> LENGTH: 54
<212> TYPE: PRT
<213> ORGANISM: Anopheles gambia

<400> SEQUENCE: 609

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Asn Gly Ala Val
    50

```
<210> SEQ ID NO 610
<211> LENGTH: 54
<212> TYPE: PRT
<213> ORGANISM: Anopheles gambia

<400> SEQUENCE: 610

Pro Glu Glu Gln Val Ile Phe Ala Glu Phe Ser Arg Lys Cys Ala Glu
1               5                   10                  15

Arg Trp Lys Thr Met Leu Asp Lys Glu Lys Gln Arg Phe His Glu Met
            20                  25                  30

Ala Glu Lys Asp Lys Ala Arg Tyr Glu Leu Glu Met Gln Ser Tyr Val
        35                  40                  45

Pro Pro Gln Gly Ala Val
    50
```